United States Patent
Hersel et al.

(10) Patent No.: US 10,729,778 B2
(45) Date of Patent: *Aug. 4, 2020

(54) CARRIER-LINKED TREPROSTINIL PRODRUGS

(71) Applicants: Ulrich Hersel, Heidelberg (DE); Harald Rau, Dossenheim (DE); Torben Lessmann, Neustadt an der Weinstrasse (DE); Nicola Bisek, Heidelberg (DE); Guillaume Maitro, Mannheim (DE); Kennett Sprogøe, Holte (DK); Thomas Wegge, Heidelberg (DE); Oliver Keil, Heidelberg (DE); Joachim Zettler, Heidelberg (DE)

(72) Inventors: Ulrich Hersel, Heidelberg (DE); Harald Rau, Dossenheim (DE); Torben Lessmann, Neustadt an der Weinstrasse (DE); Nicola Bisek, Heidelberg (DE); Guillaume Maitro, Mannheim (DE); Kennett Sprogøe, Holte (DK); Thomas Wegge, Heidelberg (DE); Oliver Keil, Heidelberg (DE); Joachim Zettler, Heidelberg (DE)

(73) Assignee: Ascendis Pharma A/S, Hellerup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/418,180

(22) Filed: Jan. 27, 2017

(65) Prior Publication Data

US 2019/0105400 A1 Apr. 11, 2019

Related U.S. Application Data

(63) Continuation of application No. 14/238,437, filed as application No. PCT/EP2012/065745 on Aug. 10, 2012, now Pat. No. 9,561,287.

(30) Foreign Application Priority Data

Aug. 12, 2011 (EP) .................................. 11177409
Dec. 23, 2011 (EP) .................................. 11195615
Apr. 25, 2012 (EP) .................................. 12165508

(51) Int. Cl.
*A61K 47/60* (2017.01)
*A61K 47/64* (2017.01)

(52) U.S. Cl.
CPC ............ *A61K 47/60* (2017.08); *A61K 47/641* (2017.08); *A61K 47/645* (2017.08)

(58) Field of Classification Search
CPC ..... A61K 47/60; A61K 47/645; A61K 47/641
See application file for complete search history.

(56) References Cited

U.S. PATENT DOCUMENTS

| 4,306,075 A | 12/1981 | Aristoff |
| 9,561,287 B2 * | 2/2017 | Hersel .................... A61K 47/60 |

FOREIGN PATENT DOCUMENTS

| EP | 0159784 | 3/1985 |
| EP | 1625856 | 2/2006 |
| WO | WO 2000/057701 | 10/2000 |
| WO | WO 2004/089280 | 10/2004 |
| WO | WO 2005/058329 | 6/2005 |
| WO | WO 2006/003014 | 1/2006 |
| WO | WO 2008/098196 | 8/2008 |
| WO | WO 2008/155134 | 12/2008 |
| WO | WO 2010/014258 | 2/2010 |
| WO | WO 2010/019233 | 2/2010 |
| WO | WO 2010/033207 | 3/2010 |
| WO | WO 2010/068754 | 6/2010 |
| WO | WO 2010/144508 | 12/2010 |
| WO | WO 2011/012715 | 2/2011 |
| WO | WO 2011/042450 | 4/2011 |
| WO | WO2004089280 | * 10/2014 |

OTHER PUBLICATIONS

McLaughlin et al., "Addition of Inhaled Treprostinil to Oral Theraphy for Pulmonary Arterial Hypertension," Journal of the American College of Cardiology, 55(18), 1915-1922, 2010. (Year: 2010).*
Obata et al., *Single Injection of a Sustained-release Prostacyclin Analog Improves Pulmonary Hypertension in Rats*, Am J Respir Crit Care Med, 2008, 177, 2, 195-201.
Riley et al. *The Benefits and Challenges of PEGylating Small Molecules*, Pharmaceutical Technology, Jul. 2008, 88-94.

* cited by examiner

*Primary Examiner* — Paul A Zucker
(74) *Attorney, Agent, or Firm* — Haug Partners LLP

(57) ABSTRACT

Prodrugs or a pharmaceutically acceptable salt thereof which comprise a covalent treprostinil carrier conjugate, as well as their pharmaceutical composition, may be used as medicaments, especially for diseases or disorders which can be treated by treprostinil, such as pulmonary arterial hypertension (PAH).

24 Claims, 5 Drawing Sheets

Specification includes a Sequence Listing.

CARRIER-LINKED TREPROSTINIL PRODRUGS

The present application is a continuation of U.S. patent application Ser. No. 14/238,437 filed on Feb. 11, 2014, which claims priority from PCT Patent Application No. PCT/EP2012/065745 filed on Aug. 10, 2012, which claims priority from European Patent Application No. EP 11177409.7 filed on Aug. 12, 2011, European Patent Application No. EP 11195615.7 filed on Dec. 23, 2011, and European Patent Application No. EP 12165508.8 filed on Apr. 25, 2012 the disclosures of which are incorporated herein by reference in their entirety.

FIELD OF THE INVENTION

It is noted that citation or identification of any document in this application is not an admission that such document is available as prior art to the present invention.

Pulmonary arterial hypertension (PAH) is an increase in blood pressure in the pulmonary artery, pulmonary vein, or pulmonary capillaries, leading to shortness of breath, dizziness, fainting, and other symptoms, all of which are exacerbated by exertion. PAH can be a severe disease with a markedly decreased exercise tolerance and heart failure. It is an orphan disease with an incidence of about 2-3 per million per year and a prevalence of about 15 per million. Median survival of patients with untreated PAH is in the range of 2-3 years from time of diagnosis, with the cause of death usually being right ventricular failure.

Pulmonary arterial hypertension involves the vasoconstriction or tightening of blood vessels connected to and within the lungs. Over time, fibrosis causes the affected blood vessels to become both stiffer and thicker which further increases the blood pressure within the lungs and impairs their blood flow. In addition, the increased workload of the heart causes hypertrophy of the right ventricle which ultimately causes right heart failure. As the blood flowing through the lungs decreases, the left side of the heart receives less blood and thus oxygen supply is below the required level, especially during physical activity.

A number of agents have been introduced for the treatment of PAH of which prostacyclins are commonly considered to be the most effective. One prostacyclin is Epoprostenol which is a synthetic prostacyclin and marketed as Flolan® (GlaxoSmithKline). It is given to patients via continuous infusion and requires a semi-permanent central venous catheter which can cause sepsis and thrombosis. Flolan® is unstable, and therefore has to be kept on ice during administration. Since it has a half-life of only 3 to 5 minutes, the infusion has to be continuous night and day and any interruption can be fatal. Thus, treatment of PAH with Flolan® is a huge burden for the patient.

Another prostacyclin, Iloprost (Ilomedin) which is marketed as Ventavis® (Bayer), was the only inhaled form of prostacyclin approved for use in the US and Europe, until the inhaled form of treprostinil was approved by the FDA in July 2009 which is marketed under the trade name TYVASO® (United Therapeutics).

Inhaled prostacyclin suffer from the drawback of not providing fully efficacious plasma levels of drug throughout the dosing period, making inhaled therapy less desired in severe patients.

Therefore, there was a need to develop other prostanoids, as has been described for example in U.S. Pat. No. 4,306,075A and EP159784B1. One such prostaglandin is treprostinil with the trade name Remodulin® (United Therapeutics). The half-life of treprostinil is 4 hours but treprostinil is still required to be administered as a continuous subcutaneous infusion or continuous intravenous infusion via an infusion pump that the patient must wear at all times.

Subcutaneous infusion of treprostinil is frequently painful to the extent that the patient cannot tolerate the pain and consequently the mode of administration is switched to intravenous infusion. However, an increased risk of sepsis with intravenous Remodulin has been reported.

As subcutaneous infusion is associated with pain, there is a need for developing a prostacyclin that can be administered by subcutaneous administration but with reduced rates of pain. This can be achieved by administering a carrier linked prodrug of a prostacyclin, in which the absorption of the prodrug is sufficiently fast, and release of prostacyclin from the prodrug is sufficiently slow, such the subcutaneous exposure to free prostacyclin molecules is minimized.

Prostacyclins are the standard treatment of PAH, particularly in more severe patients. Although inhaled treprostinil is more convenient and without the strong pain that is frequently associated with subcutaneously infused treprostinil, inhalation is considered to be less effective and therefore less often prescribed.

Treprostinil has the following structure:

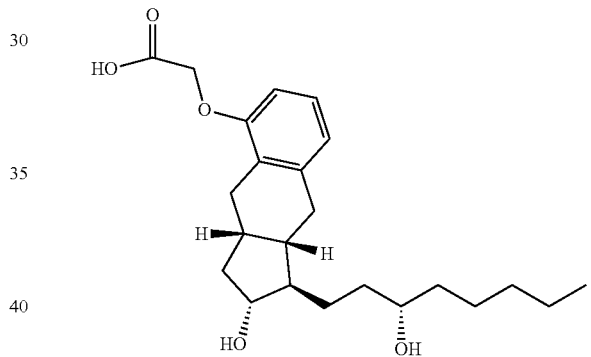

Therefore, there exists a need to provide a more efficacious and/or more comfortable treprostinil treatment for patients.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right to disclaim, and hereby disclose a disclaimer of, any previously described product, method of making the product, or process of using the product.

SUMMARY OF THE INVENTION

This object is achieved with carrier-linked treprostinil prodrugs of formula (I):

$$Z^1\text{-}(X^0\text{-}T)_y \qquad (I),$$

wherein each T is independently selected from structures (i) to (v):

(i)

(ii)

(iii)

(iv)

(v)

wherein dashed lines indicating attachment to $X^0$;

y is an integer ranging of from 1 to 64, preferably ranging from 1 to 16, more preferably y selected from 1, 2, 3, 4, 5, 6, 7, 8, 9, 10, 11, 12, 13, 14, 15 and 16, even more preferably y is 4, 6, or 8, most preferably, 8, each $X^0$ is independently $(X^{0A})_{m1}$—$(X^{0B})_{m2}$;

m1; m2 are independently 0; or 1;

$X^{0A}$ is $T^0$;

$X^{0B}$ is a branched or unbranched or cyclic $C_{1-15}$ alkylene group which is unsubstituted or substituted with one or more $R^3$, which are the same or different; more preferably, $X^{0B}$ is a branched or unbranched cyclic $C_{1-15}$ alkylene group which is unsubstituted or substituted with one or more $R^3$, which are the same or different $R^3$ is halogen; $C_{1-6}$alkyl; CN; $C(O)R^4$; $C(O)OR^4$; $OR^4$; $C(O)R^4$; $C(O)N(R^4R^{4a})$; $S(O)_2N(R^4R^{4a})$; $S(O)N(R^4R^{4a})$; $S(O)_2R^4$; $S(O)R^4$; $N(R^4)S(O)_2N(R^{4a}R^{4b})$; $SR^4$; $N(R^4R^{4a})$; $NO_2$; $OC(O)R^4$; $N(R^4)C(O)R^{4a}$; $N(R^4)SO_2R^{4a}$; $N(R^4)S(O)R^{4a}$; $N(R^4)C(O)N(R^{4a}R^{4b})$; $N(R^4)C(O)OR^{4a}$; $OC(O)N(R^4R^{4a})$; or $T^0$;

$R^4$, $R^{4a}$, $R^{4b}$ are independently selected from the group consisting of H; $T^0$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^5$, which are the same of different;

$R^5$ is halogen; CN; $C(O)R^6$; $C(O)OR^6$; $OR^6$; $C(O)R^6$; $C(O)N(R^6R^{6a})$; $S(O)_2N(R^6R^{6a})$; $S(O)N(R^6R^{6a})$; $S(O)_2R^6$; $S(O)R^6$; $N(R^6)S(O)_2N(R^{6a}R^{6b})$; $SR^6$; $N(R^6R^{6a})$; $NO_2$; $OC(O)R^6$; $N(R^6)C(O)R^{6a}$; $N(R^6)SO_2R^{6a}$; $N(R^6)S(O)R^{6a}$; $N(R^6)C(O)N(R^{6a}R^{6b})$; $N(R^6)C(O)OR^{6a}$; $OC(O)N(R^6R^{6a})$;

$R^6$, $R^{6a}$, $R^{6b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same of different;

$T^0$ is phenyl; naphthyl; azulenyl; indenyl; indanyl; $C_{3-7}$ cycloalkyl; 3 to 7 membered heterocyclyl; or 8 to 11 membered heterobicyclyl, wherein $T^0$ is optionally substituted with one or more $R^7$, which are the same or different;

$R^7$ is halogen; CN; $COOR^8$; $OR^8$; $C(O)R^8$; $C(O)N(R^8R^{8a})$; $S(O)_2N(R^8R^{8a})$; $S(O)N(R^8R^{8a})$; $S(O)_2R^8$; $S(O)R^8$; $N(R^8)S(O)_2N(R^{8a}R^{8b})$; $SR^8$; $N(R^8R^{8a})$; $NO_2$; $OC(O)R^8$; $N(R^8)C(O)R^{8a}$; $N(R^8)S(O)_2R^{8a}$; $N(R^8)S(O)R^{8a}$; $N(R^8)C(O)OR^{8a}$; $N(R^8)C(O)N(R^{8a}R^{8b})$; $OC(O)N(R^8R^{8a})$; oxo (=O), where the ring is at least partially saturated; $C_{1-6}$ alkyl; $C_{2-6}$ alkenyl; or $C_{2-6}$ alkynyl, wherein $C_{1-6}$ alkyl; $C_{2-6}$ alkenyl; and $C_{2-6}$ alkynyl are optionally substituted with one or more $R^9$, which are the same or different;

$R^8$, $R^{8a}$, $R^{8b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{10}$, which are the same of different;

$R^9$, $R^{10}$ are independently selected from the group consisting of halogen; CN; $C(O)R^{11}$; $C(O)OR^{11}$; $OR^{11}$; $C(O)R^{11}$; $C(O)N(R^{11}R^{11a})$; $S(O)_2N(R^{11}R^{11a})$; $S(O)N(R^{11}R^{11a})$; $S(O)_2R^{11}$; $S(O)R^{11}$; $N(R^{11})S(O)_2N(R^{11a}R^{11b})$; $SR^{11}$; $N(R^{11}R^{11a})$; $NO_2$; $OC(O)R^{11}$; $N(R^{11})C(O)R^{11a}$; $N(R^{11})SO_2R^{11a}$; $N(R^{11})S(O)R^{11a}$; $N(R^{11})C(O)N(R^{11a}R^{11b})$; $N(R^{11})C(O)OR^{11a}$; and $OC(O)N(R^{11}R^{11a})$;

$R^{11}$, $R^{11a}$, $R^{11b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same of different;

$Z^1$ is a carrier comprising a covalently bound polymer, preferably a pharmaceutically acceptable polymer, wherein the carrier is covalently attached to a moiety $X^0$, provided that one of m1, m2 is 1 and wherein the carrier is covalently attached to T in case m1, m2=0, or a pharmaceutically acceptable salt thereof.

It was surprisingly found that such carrier-linked treprostinil prodrugs can be used to obtain dosage forms of treprostinil which at least partially overcome the above mentioned shortcomings.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

Within the present invention the terms are used having the meaning as follows.

The terms "drug", "biologically active molecule", "biologically active moiety", "biologically active agent", "active agent", "active substance" and the like mean any substance which can affect any physical or biochemical properties of a biological organism, including but not limited to viruses, bacteria, fungi, plants, animals, and humans. In particular, as used herein, the terms include any substance intended for diagnosis, cure, mitigation, treatment, or prevention of disease in organisms, in particular humans or other animals, or to otherwise enhance physical or mental well-being of organisms, in particular humans or animals. Treprostinil is understood to be a biologically active molecule.

"Biologically active moiety D" means the part of the drug linker conjugate, which results after cleavage in a drug D-OH or D-H of known biological activity. Accordingly, "biologically active moiety treprostinil" or "treprostinil moiety" means the part of the carrier-linked treprostinil prodrug, which results after cleavage in a drug treprostinil of known biological activity.

"Free form" of a drug such as treprostinil refers to the drug in its unmodified, pharmacologically active form, such as after being released from a carrier-linked prodrug.

Targeting moieties are moieties that when present in a molecule, such as for example a prodrug, allow preferential localization of such larger molecule in specific target areas of the organism to which it has been administered. Such specific target areas might be organs, certain cell types or subcellular compartments. "Preferential localization" means that at least 5%, 10%, preferably at least 20% and more preferably at least 30% of the biologically active moieties administered to a patient reach said specific target areas.

Targeting moieties may be divided into 3 classes according to size:

small molecular targeting moieties, for example C-glucuronide, cobalamin, vitamins such as folic acid (folate) and analogs and derivatives, carbohydrates, bisphosphonates, N-acetylgalactosamine, peptides, for example bombesin, somatostatin, LHRH, EGF, VEGF, hCG, fragments of luteinizing hormone (LH), Octreotide, Vapreotide, Lanreotide, RC-3940 series, Decapeptyl, Lupron, Zoladex, Cetrorelix, peptides or peptidomimetics containing the NGR or RGD motifs or derived from these motifs such as CNGRC (linear), GNGRG (cyclic), ACDC RGD CFCG (cyclic), CDCRGDCFC, CNGRC (cyclic), CRGDCGG, CNGRC, or other peptides such as ATWLPPR, Thrombospondin (TSP)-1 mimetics, (RGD peptidomimetic), CTTHWGFTLC, CGNKRTRGC, neuropeptide substance P, SSP, the Sar9, Met(O2)11 analog of Substance P, Cholecystokinin (CCK), Corticotropin-releasing hormone/factor (CRH/CRF), Dermorphin, FGF-2 or basic fibroblast growth factor, Galanin, Melanopsin, Neurotension, cyclic RGDfK and cyclic RGDyV; preferably bombesin, somatostatin, LHRH, EGF, VEGF, hCG, fragments of luteinizing hormone (LH), Octreotide, Vapreotide, Lanreotide, RC-3940 series, Decapeptyl, Lupron, Zoladex, Cetrorelix, peptides or peptidomimetics containing the NGR or RGD motifs or derived from these motifs such as CNGRC (linear), GNGRG (cyclic), ACDC RGD CFCG (cyclic), CDCRGDCFC, CNGRC (cyclic), CRGDCGG, CNGRC, or other peptides such as ATWLPPR, Thrombospondin (TSP)-1 mimetics, (RGD peptidomimetic), CTTHWGFTLC, CGNKRTRGC, neuropeptide substance P, SSP, the Sar9, Met(O2)11 analog of Substance P, Cholecystokinin (CCK), Corticotropin-releasing hormone/factor (CRH/CRF), Dermorphin, FGF-2 or basic fibroblast growth factor, Galanin, Melanopsin, Neurotension and protein or macro-molecular targeting moieties, for example IL-2, GM-CSF, TNF-a, transferrin, immunoglobulins, Acetylated-LDL, Lactoferrin (Lf) (also called lactotransferrin) and lactoferricin (Lcin), Gambogic acid (GA).

In principle, any ligand of a cell surface receptor may be advantageously used as a targeting moiety. For instance, ATWLPPR peptide is a potent antagonist of VEGF; thrombospondin-1 (TSP-1) induces apoptosis in endothelial cells, RGD-motif mimics block integrin receptors, NGR-containing peptides inhibit aminopeptidase N, and cyclic peptides containing the sequence of HWGF selectively inhibit MMP-2 and MMP-9. LyP-1 peptide specifically binds to tumor lymphatic vessels. Illustrative other ligands include peptide ligands identified from library screens, tumor cell-specific peptides, tumor cell-specific aptamers, tumor cell-specific carbohydrates, tumor cell-specific monoclonal or polyclonal antibodies, Fab or scFv (i.e., a single chain variable region) fragments of antibodies such as, for example, a Fab fragment of an antibody directed to EphA2 or other proteins specifically expressed or uniquely accessible on metastatic cancer cells, small organic molecules derived from combinatorial libraries, growth factors, such as EGF, FGF, insulin, and insulin-like growth factors, and homologous polypeptides, somatostatin and its analogs, transferrin, lipoprotein complexes, bile salts, selecting, steroid hormones, Arg-Gly-Asp containing peptides, retinoids, various Galectins, δ-opioid receptor ligands, cholecystokinin A receptor ligands, ligands specific for angiotensin AT1 or AT2 receptors, peroxisome proliferator-activated receptor λ ligands, β-lactam antibiotics such as penicillin, small organic molecules including antimicrobial drugs, and other molecules that bind specifically to a receptor preferentially expressed on the surface of tumor cells or on an infectious organism, antimicrobial and other drugs designed to fit into the binding pocket of a particular receptor based on the crystal structure of the receptor or other cell surface protein, ligands of tumor antigens or other molecules preferentially expressed on the surface of tumor cells, or fragments of any of these molecules. Examples of tumor-specific antigens that can function as targeting moieties include extracellular epitopes of a member of the Ephrin family of proteins, such as EphA2. EphA2 expression is restricted to cell-cell junctions in normal cells, but EpbA2 is distributed over the entire cell surface in metastatic tumor cells. Thus, EphA2 on metastatic cells would be accessible for binding to, for example, a Fab fragment of an antibody conjugated to an immunogen, whereas the protein would not be accessible for binding to the Fab fragment on normal cells, resulting in a targeting moiety specific for metastatic cancer cells.

Further examples for such targeting moieties are: FSH-33, Allatostatin 1, Hepatocarcinoma targeting peptide, Peptide GFE, anti-EGFR antibodies and/or antibody fragments, in particular Cetuximab, CendR, iRGD peptide (RGD-CendR hybrid peptide), small molecules, antibodies and/or antibody fragments binding to cancer-specific epitopes like e.g. CEA, Gastrin-releasing peptide receptors, Somatostatin receptors, Galanin receptors, Follicle-stimulating hormone receptors, p32 protein, Fibroblast growth factor receptors, HepG2, Epidermal growth factor receptors, Integrin αcβ6, Neuropilin-1 receptor and VEGF receptors.

The phrases "in bound form", "connected to" or "moiety" refer to sub-structures which are part of a larger molecule. The phrases "in bound form" and "connected to" are used to simplify reference to moieties by naming or listing reagents, starting materials or hypothetical starting materials well known in the art, and whereby "in bound form" or "connected to" mean that for example one or more hydrogen radicals (—H), or one or more activating or protecting groups present in the reagents or starting materials are not present in the moiety when part of a larger molecule.

To enhance physicochemical or pharmacokinetic properties of a drug in vivo, such drug can be conjugated with a carrier. If the drug, such as treprostinil, is transiently bound to a carrier and/or a linker, as in the present invention, such systems are commonly assigned as "carrier-linked prodrugs". According to the definitions provided by IUPAC (as given under http://www.chem.qmul.ac.uk/iupac/medchem/ah.html, accessed on Mar. 7, 2011), a carrier-linked prodrug is a prodrug that contains a temporary linkage of a given active substance with a transient carrier group that produces improved physicochemical or pharmacokinetic properties and that can be easily removed in vivo, usually by a hydrolytic cleavage.

The term "promoiety" refers to the part of the prodrug which is not the drug, thus meaning linker and carrier and/or any optional spacer moieties.

The terms "reversible prodrug linkers" or "transient prodrug linkers" refer to linkers comprising, in particular consisting of reversible linkages that are non-enzymatically hydrolytically degradable, i.e. cleavable, under physiological conditions (aqueous buffer at pH 7.4, 37° C.) with half-lives ranging from, for example, one hour to three months. On the other hand, stable or permanent linkages are typically non-cleavable permanent bonds, meaning that they have a half-life of at least six months under physiological conditions (aqueous buffer at pH 7.4, 37° C.).

A "traceless prodrug linker" refers to a prodrug linker from which a drug is released in its free form, meaning that upon release from the promoiety the drug does not contain any traces of the promoiety.

The term "polymer" describes a molecule comprising, in particular consisting of repeating structural units connected by chemical bonds in a linear, circular, branched, cross-linked or dendrimeric way or a combination thereof, which can be of synthetic or biological origin or a combination of both. Typically, a polymer has a molecular weight of at least 500 Da. It is understood, that when the polymer is a polypeptide, then the individual amino acids of the polypeptide may be the same or may be different.

The term "polymeric" refers to a moiety comprising one or more polymer.

The term "poly(ethylene glycol)-based polymeric chain" or "PEG-based polymeric chain" refers to a polymer comprising at least 20 weight % ethylene glycol moieties, more preferably at least 50% by weight, even more preferably at least 80% by weight ethylene glycol moieties, which chain is optionally capped and/or optionally further comprises one or more functional groups, for example amine group(s). It is understood that a PEG-based polymeric chain may be terminated or interrupted by alkyl or aryl groups and optionally be substituted with heteroatoms and/or functional groups. Suitable capping or terminating groups for a PEG-based polymeric chain are for example $CH_3$—, $CH_3$—O— and $CH_3$—$CH_2$—. Accordingly, a PEG-based polymer is a polymer comprising at least 20 weight % ethylene glycol moieties, more preferably at least 50% by weight, even more preferably at least 80% by weight ethylene glycol moieties.

The term "hydrogel" may be defined as a three-dimensional, hydrophilic or amphiphilic polymeric network capable of taking up large quantities of water which causes swelling of the hydrogel in aqueous media. The networks are composed of homopolymers or copolymers and are insoluble due to the presence of covalent chemical or physical (ionic, hydrophobic interactions, entanglements) crosslinks. The crosslinks provide the network structure and physical integrity.

The terms "spacer", "spacer group", "spacer molecule", and "spacer moiety" are used interchangeably and refer to any moiety suitable for connecting two moieties, such as $C_{1-50}$ alkyl, $C_{2-50}$ alkenyl or $C_{2-50}$ alkinyl, which fragment is optionally interrupted by one or more groups selected from —NH—, —N($C_{1-4}$ alkyl)-, —O—, —S—, —C(O)—, —C(O)NH—, —C(O)N($C_{1-4}$ alkyl)-, —O—C(O)—, —S(O)—, —S(O)$_2$—, —O—C(O)NH—, —O—(CO)N($C_{1-4}$ alkyl)-, 4- to 7-membered heterocyclyl, phenyl or naphthyl. Preferably, the terms refer to $C_{1-50}$ alkyl, $C_{2-50}$ alkenyl or $C_{2-50}$ alkinyl, which fragment is optionally interrupted by one or more groups selected from —NH—, —N($C_{1-4}$ alkyl)-, —O—, —S—, —C(O)—, —C(O)NH—, —C(O)N($C_{1-4}$ alkyl)-, —O—C(O)—, —S(O)—, —S(O)$_2$—, 4- to 7-membered heterocyclyl, phenyl or naphthyl.

The term "terminus" refers to the last carbon atom or heteroatom of a linear or branched chain of carbon atoms and/or heteroatoms, i.e. "terminus" refers to a carbon or heteroatom which is connected to exactly one other carbon or heteroatom.

"Terminal/terminally" or "terminally connected" means that moieties are connected to the terminus or termini of another moiety.

"Pharmaceutical composition" or "composition" means a composition containing one or more drugs or prodrugs, and optionally one or more excipients, as well as any product which results, directly or indirectly, from combination, complexation or aggregation of any two or more of the excipients and/or the drug or prodrug, or from dissociation of one or more of the excipients and/or drug and/or prodrug, or from other types of reactions or interactions of one or more of the excipients and/or drug and/or prodrug. Accordingly, the a pharmaceutical composition of the present invention encompasses any composition obtainable by admixing a carrier-linked treprostinil prodrug of the present invention and a pharmaceutically acceptable excipient.

The term "excipient" refers to a diluent, adjuvant, or vehicle with which the carrier-linked treprostinil prodrug is administered. Such pharmaceutical excipient can be sterile liquids, such as water and oils, including those of petroleum, animal, vegetable or synthetic origin, including but not limited to peanut oil, soybean oil, mineral oil, sesame oil and the like. Water is a preferred excipient when the pharmaceutical composition is administered orally. Saline and aqueous dextrose are preferred excipients when the pharmaceutical composition is administered intravenously. Saline solutions and aqueous dextrose and glycerol solutions are preferably employed as liquid excipients for injectable solutions. Suitable pharmaceutical excipients include starch, glucose, lactose, sucrose, mannitol, trehalose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, pH buffering agents, like, for example, acetate, succinate, tris, carbonate, phosphate, HEPES (4-(2-hydroxyethyl)-1-piperazineethanesulfonic acid), MES (2-(N-morpholino)ethanesulfonic acid), or can contain detergents, like Tween, poloxamers, poloxamines, CHAPS, Igepal, or amino acids like, for example, glycine, lysine, or histidine. These compositions can take the form of solutions, suspensions, emulsions, tablets, pills, capsules, powders, sustained-release formulations and the like. The composition can be formulated as a suppository, with traditional binders and excipients such as triglycerides. Oral formulation can include standard excipients such as pharmaceutical grades of mannitol, lactose, starch, magnesium stearate, sodium saccharine, cellulose, magnesium carbonate, etc. Examples of suitable pharmaceutical excipients are described in "Remington's Pharmaceutical Sciences" by E. W. Martin. Such compositions will contain a therapeutically effective amount of treprostinil in the form of at least one carrier-linked treprostinil prodrug of the present invention, preferably in purified form, together with a suitable amount of excipient so as to provide the form for proper administration to the patient. The formulation should suit the mode of administration.

The term "pharmaceutically acceptable" means approved by a regulatory agency such as the EMEA (Europe) and/or the FDA (US) and/or any other national regulatory agency for use in animals, preferably in humans.

"Dry composition" means that the pharmaceutical composition comprising carrier-linked treprostinil prodrug according to the present invention is provided in a dry form in a container. Suitable methods for drying are spray-drying and lyophilization (freeze-drying). Such dry composition of carrier-linked treprostinil prodrug has a residual water content of a maximum of 10%, preferably less than 5% and more preferably less than 2% (determined according to Karl Fischer). The preferred method of drying is lyophilization. "Lyophilized composition" means that the pharmaceutical composition comprising carrier-linked treprostinil prodrug was first frozen and subsequently subjected to water reduction by means of reduced pressure. This terminology does not exclude additional drying steps which may occur in the manufacturing process prior to filling the composition into the final container.

"Lyophilization" (freeze-drying) is a dehydration process, characterized by freezing a composition and then reducing the surrounding pressure and, optionally, adding heat to allow the frozen water in the composition to sublime directly from the solid phase to gas. Typically, the sublimed water is collected by desublimation.

The term "functional group" refers to specific groups of atoms within molecules that can undergo characteristic chemical reactions. Examples of functional groups are hydroxyl, carbonyl, aldehyde, carboxyl, ester, ketal, hemiketal, acetal, hemiacetal, primary/secondary/tertiary amine, cyanate, disulfide, sulfhydryl, sulfonyl, phosphate.

If a functional group is coupled to another functional group, the resulting chemical structure is referred to as "linkage". For example, the reaction of an amine functional group with a carboxyl functional group results in an amide linkage. Further examples for linkages are ester, ether, ketal, acetal, primary/secondary/tertiary amine, carboxamide, sulfide, and disulfide.

"Alkyl" means a straight-chain (linear, unbranched) or branched carbon chain (unsubstituted alkyl). Optionally, one or more hydrogen atom(s) of an alkyl carbon may be replaced by a substituent as indicated herein, which will be referred to as "substituted alkyl". In general, a preferred alkyl is $C_{1-6}$ alkyl.

"$C_{1-4}$ alkyl" means an alkyl chain having 1 to 4 carbon atoms (unsubstituted $C_{1-4}$ alkyl), e.g. if present at the end of a molecule: methyl, ethyl, n-propyl, isopropyl, n-butyl, isobutyl, sec-butyl tert-butyl, or e.g. —CH$_2$—, —CH$_2$—CH$_2$—, —CH(CH$_3$)—, —CH$_2$—CH$_2$—CH$_2$—, —CH(C$_2$H$_5$)—, —C(CH$_3$)$_2$—, when two moieties of a molecule are linked by the alkyl group (also referred to as $C_{1-4}$ alkylene). Optionally, one or more hydrogen atom(s) of a $C_{1-4}$ alkyl carbon may be replaced by a substituent as indicated herein. Accordingly, "$C_{1-50}$ alkyl" means an alkyl chain having 1 to 50 carbon atoms.

"$C_{1-6}$ alkyl" means an alkyl chain having 1-6 carbon atoms, e.g. if present at the end of a molecule: $C_{1-4}$ alkyl, methyl, ethyl, n-propyl, isopropyl, n-butyl, isobutyl, sec-butyl, tert-butyl, n-pentyl, n-hexyl, or e.g. —$CH_2$—, —$CH_2$—$CH_2$—, —$CH(CH_3)$—, —$C(CH_2)$—, —$CH_2$—$CH_2$—$CH_2$—, —$CH(C_2H_5)$—, —$C(CH_3)_2$—, when two moieties of a molecule are linked by the alkyl group (also referred to as $C_{1-6}$ alkylene). One or more hydrogen atom(s) of a $C_{1-6}$ alkyl carbon may be replaced by a substituent as indicated herein. The terms $C_{1-15}$ alkyl or $C_{1-15}$ alkylene are defined accordingly.

"$C_{2-6}$ alkenyl" means an alkenyl chain having 2 to 6 carbon atoms, e.g. if present at the end of a molecule: —$CH=CH_2$, —$CH=CH-CH_3$, —$CH_2-CH=CH_2$, —$CH=CH-CH_2-CH_3$, —$CH=CH-CH=CH_2$, or e.g. —$CH=CH$—, when two moieties of a molecule are linked by the alkenyl group. One or more hydrogen atom(s) of a $C_{2-6}$ alkenyl carbon may be replaced by a substituent as indicated herein.

The term $C_{2-4}$ alkenyl is defined accordingly.

"$C_{2-6}$ alkynyl" means an alkynyl chain having 2 to 6 carbon atoms, e.g. if present at the end of a molecule: —C≡CH, —$CH_2$—C≡CH, $CH_2$—$CH_2$—C≡CH, $CH_2$—C≡C—$CH_3$, or e.g. —C≡C— when two moieties of a molecule are linked by the alkynyl group. One or more hydrogen atom(s) of a $C_{2-6}$ alkynyl carbon may be replaced by a substituent as indicated herein. The term $C_{2-4}$ alkynyl is defined accordingly.

"$C_{2-50}$ alkenyl" means a branched or unbranched alkenyl chain having 2 to 50 carbon atoms (unsubstituted $C_{2-50}$ alkenyl), e.g. if present at the end of a molecule: —$CH=CH_2$, —$CH=CH-CH_3$, —$CH_2-CH=CH_2$, —$CH=CH-CH_2-CH_3$, —$CH=CH-CH=CH_2$, or e.g. —$CH=CH$—, when two moieties of a molecule are linked by the alkenyl group. Optionally, one or more hydrogen atom(s) of a $C_{2-50}$ alkenyl carbon may be replaced by a substituent as further specified. Accordingly, the term "alkenyl" relates to a carbon chain with at least one carbon carbon double bond. Optionally, one or more triple bonds may occur. The term "$C_{2-15}$ alkenyl" is defined accordingly.

"$C_{2-50}$ alkynyl" means a branched or unbranched alkynyl chain having 2 to 50 carbon atoms (unsubstituted $C_{2-50}$ alkynyl), e.g. if present at the end of a molecule: —C≡CH, —$CH_2$—C≡CH, $CH_2$—$CH_2$—C≡CH, $CH_2$—C≡C—$CH_3$, or e.g. —C≡C— when two moieties of a molecule are linked by the alkynyl group. Optionally, one or more hydrogen atom(s) of a $C_{2-50}$ alkynyl carbon may be replaced by a substituent as further specified. Accordingly, the term "alkynyl" relates to a carbon chain with at least one carbon triple bond. Optionally, one or more double bonds may occur. The term "$C_{2-15}$ alkynyl" is used accordingly.

"$C_{3-7}$ cycloalkyl" or "$C_{3-7}$ cycloalkyl ring" means a cyclic alkyl chain having 3 to 7 carbon atoms, which may have carbon-carbon double bonds being at least partially saturated (unsubstituted $C_{3-7}$ cycloalkyl), e.g. cyclopropyl, cyclobutyl, cyclopentyl, cyclohexyl, cyclohexenyl, cycloheptyl. Optionally, one or more hydrogen atom(s) of a cycloalkyl carbon may be replaced by a substituent as indicated herein. The term "$C_{3-7}$ cycloalkyl" or "$C_{3-7}$ cycloalkyl ring" also includes bridged bicycles like norbonane (norbonanyl) or norbonene (norbonenyl). Accordingly, "$C_{3-5}$ cycloalkyl" means a cycloalkyl having 3 to 5 carbon atoms. Accordingly, "$C_{3-10}$ cycloalkyl" means a cycloalkyl having 3 to 10 carbon atoms. The term "$C_{5-6}$ cycloalkyl" is defined accordingly.

"Halogen" means fluoro, chloro, bromo or iodo. It is generally preferred that halogen is fluoro or chloro.

"4 to 7 membered heterocyclyl" or "4 to 7 membered heterocycle" means a ring with 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom (unsubstituted 4 to 7 membered heterocyclyl). For the sake of completeness it is indicated that in some embodiments of the present invention, 4 to 7 membered heterocyclyl has to fulfill additional requirements. Examples for a 4 to 7 membered heterocycles are azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine or homopiperazine. Optionally, one or more hydrogen atom(s) of a 4 to 7 membered heterocyclyl may be replaced by a substituent. The terms "3 to 7 membered heterocyclyl" and "5 or 6 membered heterocyclyl" are defined accordingly.

"8 to 11 membered heterobicyclyl" or "8 to 11 membered heterobicycle" means a heterocyclic system of two rings with 8 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom (unsubstituted 8 to 11 membered heterobicyclyl). Examples for an 8 to 11 membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine or pteridine. The term 8 to 11 membered heterobicycle also includes spiro structures of two rings like 1,4-dioxa-8-azaspiro[4.5]decane or bridged heterocycles like 8-aza-bicyclo[3.2.1]octane. The term "9 to 11 membered heterobicyclyl" or "9 to 11 membered heterobicycle" is defined accordingly.

The term "aliphatic" means fully saturated.

The term "interrupted" means that between two carbon atoms of, for example, a linker or a spacer or at the respective end of the carbon chain between the respective carbon atom and the hydrogen atom a group (such a —O— or —NH—) is inserted.

In general the term "substituted" preferably refers to substituents, which are the same or different and which are independently selected from the group consisting of halogen, CN, COOR$^{b9}$, OR$^{b9}$, C(O)R$^{b9}$, C(O)N(R$^{b9}$R$^{b9a}$), S(O)$_2$N(R$^{b9}$R$^{b9a}$), S(O)N(R$^{b9}$R$^{b9a}$), S(O)$_2$R$^{b9}$, S(O)R$^{b9}$, N(R$^{b9}$)S(O)$_2$N(R$^{b9a}$R$^{b9b}$), SR$^{b9}$, N(R$^{b9}$R$^{b9a}$), NO$_2$, OC(O)R$^{b9}$, N(R$^{b9}$)C(O)R$^{b9a}$, N(R$^{b9}$)S(O)$_2$R$^{b9a}$, N(R$^{b9}$)S(O)R$^{b9a}$, N(R$^{b9}$)C(O)OR$^{b9a}$, N(R$^{b9}$)C(O)N(R$^{b9a}$R$^{b9b}$), OC(O)N(R$^{b9}$R$^{b9a}$), T$^b$, $C_{1-50}$ alkyl, $C_{2-50}$ alkenyl, and $C_{2-50}$ alkynyl, wherein $T^b$, $C_{1-50}$ alkyl, $C_{2-50}$ alkenyl, and $C_{2-50}$ alkynyl are optionally substituted with one or more $R^{b10}$, which are the same or different, and wherein $C_{1-50}$ alkyl; $C_{2-50}$ alkenyl; and $C_{2-50}$ alkynyl are optionally interrupted by one or more groups selected from the group consisting of $T^b$, —C(O)O—; —O—; —C(O)—; —C(O)N($R^{b11}$)—; —S(O)$_2$N($R^{b11}$)—; —S(O)N($R^{b11}$)—; —S(O)$_2$—; —S(O)—; —N($R^{b11}$)S(O)$_2$N($R^{b11a}$)—; —S—; —N($R^{b11}$)—; —OC(O)$R^{b11}$; —N($R^{b11}$)C(O)—; —N($R^{b11}$)S(O)$_2$; —N($R^{b11}$)S(O)—; —N($R^{b11}$)C(O)O—; —N($R^{b11}$)C(O)N($R^{b11a}$)—; and —OC(O)N($R^{b11}R^{b11a}$);

$R^{b9}$, $R^{b9a}$, $R^{b9b}$ are independently selected from the group consisting of H; $T^b$; and $C_{1-50}$ alkyl; $C_{2-50}$ alkenyl; and $C_{2-50}$ alkynyl, wherein $T^b$, $C_{1-50}$ alkyl, $C_{2-50}$ alkenyl, and $C_{2-50}$ alkynyl are optionally substituted with one or more $R^{b10}$, which are the same or different, and wherein $C_{1-50}$ alkyl; $C_{2-50}$ alkenyl; and $C_{2-50}$ alkynyl are optionally interrupted by one or more groups selected from the group consisting of $T^b$, —C(O)O—, —O—, —C(O)—, —C(O)N($R^b$)—, —S(O)$_2$N($R^{b11}$)—, —S(O)N($R^{b11}$)—, —S(O)$_2$—, —S(O)—, —N($R^{b11}$)S(O)$_2$N($R^{b11a}$)—, —S—, —N($R^{b11}$)—, —OC(O)$R^{b11}$, —N($R^{b11}$)C(O)—, —N($R^{b11}$)S(O)$_2$—, —N($R^{b11}$)S(O)—, —N($R^{b11}$)C(O)O—, —N($R^{b11}$)C(O)N($R^{b11a}$)—, and —OC(O)N($R^{b11}R^{b11a}$), $T^b$ is selected from the group consisting of phenyl, naphthyl, indenyl, indanyl, tetralinyl, $C_{3-10}$ cycloalkyl, 4- to 7-membered heterocyclyl, and 9- to 11-membered heterobicyclyl, wherein $T^b$ is optionally substituted with one or more $R^{b10}$, which are the same or different, $R^{b10}$ is halogen, CN, oxo (=O), COOR$^{b12}$, OR$^{b12}$, C(O)R$^{b12}$, C(O)N(R$^{b12}$R$^{b12a}$), S(O)$_2$N(R$^{b12}$R$^{b12a}$), S(O)N(R$^{b12}$R$^{b12a}$), S(O)$_2$R$^{b12}$, S(O)R$^{b12}$, N(R$^{b12}$)S(O)$_2$N(R$^{b12a}$R$^{b12b}$), SR$^{b12}$, N(R$^{b12}$R$^{b12a}$), NO$_2$, OC(O)R$^{b12}$, N(R$^{b12}$)C(O)R$^{b12a}$, N(R$^{b12}$)S(O)$_2$R$^{b12a}$, N(R$^{b12}$)S(O)R$^{b12a}$, N(R$^{b12}$)C(O)OR$^{b12a}$, N(R$^{b12}$)C(O)N(R$^{b12a}$R$^{b2b}$), OC(O)N(R$^{b12}$R$^{b12a}$), or $C_{1-6}$ alkyl, wherein $C_{1-6}$ alkyl is optionally substituted with one or more halogen, which are the same or different, $R^{b11}$, $R^{b1a}$, $R^{b12}$, $R^{b12a}$, $R^{b12b}$ are independently selected from the group consisting of H; or $C_{1-6}$ alkyl, wherein $C_{1-6}$ alkyl is optionally substituted with one or more halogen, which are the same or different.

The term "interrupted" means that between two carbons a group is inserted or that at the end of the carbon chain between the carbon and hydrogen.

Generally, the term "dashed line" which is used to indicate the connection of one moiety to another is different from a dashed bond which is used to indicate stereochemistry. The person skilled in the art will be able to distinguish between these two.

In general the term "comprise" or "comprising" also encompasses "consist of" or "consisting of".

The term "water soluble" as in a "water-soluble carrier" is a carrier that is soluble in water at room temperature. Typically, a solution of a water-soluble carrier will transmit at least about 75%, more preferably at least about 95% of light, transmitted by the same solution after filtering. On a weight basis, a water-soluble carrier or parts thereof will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble carrier or parts thereof is about 95% (by weight) soluble in water or completely soluble in water.

The carrier-linked treprostinil prodrugs according to the present invention comprise treprostinil moieties. Treprostinil as such is a drug known to a person skilled in the art either in its pure form or as a pharmaceutically acceptable salt thereof.

As used herein a single treprostinil compound dose is given in mg and concentration of a treprostinil compound in a pharmaceutical composition is given in mg/mL. As the treprostinil compound is a carrier-linked prodrug, the concentration is based on quantitative release of free treprostinil from the prodrug. By methods well-known in the art, aliquots of a composition are subjected to treprostinil-releasing conditions (aqueous buffer pH 7.4, 37° C., or accelerated conditions at elevated pH), until no significant increase in treprostinil concentration is observed and the total amount of released treprostinil is determined.

In the present invention, the carrier-linked treprostinil prodrug or a pharmaceutically acceptable salt thereof does not contain treprostinil in its free form or as a pharmaceutically acceptable salt thereof, but in bound form. Treprostinil is bound via one of its functional groups, e.g. via a hydroxyl or carboxyl, to the rest of the molecule and is as part of a moiety T which is connected to a moiety $X^0$ or—if m1 and m2 are both 0—to a moiety $Z^1$ of formula (I). This means that the carrier-linked treprostinil prodrug according to the present invention contains treprostinil as a biologically active moiety. Due to the cleavage of the biologically active moiety from the carrier-linked treprostinil prodrug when administered to a patient in need thereof, treprostinil is released either in its free form or as a pharmaceutically acceptable salt thereof. In other words, the carrier-linked treprostinil prodrug contains one or more moieties T, which moiety T is each substituted with a moiety $X^0$ (provided that at least one of m1 and m2 is 1), which in turn is covalently bound to a carrier $Z^1$. Said carrier comprises a covalently bound polymer, preferably a pharmaceutically acceptable polymer with a molecular weight of at least 500 Dalton.

In another preferred embodiment, the molecular weight of the polymer, preferably a pharmaceutically acceptable polymer is up to 160 kDa, preferably up to about 100 kDa, even more preferably up to about 50 kDa.

Preferably, a moiety $X^0$ (provided that at least one of m1 and m2 is 1) and a moiety T are connected through a carbonate or ester linkage, most preferably a moiety $X^0$ and a moiety T are connected through an ester linkage.

Preferably, a moiety $X^0$ is unsubstituted. More preferably, each moiety $X^0$ is unsubstituted.

In one preferred embodiment, m1 is 0 and m2 is 1.

In another preferred embodiment, both m1 and m2 are 0.

In another preferred embodiment, both m1 and m2 are 1.

Preferably, a sub-structure $X^0$—$Z^1$ is C($R^1R^2$)—CH$_2$—$Z^1$, wherein $R^1$, $R^2$ are independently selected from the group consisting of H and $C_{1-4}$ alkyl, provided that at least one of $R^1$, $R^2$ is other than H; or (CH$_2$)$_n$—$Z^1$, wherein n is 2, 3, 4, 5, 6, 7 or 8.

Preferably, the carrier $Z^1$ is covalently attached to a moiety $X^0$ via an amide group.

Preferably, $R^3$ is halogen; CN; C(O)R$^4$; C(O)OR$^4$; OR$^4$; C(O)R$^4$; C(O)N(R$^4$R$^{4a}$); S(O)$_2$N(R$^4$R$^{4a}$); S(O)N(R$^4$R$^{4a}$); S(O)$_2$R$^4$; S(O)R$^4$; N(R$^4$)S(O)$_2$N(R$^{4a}$R$^{4b}$); SR$^4$; N(R$^4$R$^{4a}$); NO$_2$; OC(O)R$^4$; N(R$^4$)C(O)R$^{4a}$; N(R$^4$)SO$_2$R$^{4a}$; N(R$^4$)S(O)R$^{4a}$; N(R$^4$)C(O)N(R$^{4a}$R$^{4b}$) N(R$^4$)C(O)OR$^{4a}$; OC(O)N(R$^4$R$^{4a}$); or $T^0$.

Preferably, $R^4$, $R^{4a}$, $R^{4b}$ are independently selected from the group consisting of H; $T^0$; $C_{1-4}$ alkyl; $C_{2-4}$ alkenyl; and $C_{2-4}$ alkynyl, wherein $C_{1-4}$ alkyl; $C_{2-4}$ alkenyl; and $C_{2-4}$ alkynyl are optionally substituted with one or more $R^5$, which are the same of different.

More preferably, the carrier-linked treprostinil prodrug is of formula (II):

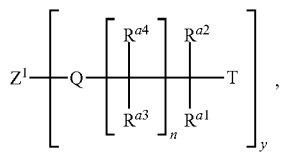

(II)

wherein each T is independently selected from structures (i) to (v) (preferably (iii)):

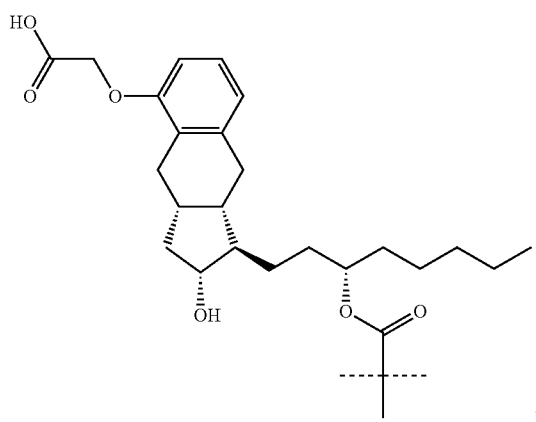

(i)

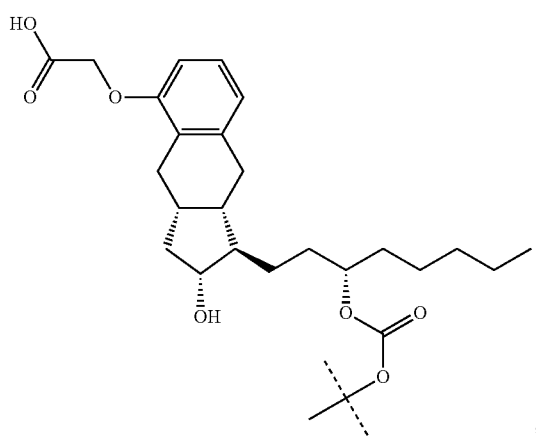

(ii)

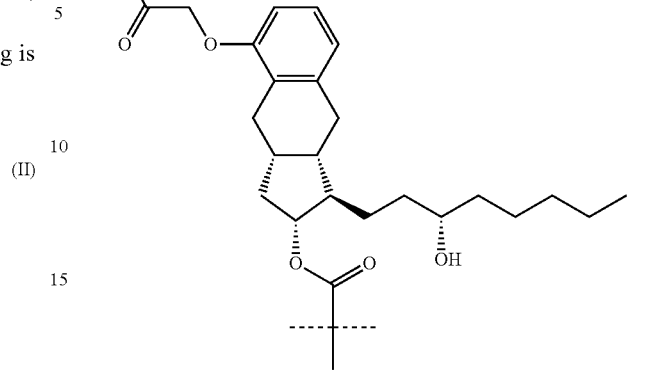

(iii)

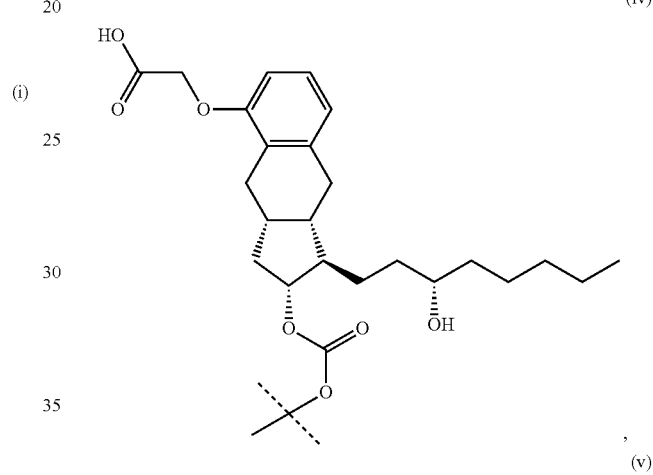

(iv)

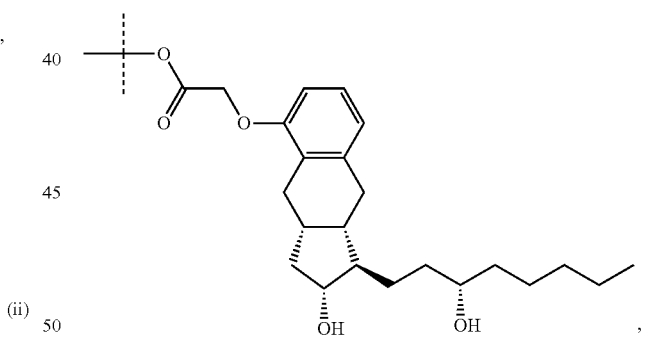

(v)

wherein dashed lines indicating attachment to the rest of the molecule;

y is an integer ranging of from 1 to 64, preferably ranging from 1 to 16, more preferably y is selected from 1, 2, 3, 4, 5, 6, 7, 8, 9, 10, 11, 12, 13, 14, 15 and 16, even more preferably y is 4, 6, 8, 10 or 12; even more preferably, y is 4, 6, or 8; most preferably 4;

$R^{a1}$ is selected from the group of unsubstituted alkyl; substituted alkyl; unsubstituted phenyl; substituted phenyl; unsubstituted naphthyl; substituted naphthyl; unsubstituted indenyl; substituted indenyl; unsubstituted indanyl; substituted indanyl; unsubstituted tetralinyl; substituted tetralinyl; unsubstituted $C_{3-10}$ cycloalkyl; substituted $C_{3-10}$ cycloalkyl; unsubstituted 4- to 7-membered heterocyclyl; substituted 4- to 7-membered heterocyclyl; unsubstituted 9- to 11-membered heterobicyclyl; and substituted 9- to 11-membered heterobicyclyl;

$R^{a2}$ is selected from H, unsubstituted alkyl, and substituted alkyl;

$R^{a3}$ and $R^{a4}$ are independently selected from the group consisting of H, unsubstituted alkyl, and substituted alkyl;

n is 0 or 1;

optionally, $R^{a1}$ and $R^{a3}$ are joined together with the atoms to which they are attached to form a ring A;

A is selected from phenyl; naphthyl; indenyl; indanyl; tetralinyl; $C_{3-10}$ cycloalkyl; 4- to 7-membered aliphatic heterocyclyl; or 9- to 11-membered aliphatic heterobicyclyl, wherein A is unsubstituted or substituted;

preferably, A is selected from the group consisting of $C_{3-10}$ cycloalkyl; 4- to 7-membered aliphatic heterocyclyl; and 9- to 11-membered aliphatic heterobicyclyl, wherein A is unsubstituted or substituted;

Q is a spacer moiety;

$Z^1$ is a carrier comprising a covalently bound polymer, preferably a pharmaceutically acceptable polymer;

or a pharmaceutical salt thereof.

Preferably, $R^{a1}$ is $C_{1-6}$ alkyl or substituted $C_{1-6}$ alkyl, more preferably $C_{1-4}$ alkyl or substituted $C_{1-4}$ alkyl.

More preferably, $R^{a1}$ is selected from methyl, ethyl, n-propyl, isopropyl, n-butyl, isobutyl, sec-butyl, t-butyl, and benzyl.

Preferably, $R^{a2}$ is H.

Preferably, $R^{a3}$ is H, $C_{1-6}$ alkyl or substituted $C_{1-6}$ alkyl, more preferably $C_{1-4}$ alkyl or substituted $C_{1-4}$ alkyl. More preferably, $R^{a3}$ is selected from methyl, ethyl, n-propyl, isopropyl, n-butyl, isobutyl, sec-butyl, t-butyl, and benzyl.

More preferably, $R^{a3}$ is H.

Preferably, $R^{a4}$ is selected from H, $C_{1-6}$ alkyl or substituted $C_{1-6}$ alkyl, more preferably $C_{1-4}$ alkyl or substituted $C_{1-4}$ alkyl. More preferably, $R^{a4}$ is selected from methyl, ethyl, n-propyl, isopropyl, n-butyl, isobutyl, sec-butyl, t-butyl, and benzyl.

More preferably, $R^{a4}$ is H.

In another preferred embodiment, $R^{a1}$ and $R^{a3}$ are joined together with the atoms to which they are attached to form a ring A; wherein A is selected from the group consisting of cyclopropane, cyclobutane, cyclopentane, cyclohexane, cycloheptane. Even more preferred is cyclohexane.

Preferably, Q in formula (II) is selected from $COOR^{a9}$; $OR^{a9}$; $C(O)R^{a9}$; $C(O)N(R^{a9}R^{a9a})$; $S(O)_2N(R^{a9}R^{a9a})$; $S(O)N(R^{a9}R^{a9a})$; $S(O)_2R^{a9}$; $S(O)R^{a9}$; $N(R^{a9})S(O)_2N(R^{a9a}R^{a9b})$; $SR^{a9}$; $N(R^{a9}R^{a9a})$; $OC(O)R^{a9}$; $N(R^9)C(O)R^{a9a}$; $N(R^{a9}))S(O)_2R^{a9a}$; $N(R^{a9})S(O)R^{a9a}$; $N(R^9)C(O)OR^{a9a}$; $N(R^{a9})C(O)N(R^{a9a}R^{a9b})$; $OC(O)N(R^{a9}R^{a9a})$; W; $C_{1-50}$ alkyl; $C_{2-50}$ alkenyl; and $C_{2-50}$ alkynyl, wherein W, $C_{1-50}$ alkyl, $C_{2-50}$ alkenyl, and $C_{2-50}$ alkynyl are optionally substituted with one or more $R^{a10}$, which are the same or different, and wherein $C_{1-50}$ alkyl; $C_{2-50}$ alkenyl; and $C_{2-50}$ alkynyl are optionally interrupted by one or more groups selected from the group consisting of —W—, —C(O)O—; —O—; —C(O)—; —C(O)N($R^{a11}$)—; —S(O)$_2$N($R^{a11}$)—; —S(O)N($R^{a9}$)—; —S(O)$_2$—; —S(O)—; —N($R^{a11}$)S(O)$_2$N($R^{a11a}$)—; —S—; —N($R^{a11}$)—; —OC(O)$R^{a11}$; —N($R^{a11}$)C(O)—; —N($R^{a11}$)S(O); —N($R^{a11}$)S(O)—; —N($R^{a11}$)C(O)O—; —N($R^{a11}$)C(O)N($R^{a11a}$)—; and —OC(O)N($R^{a11}R^{a11a}$);

$R^{a9}$, $R^{a9a}$, $R^{a9b}$ are independently selected from the group consisting of H; W; and $C_{1-50}$ alkyl; $C_{2-50}$ alkenyl; and $C_{2-50}$ alkynyl, wherein W, $C_{1-50}$ alkyl, $C_{2-50}$ alkenyl, and $C_{2-50}$ alkynyl are optionally substituted with one or more $R^{a10}$, which are the same or different, and wherein $C_{1-50}$ alkyl; $C_{2-50}$ alkenyl; and $C_{2-50}$ alkynyl are optionally interrupted by one or more groups selected from the group consisting of W, —C(O)O—; —O—; —C(O)—; —C(O)N($R^{a11}$)—; —S(O)$_2$N($R^{a11}$)—; —S(O)N($R^{a11}$)—; —S(O)$_2$—; —S(O)—; —N($R^{a11}$)S(O)$_2$N($R^{a11a}$)—; —S—; —N($R^{a11}$)—; —OC(O)$R^{a11}$; —N($R^{a11}$)C(O)—; —N($R^{a11}$)S(O)$_2$—; —N($R^{a11}$)S(O)—; —N($R^{a11}$)C(O)O—; —N($R^{a11}$)C(O)N($R^{a11a}$)—; and —OC(O)N($R^{a11}R^{a11a}$);

W is selected from the group consisting of phenyl; naphthyl; indenyl; indanyl; tetralinyl; $C_{3-10}$ cycloalkyl; 4- to 7-membered heterocyclyl; or 9- to 11-membered heterobicyclyl, wherein W is optionally substituted with one or more $R^{a10}$, which are the same or different;

$R^{a10}$ is halogen; CN; oxo (=O); $COOR^{a12}$; $OR^{a12}$; $C(O)R^{a12}$; $C(O)N(R^{a12}R^{a12a})$; $S(O)_2N(R^{a12}R^{a12a})$; $S(O)N(R^{a12}R^{a12a})$; $S(O)_2R^{a12}$; $S(O)R^{a12}$; $N(R^{a12})S(O)_2N(R^{a12a}R^{a12b})$; $SR^{a12}$; $N(R^{a12}R^{a12a})$; $NO_2$; $OC(O)R^{a12}$; $N(R^{a12})C(O)R^{a12a}$; $N(R^{a12})S(O)_2R^{a12a}$; $N(R^{a12})S(O)R^{a2a}$; $N(R^{a12})C(O)OR^{a12a}$; $N(R^{a12})C(O)N(R^{a12a}R^{a12b})$; $OC(O)N(R^{a12}R^{a12a})$; or $C_{1-6}$ alkyl, wherein $C_{1-6}$ alkyl is optionally substituted with one or more halogen, which are the same or different;

$R^{a11}$, $R^{a11a}$, $R^{a12}$, $R^{a2a}$, $R^{a12b}$ are independently selected from the group consisting of H; and $C_{1-6}$ alkyl, wherein $C_{1-6}$ alkyl is optionally substituted with one or more halogen, which are the same or different.

More preferably, each -Q- is independently -$Q^{1a}Q^1$-*, wherein the asterisk indicates the connection to $Z^1$ and wherein $Q^{1a}$ is a bond; —C(O)O—; —O—; —C(O)—; —C(O)N($R^{a9a}$)—; —S(O)$_2$N($R^{a9a}$)—; —S(O)N($R^{a9a}$)—; —S(O)—; —S(O)—; —N($R^{a9a}$)S(O)$_2$N($R^{a9b}$)—; —S—; —N($R^{a9a}$)—; —OC(O)—; —N($R^{a9a}$)C(O)—; —N($R^{a9a}$)S(O)$_2$—; —N($R^{a9a}$)S(O)—; —N($R^{a9a}$)C(O)O—; —N($R^{a9a}$)C(O)N($R^{a9b}$)—; —OC(O)N($R^{a9a}$)—; or —W—, preferably —C(O)N($R^{a9a}$)— or —N($R^{a9a}$)C(O)—;

$Q^1$ is selected from $C_{1-50}$ alkyl, $C_{2-50}$ alkenyl, and $C_{2-50}$ alkynyl which are optionally substituted with one or more $R^{a10}$, which are optionally interrupted, provided that $Q^1$ is at least $C_2$, by one or more groups selected from the group consisting of $C_{3-7}$ cycloalkyl, 4- to 7-membered heterocyclyl,

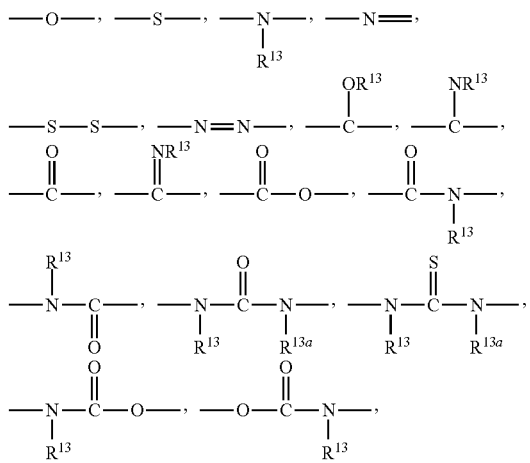

-continued

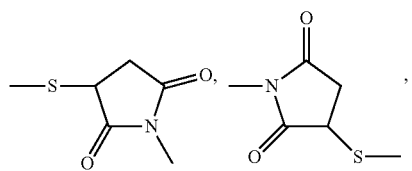

wherein each of said group may individually be present one or more times; and which $C_{1-50}$ alkyl, $C_{2-50}$ alkenyl, and $C_{2-50}$ alkynyl may optionally be terminated at the end connected to $Z^1$ by a group selected from $C_{3-7}$ cycloalkyl, 4- to 7-membered heterocyclyl,

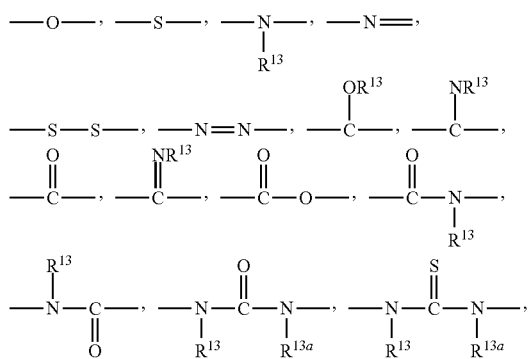

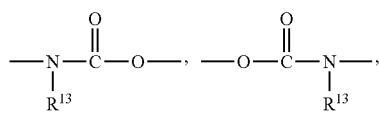

$R^{a10}$ is halogen; CN; oxo (=O); $COOR^{a12}$; $OR^{a12}$; $C(O)R^{a12}$; $C(O)N(R^{a12}R^{a12a})$; $S(O)_2N(R^{a12}R^{a12a})$; $S(O)N(R^{a12}R^{a12a})$; $S(O)_2R^{a12}$; $S(O)R^{a12}$; $N(R^{a12})S(O)_2N(R^{a12a}R^{a12b})$; $SR^{a12}$; $N(R^{a12}R^{a12a})$; $NO_2$; $OC(O)R^{a12}$; $N(R^{a12})C(O)R^{a12a}$; $N(R^{a12})S(O)_2R^{a12a}$; $N(R^{a12})S(O)R^{a12a}$; $N(R^{a12})C(O)OR^{a12a}$; $N(R^{a12})C(O)N(R^{a12a}R^{a12b})$; $OC(O)N(R^{a12}R^{a12a})$; or $C_{1-6}$ alkyl, wherein $C_{1-6}$ alkyl is optionally substituted with one or more halogen, which are the same or different;

$R^{a12}$, $R^{a12a}$ and $R^{a12b}$ are independently selected from the group consisting of H; and $C_{1-6}$ alkyl, wherein $C_{1-6}$ alkyl is optionally substituted with one or more halogen, which are the same or different, $R^{13}$ and $R^{13a}$ are independently selected from H, $C_{1-6}$ alkyl, $C_{2-6}$ alkenyl, or $C_2$ alkynyl; preferably, $R^{13}$ and $R^{13a}$ are independently selected from $C_{1-6}$ alkyl, $C_{2-6}$ alkenyl, or $C_2$ alkynyl.

In formula (I) the moiety $X^0$ is of formula (IIa):

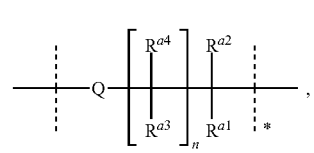

wherein
the dashed line marked with the asterisk indicates attachment to T and the unmarked dashed line indicates attachment to the rest of the carrier-linked treprostinil prodrug; and
wherein Q, $R^{a1}$, $R^{a2}$, $R^{a3}$, and $R^{a4}$ are used as defined in formula (II).

Even more preferably, the carrier-linked treprostinil prodrug has the structure of formula (II-A):

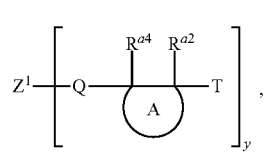

wherein
each T is independently selected from structures (i) to (v):

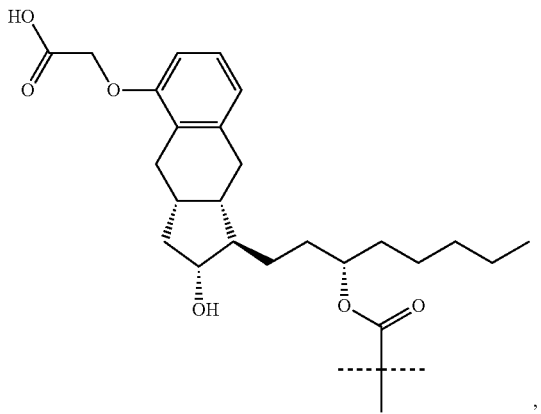

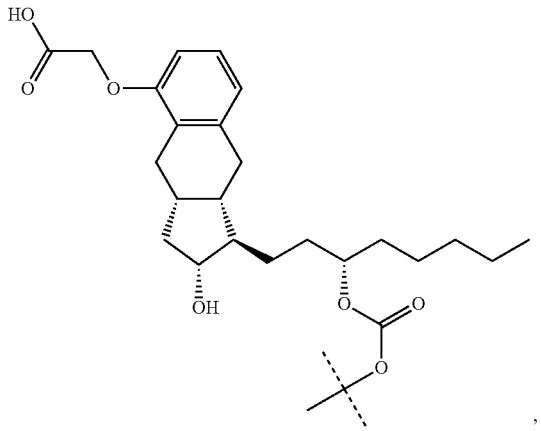

-continued (iii)

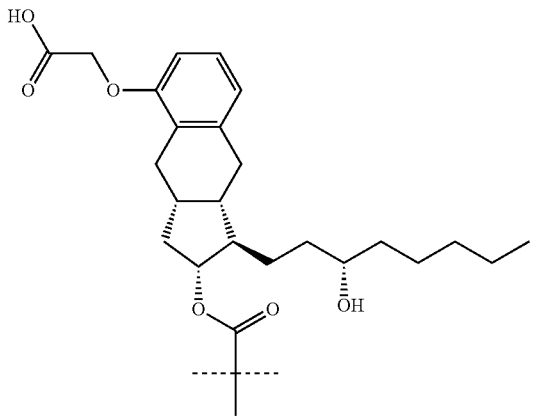

(iv)

(v)

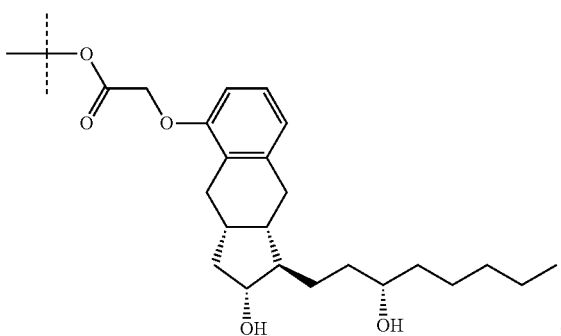

wherein dashed lines indicating attachment to the rest of the molecule;

y is an integer ranging of from 1 to 64, preferably ranging from 1 to 16, more preferably y is selected from 1, 2, 3, 4, 5, 6, 7, 8, 9, 10, 11, 12, 13, 14, 15 and 16, even more preferably y is 4, 6, 8, 10 or 12; most preferably 4;

$R^{a2}$ is selected from H, unsubstituted alkyl, and substituted alkyl;

$R^{a4}$ is selected from the group consisting of H, unsubstituted alkyl, and substituted alkyl;

A is selected from phenyl; naphthyl; indenyl; indanyl; tetralinyl; $C_{3-10}$ cycloalkyl; 4- to 7-membered aliphatic heterocyclyl; or 9- to 11-membered aliphatic heterobicyclyl, wherein A is unsubstituted or substituted;

Q is a spacer moiety;

$Z^1$ is a carrier comprising a covalently bound polymer, preferably a pharmaceutically acceptable polymer.

Preferably, $R^{a2}$ of formula (I-A) is H.

Preferably, $R^{a4}$ of formula (I-A) is selected from H, $C_{1-6}$ alkyl or substituted $C_{1-6}$ alkyl, more preferably $C_{1-4}$ alkyl or substituted $C_{1-4}$ alkyl. More preferably, $R^{a4}$ is selected from methyl, ethyl, n-propyl, isopropyl, n-butyl, isobutyl, sec-butyl, t-butyl, and benzyl.

More preferably, $R^{a4}$ of formula (I-A) is H.

Preferably, Q in formula (II-A) is selected from $COOR^{a9}$; $OR^9$; $C(O)R^{a9}$; $C(O)N(R^{a9}R^{a9a})$; $S(O)_2N(R^{a9}R^{a9a})$; $S(O)N(R^{a9}R^{a9a})$; $S(O)_2R^{a9}$; $S(O)R^{a9}$; $N(R^{a9})S(O)_2N(R^{a9a}R^{a9b})$; $SR^{a9}$; $N(R^{a9}R^{a9a})$; $OC(O)R^{a9}$; $N(R^{a9})C(O)R^{a9a}$; $N(R^{a9})S(O)_2R^{a9a}$; $N(R^{a9})S(O)R^{a9a}$; $N(R^{a9})C(O)OR^{a9a}$; $N(R^{a9})C(O)N(R^{a9a}R^{a9b})$; $OC(O)N(R^{a9}R^{a9a})$; W; $C_{1-50}$ alkyl; $C_{2-50}$ alkenyl; and $C_{2-50}$ alkynyl, wherein W, $C_{1-50}$ alkyl, $C_{2-50}$ alkenyl, and $C_{2-50}$ alkynyl are optionally substituted with one or more $R^{a10}$, which are the same or different, and wherein $C_{1-50}$ alkyl; $C_{2-50}$ alkenyl; and $C_{2-50}$ alkynyl are optionally interrupted by one or more groups selected from the group consisting of —W—, —C(O)O—; —O—; —C(O)—; —C(O)N($R^{a11}$)—; —S(O)$_2$N($R^{a11}$)—; —S(O)N($R^{a11}$)—; —S(O)$_2$—; —S(O)—; —N($R^{a11}$)S(O)$_2$N($R^{a11a}$)—; —S—; —N($R^{a11}$)—; —OC(O)$R^{a11}$; —N($R^{a11}$)C(O)—; —N($R^{a11}$)S(O)$_2$—; —N($R^{a11}$)S(O)—; —N($R^{a11}$)C(O)O—; —N($R^{a11}$)C(O)N($R^{a11a}$)—; and —OC(O)N($R^{a11}R^{a11a}$);

$R^{a9}$, $R^{a9a}$, $R^{a9b}$ are independently selected from the group consisting of H; W; and $C_{1-50}$ alkyl; $C_{2-50}$ alkenyl; and $C_{2-50}$ alkynyl, wherein W, $C_{1-50}$ alkyl, $C_{2-50}$ alkenyl, and $C_{2-50}$ alkynyl are optionally substituted with one or more $R^{a10}$, which are the same or different, and wherein $C_{1-50}$ alkyl; $C_{2-50}$ alkenyl; and $C_{2-50}$ alkynyl are optionally interrupted by one or more groups selected from the group consisting of W, —C(O)O—; —O—; —C(O)—; —C(O)N($R^{a11}$)—; —S(O)$_2$N($R^{a11}$)—; —S(O)N($R^{a9}$)—; —S(O)$_2$—; —S(O)—; —N($R^{a11}$)S(O)$_2$N($R^{a11a}$)—; —S—; —N($R^{a11}$)—; —OC(O)$R^{a11}$; —N($R^{a11}$)C(O)—; —N($R^{a11}$)S(O)$_2$—; —N($R^{a11}$)S(O)—; —N($R^{a11}$)C(O)O—; —N($R^{a11}$)C(O)N($R^{a11a}$)—; and —OC(O)N($R^{a11}R^{a11a}$);

W is selected from the group consisting of phenyl; naphthyl; indenyl; indanyl; tetralinyl; $C_{3-10}$ cycloalkyl; 4- to 7-membered heterocyclyl; or 9- to 11-membered heterobicyclyl, wherein W is optionally substituted with one or more $R^{a10}$, which are the same or different;

$R^{a10}$ is halogen; CN; oxo (=O); $COOR^{a12}$; $OR^{a12}$; $C(O)R^{a12}$; $C(O)N(R^{a12}R^{a12a})$; $S(O)_2N(R^{a12}R^{a12a})$; $S(O)N(R^{a12}R^{a12a})$; $S(O)_2R^{a12}$; $S(O)R^{a12}$; $N(R^{a12})S(O)_2N(R^{a12a}R^{a12b})$; $SR^{a12}$; $N(R^{a12}R^{a12a})$; $NO_2$; $OC(O)R^{a12}$; $N(R^{a12})C(O)R^{a12a}$; $N(R^{a12})S(O)_2R^{a12a}$; $N(R^{a12})S(O)R^{a12a}$; $N(R^{a12})C(O)OR^{a12a}$; $N(R^{a12})C(O)N(R^{a12a}R^{a12b})$; $OC(O)N(R^{a12}R^{a12a})$; or $C_{1-6}$ alkyl, wherein $C_{1-6}$ alkyl is optionally substituted with one or more halogen, which are the same or different;

$R^{a11}$, $R^{a11a}$, $R^{a12}$, $R^{a12a}$, $R^{a12b}$ are independently selected from the group consisting of H; and $C_{1-6}$ alkyl, wherein $C_{1-6}$ alkyl is optionally substituted with one or more halogen, which are the same or different.

More preferably, the carrier-linked treprostinil prodrug is of formula (IIaa):

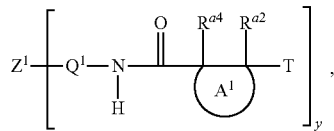
(IIaa)

wherein
each T is independently selected from structures (i) or (iii):

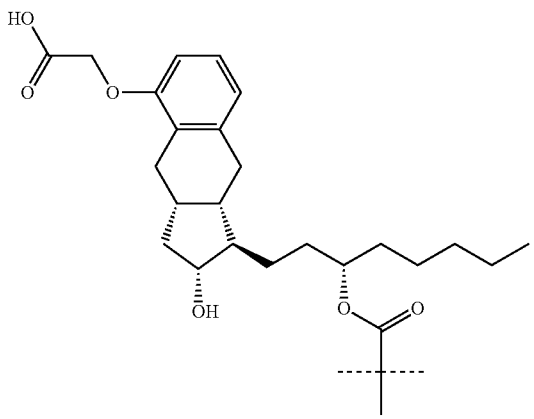
(i)

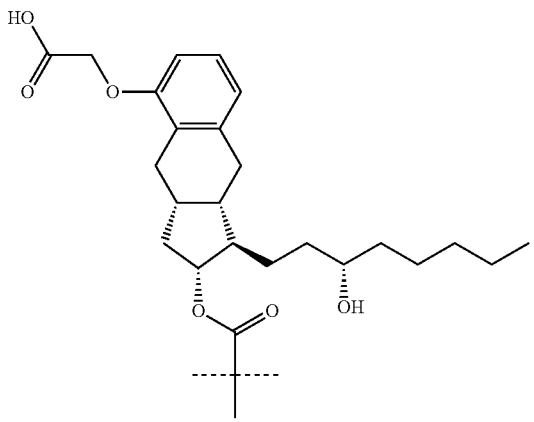
(iii)

wherein dashed lines indicate attachment to the rest of the molecule;
y is an integer ranging of from 1 to 64, preferably ranging from 1 to 16, more preferably y is selected from 1, 2, 3, 4, 5, 6, 7, 8, 9, 10, 11, 12, 13, 14, 15 and 16, even more preferably y is 4, 6, 8, 10 or 12; most preferably 4;
$R^{a2}$ is selected from H, unsubstituted alkyl, and substituted alkyl; preferably, $R^{a2}$ is selected from H and substituted or unsubstituted $C_{1-6}$ alkyl;
$R^{a4}$ is selected from the group consisting of H, unsubstituted alkyl, and substituted alkyl; preferably, $R^{a4}$ is selected from H and substituted or unsubstituted $C_{1-6}$ alkyl;

ring $A^1$ is a $C_{3-10}$ cycloalkyl; 4- to 7-membered aliphatic heterocyclyl; or 9- to 11-membered aliphatic heterobicyclyl, wherein $A^1$ is unsubstituted or substituted;
$Q^1$ is selected from $C_{1-50}$ alkyl, $C_{2-50}$ alkenyl, and $C_{2-50}$ alkynyl which are optionally substituted with one or more $R^{a10}$, which are optionally interrupted, provided that $Q^1$ is at least $C_2$, by one or more groups selected from the group consisting of $C_{3-7}$ cycloalkyl, 4- to 7-membered heterocyclyl,

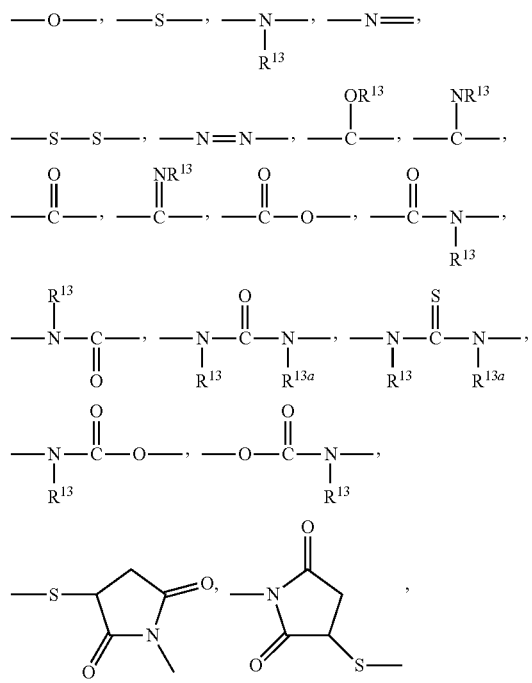

wherein each of said group may individually be present one or more times; and which $C_{1-50}$ alkyl, $C_{2-50}$ alkenyl, and $C_{2-50}$ alkynyl may optionally be terminated at the end connected to $Z^1$ by a group selected from $C_{3-7}$ cycloalkyl, 4- to 7-membered heterocyclyl,

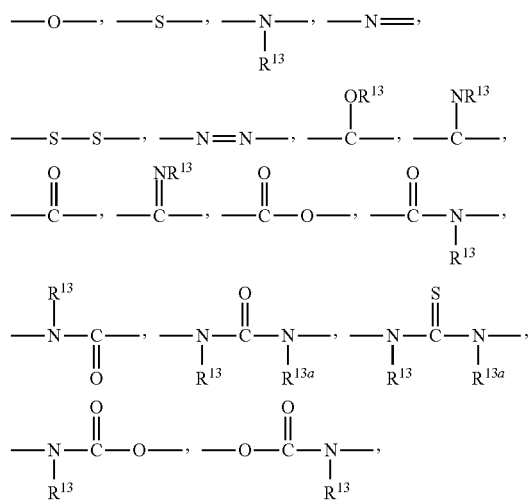

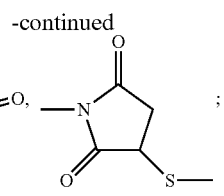

$R^{a10}$ is halogen; CN; oxo (=O); COOR$^{a12}$; OR$^{a12}$; C(O)R$^{a12}$; C(O)N(R$^{a12}$R$^{a2a}$); S(O)$_2$N(R$^{a12}$R$^{a12a}$); S(O)N(R$^{a12}$R$^{a12a}$); S(O)$_2$R$^{a12}$; S(O)R$^{a12}$; N(R$^{a12}$)S(O)$_2$N(R$^{a12a}$R$^{a12b}$); SR$^{a12}$; N(R$^{a12}$R$^{a12a}$); NO$_2$; OC(O)R$^{a12}$; N(R$^{a12}$)C(O)R$^{a12a}$; N(R$^{a12}$)S(O)$_2$R$^{a12a}$; N(R$^{a12}$)S(O)R$^{a12a}$; N(R$^{a12}$)C(O)OR$^{a12a}$; N(R$^{a12}$)C(O)N(R$^{a12a}$R$^{a12b}$); OC(O)N(R$^{a12}$R$^{a12a}$); or C$_{1-6}$ alkyl, wherein C$_{1-6}$ alkyl is optionally substituted with one or more halogen, which are the same or different;

$R^{a12}$, $R^{a12a}$ and $R^{a12b}$ are independently selected from the group consisting of H; and C$_{1-6}$ alkyl, wherein C$_{1-6}$ alkyl is optionally substituted with one or more halogen, which are the same or different, $R^{13}$ and $R^{13a}$ are independently selected from H, C$_{1-6}$ alkyl, C$_{2-6}$ alkenyl, or C$_{2-6}$ alkynyl; preferably, R$^{13}$ and R$^{13a}$ are independently selected from C$_{1-6}$ alkyl, C$_{2-6}$ alkenyl, or C$_{2-6}$ alkynyl;

$Z^1$ is a carrier comprising a covalently bound polymer, preferably a pharmaceutically acceptable polymer.

It is understood that $R^{a4}$ and $R^{a2}$ of formula (IIaa) are vicinal.

Preferably, the carrier-linked treprostinil prodrug is of formula (IIab):

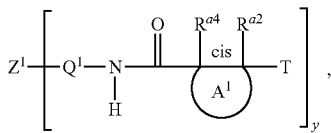

(IIab)

wherein

T, $R^{a2}$, $R^{a4}$, $A^1$, $Q^1$, $Z^1$ and y are used as defined in formula (IIaa).

It is understood that $R^{a4}$ and $R^{a2}$ of formula (IIab) are vicinal.

Preferably, $A^1$ of formula (IIaa) or (IIab) is selected from cyclopentane, cyclohexane or cycloheptane. More preferably, $A^1$ is cyclohexan.

Preferably, $R^{a2}$ and $R^{a4}$ of formula (IIaa) or (IIab) are both H.

Preferably, $Q^1$ of formula (IIaa) or (IIab) is selected from C$_{1-50}$ alkyl, which is optionally substituted with one or more R$^{a10}$, which are the same or different; and wherein the C$_{1-50}$ alkyl is optionally interrupted, provided that Q$^1$ is at least C$_2$, by one or more groups selected from the group consisting of C$_3$, cycloalkyl, 4 to 7 membered heterocyclyl,

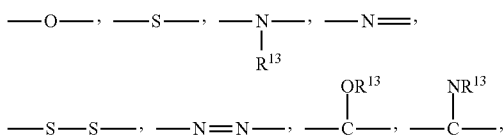

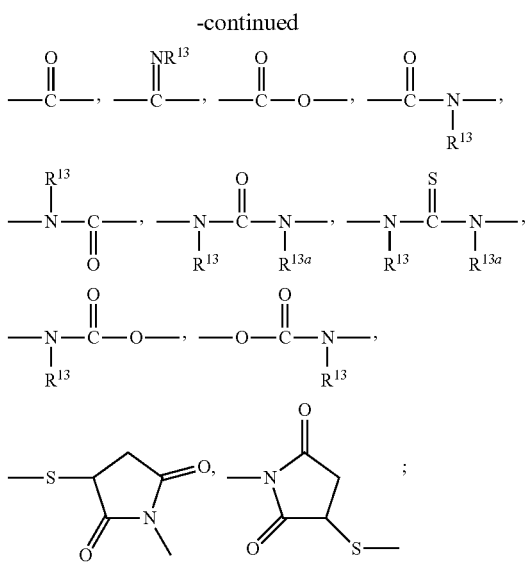

wherein each of said group may individually be present one or more times and which C$_{1-50}$ alkyl may optionally be terminated at the end connected to Z$^1$ by a group selected from C$_{3-7}$ cycloalkyl, 4- to 7-membered heterocyclyl,

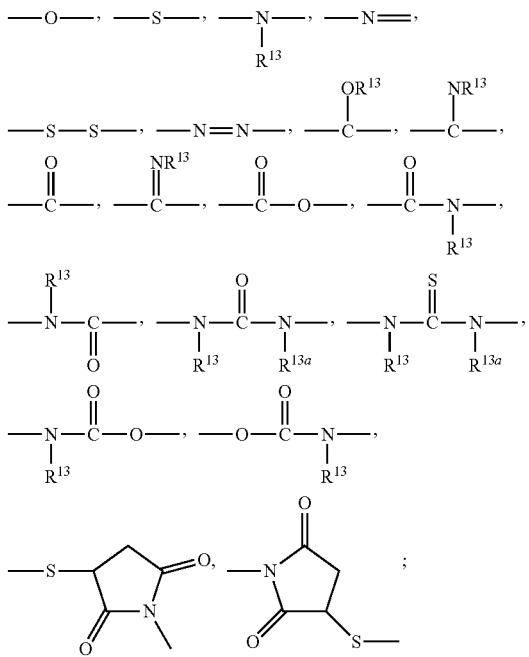

and wherein $R^{13}$ and $R^{13a}$ are used as defined for formula (IIaa);

Preferably, y of formula (IIaa) or (IIab) is 4, 6 or 8. More preferably y of formula (IIaa) or (IIab) is 4 or 8, most preferably y of formula (IIaa) or (IIab) is 4.

Even more preferably, the carrier-linked treprostinil prodrug is of formula (IIac) or (IIad):

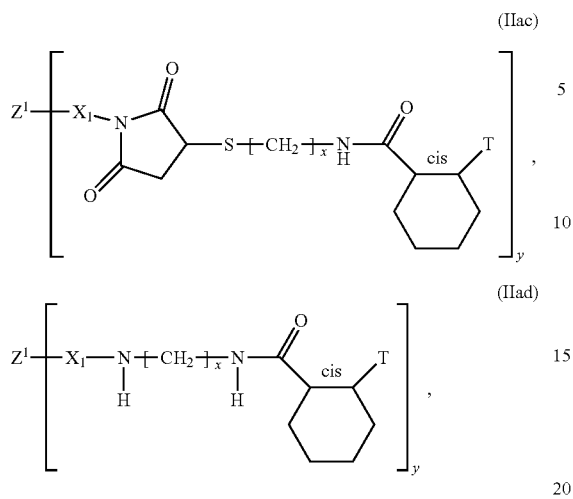

(IIac)

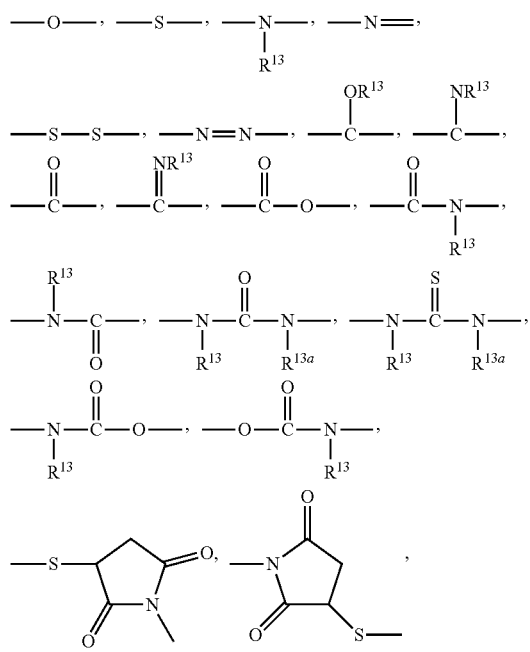

(IIad)

wherein

T, $Z^1$ and y are used as defined in formula (IIaa), x is selected from 2, 3, 4, 5, 6, 7 or 8, more preferably, x is selected from 3, 4, 5, 6, 7, or 8, $X_1$ is selected from $C_{1-50}$ alkyl, $C_{2-50}$ alkenyl, and $C_{2-50}$ alkynyl which are optionally substituted with one or more $R^{a10}$, and which $C_{1-50}$ alkyl, $C_{2-50}$ alkenyl, and $C_{2-50}$ alkynyl are optionally interrupted, provided that $X_1$ is at least $C_2$, by one or more groups selected from the group consisting of $C_{3-7}$ cycloalkyl, 4- to 7-membered heterocyclyl,

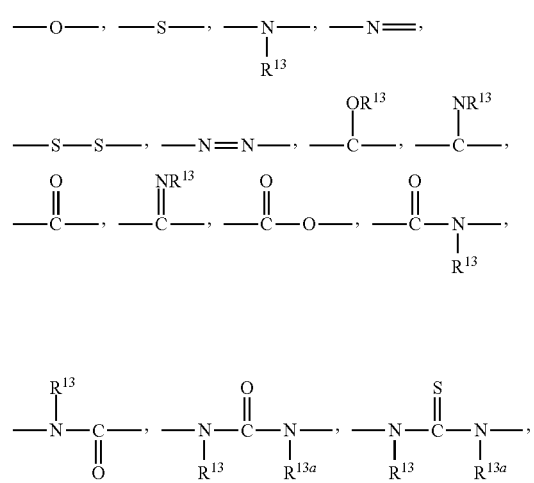

wherein each of said groups may individually be present one or more times; and which $C_{1-50}$ alkyl, $C_{2-50}$ alkenyl, and $C_{2-50}$ alkynyl may optionally be terminated at the end connected to $Z^1$ by a group selected from $C_{3-7}$ cycloalkyl, 4- to 7-membered heterocyclyl,

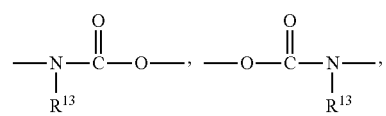

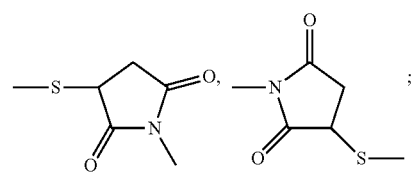

$R^{a10}$ is halogen; CN; oxo (=O); $COOR^{a12}$; $OR^{a12}$; $C(O)R^{a12}$; $C(O)N(R^{a12}R^{a12a})$; $S(O)_2N(R^{a12}R^{a12a})$; $S(O)N(R^{a12}R^{a12a})$; $S(O)_2R^{a12}$; $S(O)R^{a12}$; $N(R^{a12})S(O)_2N(R^{a12a}R^{a12b})$; $SR^{a12}$; $N(R^{a12}R^{a12a})$; $NO_2$; $OC(O)R^{a12}$; $N(R^{a12})C(O)R^{a12a}$; $N(R^{a12})S(O)_2R^{a12a}$; $N(R^{a12})S(O)R^{a12a}$; $N(R^{a12})C(O)OR^{a12a}$; $N(R^{a12})C(O)N(R^{a12a}R^{a12b})$; $OC(O)N(R^{a12}R^{a12a})$; or $C_{1-6}$ alkyl, wherein $C_{1-6}$ alkyl is optionally substituted with one or more halogen, which are the same or different;

$R^{a12}$, $R^{a12a}$ and $R^{a12b}$ are independently selected from the group consisting of H; and $C_{1-6}$ alkyl, wherein $C_{1-6}$ alkyl is optionally substituted with one or more halogen, which are the same or different, and wherein $R^{13}$ and $R^{13a}$ are used as defined for formula (IIaa).

Preferably, $X_1$ of formula (IIac) and (IIad) is selected from $C_{1-15}$ alkyl, $C_{2-15}$ alkenyl and $C_{2-15}$ alkynyl, which are optionally substituted or interrupted by one or more groups selected from the group consisting of $C_{3-7}$ cycloalkyl, 4- to 7-membered heterocyclyl,

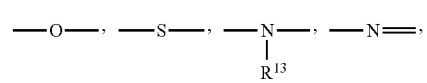

-continued

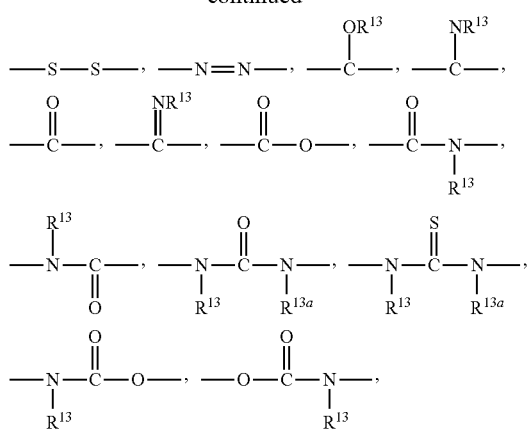
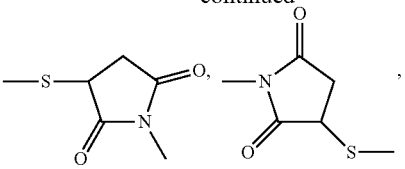

wherein
$R^{13}$ and $R^{13a}$ are independently selected from H, $C_{1-6}$ alkyl, $C_{2-6}$ alkenyl, or $C_{2-6}$ alkynyl.

More preferably, y of formulas (IIac) or (IIad) is 4, 6, or 8, even more preferabably y is 4 or 8, most preferably y is 4.

More preferably, x of formulas (IIac) or (IIad) is 4, 5, or 6, most preferably x is 6.

Even more preferably, the carrier-linked treprostinil prodrug is of formula (IIb):

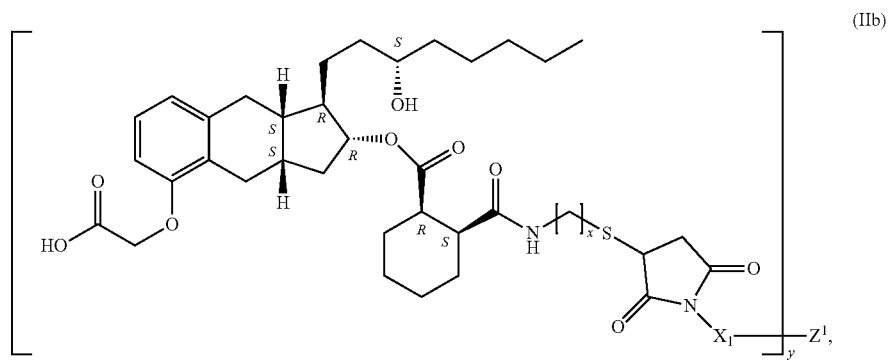

(IIb)

wherein
$Z^1$ is a carrier comprising a covalently bound polymer, preferably a pharmaceutically acceptable polymer,
$X_1$ and y are used as defined in formula (IIac) and (IIad), and
x is selected from 2, 3, 4, 5, 6, 7 or 8.

More preferably, y of formula (IIb) is 4, 6, or 8, even more preferabably y is 4 or 8, and most preferably y is 4.

More preferably, x of formula (IIb) is 4, 5, or 6, even more preferably x is 5 or 6, and most preferably x is 6.

Most preferably, y in formula (IIb) is 4 and x in formula (IIb) is 6.

More preferably, the carrier-linked treprostinil prodrug of formula (IIb) has the structure of formula (IIba):

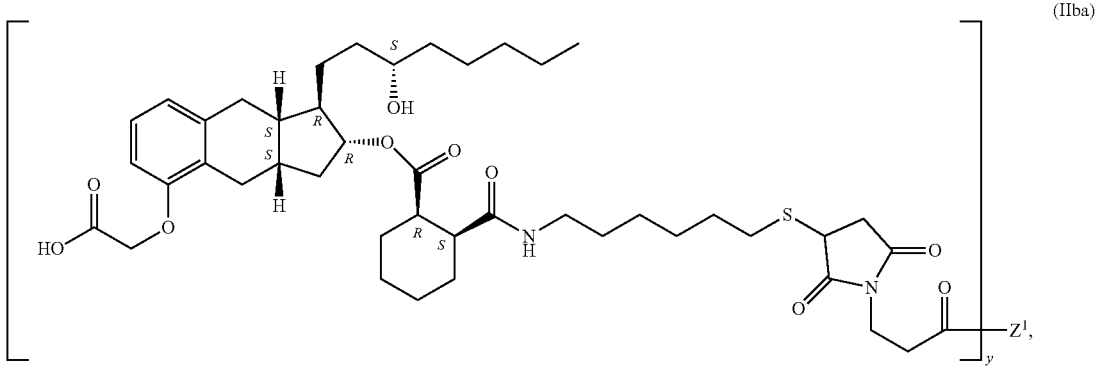

(IIba)

wherein $Z^1$ is used as defined in formula (IIaa) and y is used as defined in formula (IIac) and (IIad).

Preferably, y of formula (IIba) is 4, 6 or 8. More preferably y of formula (IIba) is 4 or 8, most preferably y of formula (IIba) is 4.

More preferably, $X_1$ of formula (IIac) is

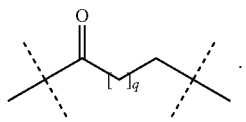

wherein q is selected from 1 to 4; preferably, q is 1.

More preferably, $X^1$ of formula (IIad) is

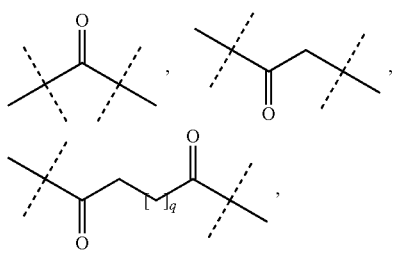

wherein q is selected from 1, 2, 3, or 4 and preferably is 2.

Preferably, $X^0$ of formula (I) is selected from the following structures:

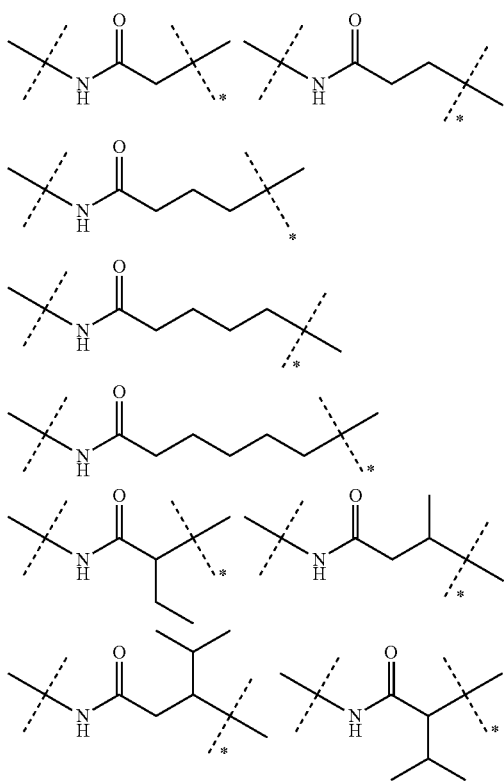

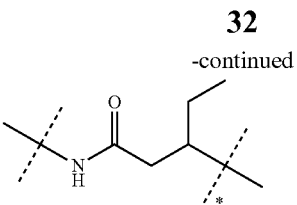

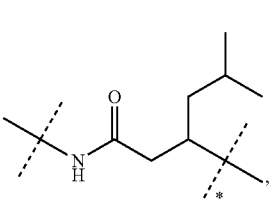

wherein dashed lines marked with an asterisk indicate attachment to T and unmarked dashed lines indicate attachment to the rest of the carrier-linked treprostinil prodrug.

Preferably, all moieties T of the carrier-linked treprostinil prodrug of formula (I), (II), (IIaa), (IIab), (IIac) and (IIad) have the same structure.

Preferably, all moieties T of formula (I) have the structure of formula (v) or formula (ii) or formula (iii), more preferably the structure of formula (v).

Preferably, all moieties T of formula (II), (IIaa), (IIab), (IIac) and (IIad) have the same structure and are either of formula (ii), (iii) or (iv). More preferably, all moieties T of formula (II), (IIaa), (IIab), (IIac) and (IIad) have the same structure and are either of formula (ii) or (iv).

Preferred sub-structures —$X^0$-T of formula (I) are selected from the following structures:

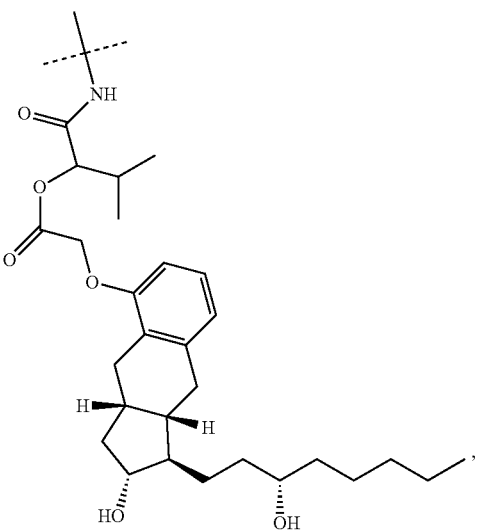

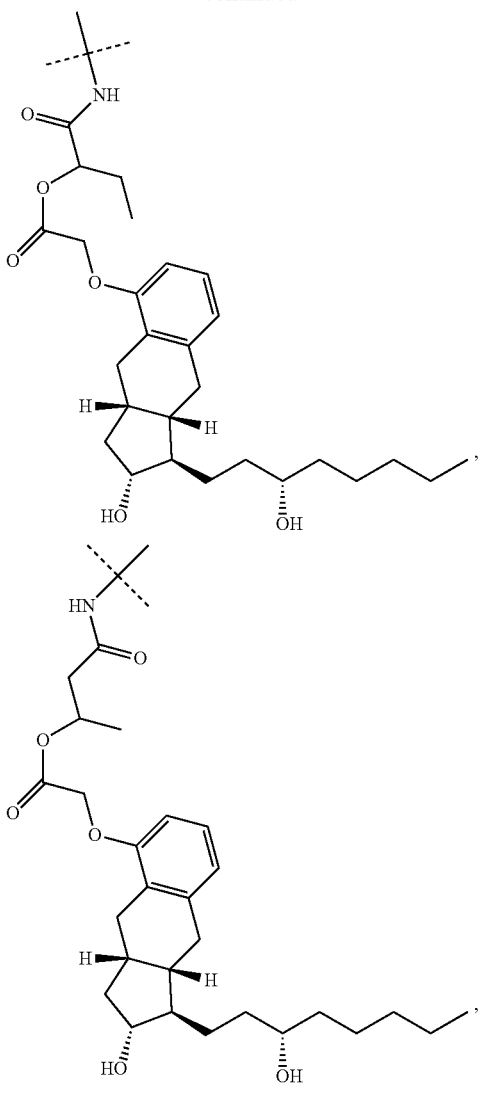

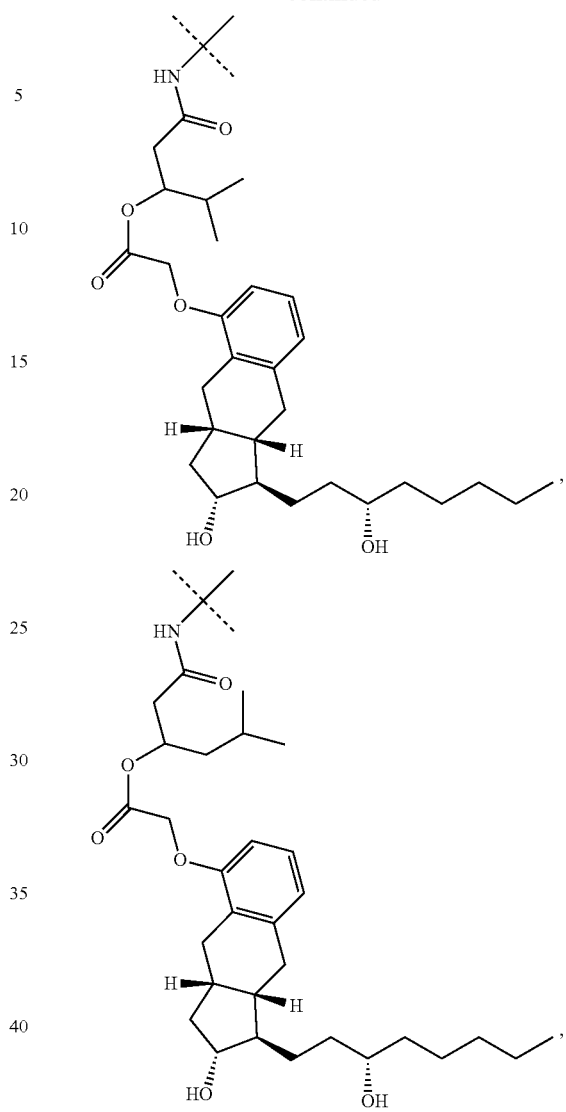

wherein the dashed lines indicate attachment to $Z^1$.

In another preferred embodiment the carrier-linked treprostinil prodrug has the structure of formula (IId):

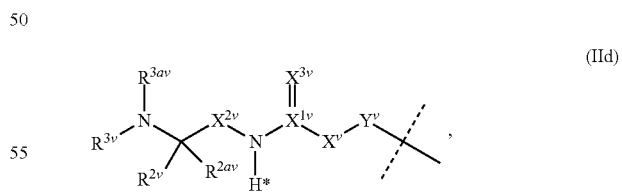

wherein the dashed line indicates attachment to T of formula (I);

$Y^v$ is —N(R$^{1v}$)—;

$X^v$ is —C(R$^{4v}$)(R$^{4av}$)—; —N(R$^{4v}$)—; —O—; —C(R$^{4v}$)(R$^{4av}$)—C(R$^{5v}$)(R$^{5av}$)—; —C(R$^{4v}$)(R$^{4av}$)—N(R$^{6v}$)—; —N(R$^{6v}$)—C(R$^{4v}$)(R$^{4av}$)—; —C(R$^{4v}$)(R$^{4av}$)—O—; —O—C(R$^{4v}$)(R$^{4av}$)—; —C(O)—N(R$^{6v}$)—; or —N(R$^{6v}$)—C(O)—;

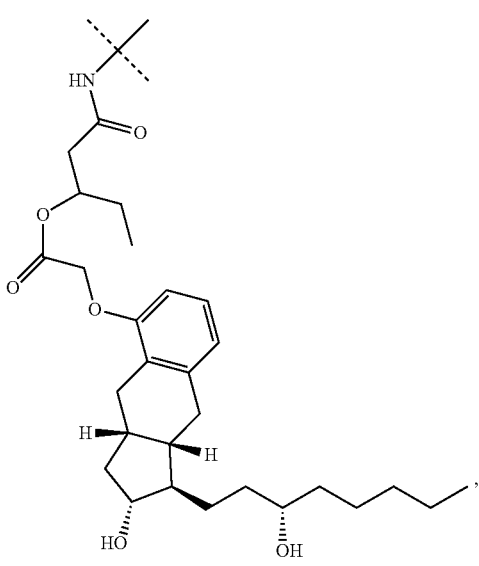

$X^{1v}$ is

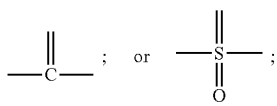

$X^{2v}$ is —C($R^{7v}$)($R^{7av}$)—; or —C($R^{7v}$)($R^{7av}$)—C($R^{8v}$)($R^{8av}$)—;

$X^{3v}$ is =O; =S; or =N—CN;

$R^{1v}$, $R^{1av}$, $R^{2v}$, $R^{2av}$, $R^{3v}$, $R^{3av}$, $R^{4v}$, $R^{4av}$, $R^{5av}$, $R^{6v}$, $R^{7v}$, $R^{7av}$, $R^{8v}$, $R^{8av}$ are independently selected from the group consisting of H; $C_{1-6}$ alkyl, $C_{2-6}$ alkenyl, $C_{2-6}$ alkynyl, $C_{1-20}$ heteroalkyl and $Y_1$-$T^v$; and independently none, one or more of the pairs $R^{1av}/R^{4av}$, $R^{1av}/R^{5av}$, $R^{4av}/R^{5av}$, $R^{7av}/R^{8av}$ are absent and the corresponding carbon atoms to which they are attached form a cis double bond;

$Y^{1v}$ is a chemical bond or $C_{1-6}$ alkyl, $C_{2-6}$ alkenyl, $C_{2-6}$ alkynyl;

$T^v$ is selected from the group consisting of phenyl; naphthyl; indenyl; indanyl; tetralinyl; $C_{3-10}$ cycloalkyl; 4- to 7-membered heterocyclyl; or 9- to 11-membered heterobicyclyl, wherein $T^v$ is optionally substituted with one or more $R^9$, which are the same or different;

$R^{9v}$ is halogen; —CN; oxo (=O); —C(O)OH; —OH; —S(O)$_2$NH$_2$; —S(O)NH$_2$; —S(O)$_2$OH; —S(O)OH; —SH; —NH$_2$; —NO$_2$; $C_{1-6}$ alkyl, or $C_{1-10}$ heteroalkyl;

optionally, one or more of the pairs $R^{1v}/R^{1av}$, $R^{1v}/R^{4v}$, $R^{1v}/R^{6v}$, $R^{1v}/R^{5v}$, $R^{2v}/R^{2v}$, $R^{2v}/R^{3v}$, $R^{4v}/R^{4av}$, $R^{4v}/R^{5v}$, $R^{5v}/R^{5av}$, $R^{7v}/R^{7av}$, $R^{7v}/R^{8v}$, $R^{8v}/R^{8av}$ are joined together with the atom to which they are attached to form a ring T;

optionally, $R^{3v}/R^{3av}$ are joined together with the nitrogen atom to which they are attached to form a 4- to 7-membered heterocycle;

and wherein one of $R^{1v}$, $R^{1av}$, $R^{2v}$, $R^{2av}$, $R^{3v}$, $R^{3av}$, $R^{4v}$, $R^{4av}$, $R^{5v}$, $R^{5av}$, $R^{6v}$, $R^{7v}$, $R^{7av}$, $R^{8v}$, $R^{8av}$ are substituted with $Z^0$ of formula (I).

The carrier $Z^1$ of formulas (I), (II), (IIaa), (IIab), (IIac), (IIad), (IIb) and (IIba) comprises a covalently bound polymer, preferably a pharmaceutically acceptable polymer.

Preferred polymers are selected from 2-methacryloyloxyethyl phosphoyl cholins, hydrogels, PEG-based hydrogels, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyloxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, mannans, pectins, rhamnogalacturonans, starches, hydroxyalkyl starches, hydroxyethyl starches and other carbohydrate-based polymers, xylans, and copolymers thereof.

Preferably, the carrier $Z^1$ of formulas (I), (II), (IIaa), (IIab), (IIac), (IIad), (IIb) and (IIba) comprises a poly(oxazoline) or a PEG-based polymer. Most preferably, the carrier $Z^1$ comprises a PEG-based polymer.

In one embodiment the carrier $Z^1$ of formulas (I), (II), (IIaa), (IIab), (IIac), (IIad), (IIb) and (IIba) may be a hydrogel (as one option for a polymer) which are known in the art. Suitable hydrogels are described in WO-A 2006/003014 or EP-A 1 625 856. If the carrier $Z^1$ is a hydrogel it is preferred that it is a PEG-based hydrogel as disclosed in WO-A 2011/012715 which is incorporated by reference herewith.

Preferably, the carrier $Z^1$ of formulas (I), (II), (IIaa), (IIab), (IIac), (IIad), (IIb) and (IIba) is a water-soluble carrier.

In one embodiment the carrier $Z^1$ of formulas (I), (II), (IIaa), (IIab), (IIac), (IIad), (IIb) and (IIba) has the structure of formula (III):

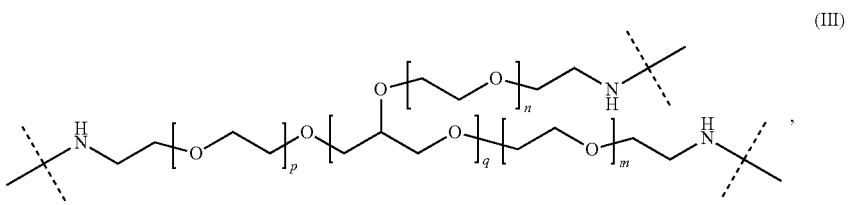

(III)

wherein dashed lines indicate attachment to $X^0$ (if the carrier-linked treprostinil prodrug is of formula (I)), to Q (if the carrier-linked treprostinil prodrug is of formula (II)), to $Q^1$ (if the carrier-linked treprostinil prodrug is of formula (IIaa) or (IIab)) or to $X_1$ (if the carrier-linked treprostinil prodrug is of formula (IIac), (IIad), and (IIb)) or to the rest of the molecule (if the carrier-linked treprostinil prodrug is of formula (IIba)), respectively, and wherein each of m, n, and p of formula (III) are independently an integer ranging of from 5 to 500, and wherein q of formula (III) ranges of from 2 to 32.

In one embodiment the carrier $Z^1$ of formulas (I), (II), (IIaa), (IIab), (IIac), (IIad), and (IIb) has the structure of formula (IIIa):

(IIIa)

[chemical structure]

wherein dashed lines indicate attachment to $X^0$ (if the carrier-linked treprostinil prodrug is of formula (I)), to Q (if the carrier-linked treprostinil prodrug is of formula (II)), to $Q^1$ (if the carrier-linked treprostinil prodrug is of formula (IIaa) or (IIab)) or to $X_1$ (if the carrier-linked treprostinil prodrug is of formula (IIac), (IIad), and (IIb)), respectively, and wherein each of m, n, and p of formula (IIIa) are independently an integer ranging of from 5 to 500, and wherein q of formula (IIIa) ranges of from 2 to 32.

Preferably, q in formula (III) and (IIIa) is an integer ranging of from 2 to 14 and more preferably q of formula (III) and (IIIa) is 6.

Preferably, each of m, n, and p in formula (III) and (IIIa) independently range of from 10 to 250, more preferably from 50 to 150. Preferably, m, n, and p in formula (III) and formula (IIIa) are the same.

In an alternative embodiment the carrier $Z^1$ of formulas (I), (II), (IIaa), (IIab), (IIac), (IIad), (IIb), and (IIba) has the structure of formula (IV):

In another preferred embodiment $Z^1$ of formulas (I), (II), (IIaa), (IIab), (IIac), (IIad), (IIb), and (IIba) has the structure of formula (V):

$$\text{Hyp}^1{}_{mx}\text{-POL}^x\text{-Hyp}^2 \quad (V),$$

wherein $POL^x$ is a polymeric moiety having a molecular weight ranging from 0.5 kDa to 160 kDa, $Hyp^1$ and $Hyp^2$ are independently a hyperbranched moiety, and mx is 0 or 1.

The polymeric moiety $POL^x$ has a molecular weight of from 0.5 kDa to 160 kDa, preferably of from 2 kDa to 80 kDa and more preferably of from 5 kDa to 40 kDa.

$POL^x$ may be selected from the group of polymers consisting of, for example, polypeptides, 2-methacryloyl-oxyethyl phosphoyl cholins, water-soluble hydrogels, water-soluble PEG-based hydrogels, water-soluble hyaluronic acid-based hydrogels, poly(acrylic acids), poly(acrylates), poly(acrylamides), poly(alkyloxy) polymers, poly(amides), (IV)

[chemical structure]

wherein dashed lines indicate attachment to $X^0$ (if the carrier-linked treprostinil prodrug is of formula (I)), to Q (if the carrier-linked treprostinil prodrug is of formula (II)), to $Q^1$ (if the carrier-linked treprostinil prodrug is of formula (IIaa) or (IIab)) or to $X_1$ (if the carrier-linked treprostinil prodrug is of formula (IIac), (IIad) or (IIb)), or to the rest of the molecule (if the carrier-linked treprostinil prodrug is of formula (IIba)), respectively, provided that one of m1, m2 is 1 and wherein the carrier is covalently attached to T in case m1, m2=0, and wherein each of m, n, and p of formula (IV) are independently an integer ranging of from 5 to 500 and wherein q of formula (IV) ranges of from 0 to 14.

Preferably, q in formula (IV) is an integer ranging of from 2 to 6 and more preferably q of formula (IV) is 2.

Preferably, each of m, n, and p in formula (IV) independently range of from 10 to 250, more preferably from 50 to 150. Preferably, m, n, and p in formula (IV) are the same.

poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyloxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

The polymeric moiety $POL^x$ of formula (V) may comprise a linear or branched polymer. Preferably, $POL^x$ of formula (V) comprises, in particular consists of a linear polymer.

In one preferred embodiment, $POL^x$ of formula (V) comprises, in particular consists of a PEG-based polymer or a poly(oxazoline)-based polymer, more preferably a linear PEG-based polymer. Even more preferably, $POL^x$ of formula (V) consists of a PEG-based linear polymer.

If m in formula (V) is 0, it is preferred that $POL^x$ of formula (V) comprises, preferably consists of a structure of the formula X1-$(OCH_2CH_2)_p$—O—$(CH_2)_n$—X2-, wherein n is selected from 2, 3, or 4; p is an integer in the range of from 5 to 2000, preferably p is an integer in the range of from 10 to 1000, more preferably p is an integer in the range of from 100 to 1000; and X2 is a functional group covalently linking $POL^x$ and $Hyp^2$ of formula (V); and X1 is selected from H, $CH_3$ and $C_2H_5$.

If m in formula (V) is 1, it is preferred that $POL^x$ of formula (V) comprises, preferably consists of a structure of the formula X3-$(CH_2)_{n1}$—$(OCH_2CH)_p$—O—$(CH_2)_{n2}$—X2-, wherein n1 and n2 are independently selected from 2, 3, and 4; p is an integer in the range of from 5 to 2000, preferably p is an integer in the range of from 10 to 1000, more preferably p is an integer in the range of from 100 to 1000; and X2 and X3 are functional groups covalently linking $POL^x$ to $Hyp^1$ and $Hyp^2$ of formula (V), respectively.

In a preferred embodiment mx in formula (V) is 0.

In another preferred embodiment, $POL^x$ of formula (V) is a polypeptide (or protein), in particular a non-immunogenic polypeptide as described below.

Preferably, the polymeric moiety $POL^x$ of formula (V) is a polypeptide which comprises at least about 100 amino acid residues, in particular which consists of at least about 100 amino acid residues. In a preferred embodiment, amino acids selected from alanine, serine and/or proline residues are present, in particular are mainly present, and which polypeptide moiety preferably has a random coil conformation at physiological conditions. It is understood that such a polypeptide moiety $POL^x$ of formula (V) may transiently or temporarily not form a random coil, for example when present in a lyophilisate or dried composition.

A polypeptide moiety $POL^x$ of formula (V) may have a random coil conformation with an amino acid sequence consisting of maximally about 1000 amino acid residues, preferably of maximally about 900 amino acid residues, more preferably of maximally about 800 amino acid residues, even more preferably of maximally about 700 amino acid residues, particularly preferably of maximally about 600 amino acid residues. Thus, the amino acid sequence forming random coil conformation may consist of maximally about 500 amino acid residues or of maximally about 450 amino acid residues.

It is also envisaged herein that the amino acid sequence forming random coil conformation may consist of maximally about 1200 and up to about 1500 amino acid residues.

Accordingly, the amino acid sequence forming random coil conformation may consist of about 100 to about 1500 amino acid residues.

In particular embodiments said amino acid sequence forming random coil conformation consists of about 100 to 1000 amino acid residues as characterized herein, i.e. comprising alanine, serine and/or proline as main or unique residues as defined below.

In a preferred embodiment, a polypeptide moiety $POL^x$ of formula (V) consists mainly of one, two or three of the amino acid residues alanine, serine and proline, whereby proline residues represent preferably about 4% to about 40% of the polypeptide moiety $POL^x$ of formula (V). The alanine and serine residues comprise the remaining at least 60% to 96% of the polypeptide moiety $POL^x$ of formula (V). However, as will be detailed herein below said polypeptide moiety $POL^x$ of formula (V) may also comprise further amino acids differing from alanine, serine, and proline, i.e. as minor constituents.

The term "minor constituent" as used herein means that maximally 10% (i.e. maximally 10 of 100 amino acids) may be different from alanine, serine and proline, preferably maximally 8% (i.e. maximally 8 of 100 amino acids) may be different than alanine, serine and proline, more preferably maximally 6% (i.e. maximally 6 of 100 amino acids) may be different from alanine, serine and proline, even more preferably maximally 5% (i.e. maximally 5 of 100 amino acids) may be different from alanine, serine and proline, particularly preferably maximally 4% (i.e. maximally 4 of 100 amino acids) may be different from alanine, serine and proline, more particularly preferably maximally 3% (i.e. maximally 3 of 100 amino acids) may be different from alanine, serine and proline, even more particularly preferably maximally 2% (i.e. maximally 2 of 100 amino acids) may be different from alanine, serine and proline and most preferably maximally 1% (i.e. maximally 1 of 100 of the amino acids) may be different from alanine, serine and proline. Said amino acids different from alanine, serine and proline may be selected from the group consisting of different from alanine, serine and proline may be selected from the group of natural or proteinogenic amino-acids comprising Arg, Asn, Asp, Cys, Gln, Glu, Gly, His, Ile, Leu, Lys, Met, Phe, Thr, Trp, Tyr, Val, selenocystein, selenomethionin, and hydroxyproline. Minor constituents may also be selected from non-naturally occurring amino acids.

The term "at least about 100/150/200/250/300/300/350 (etc) amino acid residues" is not limited to the concise number of amino acid residues but also comprises amino acid stretches that comprise an additional 10% to 20% or comprise 10% to 20% less residues.

For example "at least about 100 amino acid residues" may also encompass 80 to 100 and about 100 to 120 amino acid residues without deferring from the gist of the present invention.

In one embodiment, the polypeptide moiety $POL^x$ of formula (V) comprises a plurality of polymer cassettes wherein said polymer cassettes consist of one, two or three of the amino acids selected from Ala, Ser, and Pro and wherein no more than 6 consecutive amino acid residues are identical and wherein said proline residues constitute more than 4% and less than 40% of the amino acids of said polypeptide moiety $POL^x$ of formula (V).

A polypeptide moiety $POL^x$ of formula (V) may comprise a plurality, in particular 2, 3, 4, 5 or more of identical polymer cassettes or a plurality of non-identical polymer cassettes. Non-limiting examples of polymer cassettes consisting of Ala, Ser and Pro residues are provided herein below; see SEQ ID NO:9, SEQ ID NO:10, SEQ ID NO:11, SEQ ID NO:12, SEQ ID NO:13 and SEQ ID NO:14 or peptide fragments or multimers of these sequences. A polymer cassette may consist of at least 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid residues, wherein each polymer cassette comprises (an) Ala, Ser, and Pro residue(s).

In one embodiment, the polymer cassette according to the present invention does not comprise more than 100 amino acid residues. Preferably, a polymer cassette as defined herein comprises more than about 4%, preferably more than about 5%, even more preferably more than about 6%, particularly preferably more than about 8%, more particularly preferably more than about 10%, even more particularly preferably more than about 15% and most preferably more than about 20% proline residues. Such polymer cassette as defined herein preferably comprises less than about 40% or less than about 35% proline residues.

In one preferred embodiment the polypeptide moiety POL$^x$ of formula (V) comprises, in particular consists of formula (a):

$$\text{Ser}_x[\text{Ala}_y\text{Ser}_z]_n \qquad (a),$$

which formula further comprises proline residues as defined herein and wherein
x is independently selected from integer 0 to 6,
each y is independently selected from integer ranging of from 1 to 6,
each z is independently selected from integer ranging of from 1 to 6.
n is any integer so that a polypeptide moiety POL$^x$ of formula (V) consists of at least about 100 amino acid residues, and in particular of at least about 100 to about 3000 amino acid residues, preferably to about 2000 and more preferably to about 1000 amino acid residues.

In another preferred embodiment, a polypeptide moiety POL$^x$ of formula (V) comprises no more than 5 identical consecutive amino acid residues, more preferably no more than 4 identical consecutive amino acid residues and most preferably no more than 3 identical consecutive amino acid residues.

As already indicated herein above, a polypeptide moiety POL$^x$ of formula (V) comprises in one embodiment proline residues, wherein said proline residues constitute more than about 4%, preferably more than about 5%, even more preferably more than about 6%, particularly preferably more than about 8%, more particularly preferably more than about 10%, even more particularly preferably more than about 15% and most preferably more than about 20% of the amino acids of POL$^x$ of formula (V).

In another preferred embodiment, a polypeptide moiety POL$^x$ of formula (V) comprises more than about 4% but less than about 50%, preferably more than about 10% but less than about 50% and most preferably more than about 20% but less than about 50% alanine residues of the amino acids constituting the polypeptide moiety POL$^x$ of formula (V).

In a further preferred embodiment, a polypeptide moiety POL$^x$ of formula (V) comprises more than about 4% and less than about 50%, preferably more than about 10% but less than about 50% and most preferably more than about 20% but less than about 50% serine residues of the amino acids constituting the polypeptide moiety POL$^x$ of formula (V).

Preferably, a polypeptide moiety POL$^x$ of formula (V) comprises about 35% proline residues, about 50% alanine residues and about 15% serine residues of the amino acids constituting the polypeptide moiety POL$^x$ of formula (V). Alternatively, a polypeptide moiety POL$^x$ of formula (V) may comprise about 35% proline residues, about 15% alanine residues and about 50% serine residues of the amino acids constituting the polypeptide moiety POL$^x$ of formula (V).

Preferably, a polypeptide moiety POL$^x$ of formula (V) comprises one or more of the following alanine-serine polymer cassettes:

AAAASSASSASSSSSAAASA   SEQ ID NO: 1

AASAAASSAAASAAAASASS   SEQ ID NO: 2

ASASASASASASSAASAASA   SEQ ID NO: 3

SAASSSASSSSAASSASAAA   SEQ ID NO: 4

SSSSAASAASAAAAASSSAS   SEQ ID NO: 5

SSASSSAASSSASSSSASAA   SEQ ID NO: 6

SASASASASASAASSASSAS   SEQ ID NO: 7

ASSAAASAAAASSAASASSS   SEQ ID NO: 8

The multimers of these alanine-serine polymer cassettes may form random coil conformation in case the resulting amino acid sequence further comprises proline residues as defined herein above.

In a preferred embodiment, a polypeptide moiety POL$^x$ of formula (V) comprises one or more of the following polymer cassettes:

ASPAAPAPASPAAPAPSAPA   SEQ ID NO: 9

AAPASPAPAAPSAPAPAAPS   SEQ ID NO: 10

APSSPSPSAPSSPSPASPSS   SEQ ID No: 11

SAPSSPSPSAPSSPSPASPS   SEQ ID NO: 15

SEQ ID NO:15 corresponds to the herein provided SEQ ID No:11 in a circularly permuted form, wherein the last serine was removed and another serine was appended as starting amino acid. As a consequence, multimers of this modified sequence possess essentially the same internal repeating unit as multimers of the non-modified sequence, except for the very first and the very last residue. Accordingly, SEQ ID NO:15 may be considered as an example of a further polymer cassette for a polypeptide moiety POL$^x$ of formula (V). It is clear for the person skilled in the art that also other polymer cassettes and (shorter) peptide fragments or circularly permuted versions of the herein provided amino acid polymers may be used as polymer cassettes for a polypeptide moiety POL$^x$ of formula (V).

Yet, even further and illustrative amino acid polymers forming random coil conformation may comprise amino acid sequences that may be selected from the group consisting of the following sequences:

SSPSAPSPSSPASPSPSSPA   SEQ ID NO: 12

AASPAAPSAPPAAASPAAPSAPPA   SEQ ID NO: 13

ASAAAPAAASAAASAPSAAA   SEQ ID NO: 14

Therefore, preferred polymer cassettes for a polypeptide moiety POL$^x$ of formula (V) are selected from the following sequences:

```
                                  (SEQ ID NO: 9)
ASPAAPAPASPAAPAPSAPA, (SEQ ID NO: 10)
AAPASPAPAAPSAPAPAAPS, (SEQ ID NO: 11)
APSSPSPSAPSSPSPASPSS, (SEQ ID NO: 12)
SSPSAPSPSSPASPSPSSPA, (SEQ ID NO: 13)
AASPAAPSAPPAAASPAAPSAPPA,
and (SEQ ID NO: 14)
ASAAAPAAASAAASAPSAAA;
``` or circular permuted versions or (a) multimer(s) of these sequences as a whole or parts of these sequences.

Again, also (a) peptide fragment(s) or (a) multimer(s) or circularly permuted versions of these sequences and the sequences provided herein above may be employed in context of the present invention as polymer cassettes for a polypeptide moiety POL$^x$ of formula (V). The person skilled in the art is readily in a position to generate further amino acid polymer cassettes that form random coil conformation under physiological conditions and are constituted of mainly alanine, serine, and proline as defined herein. Such other and further examples of random coil conformation forming amino acid polymer cassettes to be used for a polypeptide moiety POL$^x$ of formula (V) may, inter alia, comprise combinations and/or peptide fragments or circularly permuted versions of the specific polymer cassettes shown above.

Accordingly, the exemplified polymer cassettes may also provide for individual peptide fragments which may be newly combined to form further polymer cassettes.

In accordance with the above, a polypeptide moiety POL$^x$ of formula (V) may comprise a multimer of sequences consisting of either one of the amino acid sequences with SEQ ID NO:9, 10, 11, 12, 13 or 14 as disclosed herein above or may comprise a multimer of sequences consisting of more than one of amino acid sequences SEQ ID NOs:9, 10, 11, 12, 13 and 14. Furthermore, it is envisaged that also peptide fragments or circularly permuted versions of these exemplified sequences may be used to build up further polymer cassettes of a polypeptide moiety POL$^x$ of formula (V).

In another embodiment, a polypeptide moiety POL$^x$ of formula (V) may comprise a multimer of sequences consisting of a (circular) permutation of the amino acid sequence selected from the group consisting of SEQ ID NO:9, 10, 11, 12, 13, 14, 15 or (a) multimers(s) of these (circular) permutated sequences.

In yet another embodiment, a polypeptide moiety POL$^x$ of formula (V) may comprise a multimer consisting of a peptide fragment/part of the amino acid sequence selected from the group consisting of SEQ ID NOs: 9, 10, 12, 13, 14, 15 or (a) multimers(s) of these exemplified polymer cassettes.

Peptide fragments of these sequences to be employed for the generation of a polypeptide moiety POL$^x$ of formula (V) may consist of at least 3, preferably of at least 4, more preferably of at least 5, even more preferably of at least 6, still more preferably of at least 8, particularly preferably of at least 10, more particularly preferably of at least 12, even more particularly preferably of at least 14, preferably of at least 6, still more preferably of at least 8, particularly preferably of at least 10, more particularly preferably of at least 12, even more particularly preferably of at least 14, even more particularly preferably of at least 16, and most preferably of at least 18 consecutive amino acids of the amino acid sequence selected from the group consisting of said SEQ ID NOs: 9, 10, 11, 12, 13 and 14.

For example, individual peptide fragments of the inventive polymer cassettes may be combined to further individual polymer cassettes as long as the above-identified rules for the overall distribution and amount of alanine, serine and proline are respected. Again, these polymer cassettes may also comprise further amino acid residues, however only as minimal or minor constituents, i.e. maximally 10%, preferably maximally 2% of the individual polymer cassette. POL$^x$ of formula (V) moieties comprising polymer cassettes consist, in one embodiment of the present invention, of at least about 100 amino acid residues. Individual polymer cassettes may be combined in order to form longer random coil forming amino acid polymers, whereby a maximal length of a polypeptide moiety POL$^x$ of formula (V) is about 3000 amino acids.

Preferably, POL$^x$ of formula (V) is covalently linked to Hyp$^1$ and Hyp$^2$ of formula (V), in particular by a permanent linkage, more preferably by a permanent amide linkage.

In the carrier-linked treprostinil prodrugs of the present invention functional groups of Hyp$^1$ and Hyp$^2$ of formula (V) are connected to a moiety X$^0$ of formula (I), to a moiety Q (if the carrier-linked treprostinil prodrug is of formula (II)), to a moiety Q$^1$ (if the carrier-linked treprostinil prodrug is of formula (IIaa) or (IIab)) or to a moiety X$_1$ (if the carrier-linked treprostinil prodrug is of formula (IIac), (IIad), or (IIb)), or to the rest of the molecule (if the carrier-linked treprostinil prodrug is of formula (IIba)), respectively.

The hyperbranched moieties Hyp$^1$ and Hyp$^2$ of formula (V) are each independently selected from the group comprising, in particular consisting of, in bound form glycerol, pentaerythritol, dipentaerythritol, tripentaerythritol, hexaglycerine, sucrose, sorbitol, fructose, mannitol, glucose, cellulose, amyloses, starches, hydroxyalkyl starches, polyvinylalcohols, dextranes, hyualuronans, dilysine, trilysine, tetralysine, pentalysine, hexalysine, heptalysine, octalysine, nonalysine, decalysine, undecalysine, dodecalysine, tridecalysine, tetradecalysine, pentadecalysine, hexadecalysine, heptadecalysine, octadecalysine, nonadecalysine, triornithine, tetraornithine, pentaornithine, hexaornithine, heptaornithine, octaornithine, nonaornithine, decaornithine, undecaornithine, dodecaornithine, tridecaornithine, tetradecaornithine, pentadecaornithine, hexadecaornithine, heptadecaornithine, octadecaornithine, nonadecaornithine, tridiaminobutyric acid, tetradiaminobutyric acid, pentadiaminobutyric acid, hexadiaminobutyric acid, heptadiaminobutyric acid, octadiaminobutyric acid, nonadiaminobutyric acid, decadiaminobutyric acid, undecadiaminobutyric acid, dodecadiaminobutyric acid, tridecadiaminobutyric acid, tetradecadiaminobutyric acid, pentadecadiaminobutyric acid, hexadecadiaminobutyric acid, heptadecadiaminobutyric acid, octadecadiaminobutyric acid, nonadecadiaminobutyric acid, di(glutamic acid), tri(glutamic acid), tetra(glutamic acid), penta(glutamic acid), hexa(glutamic acid), hepta(glutamic acid), octa(glutamic acid), nona(glutamic acid), deca (glutamic acid), undeca(glutamic acid), dodeca(glutamic acid), trideca(glutamic acid), tetradeca(glutamic acid), pentadeca(glutamic acid), hexadeca(glutamic acid), heptadeca (glutamic acid), octadeca(glutamic acid), nonadeca(glutamic acid), di(aspartic acid), tri(aspartic acid), tetra(aspartic acid), penta(aspartic acid), hexa(aspartic acid), hepta(aspartic acid), octa(aspartic acid), nona(aspartic acid), deca(aspartic acid), undeca(aspartic acid), dodeca(aspartic acid), trideca(aspartic acid), tetradeca(aspartic acid), pentadeca(aspartic acid), hexadeca(aspartic acid), heptadeca(aspartic acid), octadeca(aspartic acid), nonadeca(aspartic acid), polyethyleneimines, and low-molecular weight PEI.

In a preferred embodiment, the hyperbranched moieties $Hyp^1$ and $Hyp^2$ of formula (V) are each independently selected from the group comprising, in particular consisting of, in bound form dilysine, trilysine, tetralysine, pentalysine, hexalysine, heptalysine, octalysine, nonalysine, decalysine, undecalysine, dodecalysine, tridecalysine, tetradecalysine, pentadecalysine, hexadecalysine, heptadecalysine, octadecalysine, nonadecalysine, triornithine, tetraornithine, pentaornithine, hexaornithine, heptaornithine, octaornithine, nonaornithine, decaornithine, undecaornithine, dodecaornithine, tridecaornithine, tetradecaornithine, pentadecaornithine, hexadecaornithine, heptadecaornithine, octadecaornithine, nonadecaornithine, tridiaminobutyric acid, tetradiaminobutyric acid, pentadiaminobutyric acid, hexadiaminobutyric acid, heptadiaminobutyric acid, octadiaminobutyric acid, nonadiaminobutyric acid, decadiaminobutyric acid, undecadiaminobutyric acid, dodecadiaminobutyric acid, tridecadiaminobutyric acid, tetradecadiaminobutyric acid, pentadecadiaminobutyric acid, hexadecadiaminobutyric acid, heptadecadiaminobutyric acid, octadecadiaminobutyric acid, nonadecadiaminobutyric acid, di(glutamic acid), tri(glutamic acid), tetra(glutamic acid), penta(glutamic acid), hexa(glutamic acid), hepta(glutamic acid), octa(glutamic acid), nona(glutamic acid), deca(glutamic acid), undeca(glutamic acid), dodeca(glutamic acid), trideca(glutamic acid), tetradeca(glutamic acid), pentadeca(glutamic acid), hexadeca(glutamic acid), heptadeca(glutamic acid), octadeca(glutamic acid), nonadeca(glutamic acid), di(aspartic acid), tri(aspartic acid), tetra(aspartic acid), penta(aspartic acid), hexa(aspartic acid), hepta(aspartic acid), octa(aspartic acid), nona(aspartic acid), deca(aspartic acid), undeca(aspartic acid), dodeca(aspartic acid), trideca(aspartic acid), tetradeca(aspartic acid), pentadeca(aspartic acid), hexadeca(aspartic acid), heptadeca(aspartic acid), octadeca(aspartic acid), nonadeca(aspartic acid), polyethyleneimines, and low-molecular weight PEI.

More preferably, the hyperbranched moieties $Hyp^1$ and $Hyp^2$ of formula (V) are independently selected from the group comprising, more preferably consisting of, in bound form, trilysine, tetralysine, pentalysine, hexalysine, heptalysine, octalysine, nonalysine, decalysine, undecalysine, dodecalysine, tridecalysine, tetradecalysine, pentadecalysine, hexadecalysine, and heptadecalysine, even more preferably $Hyp^1$ and $Hyp^2$ are independently comprising, preferably consisting of, in bound form, trilysine, heptalysine or pentadecalysine.

More preferably, $Hyp^1$ and $Hyp^2$ of formula (V) are independently selected from any one of the following structures:

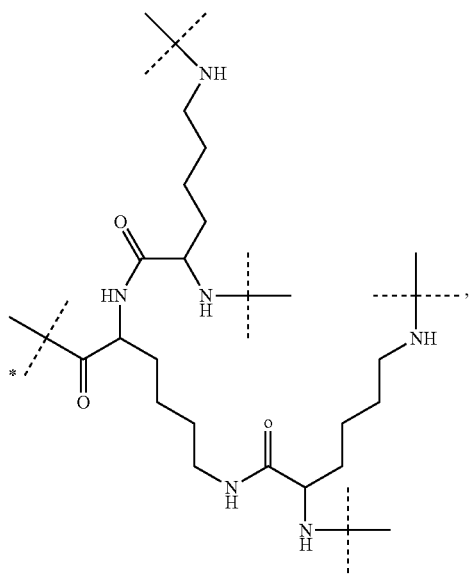

(i-x)

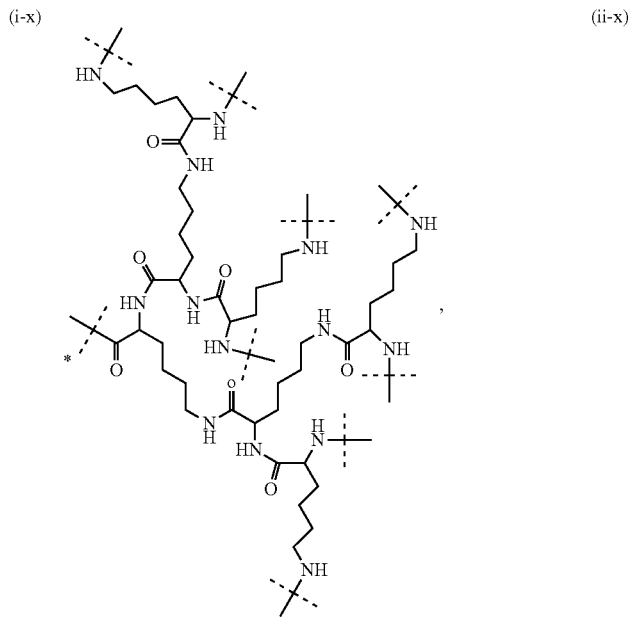

(ii-x)

-continued
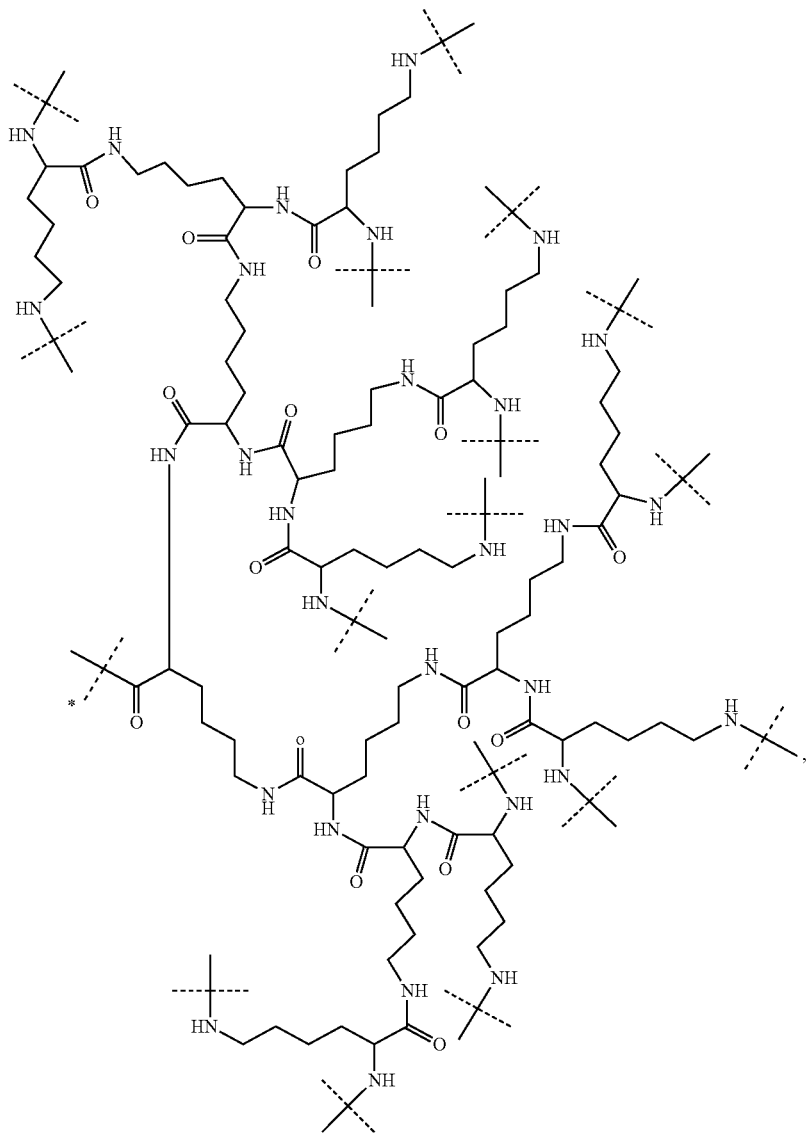
(iii-x)
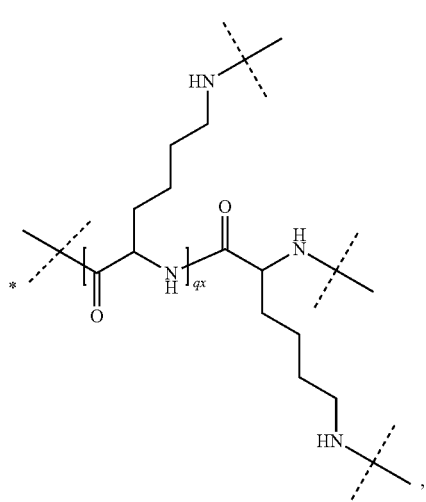
(iv-x)

wherein
dashed lines marked with an asterisk indicate attachment to POL$^x$ of formula (V),
unmarked dashed lines indicate attachment to X$^0$ (if the carrier-linked treprostinil prodrug is of formula (I)), to Q (if the carrier-linked treprostinil prodrug is of formula (II)), to Q$^1$ (if the carrier-linked treprostinil prodrug is of formula (IIaa) or (IIab)) or to X$_1$ (if the carrier-linked treprostinil prodrug is of formula (IIac), (IIad), or (IIb)), or to the rest of the molecule (if the carrier-linked treprostinil prodrug is of formula (IIba)), respectively, and qx is an integer of from 0 to 15, preferably 3 to 7, and even more preferably 6.

Preferably, Hyp$^1$ and Hyp$^2$ of formula (V) are each a heptalysinyl group, in particular Hyp$^1$ and Hyp$^2$ of formula (V) each have the structure of formula (ii-x) above.

Preferably, Hyp$^1$ and Hyp$^2$ of formula (V) have the same structure.

Functional groups of Hyp$^1$ and Hyp$^2$ of formula (V) serve as attachment points for direct linkage of Hyp$^1$ and Hyp$^2$ of formula (V) to X$^0$ (if the carrier-linked treprostinil prodrug is of formula (I)), to Q (if the carrier-linked treprostinil prodrug is of formula (II)), to Q$^1$ (if the carrier-linked treprostinil prodrug is of formula (IIaa) or (IIab)) or to X$_1$ (if the carrier-linked treprostinil prodrug is of formula (IIac), (IIad), or (IIb)), or to the rest of the molecule (if the carrier-linked treprostinil prodrug is of formula (IIba)), respectively. Remaining functional groups which are not connected to X$^0$, Q, Q$^1$ or X$_1$, respectively, may, independently of each other, be capped with suitable capping reagents or may optionally be connected to at least one targeting moiety, in particular through permanent linkages Therefore, in the water-soluble carrier-linked prodrugs of the present invention the hyperlinked moieties Hyp$^1$ and Hyp$^2$ of formula (V) are connected to POL$^x$ of formula (V) and functional groups of Hyp$^1$ and Hyp$^2$ of formula (V) are connected to X$^0$ of formula (I), to Q (if the carrier-linked treprostinil prodrug is of formula (II)), to Q$^1$ (if the carrier-linked treprostinil prodrug is of formula (IIaa) or (IIab)) or to X$_1$ (if the carrier-linked treprostinil prodrug is of formula (IIac), (IIad), or (IIb)), or to the rest of the molecule (if the carrier-linked treprostinil prodrug is of formula (IIba)), respectively, permanent linkages, targeting moieties and/or capping groups.

In a preferred embodiment, all functional groups of the hyperbranched moieties Hyp$^1$ and Hyp$^2$ of formula (V) are connected to X$^0$ of formula (I), to Q (if the carrier-linked treprostinil prodrug is of formula (II)), to Q$^1$ (if the carrier-linked treprostinil prodrug is of formula (IIaa) or (IIab)) or to X$_1$ (if the carrier-linked treprostinil prodrug is of formula (IIac), (IIad) or (IIb)), or to the rest of the molecule (if the carrier-linked prodrug is of formula (IIba)), respectively.

Preferably, the hyperbranched moieties Hyp$^1$ and Hyp$^2$ of formula (V) have independently a molecular weight in the range of from 0.1 kDa to 4 kDa, more preferably 0.4 kDa to 2 kDa. Preferably, the hyperbranched moieties Hyp$^1$ and Hyp$^2$ of formula (V) have each independently at least 3 branchings and are each independently conjugated to at least 4 X$^0$, Q, Q$^1$, X$_1$ or the rest of the molecule, respectively, permanent linkages, and/or capping groups and each independently have at most 63 branchings and are each independently at most conjugated to 64 X$^0$, Q, Q$^1$, X$^1$ or the rest of the molecule, respectively, permanent linkages, and/or capping groups. It is preferred that the hyperbranched moieties Hyp$^1$ and Hyp$^2$ of formula (V) have each independently at least 7 branchings and are each independently conjugated to at least 8 X$^0$, Q, Q$^1$, X$_1$ or the rest of the molecule, respectively, permanent linkages, and/or capping groups and have each independently at most 31 branchings and are each independently at most conjugated to 32 X$^0$, Q, Q$^1$, X$^1$ or the rest of the molecule, respectively, permanent linkages, and/or capping groups.

Preferably, the hyperbranched moieties Hyp$^1$ and Hyp$^2$ of formula (V) are each independently a hyperbranched polypeptide. Preferably, such hyperbranched polypeptide comprises lysine in bound form. Preferably, each hyperbranched moiety Hyp$^1$ and Hyp$^2$ of formula (V) independently have a molecular weight in the range of from 0.1 kDa to 4 kDa, in particular 0.4 kDa to 2 kDa.

Preferably, mx is 0 and POL-Hyp$^2$- of formula (V) is selected from the following structures:

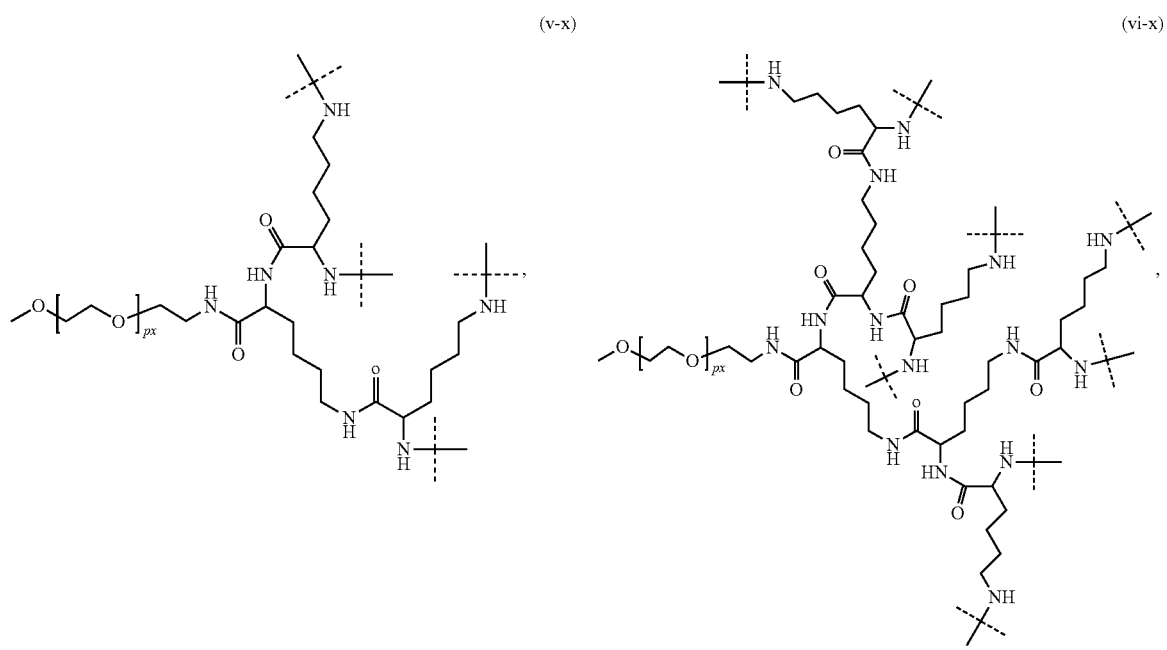

(v-x)

(vi-x)

-continued
(vii-x)
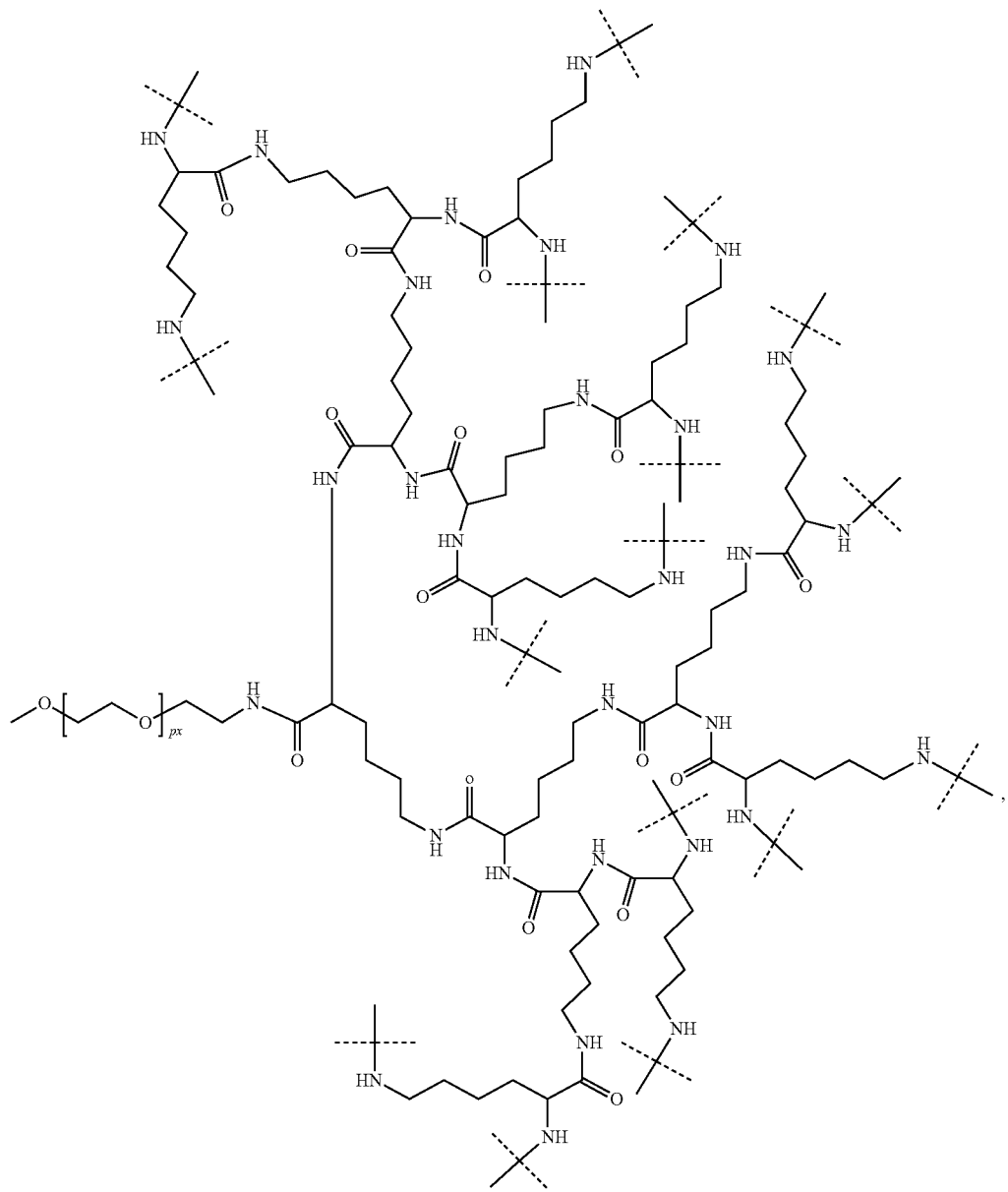

(viii-x)

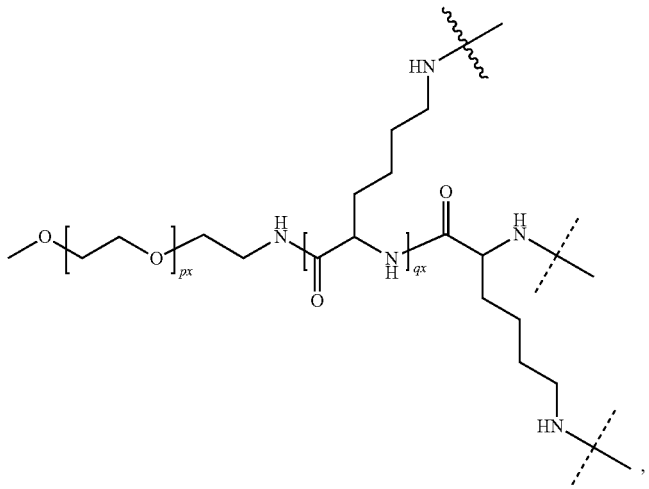

wherein
dashed lines indicate attachment to $X^0$ (if the carrier-linked treprostinil prodrug is of formula (I)), to Q (if the carrier-linked treprostinil prodrug is of formula (II)), to $Q^1$ (if the carrier-linked treprostinil prodrug is of formula (IIaa) or (IIab)) or to $X^1$ (if the carrier-linked treprostinil prodrug is of formula (IIac) or (IIad)), respectively, provided that one of m1, m2 of formula (I) is 1 and wherein the carrier is covalently attached to T of formula (I) in case m1, m2=0,
px is an integer of from 5 to 2000, preferably 10 to 1000, in particular 100 to 1000, and
qx is an integer of from 0 to 15, preferably 3 to 7, more preferably, qx is 6.

In another preferred embodiment $Z^1$ of formula (I), (II), (IIaa), (IIab), (IIac), (IIad), (IIb) and (IIba) has the structure of formula (VI):

wherein
B is a branching core,
each A is independently a poly(ethylene glycol)-based polymeric chain,
each $Hyp^y$ is independently a branched moiety, and
n is an integer of from 3 to 32;

In a preferred embodiment, the branching core B of formula (VI) comprises, preferably consists of a moiety selected from:
a polyalcohol comprising at least 2 hydroxyl groups (preferably further comprising a functional group, which is preferably an additional amino group or a carboxylic acid group, more preferably an additional carboxylic acid group),
preferably B is selected from glycerol, pentaerythritol, dipentaerythritol, tripentaerythritol, hexaglycerine, sucrose, sorbitol, fructose, mannitol, glucose, cellulose, amyloses, starches, hydroxyalkyl starches, polyvinylalcohols, dextranes, and hyualuronans, erythritol, threitol, arabitol, xylitol, ribitol, dulcitol, iditol; more preferably from glycerol, pentaerythritol, dipentaerythritol, tripentaerythritol, hexaglycerine, sucrose, sorbitol, fructose, mannitol, glucose, cellulose, amyloses, starches, hydroxyalkyl starches, polyvinylalcohols, dextranes, and hyualuronans.

or a polyamine comprising at least 2 amine groups (preferably further comprising a functional group, which is preferably an additional hydroxyl group or a carboxylic acid group, more preferably a carboxylic acid group),
preferably selected from ornithine, diornithine, triornithine, tetraornithine, pentaornithine, hexaornithine, heptaornithine, octaornithine, nonaornithine, decaornithine, undecaornithine, dodecaornithine, tridecaornithine, tetradecaornithine, pentadecaornithine, hexadecaornithine, heptadecaornithine, octadecaornithine, nonadecaornithine, diaminobutyric acid, di(diaminobutyric acid), tri(diaminobutyric acid), tetra(diaminobutyric acid), penta(diaminobutyric acid), hexa(diaminobutyric acid), hepta(diaminobutyric acid), octa(diaminobutyric acid), nona(diaminobutyric acid), deca(diaminobutyric acid), undeca(diaminobutyric acid), dodeca(diaminobutyric acid), trideca(diaminobutyric acid), tetradeca(diaminobutyric acid), pentadeca(diaminobutyric acid), hexadeca(diaminobutyric acid), heptadeca(diaminobutyric acid), octadeca(diaminobutyric acid), nonadeca(diaminobutyric acid), lysine, dilysine, trilysine, tetralysine, pentalysine, hexalysine, heptalysine, octalysine, nonalysine, decalysine, undecalysine, dodecalysine, tridecalysine, tetradecalysine, pentadecalysine, hexadecalysine, heptadecalysine, octadecalysine, nonadecalysine, oligolysines, polyethyleneimines, and polyvinylamines;
wherein the polyalcohol or polyamine is in bound form.

In a preferred embodiment, the branching core B of formula (VI) comprises, preferably consists of pentaerithritol.

Preferably, a poly(ethylene glycol)-based polymeric chain A connected to the branching core B of formula (VI) consists of a linear PEG chain, of which one terminus is connected to B of formula (VI) and the other terminus is connected to $Hyp^y$ of formula (VI). It is understood that a PEG-based chain A of formula (VI) may optionally be terminated in case of a branched PEG chain and/or may optionally be interrupted in case of a branched or linear PEG chain by alkyl or aryl groups and may optionally be substituted with heteroatoms and/or functional groups.

Each sub-structure A-$Hyp^y$ of formula (VI) extending from the branching core B of formula (VI) may be independently of each other the same or different sub-structures A-Hyp$^y$. In a preferred embodiment, the all sub-structures A-Hyp$^y$ of formula (VI) are the same.

Each A and each Hyp$^y$ of formula (VI) may be independently selected from the other moieties A and Hyp$^y$. Preferably, all sub-structures A-Hyp$^y$ connected to B of formula (VI) have an identical structure.

Preferably, the PEG-based polymeric chains A of formula (VI) are connected to B through permanent linkages.

n of formula (VI) is an integer from 3 to 32. Preferably, n is an integer from 3 to 16, more preferably n is an integer from 4 to 8 and most preferably n is 4.

In a preferred embodiment n of formula (VI) is 4 and m is 2.

In one embodiment, a PEG-based polymeric chain A of formula (VI) is selected from a linear or branched PEG-based polymeric chain. Preferably, A is a linear PEG-based polymeric chain.

Preferably, each A of formula (VI) is independently selected from the formula

—X3-(CH$_2$)$_{n1}$—(OCH$_2$CH$_2$)$_p$—O—(CH$_2$)$_{n2}$—X2-, wherein
n1 and n2 are independently selected from 1, 2, 3, and 4, preferably from 1, 2, and 3;
p is an integer in the range of from 5 to 2000, preferably p is an integer in the range of from 10 to 1000, more preferably p is an integer in the range of from 100 to 1000; and
X3 and X2 are independently functional groups covalently linked to B or Hyp$^y$, respectively.

Preferably, a linkage between a moiety A and a moiety Hyp$^y$ of formula (VI) is a permanent linkage, more preferably a permanent linkage comprising a linkage group comprising, in particular consisting of a group selected from amine groups, amide groups, carbamate groups, thioether groups, ether groups, and most preferably a permanent linkage between a moiety A and a moiety Hyp$^y$ of formula (VI) is an amide linkage.

In a preferred embodiment, a sub-structure B (A)$_n$ formula (VI) is a multi-arm PEG derivative as, for instance, detailed in the products list of JenKem Technology, USA (accessed by download from http://jenkemusa.net/pegproducts2.aspx on Mar. 8, 2011), such as a 4-arm-PEG derivative, in particular comprising a pentaerythritol core, an 8-arm-PEG derivative comprising a hexaglycerin core, and an 8-arm-PEG derivative comprising a tripentaerythritol core. Most preferred are sub-structures B (A)$_n$ of formula (VI) comprising, in particular consisting of, moieties selected from:

a 4-arm PEG Amine comprising a pentaerythritol core:

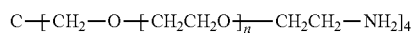
C—[CH$_2$—O—[CH$_2$CH$_2$O]$_n$—CH$_2$CH$_2$—NH$_2$]$_4$ with n ranging from 400 to 2000;
a 4-arm PEG Carboxyl comprising a pentaerythritol core:

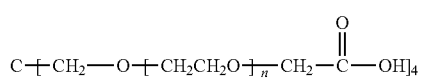
C—[CH$_2$—O—[CH$_2$CH$_2$O]$_n$—CH$_2$—C(=O)—OH]$_4$ with n ranging from 400 to 2000;

an 8-arm PEG Amine comprising a hexaglycerin core:

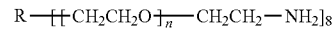
R—[[CH$_2$CH$_2$O]$_n$—CH$_2$CH$_2$—NH$_2$]$_8$ with n ranging from 400 to 2000 and
R=hexaglycerin core structure;
an 8-arm PEG Carboxyl comprising a hexaglycerin core:

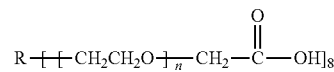
R—[[CH$_2$CH$_2$O]$_n$—CH$_2$—C(=O)—OH]$_8$ with n ranging from 400 to 2000 and
R=hexaglycerin core structure;
an 8-arm PEG Amine comprising a tripentaerythritol core:

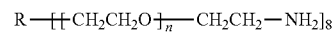
R—[[CH$_2$CH$_2$O]$_n$—CH$_2$CH$_2$—NH$_2$]$_8$ with n ranging from 400 to 2000
and R=tripentaerythritol core structure;
and an 8-arm PEG Carboxyl comprising a tripentaerythritol core:

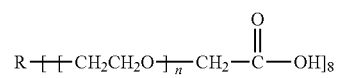
R—[[CH$_2$CH$_2$O]$_n$—CH$_2$—C(=O)—OH]$_8$ with n ranging from 400 to 2000 and
R=tripentaerythritol core structure;
a 6-arm PEG Amine comprising a sorbitol or dipentaerythritol core:

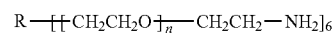
R—[[CH$_2$CH$_2$O]$_n$—CH$_2$CH$_2$—NH$_2$]$_6$ with n ranging from 400 to 2000 and
R=sorbitol or dipentaerythritol;
an 8-arm PEG Carboxyl comprising a sorbitol or dipentaerythritol core:

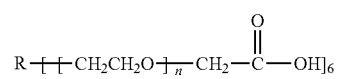
R—[[CH$_2$CH$_2$O]$_n$—CH$_2$—C(=O)—OH]$_6$ with n ranging from 400 to 2000 and
R=sorbitol or dipentaerythritol;
an 8-arm PEG Amine comprising a sorbitol or dipentaerythritol core:

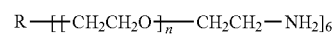
R—[[CH$_2$CH$_2$O]$_n$—CH$_2$CH$_2$—NH$_2$]$_6$ with n ranging from 400 to 2000
and R=sorbitol or dipentaerythritol;

and an 8-arm PEG Carboxyl comprising a sorbitol or dipentaerythritol core:

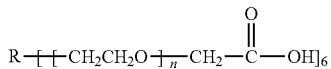

with n ranging from 400 to 2000 and
R=sorbitol or dipentaerythritol;
each in bound form.
Also preferred are sub-structures B (A)$_n$ of the following formulas:
a 4-arm PEG Amine comprising a pentaerythritol core:

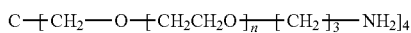

with n ranging from 400 to 2000;
a 4-arm PEG Carboxyl comprising a pentaerythritol core:

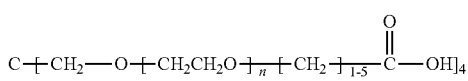

with n ranging from 400 to 2000;
an 8-arm PEG Amine comprising a hexaglycerin core:

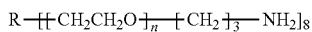

with n ranging from 400 to 2000 and
R=hexaglycerin core structure;
an 8-arm PEG Carboxyl comprising a hexaglycerin core:

with n ranging from 400 to 2000 and
R=hexaglycerin core structure;
an 8-arm PEG Amine comprising a tripentaerythritol core:

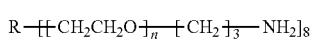

with n ranging from 400 to 2000
and R=tripentaerythritol core structure;
and an 8-arm PEG Carboxyl comprising a tripentaerythritol core:

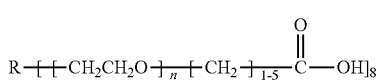

with n ranging from 400 to 2000 and
R=tripentaerythritol core structure;

a 6-arm PEG Amine comprising a sorbitol or dipentaerythritol core:

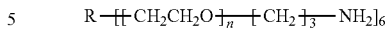

with n ranging from 400 to 2000 and
R=sorbitol or dipentaerythritol;
a 6-arm PEG Carboxyl comprising a sorbitol or dipentaerythritol core:

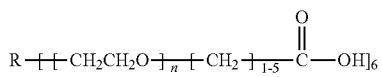

with n ranging from 400 to 2000 and
R=sorbitol or dipentaerythritol;
a 6-arm PEG Amine comprising a sorbitol or dipentaerythritol core:

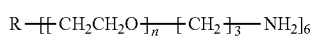

with n ranging from 400 to 2000
and R=sorbitol or dipentaerythritol;
and a 6-arm PEG Carboxyl comprising a sorbitol or dipentaerythritol core:

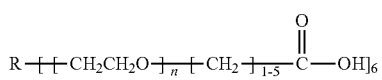

with n ranging from 400 to 2000 and
R=sorbitol or dipentaerythritol;
each in bound form.
Also preferred are sub-structures B (A)$_n$ of formula (VI) comprising, in particular consisting of, moieties selected from:
a 4-arm PEG Amine comprising a pentaerythritol core:

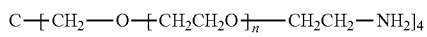

with n ranging from 20 to 500;
a 4-arm PEG Carboxyl comprising a pentaerythritol core:

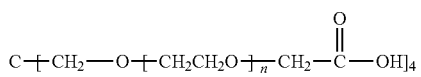

with n ranging from 20 to 500;
an 8-arm PEG Amine comprising a hexaglycerin core:

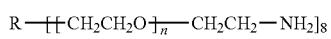

with n ranging from 20 to 500; and
R=hexaglycerin core structure;

an 8-arm PEG Carboxyl comprising a hexaglycerin core:

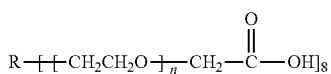

with n ranging from 20 to 500; and
R=hexaglycerin core structure;
an 8-arm PEG Amine comprising a tripentaerythritol core:

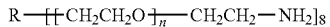

with n ranging from 20 to 500;
and R=tripentaerythritol core structure;
and an 8-arm PEG Carboxyl comprising a tripentaerythritol core:

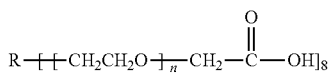

with n ranging from 20 to 500; and
R=tripentaerythritol core structure;
a 6-arm PEG Amine comprising a sorbitol or dipentaerythritol core:

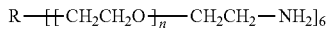

with n ranging from 20 to 500; and
R=sorbitol or dipentaerythritol;
an 8-arm PEG Carboxyl comprising a sorbitol or dipentaerythritol core:

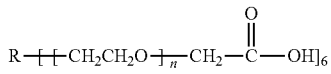

with n ranging from 20 to 500; and
R=sorbitol or dipentaerythritol;
an 8-arm PEG Amine comprising a sorbitol or dipentaerythritol core:

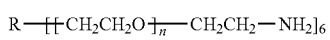

with n ranging from 20 to 500;
and R=sorbitol or dipentaerythritol;
and an 8-arm PEG Carboxyl comprising a sorbitol or dipentaerythritol core:

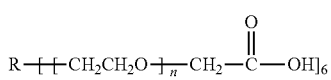

with n ranging from 20 to 500; and
R=sorbitol or dipentaerythritol;
each in bound form.

Also preferred are sub-structures B (A)$_n$ of the following formulas:
a 4-arm PEG Amine comprising a pentaerythritol core:

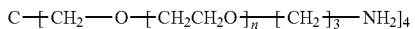

with n ranging from 20 to 500;
a 4-arm PEG Carboxyl comprising a pentaerythritol core:

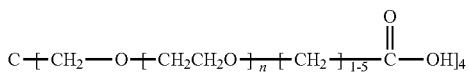

with n ranging from 20 to 500;
an 8-arm PEG Amine comprising a hexaglycerin core:

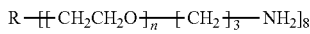

with n ranging from 20 to 500; and
R=hexaglycerin core structure;
an 8-arm PEG Carboxyl comprising a hexaglycerin core:

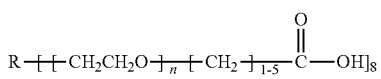

with n ranging from 20 to 500; and
R=hexaglycerin core structure;
an 8-arm PEG Amine comprising a tripentaerythritol core:

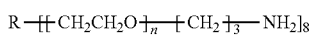

with n ranging from 20 to 500;
and R=tripentaerythritol core structure;
and an 8-arm PEG Carboxyl comprising a tripentaerythritol core:

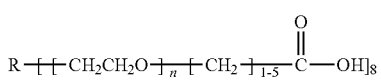

with n ranging from 20 to 500; and
R=tripentaerythritol core structure;
a 6-arm PEG Amine comprising a sorbitol or dipentaerythritol core:

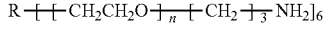

with n ranging from 20 to 500; and
R=sorbitol or dipentaerythritol;

a 6-arm PEG Carboxyl comprising a sorbitol or dipentaerythritol core:

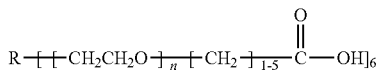

with n ranging from 20 to 500; and
R=sorbitol or dipentaerythritol;
a 6-arm PEG Amine comprising a sorbitol or dipentaerythritol core:

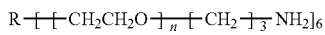

with n ranging from 20 to 500;
and R=sorbitol or dipentaerythritol;
and a 6-arm PEG Carboxyl comprising a sorbitol or dipentaerythritol core:

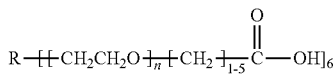

with n ranging from 20 to 500; and
R=sorbitol or dipentaerythritol;
each in bound form.

In a preferred embodiment, the molecular weight of a sub-structure B-(A)$_n$ of formula (VI) ranges from 1 kDa to 80 kDa, more preferably 1 kDa to 40 kDa and even more preferably 10 kDa to 40 kDa. It is understood that the terminal amine groups or carboxyl groups, respectively, are used for conjugation to a moiety Hyp$^y$ of formula (VI).

Functional groups of a moiety Hyp$^y$ of formula (VI) are connected to moieties $X^0$ of formula (I), to Q (if the carrier-linked treprostinil prodrug is of formula (II)), to $Q^1$ (if the carrier-linked treprostinil prodrug is of formula (IIaa) or (IIab)) or to $X_1$ (if the carrier-linked treprostinil prodrug is of formula (IIac), (IIad), or (IIb)), or to the rest of the molecule (if the carrier-linked treprostinil prodrug is of formula (IIba)), respectively.

In a preferred embodiment, a moiety Hyp$^y$ of formula (VI) is connected to a moiety $X^0$ of formula (I), to Q (if the carrier-linked treprostinil prodrug is of formula (II)), to $Q^1$ (if the carrier-linked treprostinil prodrug is of formula (IIaa) or (IIab)) or to $X_1$ (if the carrier-linked treprostinil prodrug is of formula (IIac), (IIad), or (IIb)), or to the rest of the molecule (if the carrier-linked treprostinil prodrug is of formula (IIba)), respectively, through a functional group selected from amide groups, carbamate groups, ester groups, ether groups, amine groups, thioether groups. Preferably, a moiety Hyp$^y$ of formula (VI) is connected to a moiety $X^0$ of formula (I), to a moiety Q of formula (II), to a moiety $Q^1$ of either formula (IIaa) or (IIab) or to a moiety $X_1$ of formula (IIac), (IIad), or (IIb), or to the rest of the molecule of formula (IIba), respectively, through amide groups, thioether groups and/or ether groups, even more preferably through amide groups.

Optionally, functional groups of a moiety Hyp$^y$ of formula (VI) which are not connected to a moiety $X^0$ of formula (I), to a moiety Q of formula (II), to a moiety $Q^1$ of either formula (IIaa) or (IIab) or to a moiety $X_1$ of formula (IIac), (IIad), (IIb), or to the rest of the molecule of formula (IIba) respectively, may be capped with suitable capping reagents and/or may optionally be connected to at least one targeting moiety, in particular through permanent linkages. Therefore, a moiety Hyp$^y$ of formula (VI) may be connected to a moiety $X^0$ of formula (I), to a moiety Q of formula (II), to a moiety $Q^1$ of either formula (IIaa) or (IIab) or to a moiety $X_1$ of formula (IIac), (IIad), (IIb), or to the rest of the molecule of formula (IIba), respectively, capping moieties and/or targeting moieties. Preferably, functional groups of a moiety Hyp$^y$ of formula (VI) are connected to a moiety $X^0$ of formula (I), to a moiety Q of formula (II), to a moiety $Q^1$ of either formula (IIaa) or (IIab) or to a moiety $X_1$ of formula (IIac), (IIad), or (IIb), or to the rest of the molecule of formula (IIba), respectively, and are not connected to capping moieties and/or targeting moieties. Targeting moieties, if present, may be conjugated to a moiety Hyp$^y$ of formula (VI) either directly or indirectly through spacer moieties.

Examples of suitable capping moieties are linear, branched or cyclic $C_{1-8}$ alkyl groups.

In one embodiment, each branched moiety Hyp$^y$ of formula (VI) is directly or indirectly connected to at least two moieties $X^0$ of formula (I), to at least two moieties Q of formula (II), to at least two moieties $Q^1$ of either formula (IIaa) or (IIab) or to at least two moieties $X^1$ of formula (IIac), (IIad), or (IIb), or to the rest of the molecule of formula (IIba), respectively. More preferably, each branched moiety Hyp$^y$ of formula (VI) is directly or indirectly connected to at least three moieties $X^0$ of formula (I), to at least three moieties Q of formula (II), to at least three moieties $Q^1$ of either formula (IIaa) or (IIab) or to at least three moieties $X_1$ of formula (IIac), (IIad), or (IIb), or to the rest of the molecule of formula (IIba), respectively. Most preferably, each branched moiety Hyp$^y$ of formula (VI) is directly or indirectly connected to at least four moieties $X^0$ of formula (I), to at least four moieties Q of formula (II), to at least four moieties $Q^1$ of either formula (IIaa) or (IIab) or to at least four moieties $X_1$ of formula (IIac), (IIad) or (IIb), or to the rest of the molecule of formula (IIba), respectively.

The branched moiety Hyp$^y$ of formula (VI) comprises, preferably consists of a moiety in bound form selected from:
a polyalcohol in bound form comprising at least 2 hydroxyl groups (preferably further comprising a functional group, which is preferably an additional hydroxyl group or a carboxylic acid group, more preferably an additional hydroxyl group),
preferably selected from glycerol, pentaerythritol, dipentaerythritol, tripentaerythritol, hexaglycerine, sucrose, sorbitol, fructose, mannitol, glucose, cellulose, amyloses, starches, hydroxyalkyl starches, polyvinylalcohols, dextranes, and hyualuronans, erythritol, threitol, arabitol, xylitol, ribitol, dulcitol, iditol; more preferably from glycerol, pentaerythritol, dipentaerythritol, tripentaerythritol, hexaglycerine, sucrose, sorbitol, fructose, mannitol, glucose, cellulose, amyloses, starches, hydroxyalkyl starches, polyvinylalcohols, dextranes, and hyualuronans;
or a polyamine in bound form comprising at least 2 amine groups (preferably further comprising a functional group, which is preferably an additional amine group or a carboxylic acid group, more preferably a carboxylic acid group),
preferably selected from ornithine, diornithine, triornithine, tetraornithine, pentaornithine, hexaornithine, heptaornithine, octaornithine, nonaornithine, decaornithine, undecaornithine, dodecaornithine, tridecaornithine, tetradecaornithine, pentadecaornithine, hexadecaornithine, heptadecaornithine, octadecaornithine, nonadecaornithine, diaminobutyric acid, di(diaminobutyric acid), tri(diaminobutyric acid), tetra(diaminobutyric acid), penta(diaminobutyric acid), hexa(diaminobutyric acid), hepta(diaminobutyric acid), octa(diaminobutyric acid), nona(diaminobutyric acid), deca(diaminobutyric acid), undeca(diaminobutyric acid), dodeca(diaminobutyric acid), trideca(diaminobutyric acid), tetradeca(diaminobutyric acid), pentadeca(diaminobutyric acid), hexadeca(diaminobutyric acid), heptadeca(diaminobutyric acid), octadeca(diaminobutyric acid), nonadeca(diaminobutyric acid), lysine, dilysine, trilysine, tetralysine, pentalysine, hexalysine, heptalysine, octalysine, nonalysine, decalysine, undecalysine, dodecalysine, tridecalysine, tetradecalysine, pentadecalysine, hexadecalysine, heptadecalysine, octadecalysine, nonadecalysine, oligolysines, triornithine, tetraornithine, pentaornithine, hexaornithine, heptaornithine, octaornithine, nonaornithine, decaornithine, undecaornithine, dodecaornithine, tridecaornithine, tetradecaornithine, pentadecaornithine, hexadecaornithine, heptadecaornithine, octadecaornithine, nonadecaornithine, tridiaminobutyric acid, tetradiaminobutyric acid, pentadiaminobutyric acid, hexadiaminobutyric acid, heptadiaminobutyric acid, octadiaminobutyric acid, nonadiaminobutyric acid, decadiaminobutyric acid, undecadiaminobutyric acid, dodecadiaminobutyric acid, tridecadiaminobutyric acid, tetradecadiaminobutyric acid, pentadecadiaminobutyric acid, hexadecadiaminobutyric acid, heptadecadiaminobutyric acid, octadecadiaminobutyric acid, nonadecadiaminobutyric acid, or a polycarboxylate in bound form comprising at least 2 carboxylate groups (preferably further comprising a functional group, which is preferably an additional amino group or a carboxylic acid group, more preferably an additional carboxylic acid group), preferably selected from di(glutamic acid), tri(glutamic acid), tetra(glutamic acid), penta(glutamic acid), hexa(glutamic acid), hepta(glutamic acid), octa(glutamic acid), nona(glutamic acid), deca(glutamic acid), undeca(glutamic acid), dodeca(glutamic acid), trideca(glutamic acid), tetradeca(glutamic acid), pentadeca(glutamic acid), hexadeca(glutamic acid), heptadeca(glutamic acid), octadeca(glutamic acid), nonadeca(glutamic acid), di(aspartic acid), tri(aspartic acid), tetra(aspartic acid), penta(aspartic acid), hexa(aspartic acid), hepta(aspartic acid), octa(aspartic acid), nona(aspartic acid), deca(aspartic acid), undeca(aspartic acid), dodeca(aspartic acid), trideca(aspartic acid), tetradeca(aspartic acid), pentadeca(aspartic acid), hexadeca(aspartic acid), heptadeca(aspartic acid), octadeca(aspartic acid), nonadeca(aspartic acid), polyethyleneimines, and polyvinylamines.

In a preferred embodiment, a moiety $Hyp^y$ of formula (VI) is selected from the group comprising, in particular consisting of, in bound form, dilysine, trilysine, tetralysine, pentalysine, hexalysine, heptalysine, octalysine, nonalysine, decalysine, undecalysine, dodecalysine, tridecalysine, tetradecalysine, pentadecalysine, hexadecalysine, heptadecalysine, octadecalysine, nonadecalysine, triornithine, tetraornithine, pentaornithine, hexaornithine, heptaornithine, octaornithine, nonaornithine, decaornithine, undecaornithine, dodecaornithine, tridecaornithine, tetradecaornithine, pentadecaornithine, hexadecaornithine, heptadecaornithine, octadecaornithine, nonadecaornithine, tridiaminobutyric acid, tetradiaminobutyric acid, pentadiaminobutyric acid, hexadiaminobutyric acid, heptadiaminobutyric acid, octadiaminobutyric acid, nonadiaminobutyric acid, decadiaminobutyric acid, undecadiaminobutyric acid, dodecadiaminobutyric acid, tridecadiaminobutyric acid, tetradecadiaminobutyric acid, pentadecadiaminobutyric acid, hexadecadiaminobutyric acid, heptadecadiaminobutyric acid, octadecadiaminobutyric acid, nonadecadiaminobutyric acid, di(glutamic acid), tri(glutamic acid), tetra(glutamic acid), penta(glutamic acid), hexa(glutamic acid), hepta(glutamic acid), octa(glutamic acid), nona(glutamic acid), deca(glutamic acid), undeca(glutamic acid), dodeca(glutamic acid), trideca(glutamic acid), tetradeca(glutamic acid), pentadeca(glutamic acid), hexadeca(glutamic acid), heptadeca(glutamic acid), octadeca(glutamic acid), nonadeca(glutamic acid), di(aspartic acid), tri(aspartic acid), tetra(aspartic acid), penta(aspartic acid), hexa(aspartic acid), hepta(aspartic acid), octa(aspartic acid), nona(aspartic acid), deca(aspartic acid), undeca(aspartic acid), dodeca(aspartic acid), trideca(aspartic acid), tetradeca(aspartic acid), pentadeca(aspartic acid), hexadeca(aspartic acid), heptadeca(aspartic acid), octadeca(aspartic acid), nonadeca(aspartic acid), polyethyleneimines, and low-molecular weight PEI.

More preferably, a moiety $Hyp^y$ of formula (VI) is selected from the group comprising, more preferably consisting of, in bound form, trilysine, tetralysine, pentalysine, hexalysine, heptalysine, octalysine, nonalysine, decalysine, undecalysine, dodecalysine, tridecalysine, tetradecalysine, pentadecalysine, hexadecalysine, and heptadecalysine, even more preferably a moiety $Hyp^y$ of formula (VI) comprises, preferably consists of, in bound form, trilysine, heptalysine or pentadecalysine.

In a preferred embodiment, a moiety $Hyp^y$ of formula (VI) has a molecular weight in the range of from 0.1 kDa to 4 kDa, more preferably 0.2 kDa to 2 kDa.

In a further preferred embodiment, each branched moiety $Hyp^y$ of formula (VI) has at least 1 branching and is conjugated to at least 2 moieties $X^0$ of formula (I), to at least two moieties Q of formula (II), to at least two moieties $Q^1$ of either formula (IIaa) or (IIab) or to at least two moieties $X_1$ of formula (IIac), (IIad), or (IIb), or to the rest of the molecule of formula (IIba), respectively, and has at most 63 branchings and is at most conjugated to 64 moieties $X^0$ of formula (I), to at least 64 moieties Q of formula (II), to at least 64 moieties $Q^1$ of either formula (IIaa) or (IIab) or to at least 64 moieties $X_1$ of formula (IIac), (IIad), or (IIb), or to the rest of the molecule of formula (IIba), respectively, more preferably each branched moiety $Hyp^y$ of formula (VI) has at least 1 branching and is conjugated to at least 2 moieties $X^0$ of formula (I), to at least two moieties Q of formula (II), to at least two moieties $Q^1$ of either formula (IIaa) or (IIab) or to at least two moieties $X_1$ of formula (IIac), (IIad), or (IIb), or to the rest of the molecule of formula (IIba), respectively, and has at most 31 branchings and is at most conjugated to 32 moieties $X^0$ of formula (I), to at least 32 moieties Q of formula (II), to at least 32 moieties $Q^1$ of either formula (IIaa) or (IIab) or to at least 32 moieties $X^1$ of formula (IIac), (IIad), or (IIb), or to the rest of the molecule of formula (IIba), respectively.

In a preferred embodiment, $Z^1$ of formula (VI) comprises a quaternary carbon, in particular a quaternary carbon of a branching core moiety B, wherein B of formula (VI) is pentarythritol in bound form. Preferably, each A of formula (VI) is independently a PEG-based polymeric chain terminally attached to the quaternary carbon of pentaerythritol via the —$CH_2$—O— moieties of the branching core moiety pentaerythritol by a permanent covalent linkage, and the distal end of the PEG-based polymeric chain is covalently bound to a branched moiety $Hyp^y$ of formula (VI), each branched moiety $Hyp^y$ of formula (VI) is conjugated to the moieties $X^0$ of formula (I), to the moieties Q of formula (II), to the moieties $Q^1$ of either formula (IIaa) or (IIab) or to the moieties $X_1$ of formula (IIac), (IIad), or (IIb) or to the rest of the molecule of formula (IIba), respectively.

In one preferred embodiment, a branched moiety $Hyp^y$ of formula (VI) comprises, preferably consists of branched polyamines comprising at least 2 amine groups. Preferably, the branched polyamine comprising at least 2 amine groups, comprises one or more lysine residues in bound form. Preferably, each branched moiety $Hyp^y$ of formula (VI) has a molecular weight in the range of from 0.1 kDa to 4 kDa, particular 0.2 to 2 kDa. In a preferred embodiment, a moiety B $(A-Hyp^y)_n$ of formula (VI), wherein n=4, consist of the same or different branched moieties $Hyp^y$ and that each moiety $Hyp^y$ can be chosen independently. In a preferred embodiment, all moieties $Hyp_y$ of formula (VI) are the same.

In a preferred embodiment, a moiety $Hyp^y$ of formula (VI) comprises, in particular consists of, between 1 and 32 lysines in bound form, preferably of 1, 3, 7 or 15 lysines in bound form, more preferably of 1, 3 or 7 lysines in bound form. Most preferably, $Hyp^y$ of formula (VI) comprises, in particular consists of heptalysinyl.

Preferably, the moiety B $(A-Hyp^y)_n$ of formula (VI), wherein n is preferably 4, has a molecular weight in the range of from 1 kDa to 160 kDa, more preferably 1 kDa to 80 kDa and even more preferably 10 kDa to 40 kDa.

Preferred moieties B—$(A-Hyp^y)_4$ of formula (VI) are selected from structures (i-y) to (iii-y):

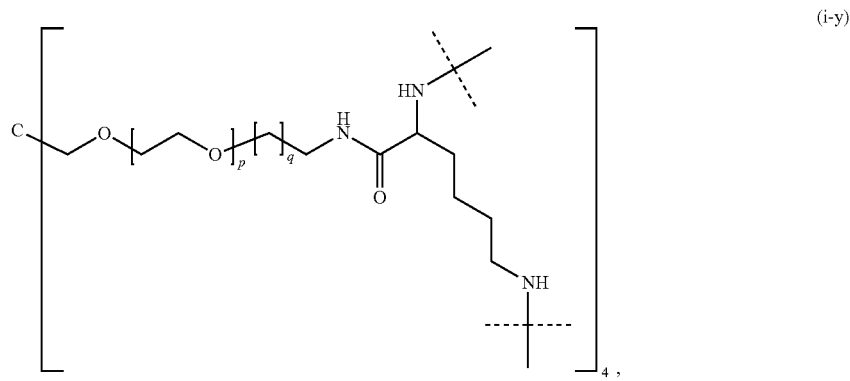

(i-y)

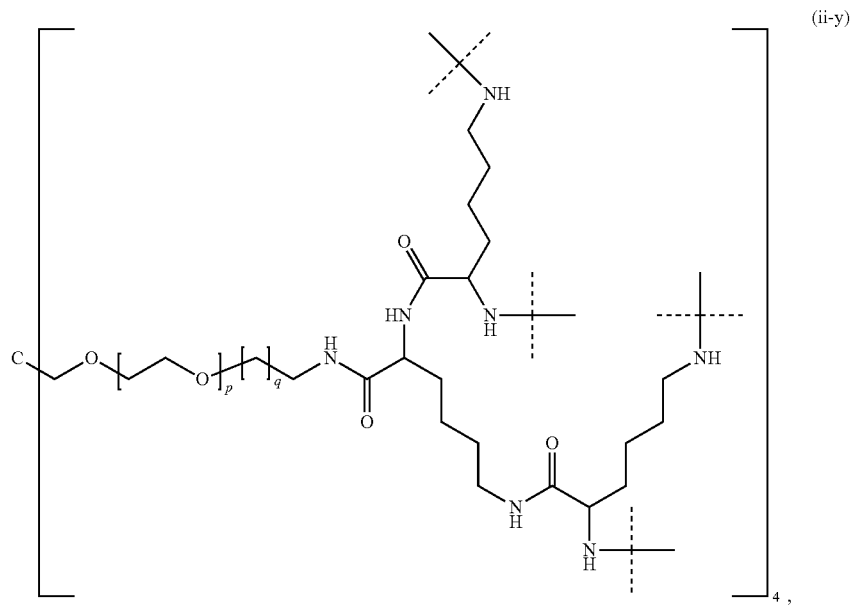

(ii-y)

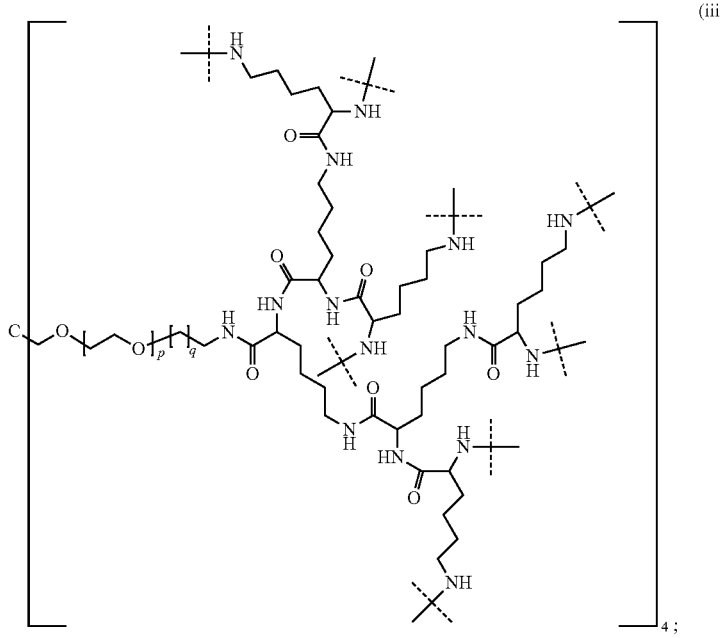

wherein
dashed lines indicate attachment to a moiety $X^0$ of formula (I), to a moiety Q of formula (II), to a moiety $Q^1$ of formula (IIaa) or (IIab) or to a moiety $X_1$ of formula (IIac), (IIad) or (IIb), or to the rest of the molecule of formula (IIba), respectively, provided that one of m1, m2 of formula (I) is 1 and wherein the carrier is covalently attached to T in case m1, m2=0, p is an integer of from 5 to 2000, preferably from 10 to 1000, more preferably from 10 to 500, most preferably from 100 to 1000, q is 1 or 2.

In a preferred embodiment, B of formula (VI) is pentaerythritol.

In another preferred embodiment, $Z^1$ of formula (I), (II), (IIaa), (IIab), (IIac), (IIad), (IIb), or (IIba) is a protein carrier which comprises, in particular consists of an amino acid sequence of at least 100 amino acid residues.

In another preferred embodiment, the protein carrier $Z^1$ of formula (I), (II), (IIaa), (IIab), (IIac), (IIad), (IIb) or (IIba) is in random coil conformation.

In another preferred embodiment, the protein carrier $Z^1$ of formula (I), (II), (IIaa), (IIab), (IIac), (IIad), (IIb) or (IIba) comprises, in particular consists of alanine, serine and proline residues.

In the preferred embodiment, the protein carrier $Z^1$ of formula (I), (II), (IIaa), (IIab), (IIac), (IIad), (IIb) or (IIba) comprises, in particular consists of an amino acid sequence of at least 100 amino acid residues, and
  wherein the amino acid sequence of at least 100 amino acid residues is in random coil conformation, and,
  wherein the amino acid sequence of at least 100 amino acid residues comprises alanine, serine and proline residues.

Preferably, the protein carrier a protein carrier $Z^1$ of formula (I), (II), (IIaa), (IIab), (IIac), (IIad), (IIb) or (IIba) is composed of an amino acid sequence comprising at least about 100 amino acid residues, at least 100 amino acid residues, consisting of alanine, serine and proline residues which have a random coil conformation at physiological conditions. It is understood that the protein carrier $Z^1$ of formula (I), (II), (IIaa), (IIab), (IIac), (IIad), (IIb) or (IIba) may transiently or temporarily not form a random coil, for example when present in a lyophilisate or dried composition.

In one embodiment the protein carrier $Z^1$ of formula (I), (II), (IIaa), (IIab), (IIac), (IIad), (IIb) or (IIba) has a random coil conformation with an amino acid sequence of maximally about 3000 amino acid residues, preferably of maximally about 1500 amino acid residues, more preferably of maximally about 900 amino acid residues, even more preferably of maximally about 700 amino acid residues, particularly preferably of maximally about 600 amino acid residues. Thus, the amino acid sequence forming random coil conformation is maximally about 500 amino acid residues or of maximally about 450 amino acid residues in length.

Accordingly, the protein carrier $Z^1$ of formula (I), (II), (IIaa), (IIab), (IIac), (IIad), (IIb) or (IIba) in particular the amino acid sequence forming random coil conformation of the protein carrier $Z^1$ of formula (I), (II), (IIaa), (IIab), (IIac), (IIad), (IIb) or (IIba) is about 100 to about 3000 amino acid residues in length.

In particular embodiments said amino acid sequence forming random coil conformation of about 100 to 1000 amino acid residues is as characterized herein, i.e. comprising alanine, serine and proline as main or unique residues as defined below.

The protein carrier moiety $Z^1$ of formula (I), (II), (IIaa), (IIab), (IIac), (IIad), (IIb) or (IIba) consists mainly of the three amino acid residues alanine, serine and proline, and wherein all three amino acids are present in a protein carrier moiety $Z^1$ of formula (I), (II), (IIaa), (IIab), (IIac) (IIad), (IIb) or (IIba), whereby proline residues represent preferably about 4% to about 40% of the protein carrier $Z^1$ of formula (I), (II), (IIaa), (IIab), (IIac), (IIad), (IIb), and (IIba). The alanine and serine residues preferably comprise the remaining at least 60% to 96% of the protein carrier $Z^1$ of formula (I), (II), (IIaa), (IIab), (IIac) or (IIad). However, as will be detailed herein below said protein carrier $Z^1$ of formula (I), (II), (IIaa), (IIab), or (IIac) may also comprise further amino acids differing from alanine, serine, and proline, i.e. as minor constituents.

The term "minor constituent" as used herein means that maximally 10% (i.e. maximally 10 of 100 amino acids) may be different from alanine, serine and proline, preferably maximally 8% (i.e. maximally 8 of 100 amino acids) may be different than alanine, serine and proline, more preferably maximally 6% (i.e. maximally 6 of 100 amino acids) may be different from alanine, serine and proline, even more preferably maximally 5% (i.e. maximally 5 of 100 amino acids) may be different from alanine, serine and proline, particularly preferably maximally 4% (i.e. maximally 4 of 100 amino acids) may be different from alanine, serine and proline, more particularly preferably maximally 3% (i.e. maximally 3 of 100 amino acids) may be different from alanine, serine and proline, even more particularly preferably maximally 2% (i.e. maximally 2 of 100 amino acids) may be different from alanine, serine and proline and most preferably maximally 1% (i.e. maximally 1 of 100 of the amino acids) that encode the protein carrier $Z^1$ of formula (I), (II), (IIaa), (IIab), (IIac) or (IIad) may be different from alanine, serine and proline. Said amino acids different from alanine, serine and proline may be selected from the group of natural or proteinogenic amino-acids consisting of Arg, Asn, Asp, Cys, Gln, Glu, Gly, His, Ile, Leu, Lys, Met, Phe, Thr, Trp, Tyr, and Val. Minor constituents may also be selected from non-naturally occurring amino acids, such as, for example, hydroxyproline or selenomethionine or other modified natural amino acids.

The term "at least about 100/150/200/250/300/300/350 (etc) amino acid residues" is not limited to the concise number of amino acid residues but also comprises amino acid stretches that comprise an additional 10% to 20% or comprise 10% to 20% less residues. For example "at least about 100 amino acid residues" may also comprise 80 to 100 and about 100 to 120 amino acid residues.

In one embodiment, the protein carrier $Z^1$ of formula (I), (II), (IIaa), (IIab), (IIac) or (IIad) comprises a plurality of polymer cassettes wherein said polymer cassettes consist of Ala, Ser, and/or Pro, and wherein no more than 6 consecutive amino acid residues of the polymer cassettes, preferably of the protein carrier $Z^1$ of formula (I), (II), (IIaa), (IIab), (IIac) or (IIad) are identical and wherein said proline residues constitute more than 4% and less than 40% of the amino acids of said protein carrier $Z^1$ of formula (I), (II), (IIaa), (IIab), (IIac) or (IIad).

In one embodiment, the protein carrier moiety $Z^1$ of formula (I), (II), (IIaa), (IIab), or (IIIac) comprises, preferably consists of a plurality of amino acid repeats,
wherein said repeats consist of Ala, Ser, and Pro residues, and wherein no more than 6 consecutive amino acid residues of the carrier moiety $Z^1$ of formula (I), (II), (IIaa), (IIab), (IIac), or (IIad) (IIb) or (IIba) are identical.

In a preferred embodiment, said proline residues constitute more than 4% and less than 40% of the amino acids of the protein carrier moiety $Z^1$ of formula (I), (II), (IIaa), (IIab), (IIac), (IIad), (IIb) or (IIba).

In a further preferred embodiment, the protein carrier moiety $Z^1$ of formula (I), (II), (IIaa), (IIab), (IIac), (IIad), (IIb), or (IIba) comprises, in particular consists of an amino acid sequence of about 100 to 3000 amino acid residues forming random coil conformation.

The protein carrier $Z^1$ of formula (I), (II), (IIaa), (IIab), (IIac), (IIad), (IIb) or (IIba) may comprise a plurality of identical polymer cassettes or a plurality of non-identical polymer cassettes. Non-limiting examples of polymer cassettes consisting of Ala, Ser and/or Pro residues are provided herein below; see SEQ ID NO:9, SEQ ID NO:10, SEQ ID NO:11, SEQ ID NO:12, SEQ ID NO:13 and SEQ ID NO:14 or peptide fragments or multimers of these sequences. A polymer cassette may consist of at least 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid residues, wherein each polymer cassette comprises (an) Ala, Ser, and/or Pro residue(s), preferably (an) Ala, Ser, and Pro residue(s).

In one embodiment, the polymer cassette does not comprise more than 100 amino acid residues. Preferably, a polymer cassette as defined herein comprises more than about 4%, preferably more than about 5%, even more preferably more than about 6%, particularly preferably more than about 8%, more particularly preferably more than about 10%, even more particularly preferably more than about 15% and most preferably more than about 20% proline residues. Such polymer cassette as defined herein preferably comprises less than about 40% or less than about 35% proline residues.

In one embodiment the protein carrier $Z^1$ of formula (I), (II), (IIaa), (IIab), (IIac), (IIad), (IIb) or (IIba) is of formula (b):

$$\text{Ser}_x[\text{Ala}_y\text{Ser}_z]_v \tag{b}$$

which formula further comprises proline residues as defined herein and wherein
x is independently selected from integer 0 to 6,
each y is independently selected from integer ranging of from 1 to 6,
each z is independently selected from integer ranging of from 1 to 6.
v is any integer so that the protein carrier $Z^1$ of formula (I), (II), (IIaa), (IIab), (IIac), (IIad), (IIb) or (IIba) consists of at least about 100 amino acid residues, and in particular of at least about 100 to about 3000 amino acid residues, preferably to about 2000 and more preferably to about 1000 amino acid residues.

In one embodiment, all y of formula (b) and z of formula (b) of the v $\text{Ala}_y$, $\text{Ser}_z$ monomer moieties of formula (b) are identical. In another embodiment, the y of formula (b) and z of formula (b) of the v $\text{Ala}_y$, $\text{Ser}_z$ monomer moieties of formula (b) are different.

In preferred embodiments, the protein carrier $Z^1$ of formula (I), (II), (IIaa), (IIab), (IIac), (IIad), (IIb) or (IIba) comprises no more than 5 identical consecutive amino acid residues, more preferably no more than 4 identical consecutive amino acid residues and most preferably no more than 3 identical consecutive amino acid residues.

As already indicated herein above, the protein carrier $Z^1$ of formula (I), (II), (IIaa), (IIab), (IIac), (IIad), (IIb) or (IIba) comprises proline residues, wherein said proline residues constitute more than about 4%, preferably more than about 5%, even more preferably more than about 6%, particularly preferably more than about 8%, more particularly preferably more than about 10%, even more particularly preferably more than about 15% and most preferably more than about 20% of the amino acids constituting the protein carrier $Z^1$ of formula (I), (II), (IIaa), (IIab), (IIac), (IIad), (IIb) or (IIba). Such proline residues may be introduced at any position in formula (b). Preferably, the proline residues may be present in one or more of the v $\text{Ala}_y$, $\text{Ser}_z$ monomers of formula (b), and they may be present at the same or at different positions.

In another preferred embodiment, the protein carrier $Z^1$ of formula (I), (II), (IIaa), (IIab), (IIac), (IIad), (IIb) or (IIba) comprises more than about 4% but less than about 50%, preferably more than about 10% but less than about 50% and most preferably more than about 20% but less than about 50% alanine residues of the amino acids constituting the protein carrier $Z^1$ of formula (I), (II), (IIaa), (IIab), (IIac), (IIad), (IIb) or (IIba).

In a further preferred embodiment, the protein carrier $Z^1$ of formula (I), (II), (IIaa), (IIab), (IIac), (IIad), (IIb) or (IIba) comprises more than about 4% and less than about 50%, preferably more than about 10% but less than about 50% and most preferably more than about 20% but less than about 50% serine residues of the amino acids constituting the protein carrier $Z^1$ of formula (I), (II), (IIaa), (IIab), (IIac), (IIad), (IIb) or (IIba).

Accordingly, the protein carrier $Z^1$ of formula (I), (II), (IIaa), (IIab), (IIac), (IIad), (IIb) or (IIba) comprises about 35% proline residues, about 50% alanine residues and about 15% serine residues of the amino acids constituting the protein carrier $Z^1$ of formula (I), (II), (IIaa), (IIab), (IIac), (IIad), (IIb) or (IIba). Alternatively, the protein carrier $Z^1$ of formula (I), (II), (IIaa), (IIab), (IIac), (IIad), (IIb) or (IIba) may comprise about 35% proline residues, about 15% alanine residues and about 50% serine residues of the amino acids constituting the protein carrier $Z^1$ of formula (I), (II), (IIaa), (IIab), (IIac), (IIad), (IIb) or (IIba).

Preferably, the protein carrier $Z^1$ of formula (I), (II), (IIaa), (IIab), (IIac), (IIad), (IIb) or (IIba) is comprises one or more of the following alanine-serine polymer cassettes:

```
AAAASSASSASSSSSAAASA        SEQ ID NO: 1

AASAAASSAAASAAAASASS        SEQ ID NO: 2

ASASASASASASSAASAASA        SEQ ID NO: 3

SAASSSASSSSAASSASAAA        SEQ ID NO: 4

SSSSAASAASAAAAASSSAS        SEQ ID NO: 5

SSASSSAASSSASSSSASAA        SEQ ID NO: 6

SASASASASASAASSASSAS        SEQ ID NO: 7

ASSAAASAAAASSAASASSS        SEQ ID NO: 8
``` provided that the protein carrier $Z^1$ of formula (I), (II), (IIaa), (IIab), (IIac), (IIad), (IIb) or (IIba) further comprises proline residues as described herein.

The multimers of these alanine-serine polymer cassettes may form random coil conformation in case the resulting amino acid sequence further comprises proline residues as defined herein above.

In a preferred embodiment, the protein carrier $Z^1$ of formula (I), (II), (IIaa), (IIab), (IIac), (IIad), (IIb) or (IIba) comprises, preferably consists of one or more of the following polymer cassettes:

```
ASPAAPAPASPAAPAPSAPA        SEQ ID NO: 9

AAPASPAPAAPSAPAPAAPS        SEQ ID NO: 10

APSSPSPSAPSSPSPASPSS        SEQ ID No: 11

SAPSSPSPSAPSSPSPASPS        SEQ ID NO: 15
```

SEQ ID NO:15 corresponds to the herein provided SEQ ID No:11 in a circularly permuted form, wherein the last serine was removed and another serine was appended as starting amino acid. As a consequence, multimers of this modified sequence possess essentially the same internal repeating unit as multimers of the non-modified sequence, except for the very first and the very last residue. Accordingly, SEQ ID NO:15 may be considered as an example of a further polymer cassette for the protein carrier $Z^1$ of formula (I), (II), (IIaa), (IIab), (IIac), (IIad), (IIb) or (IIba). It is clear for the person skilled in the art that also other polymer cassettes and (shorter) peptide fragments or circularly permuted versions of the herein provided amino acid polymers may be used as polymer cassettes for the protein carrier $Z^1$ of formula (I), (II), (IIaa), (IIab), (IIac), (IIad), (IIb) or (IIba).

Yet, even further and illustrative amino acid polymers forming random coil conformation may comprise amino acid sequences that may be selected from the group consisting of:

```
SSPSAPSPSSPASPSPSSPA,       SEQ ID NO: 12

AASPAAPSAPPAAASPAAPSAPPA,   SEQ ID NO: 13
and

ASAAAPAAASAAASAPSAAA.       SEQ ID NO: 14
```

Therefore, preferred polymer cassettes for $Z^1$ of formula (I), (II), (IIaa), (IIab), (IIac), (IIad), (IIb) or (IIba) are selected from the following sequences:

```
ASPAAPAPASPAAPAPSAPA,       (SEQ ID NO: 9)

AAPASPAPAAPSAPAPAAPS,       (SEQ ID NO: 10)

APSSPSPSAPSSPSPASPSS,       (SEQ ID NO: 11)

SSPSAPSPSSPASPSPSSPA,       (SEQ ID NO: 12)

AASPAAPSAPPAAASPAAPSAPPA,   (SEQ ID NO: 13)
and

ASAAAPAAASAAASAPSAAA;       (SEQ ID NO: 14)
``` or circular permuted versions or (a) multimer(s) of these sequences as a whole or parts of these sequences.

In one embodiment, the protein carrier moiety $Z^1$ of formula (I), (II), (IIaa), (IIab), (IIac), (IIad), (IIb) or (IIba) comprises at least one amino acid sequence selected from the group consisting of:

ASPAAPAPASPAAPAPSAPA, (SEQ ID NO: 9)

AAPASPAPAAPSAPAPAAPS, (SEQ ID NO: 10)

APSSPSPSAPSSPSPASPSS, (SEQ ID NO: 11)

SSPSAPSPSSPASPSPSSPA, (SEQ ID NO: 12)

AASPAAPSAPPAAASPAAPSAPPA, (SEQ ID NO: 13)
and

ASAAAPAAASAAASAPSAAA; (SEQ ID NO: 14)

and circular permuted versions or (a) multimer(s) of these sequences as a whole or parts of these sequences.

Again, also (a) peptide fragment(s) or (a) multimer(s) or circularly permuted versions of these sequences and the sequences provided herein above may be employed as polymer cassettes for the protein carrier $Z^1$ of formula (I), (II), (IIaa), (IIab), (IIac), (IIad), (IIb) or (IIba).

Accordingly, the exemplified polymer cassettes may also provide for individual peptide fragments which may be newly combined to form further polymer cassettes.

In accordance with the above, the protein carrier $Z^1$ of formula (I), (II), (IIaa), (IIab), (IIac), (IIad), (IIb) or (IIba) may comprise a multimer consisting of either one of the amino acid sequences with SEQ ID NO:9, 10, 11, 12, 13 or 14 as disclosed herein above or may comprise a multimer consisting of more than one of amino acid sequences SEQ ID NO:9, 10, 11, 12, 13 and 14. Furthermore, it is envisaged that also peptide fragments or circularly permuted versions of these exemplified sequences may be used to build up further polymer cassettes of the protein carrier $Z^1$ of formula (I), (II), (IIaa), (IIab), (IIac), (IIad), (IIb) or (IIba).

In another embodiment, the protein carrier $Z^1$ of formula (I), (II), (IIaa), (IIab), (IIac), (IIad), (IIb) or (IIba) may comprise a multimer comprising, preferably consisting of a (circular) permutation of the amino acid sequence selected from the group consisting of SEQ ID NOs:9, 10, 11, 12, 13, 14, 15 and (a) multimers(s) of these (circular) permutated sequences.

In yet another embodiment, the protein carrier $Z^1$ of formula (I), (II), (IIaa), (IIab), (IIac), (IIad), (IIb) or (IIba) may comprise, preferably consist of a multimer consisting of a peptide fragment/part of the amino acid sequence selected from the group consisting of SEQ ID NO: 9, 10, 12, 13, 14, 15 and (a) multimers(s) of these exemplified polymer cassettes.

Peptide fragments of these sequences to be employed for the generation of the protein carrier $Z^1$ of formula (I), (II), (IIaa), (IIab), (IIac), (IIad), (IIb) or (IIba) may consist of at least 3, preferably of at least 4, more preferably of at least 5, even more preferably of at least 6, still more preferably of at least 8, particularly preferably of at least 10, more particularly preferably of at least 12, even more particularly preferably of at least 14, preferably of at least 6, still more preferably of at least 8, particularly preferably of at least 10, more particularly preferably of at least 12, even more particularly preferably of at least 14, even more particularly preferably of at least 16, and most preferably of at least 18 consecutive amino acids of the amino acid sequence selected from the group consisting of said SEQ ID NOs: 9, 10, 11, 12, 13 and 14.

For example, individual peptide fragments of the polymer cassettes may be combined to further individual polymer cassettes as long as the above-identified rules for the overall distribution and amount of alanine, serine and proline are respected. Again, these polymer cassettes may also comprise further amino acid residues, however only as minimal or minor constituents, i.e. maximally 10%, preferably maximally 2% of the individual polymer cassette. Said individual polymer cassettes consist of at least about 100 amino acid residues. Individual polymer cassettes may be combined in order to form longer random coil forming amino acid polymers, whereby a maximal length of the protein carrier $Z^1$ of formula (I), (II), (IIaa), (IIab), (IIac), (IIad), (IIb) or (IIba) is about 3000 amino acids. A preferred minor constituent of the protein carrier $Z^1$, (II), (IIaa), (IIab), (IIac), (IIad), (IIb) or (IIba) is lysine.

In another embodiment the carrier $Z^1$ is a $C_{10\text{-}24}$ fatty acid, i.e. a carboxylic acid with a linear carbon chain having 10, 11, 12, 13, 14, 15, 16, 17, 18, 19, 20, 21, 22, 23 or 24 carbon atoms, which is either saturated or partially or fully unsaturated.

In another embodiment the carrier $Z^1$ has the structure of formula (VII):

$$B\text{--}(A)_n \quad (VII),$$

wherein

B is branching core,

A is a poly(ethylene glycol)-based polymeric chain, and n is an integer of from 3 to 32.

In a preferred embodiment, the branching core B of formula (VII) comprises, preferably consists of a moiety selected from:

a polyalcohol comprising at least 2 hydroxyl groups (preferably further comprising a functional group, which is preferably an additional amino group or a carboxylic acid group, more preferably an additional carboxylic acid group), preferably B is selected from glycerol, pentaerythritol, dipentaerythritol, tripentaerythritol, hexaglycerine, sucrose, sorbitol, fructose, mannitol, glucose, cellulose, amyloses, starches, hydroxyalkyl starches, polyvinylalcohols, dextranes, and hyualuronans, erythritol, threitol, arabitol, xylitol, ribitol, dulcitol, iditol; more preferably from glycerol, pentaerythritol, dipentaerythritol, tripentaerythritol, hexaglycerine, sucrose, sorbitol, fructose, mannitol, glucose, cellulose, amyloses, starches, hydroxyalkyl starches, polyvinylalcohols, dextranes, and hyualuronans.

or a polyamine comprising at least 2 amine groups (preferably further comprising a functional group, which is preferably an additional hydroxyl group or a carboxylic acid group, more preferably a carboxylic acid group), preferably selected from ornithine, diornithine, triornithine, tetraornithine, pentaornithine, hexaornithine, heptaornithine, octaornithine, nonaornithine, decaornithine, undecaornithine, dodecaornithine, tridecaornithine, tetradecaornithine, pentadecaornithine, hexadecaornithine, heptadecaornithine, octadecaornithine, nonadecaornithine, diaminobutyric acid, di(diaminobutyric acid), tri(diaminobutyric acid), tetra(diaminobutyric acid), penta(diaminobutyric acid), hexa(diaminobutyric acid), hepta(diaminobutyric acid), octa(diaminobutyric acid), nona(diaminobutyric acid), deca(diaminobutyric acid), undeca(diaminobutyric acid), dodeca(diaminobutyric acid), trideca(diaminobutyric acid), tetradeca(diaminobutyric acid), pentadeca(diaminobutyric acid), hexadeca(diaminobutyric acid), heptadeca(diaminobutyric acid), octadeca(diaminobutyric acid), nonadeca(diaminobutyric acid), lysine, dilysine, trilysine, tetralysine, pentalysine, hexalysine, heptalysine, octalysine, nonalysine, decalysine, undecalysine, dodecalysine, tridecalysine, tetradecalysine, pentadecalysine, hexadecalysine, heptadecalysine, octadecalysine, nonadecalysine, oligolysines, polyethyleneimines, and polyvinylamines;

wherein the polyalcohol or polyamine is in bound form.

In a preferred embodiment, the branching core B of formula (VII) comprises, preferably consists of pentaerithritol.

Preferably, a poly(ethylene glycol)-based polymeric chain A connected to the branching core B of formula (VII) consists of a linear PEG chain, of which one terminus is connected to B of formula (VII) and the other terminus is connected to $X^0$ of formula (I), to Q (if the carrier-linked treprostinil prodrug is of formula (II)), to $Q^1$ (if the carrier-linked treprostinil prodrug is of formula (IIaa) or (IIab)) or to $X_1$ (if the carrier-linked treprostinil prodrug is of formula (IIac), (IIad), or (IIb)), or to the rest of the molecule (if the carrier-linked treprostinil prodrug is of formula (IIba)), respectively.

It is understood that a PEG-based chain A of formula (VII) may optionally be terminated in case of a branched PEG chain and/or may optionally be interrupted in case of a branched or linear PEG chain by alkyl or aryl groups and may optionally be substituted with heteroatoms and/or functional groups.

Preferably, the carrier $Z^1$ of formula (VII) is a multi-arm PEG derivative as, for instance, detailed in the products list of JenKem Technology, USA (accessed by download from http://jenkemusa.net/pegproducts2.aspx on Mar. 8, 2011), such as a 4-arm-PEG derivative, in particular comprising a pentaerythritol core, an 8-arm-PEG derivative comprising a hexaglycerin core, and an 8-arm-PEG derivative comprising a tripentaerythritol core. Most preferred are sub-structures B $(A)_n$ of formula (VI) comprising, in particular consisting of, moieties selected from:

a 4-arm PEG Amine comprising a pentaerythritol core:

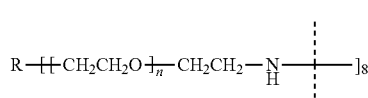

with n ranging from 20 to 500;
a 4-arm PEG Carboxyl comprising a pentaerythritol core:

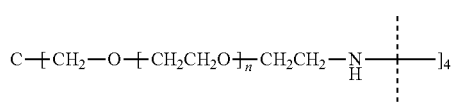

with n ranging from 20 to 500;
an 8-arm PEG Amine comprising a hexaglycerin core:

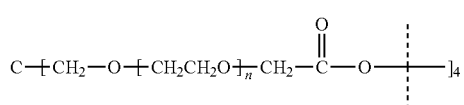

with n ranging from 20 to 500; and
R=hexaglycerin core structure;
an 8-arm PEG Carboxyl comprising a hexaglycerin core:

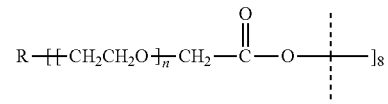

with n ranging from 20 to 500; and
R=hexaglycerin core structure;
an 8-arm PEG Amine comprising a tripentaerythritol core:

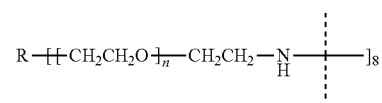

with n ranging from 20 to 500;
and R=tripentaerythritol core structure;
an 8-arm PEG Carboxyl comprising a tripentaerythritol core:

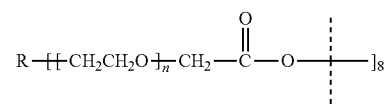

with n ranging from 20 to 500; and
R=tripentaerythritol core structure;
a 6-arm PEG Amine comprising a sorbitol or dipentaerythritol core:

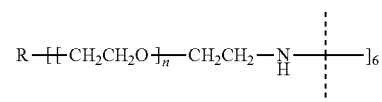

with n ranging from 20 to 500; and
R=sorbitol or dipentaerythritol;
a 6-arm PEG Carboxyl comprising a sorbitol or dipentaerythritol core:

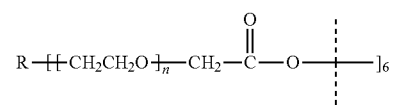

with n ranging from 20 to 500; and
R=sorbitol or dipentaerythritol;
a 6-arm PEG Amine comprising a sorbitol or dipentaerythritol core:

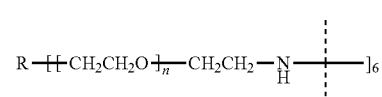

with n ranging from 20 to 500;
and R=sorbitol or dipentaerythritol;

a 6-arm PEG Carboxyl comprising a sorbitol or dipentaerythritol core:

$$R-[(CH_2CH_2O)_n-CH_2-\overset{O}{\underset{\|}{C}}-O-]_6$$

with n ranging from 20 to 500; and
R=sorbitol or dipentaerythritol;
a 4-arm PEG Amine comprising a pentaerythritol core:

$$C-[CH_2-O-(CH_2CH_2O)_n(CH_2)_3-\underset{H}{N}-]_4$$

with n ranging from 20 to 500;
a 4-arm PEG Carboxyl comprising a pentaerythritol core:

$$C-[CH_2-O-(CH_2CH_2O)_n(CH_2)_{1-5}\overset{O}{\underset{\|}{C}}-O-]_4$$

with n ranging from 20 to 500;
an 8-arm PEG Amine comprising a hexaglycerin core:

$$R-[(CH_2CH_2O)_n(CH_2)_3-\underset{H}{N}-]_8$$

with n ranging from 20 to 500; and
R=hexaglycerin core structure;
an 8-arm PEG Carboxyl comprising a hexaglycerin core:

$$R-[(CH_2CH_2O)_n(CH_2)_{1-5}\overset{O}{\underset{\|}{C}}-O-]_8$$

with n ranging from 20 to 500; and
R=hexaglycerin core structure;
an 8-arm PEG Amine comprising a tripentaerythritol core:

$$R-[(CH_2CH_2O)_n(CH_2)_3-\underset{H}{N}-]_8$$

with n ranging from 20 to 500;
and R=tripentaerythritol core structure;
and an 8-arm PEG Carboxyl comprising a tripentaerythritol core:

$$R-[(CH_2CH_2O)_n(CH_2)_{1-5}\overset{O}{\underset{\|}{C}}-O-]_8$$

with n ranging from 20 to 500; and
R=tripentaerythritol core structure;
a 6-arm PEG Amine comprising a sorbitol or dipentaerythritol core:

$$R-[(CH_2CH_2O)_n(CH_2)_3-\underset{H}{N}-]_6$$

with n ranging from 20 to 500; and
R=comprising a sorbitol or dipentaerythritol core;
a 6-arm PEG Carboxyl comprising a sorbitol or dipentaerythritol core:

$$R-[(CH_2CH_2O)_n(CH_2)_{1-5}\overset{O}{\underset{\|}{C}}-O-]_6$$

with n ranging from 20 to 500; and
R=comprising a sorbitol or dipentaerythritol core;
a 6-arm PEG Amine comprising a sorbitol or dipentaerythritol core:

$$R-[(CH_2CH_2O)_n(CH_2)_3-\underset{H}{N}-]_6$$

with n ranging from 20 to 500;
and R=comprising a sorbitol or dipentaerythritol core;
and a 6-arm PEG Carboxyl comprising a sorbitol or dipentaerythritol core:

$$R-[(CH_2CH_2O)_n(CH_2)_{1-5}\overset{O}{\underset{\|}{C}}-O-]_6$$

with n ranging from 20 to 500; and
R=comprising a sorbitol or dipentaerythritol core;
wherein dashed lines indicate attachment to $X^0$ of formula (I), to Q (if the carrier-linked treprostinil prodrug is of formula (II)), to $Q^1$ (if the carrier-linked treprostinil prodrug is of formula (IIaa) or (IIab)) or to $X_1$ (if the carrier-linked treprostinil prodrug is of formula (IIac), (IIad), or (IIb)), or to the rest of the molecule (if the carrier-linked treprostinil prodrug is of formula (IIba)), respectively.

In a preferred embodiment, the molecular weight of the carrier B-$(A)_n$ of formula (VII) ranges from 1 kDa to 80 kDa, more preferably 1 kDa to 40 kDa and even more preferably 10 kDa to 40 kDa.

More preferably, the carrier of formula (VII) has the structure of formula (VIIa):

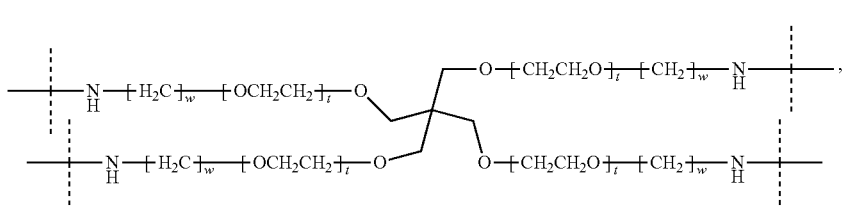

(VIIa)

wherein
t ranges from 80 to 160;
w ranges from 2 to 6;
and dashed lines indicate attachment to the rest of the carrier-linked treprostinil prodrug, i.e. a moiety $X^0$ of formula (I), to a moiety Q (if the carrier-linked treprostinil prodrug is of formula (II)), to a moiety $Q^1$ (if the carrier-linked treprostinil prodrug is of formula (IIaa) or (IIab)) or to a moiety $X_1$ (if the carrier-linked treprostinil prodrug is of formula (IIac), (IIad), or (IIb)), or to the rest of the molecule (if the carrier-linked treprostinil prodrug is of formula (IIba)), respectively.

Preferably, w is 2 or 3.

Most preferably, the carrier-linked treprostinil prodrug has the structure of formula (IIc):

The term "plasma-independent" means that the release kinetics of prostacyclin from the prostacyclin compound measured at 37° C. independently in buffer at pH 7.4 and in 80% buffered plasma at pH 7.4 varies by no more than 50%, preferably by no more than 40%, more preferably by no more than 30%, even more preferably by no more than 20% and most preferably by no more than 10%.

The term "enzyme-independent" means that the release of prostacyclin from the prostacyclin compound does not require the presence of enzymes.

Another aspect of the present invention is a pharmaceutical composition comprising a carrier-linked treprostinil prodrug or a pharmaceutically acceptable salt of the present invention, optionally together with one or more pharmaceutically acceptable excipients.

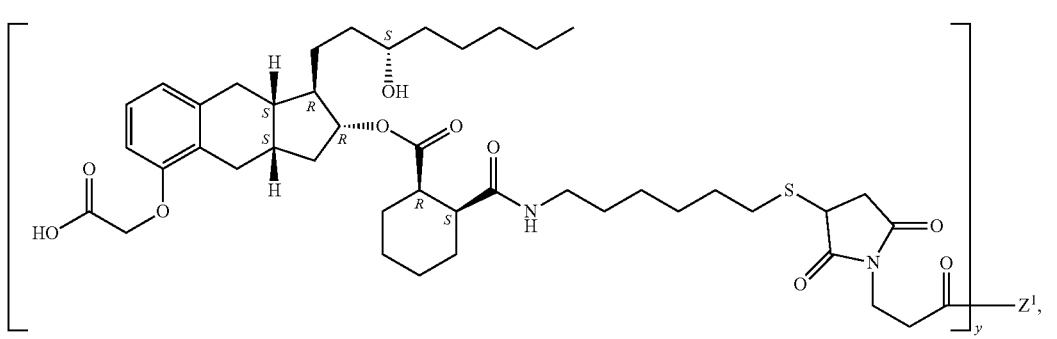

(IIc)

wherein y is 4 and $Z^1$ represents a moiety (IIc):

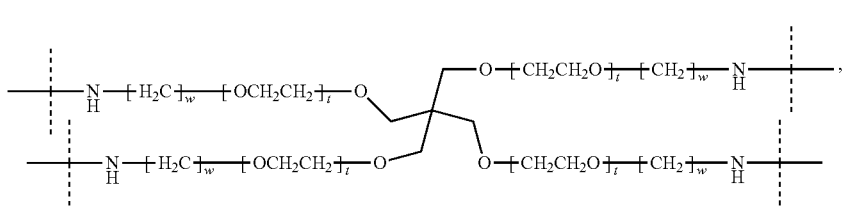

(IIca)

wherein dashed lines indicate attachment to the rest of the structure of formula (IIc), t ranges from 80 to 160 and w is 2 or 3.

In another preferred embodiment, the present invention relates to a pharmaceutical composition comprising a carrier-linked treprostinil prodrug, wherein said pharmaceutical composition is characterized in that the prostacyclin compound releases prostacyclin in a plasma-independent manner. Preferably, the prostacyclin compound releases prostacyclin in an enzyme-independent manner.

The pharmaceutical composition is further described in the following paragraphs.

The pharmaceutical composition comprising the carrier-linked treprostinil prodrug of the present invention may be provided as a liquid composition or as a dry composition. Suitable methods of drying are, for example, spray-drying and lyophilization (freeze-drying). A preferred method of drying is lyophilization.

Preferably, the carrier-linked treprostinil prodrug is sufficiently dosed in the composition to provide a therapeutically effective amount of treprostinil for at least 12 hours in one application. More preferably, one application of the pharmaceutical composition comprising the carrier-linked treprostinil prodrug is sufficient for at least 1 day, such as two days, three days, four days, five days, six days, or seven days, such as two weeks, three weeks or four weeks.

In one embodiment, the present invention relates to a pharmaceutical composition
(i) wherein the carrier-linked treprostinil prodrug of the present invention is sufficiently dosed in the pharmaceutical composition to provide a therapeutically effective amount of treprostinil for at least 12 hours in one application, and/or
(ii) wherein a single dose of the pharmaceutical composition comprises about 2 to about 6, preferably about 4 mg treprostinil.

In a preferred embodiment, the a single dose of a liquid pharmaceutical composition of the present invention has a volume of about 0.1 to about 10 ml, preferably about 0.5 to about 5 ml, even more preferably about 0.5 to about 2 ml, in particular about 1 ml.

"About" according to the present invention is understood as meaning the experimental error range, in particular ±5% or ±10%.

The pharmaceutical composition of carrier-linked treprostinil prodrug according to the present invention optionally comprises one or more excipients.

Excipients may be categorized as buffering agents, isotonicity modifiers, preservatives, stabilizers, anti-adsorption agents, oxidation protection agents, viscosifiers/viscosity enhancing agents, or other auxiliary agents. In some cases, these ingredients may have dual or triple functions. The pharmaceutical compositions of carrier-linked treprostinil prodrugs according to the present invention contain one or more excipients, selected from the groups consisting of:
(i) Buffering agents: physiologically tolerated buffers to maintain pH in a desired range, such as sodium phosphate, bicarbonate, succinate, histidine, citrate and acetate, sulphate, nitrate, chloride, pyruvate. Antacids such as Mg(OH)$_2$ or ZnCO$_3$ may be also used. Buffering capacity may be adjusted to match the conditions most sensitive to pH stability
(ii) Isotonicity modifiers: to minimize pain that can result from cell damage due to osmotic pressure differences at the injection depot. Glycerin and sodium chloride are examples. Effective concentrations can be determined by osmometry using an assumed osmolality of 285-315 mOsmol/kg for serum
(iii) Preservatives and/or antimicrobials: multidose parenteral preparations require the addition of preservatives at a sufficient concentration to minimize risk of patients becoming infected upon injection and corresponding regulatory requirements have been established. Typical preservatives include m-cresol, phenol, methylparaben, ethylparaben, propylparaben, butylparaben, chlorobutanol, benzyl alcohol, phenylmercuric nitrate, thimerosol, sorbic acid, potassium sorbate, benzoic acid, chlorocresol, and benzalkonium chloride
(iv) Stabilizers: Stabilization is achieved by strengthening of the protein-stabilizing forces, by destabilization of the denatured state, or by direct binding of excipients to the protein. Stabilizers may be amino acids such as alanine, arginine, aspartic acid, glycine, histidine, lysine, proline, sugars such as glucose, sucrose, trehalose, polyols such as glycerol, mannitol, sorbitol, salts such as potassium phosphate, sodium sulphate, chelating agents such as EDTA, hexaphosphate, ligands such as divalent metal ions (zinc, calcium, etc.), other salts or organic molecules such as phenolic derivatives. In addition, oligomers or polymers such as cyclodextrins, dextran, dendrimers, PEG or PVP or protamine or HSA may be used
(v) Anti-adsorption agents: Mainly ionic or non-ionic surfactants or other proteins or soluble polymers are used to coat or adsorb competitively to the inner surface of the composition's or composition's container. Suitable surfactants are e.g., alkyl sulfates, such as ammonium lauryl sulfate and sodium lauryl sulfate; alkyl ether sulfates, such as sodium laureth sulfate and sodium myreth sulfate; sulfonates such as dioctyl sodium sulfosuccinates, perfluorooctanesulfonates, perfluorobutanesulfonates, alkyl benzene sulfonates; phosphates, such as alkyl aryl ether phosphates and alkyl ether phosphates; carboxylates, such as fatty acid salts (soaps) or sodium stearate, sodium lauroyl sarcosinate, perfluorononanoate, perfluorooctanoate; octenidine dihydrochloride; quaternary ammonium cations such as cetyl trimethylammonium bromide, cetyl trimethylammonium chloride, cetylpyridinium chloride, polyethoxylated tallow amine, benzalkonium chloride, benzethonium chloride, 5-bromo-5-nitor-1,3-dioxane, dimethyldioctadecylammonium chloride, dioctadecyldimethylammonium bromide; zwitterionics, such as 3-[(3-cholamidopropyl)dimethylammonio]-1-propanesulfonate, cocamidopropyl hydroxysultaine, amino acids, imino acids, cocamidopropyl betaine, lecithin; fatty alcohols, such as cetyl alcohol, stearyl alcohol, cetostearyl alcohol, oleyl alcohol; polyoxyethylene glycol alkyl ethers, such as octaethylene glycol monododecyl ether, pentaethylene glycol monododecyl ether; polyoxypropylene glycol alkyl ethers; glucoside alkyl ethers, such as decyl glucoside, lauryl glucoside, octyl glucoside; polyoxyethylene glycol octylphenol ethers such as Triton X-100; polyoxyethylene glycol alkylphenol ethers such as nonoxynol-9; glycerol alkyl esters such as glyceryl laurate; polyoxyethylene glycol sorbitan alkyl esters such as polysorbates; sorbitan alkyl esters; cocamide MEA and cocamide DEA; dodecyl dimethylamine oxide; block copolymers of polyethylene glycol and polypropylene glycol, such as poloxamers (Pluronic F-68), PEG dodecyl ether (Brij 35), polysorbate 20 and 80; other anti-absorption agents are dextran, polyethylene glycol, PEG-polyhistidine, BSA and HSA and gelatines. Chosen concentration and type of excipient depends on the effect to be avoided but typically a monolayer of surfactant is formed at the interface just above the CMC value
(vi) Lyo- and/or cryoprotectants: During freeze- or spray drying, excipients may counteract the destabilizing effects caused by hydrogen bond breaking and water removal. For this purpose sugars and polyols may be used but corresponding positive effects have also been observed for surfactants, amino acids, non-aqueous solvents, and other peptides. Trehalose is particularly efficient at reducing moisture-induced aggregation and also improves thermal stability potentially caused by exposure of protein hydrophobic groups to water. Mannitol and sucrose may also be used, either as solely o/cryoprotectant or in combination with each other where higher ratios of mannitol:sucrose are known to enhance physical stability of a lyophilized cake. Mannitol may also be combined with trehalose. Trehalose may also be combined with sorbitol or sorbitol used as the sole protectant. Starch or starch derivatives may also be used (vii) Oxidation protection agents: antioxidants such as ascorbic acid, ectoine, methionine, glutathione, monothioglycerol, morin, polyethylenimine (PEI), propyl gallate, vitamin E, chelating agents such aus citric acid, EDTA, hexaphosphate, thioglycolic acid (viii) Spreading or diffusing agent: modifies the permeability of connective tissue through the hydrolysis of components of the extracellular matrix in the intrastitial space such as but not limited to hyaluronic acid, a polysaccharide found in the intercellular space of connective tissue. A spreading agent such as but not limited to hyaluronidase temporarily decreases the viscosity of the extracellular matrix and promotes diffusion of injected drugs.

(ix) Other auxiliary agents: such as wetting agents, viscosity modifiers, antibiotics, hyaluronidase. Acids and bases such as hydrochloric acid and sodium hydroxide are auxiliary agents necessary for pH adjustment during manufacture.

In a general embodiment the pharmaceutical composition comprising the carrier-linked treprostinil prodrugs of the present invention in either dry or liquid form may be provided as a single or multiple dose composition.

In one embodiment of the present invention, the liquid or dry pharmaceutical composition comprising the carrier-linked treprostinil prodrug is provided as a single dose, meaning that the container in which it is supplied contains one pharmaceutical dose.

Alternatively, the liquid or dry pharmaceutical composition comprising the carrier-linked treprostinil prodrug is a multiple dose composition, meaning that the container in which it is supplied contains more than one therapeutic dose, i.e., a multiple dose composition contains at least 2 doses. Such multiple dose composition of carrier-linked treprostinil prodrug can either be used for different patients in need thereof or can be used for one patient, wherein the remaining doses are stored after the application of the first dose until needed.

In another aspect of the present invention the pharmaceutical composition is in a container. Suitable containers for liquid or dry compositions are, for example, syringes, vials, vials with stopper and seal, ampoules, and cartridges. In particular, the liquid or dry composition comprising the carrier-linked treprostinil prodrug according to the present invention is provided in a syringe. If the pharmaceutical composition comprising the carrier-linked treprostinil prodrug is a dry pharmaceutical composition the container preferably is a dual-chamber syringe. In such embodiment, said dry pharmaceutical composition is provided in a first chamber of the dual-chamber syringe and reconstitution solution is provided in the second chamber of the dual-chamber syringe.

Prior to applying the dry composition of carrier-linked treprostinil prodrug to a patient in need thereof, the dry composition is reconstituted. Reconstitution can take place in the container in which the dry composition of carrier-linked treprostinil prodrug is provided, such as in a vial, syringe, dual-chamber syringe, ampoule, and cartridge. Reconstitution is done by adding a predefined amount of reconstitution solution to the dry composition. Reconstitution solutions are sterile liquids, such as water or buffer, which may contain further additives, such as preservatives and/or antimicrobials, such as, for example, benzyl alcohol and cresol. Preferably, the reconstitution solution is sterile water. When a dry composition is reconstituted, it is referred to as a "reconstituted pharmaceutical composition" or "reconstituted composition".

An additional aspect of the present invention relates to the method of administration of a reconstituted or liquid pharmaceutical composition comprising the carrier-linked treprostinil prodrug of the present invention. The pharmaceutical composition comprising carrier-linked treprostinil prodrug may be administered by methods of inhalation, injection or infusion, including intradermal, subcutaneous, intramuscular, intravenous, intraosseous, and intraperitoneal. Preferably, the pharmaceutical composition comprising carrier-linked treprostinil prodrug is administered subcutaneously.

The preferred method of administration for dry pharmaceutical compositions comprising the carrier-linked treprostinil prodrugs of the present invention is via inhalation.

Therefore, in a preferred embodiment, the present invention relates to a carrier-linked treprostinil prodrug or a pharmaceutically acceptable salt thereof of the present invention or a pharmaceutical composition of the present invention, for use as medicament for topical, enteral administration, parenteral administration, inhalation, injection, or infusion, intraarticular, intradermal, subcutaneous, intramuscular, intravenous, intraosseous, and intraperitoneal, intrathecal, intracapsular, intraorbital, intracardiac, transtracheal, subcuticular, intraarticular, subcapsular, subarachnoid, intraspinal, intraventricular or intrasternal administration, preferably for subcutaneous administration.

In another embodiment, a first carrier-linked treprostinil prodrug of the present invention is administered via a first method of administration and a second carrier-linked treprostinil prodrug of the present invention is administered via a second method of administration, either simultaneously or consecutively. Said first and second method of administration can be any combination of topical, enteral administration, parenteral administration, inhalation, injection, or infusion, intraarticular, intradermal, subcutaneous, intramuscular, intravenous, intraosseous, and intraperitoneal, intrathecal, intracapsular, intraorbital, intracardiac, transtracheal, subcuticular, intraarticular, subcapsular, subarachnoid, intraspinal, intraventricular or intrasternal administration.

Therefore, in another preferred embodiment, the present invention relates to a carrier-linked treprostinil prodrug or a pharmaceutically acceptable salt thereof of the present invention or a pharmaceutical composition of the present invention, wherein such water-soluble carrier-linked prodrug or pharmaceutically acceptable salt thereof or pharmaceutical composition is suitable to be administered to a patient via topical, enteral or parenteral administration and by methods of external application, inhalation, injection or infusion, including intraarticular, intradermal, subcutaneous, intramuscular, intravenous, intraosseous, and intraperitoneal, intrathecal, intracapsular, intraorbital, intracardiac, transtracheal, subcuticular, intraarticular, subcapsular, subarachnoid, intraspinal, intraventricular and intrasternal application, preferably via subcutaneous administration.

A further aspect is a method of preparing a reconstituted composition comprising a therapeutically effective amount of carrier-linked treprostinil prodrug of the present invention, and optionally one or more pharmaceutically acceptable excipients, the method comprising the step of contacting the pharmaceutical composition comprising carrier-linked treprostinil prodrug of the present invention with a reconstitution solution.

Another aspect is a reconstituted pharmaceutical composition comprising a therapeutically effective amount of the carrier-linked treprostinil prodrug of the present invention, and optionally one or more pharmaceutically acceptable excipients.

Another aspect of the present invention is the method of manufacturing a dry composition of carrier-linked treprostinil prodrug. In one embodiment, such dry composition is made by
(i) admixing the carrier-linked treprostinil prodrug with one or more excipients,
(ii) transferring amounts equivalent to single or multiple doses into a suitable container,
(iii) drying the composition in said container, and
(iv) sealing the container.

Suitable containers are vials, syringes, dual-chamber syringes, ampoules, and cartridges.

Another aspect of the present invention is a kit of parts.

If the administration device is simply a hypodermic syringe then the kit may comprise the syringe, a needle and a container comprising the dry pharmaceutical composition of carrier-linked treprostinil prodrug for use with the syringe and a second container comprising the reconstitution solution.

If the pharmaceutical composition is a liquid composition then the kit may comprise the syringe, a needle and a container comprising the liquid composition of carrier-linked treprostinil prodrug for use with the syringe.

In more preferred embodiments, the injection device is other than a simple hypodermic syringe and so the separate container with reconstituted or liquid carrier-linked treprostinil prodrug is adapted to engage with the injection device such that in use the liquid composition in the container is in fluid connection with the outlet of the injection device. Examples of administration devices include but are not limited to hypodermic syringes and pen injector devices. Particularly preferred injection devices are the pen injectors in which case the container is a cartridge, preferably a disposable cartridge. Optionally, the kit of parts comprises a safety device for the needle which can be used to cap or cover the needle after use to prevent injury.

A preferred kit of parts comprises a needle and a container containing the composition according to the present invention and optionally further containing a reconstitution solution, the container being adapted for use with the needle. Preferably, the container is a dual-chamber syringe.

In another aspect, the invention provides a cartridge comprising a pharmaceutical composition of carrier-linked treprostinil prodrug as hereinbefore described for use with a pen injector device. The cartridge may contain a single dose or multiplicity of doses of the carrier-linked treprostinil prodrug.

Yet another aspect of the present invention is a carrier-linked treprostinil prodrug of the present invention or a pharmaceutical composition of the present invention for use as a medicament.

In case the carrier-linked treprostinil prodrugs according to the invention contain one or more acidic or basic groups, the invention also comprises their corresponding pharmaceutically or toxicologically acceptable salts, in particular their pharmaceutically utilizable salts. Thus, the carrier-linked treprostinil prodrugs according to the invention which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Carrier-linked treprostinil prodrugs according to the invention which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the carrier-linked treprostinil prodrugs according to the invention simultaneously contain acidic and basic groups in the molecule, the invention also includes, in addition to the salt forms mentioned, inner salts or betaines (zwitterions). The respective salts can be obtained by customary methods which are known to the person skilled in the art like, for example by contacting these with an organic or inorganic acid or base in a solvent or dispersant, or by anion exchange or cation exchange with other salts. The present invention also includes all salts of the prodrugs which, owing to low physiological compatibility, are not directly suitable for use in pharmaceuticals but which can be used, for example, as intermediates for chemical reactions or for the preparation of pharmaceutically acceptable salts.

Yet another aspect of the present invention is a method of treating, controlling, delaying or preventing in a mammalian patient, preferably in a human, in need of the treatment of one or more conditions, diseases or disorders comprising administering to said patient a therapeutically effective amount of a carrier-linked treprostinil prodrug of the present invention or a pharmaceutical composition comprising the carrier-linked treprostinil prodrug of the present invention or a pharmaceutically acceptable salt thereof.

Said conditions, diseases or disorders that can be prevented and/or treated with the carrier-linked treprostinil prodrug of the present invention are, for example, pulmonary hypertension, ischemic diseases (e.g. peripheral vascular disease including peripheral arterial disease, Raynaud's phenomenon including Raynaud's disease and Raynaud's syndrome, scleroderma including systemic sclerosis, myocardial ischemia, ischemic stroke, renal insufficiency), ischemic ulcers including digital ulcers, heart failure (including congestive heart failure), portopulmonary hypertension, interstitial lung disease, idiopathic pulmonary fibrosis, conditions requiring anticoagulation (e.g., post MI, post cardiac surgery), thrombotic microangiopathy, extracorporeal circulation, central retinal vein occlusion, atherosclerosis, inflammatory diseases (e.g., COPD, psoriasis), hypertension (e.g., preeclampsia), reproduction and parturition, cancer or other conditions of unregulated cell growth, cell/tissue preservation and other emerging therapeutic areas where prostacyclin treatment appears to have a beneficial role, preferably pulmonary arterial hypertension.

In one embodiment, the present invention relates to a carrier-linked treprostinil prodrug or a pharmaceutically acceptable salt thereof or a pharmaceutical composition of the present invention for use in a method of treating or preventing a disease or disorder which can be treated and/or prevented by treprostinil.

In a preferred embodiment, the disease or disorder is pulmonary arterial hypertension.

In a further embodiment, the present invention relates to the use of a carrier-linked treprostinil prodrug or a pharmaceutically acceptable salt thereof or a pharmaceutical composition of the present invention for the preparation of a medicament for the treatment and/or prevention of a disease or disorder which can be treated and/or prevented by treprostinil.

In a preferred embodiment, the disease or disorder is pulmonary arterial hypertension.

In one embodiment the carrier-linked treprostinil prodrug of the present invention can be administered by different routes of administration to the same patient, for example but not limited to subcutaneous injection and inhalation.

In another embodiment the carrier-linked treprostinil prodrug of the present invention can be administered in combination with one or more additional drug(s) or biologically active moiety/moieties, either in their free form(s) or as prodrug(s). In another embodiment such one or more additional drug(s) are administered together with the carrier-linked treprostinil prodrug of the present invention using the same or different route(s) of administration. It is preferred that the one or more additional drug(s) and the carrier-linked treprostinil prodrug of the present invention are administered in a fixed dose combination.

Accordingly, such one or more additional active agents can be administered separately from the carrier-linked treprostinil prodrug. Particular additional drugs or biologically active moieties that can be administered in combination with the carrier-linked treprostinil prodrug may depend on a particular disease or condition for treatment or prevention of which the carrier-linked treprostinil prodrug can be administered. In some cases, the additional drug/biologically active moiety can be a cardiovascular agent such as a prostacyclin compound, mediators of NO activity, calcium channel blocker, a phosphodiesterase inhibitor, diuretics, an endothelial antagonist, or an antiplatelet agent.

In another object of the invention, the carrier-linked treprostinil prodrug may be administered in combination with an inhaled prostacyclin.

Another subject of the present invention is a method for the synthesis of a carrier-linked treprostinil prodrug or a pharmaceutically acceptable salt thereof of the present invention. Carrier-linked treprostinil prodrugs or precursors of such prodrugs according to the present invention may be prepared by known methods or in accordance with the reaction sequences described below. The starting materials used in the preparation (synthesis) of carrier-linked treprostinil prodrugs of the invention or precursors thereof are known or commercially available, or can be prepared by known methods or as described below.

All reactions for the synthesis of the carrier-linked treprostinil prodrugs according to the present invention including precursors are per se well-known to the skilled person and can be carried out under standard conditions according to or analogously to procedures described in the standard literature of organic chemistry. Depending on the circumstances of the individual case, in order to avoid side reactions during the synthesis of a carrier-linked treprostinil prodrug or a precursor thereof, it can be necessary or advantageous to temporarily block functional groups by introducing protective groups and to deprotect them in a later stage of the synthesis, or introduce functional groups in the form of precursor groups which in a later reaction step are converted into the desired functional groups. Such synthesis strategies and protective groups and precursor groups which are suitable in an individual case are known to the skilled person. If desired, the carrier-linked treprostinil prodrugs or precursors thereof can be purified by customary purification procedures, for example by recrystallization or chromatography.

In one embodiment, the carrier-linked treprostinil prodrugs according to the present invention (or a pharmaceutically acceptable salt thereof) may be prepared by a method comprising the steps of converting the carboxylic acid of the treprostinil to a biologically active moiety reagent D-Y, wherein Y is a leaving group, and subsequently reacting the reagent D-Y with a hydroxyl-group containing reversible prodrug linker reagent $X^0$—OH, thus generating a biologically active moiety-reversible prodrug linker conjugate T-$X^0$ by forming a carboxylic ester linkage. Afterwards, T-$X^0$ may be bound to a carrier moiety $Z^1$ to obtain the carrier-linked treprostinil prodrug of a biologically active moiety comprising a carboxylic acid group according to the present invention. Alternatively, the carrier moiety $Z^1$ may already be bound to $X^0$—OH.

It is understood that functional groups of treprostinil not involved in the synthesis of the carrier-linked treprostinil prodrugs of the present invention may be protected with suitable protecting groups known to the person skilled in the art.

Y is a leaving group. Suitable leaving groups are known to a person skilled in the art. Preferably, if attached to D, Y is chloride, bromide, fluoride, nitrophenoxy, imidazolyl, N-hydroxysuccinimidyl, N-hydroxybenzotriazolyl, N-hydroxyazobenzotriazolyl, pentafluorophenoxy, 2-thiooxo-thiazolidinyl, or N-hydroxysulfosuccinimidyl.

The carrier-linked treprostinil prodrug of the present invention can be prepared starting from a polymer by convenient methods known in the art. It is clear to a practitioner in the art that several routes exist. For example, a moiety T-$X^0$ can be reacted with the reactive functional groups of the polymer of the carrier moiety POL. Alternatively, a reagent comprising a moiety $Z^1$—$X^0$ may be prepared for subsequent reaction with a preferentially activated biologically active acid D-Y. It is understood that D is treprostinil.

BRIEF DESCRIPTION OF THE DRAWINGS

The invention is illustrated hereinafter by drawings and the working examples, the drawings and working examples serving merely for illustration but not restricting the invention.

OPERATIVE EXAMPLES

Figure 1:
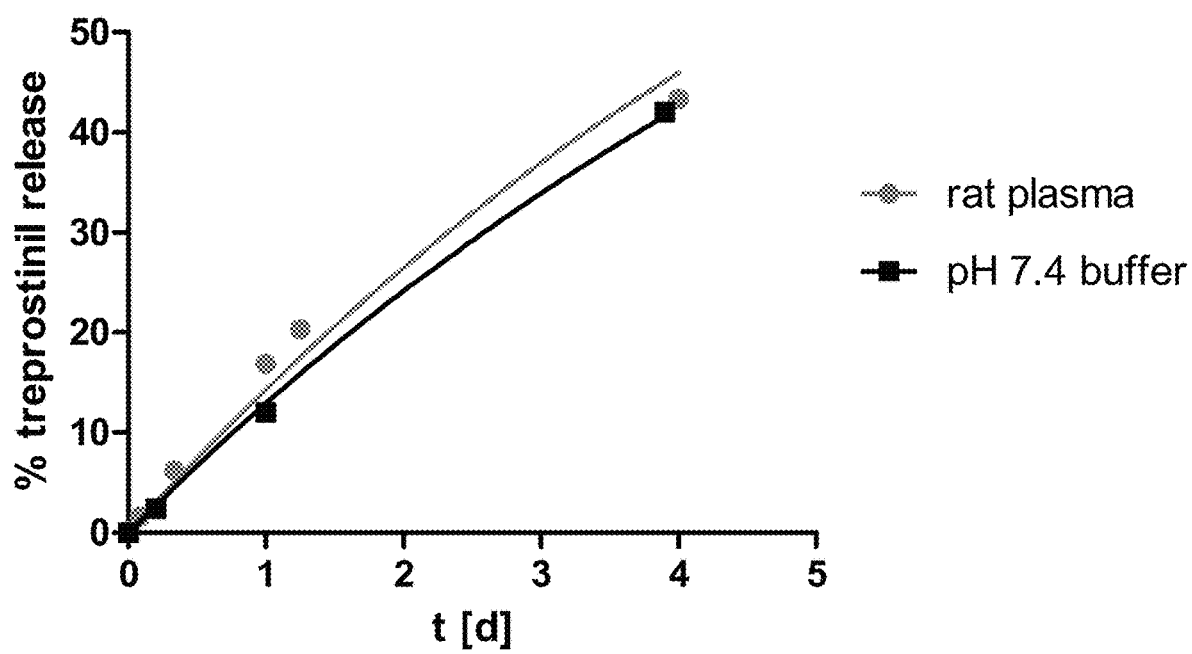
FIG. 1 shows the treprostinil release in buffer and buffered rat plasma at different time points expressed as % treprostinil release compared to total treprostinil content (see Example 29).

The subject matter of the present invention is elucidated in more detail below, using examples, without any intention that the subject matter of the invention should be confined to these exemplary embodiments.

Materials, Methods and Analytics:

Product Purification

Normal phase purification was performed on a Biotage "Isolera one" purification system Biotage AB, Sweden. Biotage KP-Sil silica cartridges. Gradients of Heptane/Ethylacetate or Dichloromethane/Methanol were used. Products were detected and collected at 254 and 280 nm.

For preparative RP-HPLC, a Waters 600 controller and a 2487 Dual Absorbance Detector was used equipped with a Waters XBridge™ BEH300 Prep C18 5 μm, 150×10 mm, flow rate 6 ml/min, or Waters XBridge™ BEH300 Prep C18 10 μm, 150×30 mm, flow rate 40 ml/min. Gradients of eluents A (water containing 0.05% TFA v/v or 0.01% HCl v/v) and B (acetonitrile containing 0.05% TFA v/v or 0.01% HCl v/v) were used.

HPLC fractions containing product were pooled and lyophilized if not stated otherwise.

Automated Flash Chromatography

Automated Flash Chromatography was performed on a Biotage "Isolera one" purification system Biotage AB, Sweden, using Biotage KP-Sil silica cartridges. Products were detected and collected at 254 and 280 nm.

LC/MS Analytics

Analytical RP-HPLC/ESI-MS was performed on waters equipment consisting of a 2695 sample manager, a 2487 Dual Absorbance Detector, and a ZQ 4000 ESI instrument equipped with a 5 μm Reprosil Pur 300 Å ODS-3 column (75×1.5 mm) (Dr. Maisch, Ammerbuch, Germany; flow rate: 350 μl/min, typical gradient: 10-90% MeCN in water, 0.05% TFA over 5 min) or on a Waters Acquity UPLC with an Acquity PDA detector coupled to a Thermo LTQ Orbitrap Discovery high resolution/high accuracy mass spectrometer equipped with a Waters ACQUITY UPLC BEH300 C18 RP column (2.1×50 mm, 300 Å, 1.7 μm, flow: 0.25 mL/min; solvent A: UP-H$_2$O+0.04% TFA, solvent B: UP-Acetonitrile+0.05% TFA.

RP-UPLC/ESI-MS was performed on Waters/Thermo equipment consisting of a Waters Acquity UPLC with an Acquity PDA detector coupled to a Thermo LTQ Orbitrap Discovery high resolution/high accuracy mass spectrometer equipped with a ACQUITY UPLC® BEH300 C18 RP column (Waters Corporation, 2.1×50 mm, 300 Å, 1.7 μm, Flow: 0.25 mL/min; solvent A: UP-H$_2$O+0.04% TFA, solvent B: UP-MeCN+0.05% TFA. Typical gradients for determination of released treprostinil from TransCon 5 kDa PEG linker treprostinil are: 0.25 mL flow rate, gradient: 30-50% B over 10 min RP-HPLC Purification:

For preparative RP-HPLC a Waters 600 controller and a 2487 Dual Absorbance Detector was used equipped with the following columns: Waters XBridge™ BEH300 Prep C18 5 μm, 150×10 mm, flow rate 6 ml/min, or Waters XBridge™ BEH300 Prep C18 10 μm, 150×30 mm, flow rate 40 ml/min. Linear gradients of solvent system A (water containing 0.05% TFA v/v or 0.01% HCl v/v) and solvent system B (acetonitrile containing 0.05% TFA v/v or 0.01% HCl v/v)

Typical gradients for purification procedures are:

6 mL/min flow rate, solvent A: H$_2$O+0.05% TFA, solvent B: MeCN+0.05% TFA, typical gradient: 1-95% B over 14 min 6 mL/min flow rate, solvent A: H$_2$O+0.05% TFA, solvent B: MeCN+0.05% TFA, typical gradient: 10-80% B over 14 min 40 mL/min flow rate, solvent A: H$_2$O+0.05% TFA, solvent B: MeCN+0.05% TFA, typical gradient: 40-95% B over 14 min HPLC fractions containing product were pooled and lyophilized if not stated otherwise.

Chemicals and Drug Substances:

Treprostinil acid was purchased from Shanghai Techwell Biopharmaceutical Co., Ltd., Shanghai, Peoples Republic of China or Chirogate International Inc. Yangmei, Taiwan. 6-(S-Tritylmercapto)hexanoic acid was purchased from Polypeptide, Strasbourg, France. Cis-cyclohexanedicarboxylic anhydride was purchased from Alfa Aesar GmbH & Co KG, Karlsruhe, Germany. 2-Chlorotrityl chloride resin (1%, Novabiochem® DVB) was obtained from Merck Biosciences GmbH, Germany. 6-(S-Tritylsulfanyl)-hexaneamine was synthesized according to WO-A 2009/133137. PEGs used in this work were acquired from NOF Europe N.V., Grobbendonk, Belgium. All other chemicals were purchased from Sigma Aldrich GmbH, Taufkirchen, Germany. Water and acetonitrile for analytical RP-HPLC were purchased from Biosolve B.V. and TFA from Thermo scientific.

Example 1

Benzyl Protection of 3-Hydroxybutanoic Acid 1:

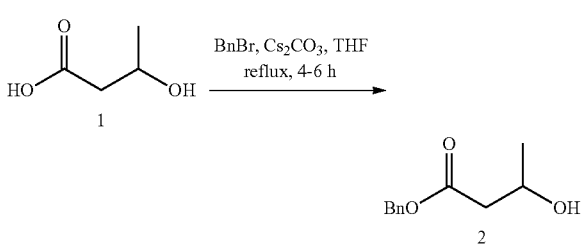

3-Hydroxybutanoic acid 1 (434 mg, 4.17 mmol) was dissolved in THF (10 mL) and BnBr (700 μL, 5.89 mmol) and Cs$_2$CO$_3$ (2.5 g, 7.67 mmol) were added. The reaction mixture was refluxed in a sealed tube for 4-6 hours. After cooling down to room temperature the reaction mixture was filtrated and the residue was washed several times with EtOAc. The organic solvents were removed and the product was purified by automated flash chromatography on silica in one portion (SNAP 25 g cartridge, flow 30 ml/min, solvent A: DCM, solvent B: MeOH; gradient: 0-5% B over 19 CV) to remove starting material and obtain desired benzyl protected 3-hydroxybutanoic acid 2 as yellow oil.

Yield: 361 mg (45%)

MS: m/z 217.1=[M+Na]$^+$ (MW+Na calculated=217.2).

Example 2

Coupling Reaction of Benzylated 3-Hydroxybutanoic Acid 2 with Treprostinil:

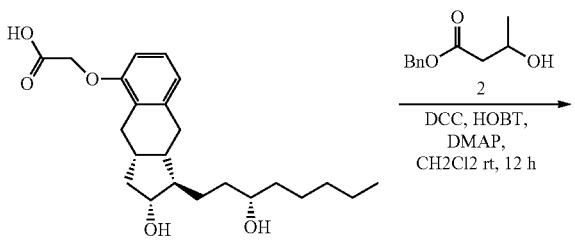

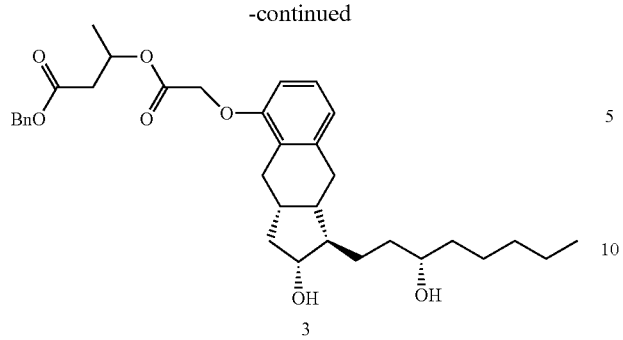

3

Treprostinil acid (10.5 mg, 0.0268 mmol) was dissolved in DCM (4.5 mL) and DCC (9.4 mg, 0.0455 mmol), HOBT (7.5 mg, 0.0489 mmol) and DMAP (7.5 mg, 0.0613 mmol) were added to the solution. Then benzylated 3-hydroxybutanoic acid 2 (15 mg, 0.0772 mmol) was dissolved in DCM (0.5 mL) and added to the reaction mixture. The mixture was stirred at RT until the consumption was complete (analytical RP-HPLC). Volatile solvents were removed in vacuo and the residue was purified over a small silica column (3 ml silica, DCM/MeOH (100:0)-DCM/MeOH (95:5) to obtain the desired linker treprostinil 3 as yellow oil.

Yield: 8 mg (50%)

MS: m/z 589.3=[M+Na]$^+$ (MW+Na calculated=589.7)

Example 3

Hydrogenation Reaction of Benzylester 3:

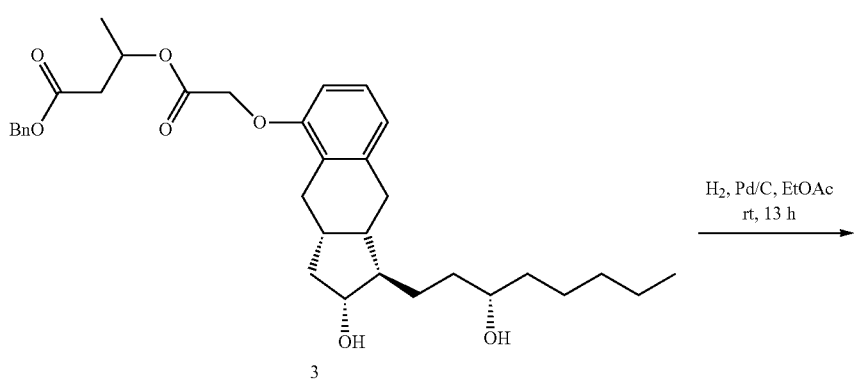

3

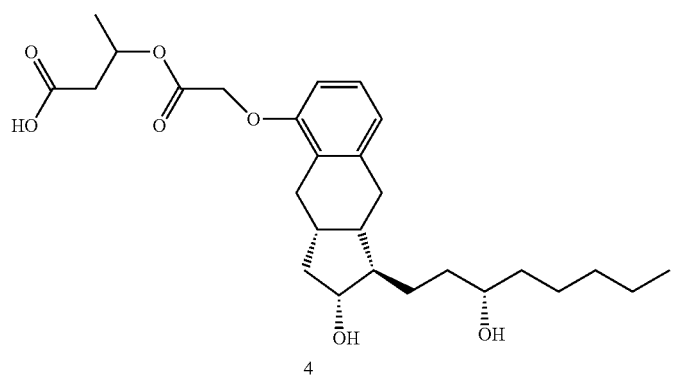

4

Benzylester 3 (13 mg, 0.0229 mmol) was dissolved in EtOAc (4 Å MS, 2 mL) and 5% palladium on charcoal (5% Pd, 15 mg) was added. Hydrogen was bubbled through the solution for 30 min. The reaction mixture was stirred further 12.5 h under hydrogen atmosphere until the consumption was complete (analytical RP-HPLC). The mixture was filtered over celite and washed several times with EtOAc. Organic solvents were removed in vacuo and the residue was purified using RP-HPLC (solvent A: H$_2$O with 0.05% TFA, solvent B: MeCN with 0.05% TFA, gradient: 1-95% B over 20 min, flow: 6 mL/min). The product containing fractions were pooled and lyophilized to obtain 4 as white solid.

Yield: 1.9 mg (29%).

MS: m/z 499.3=[M+Na]$^+$ (MW+Na calculated=499.6).

Example 4

Coupling Reaction of Linear PEG 5 kDa Amine with Linker Treprostinil 4:

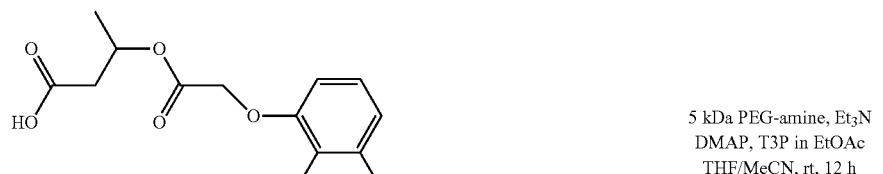

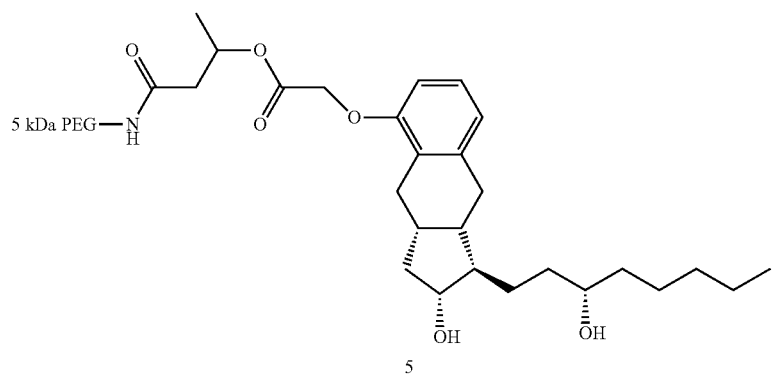

Linker treprostinil 4 (1.9 mg, 3.98 µmol) and linear PEG 5 kDa amine (86 mg, 17.2 µmol) were dissolved in THF/MeCN (4 Å MS; 1.5 mL: 0.5 mL) and Et₃N (40 µL), a catalytic amount of DMAP and T3P (50% in EtOAc, 50 µL, 73.2 µmol) were successively added. The reaction mixture was allowed to stir at rt for 12 h. The reaction mixture was diluted with 20 µL H₂O and volatile solvents were removed in vacuo. The residue was purified using RP-HPLC (solvent A: H₂O with 0.05% TFA, solvent B: MeCN with 0.05% TFA, gradient: 10-80% B over 20 min, flow: 6 mL/min). The product containing fractions were pooled and lyophilized to obtain TransCon PEG linker treprostinil 5 as white solid.

Yield: 12.5 mg (58%).

MS: m/z 1378.6=$[M+4H]^{4+}$ (calculated=1378.9) for one representative peak in the polymer distribution.

Example 5

Treprostinil Release Kinetics of TransCon PEG Linker Treprostinil 5:

TransCon PEG linker treprostinil 5 (0.5-1.5 mg) was incubated in pH 7.4 hydrolysis buffer (60 mM sodium phosphate, 3 mM EDTA, 0.05% Tween-20, 1 mL) at 37° C. and aliquots were analyzed by UPLC at various time points for released treprostinil.

Half Life Determination of Hydrolysis Kinetics of TransCon PEG Linker Treprostinil 5:

The percentage of released treprostinil after incubation at pH 7.4 and 37° C. for a given time period was determined by integrating the corresponding peaks (released material versus conjugate) in the RP-UPLC chromatogram. The data as shown in table 1 were subsequently plotted against time. By using a first order kinetics fit a half life of 4.20 d for the treprostinil release from 5 was obtained.

TABLE 1

| entry | Incubation time [d] | released treprostinil [%] |
| --- | --- | --- |
| 1 | 0.000 | 2 |
| 2 | 0.83 | 5 |
| 3 | 1.11 | 18 |
| 4 | 1.81 | 27 |
| 5 | 2.06 | 29 |
| 6 | 5.13 | 59 |
| 7 | 6.10 | 64 |
| 8 | 8.80 | 77 |
| 9 | 11.90 | 86 |

Example 6

Synthesis of Intermediates 6a/6b:

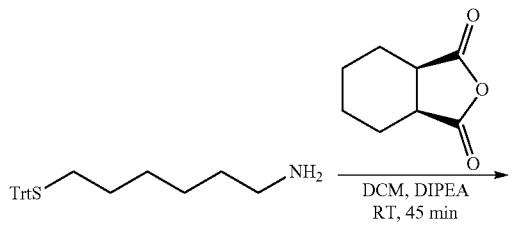

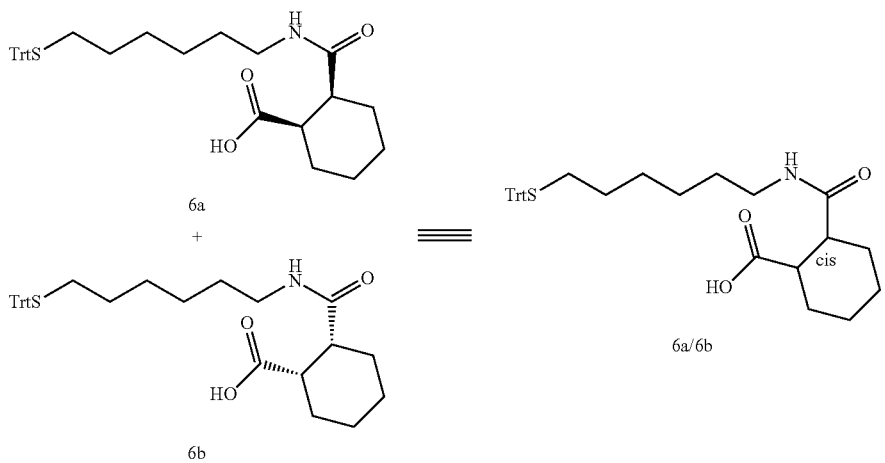

6-(S-Tritylsulfanyl)-hexaneamine (for synthesis see WO-A 2009/133137) (507 mg, 1.35 mmol) was dissolved in DCM (4 ml) and cis-1,2-cyclohexanedicarboxylic anhydride (251 mg, 1.63 mmol) was added to the reaction mixture at RT. DIPEA (0.70 mL, 4.06 mmol) was added and the mixture was stirred at RT until complete consumption of 6-(S-Tritylsulfanyl)-hexaneamine (LC/MS). Volatile solvents were removed in vacuo, the residue was dissolved in H$_2$O/MeCN (6:1, 18 mL) and the product was purified by RP-HPLC (solvent A: H$_2$O with 0.05% TFA, solvent B: MeCN with 0.05% TFA, gradient: 40-95% B over 16 min, flow: 40 ml/min). The pooled fractions were neutralized with sat. NaHCO$_3$ soln. (pH approx. 6) and the organic solvents were removed in vacuo. The remaining aqueous phase was extracted twice with DCM. Combined organic layers were dried with MgSO$_4$ and the solvent was removed in vacuo obtaining 6a/6b as a racemic mixture.

Yield: 580 mg (81%).

MS: m/z 552.23=[M+Na]$^+$ (MW+Na calculated=552.62 g/mol).

Example 7

Synthesis of Intermediates 7a/7b:

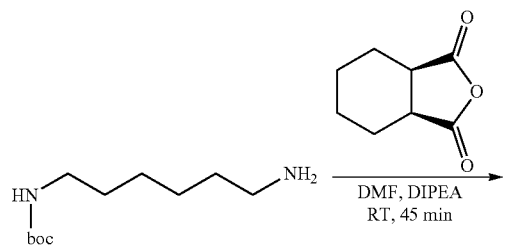

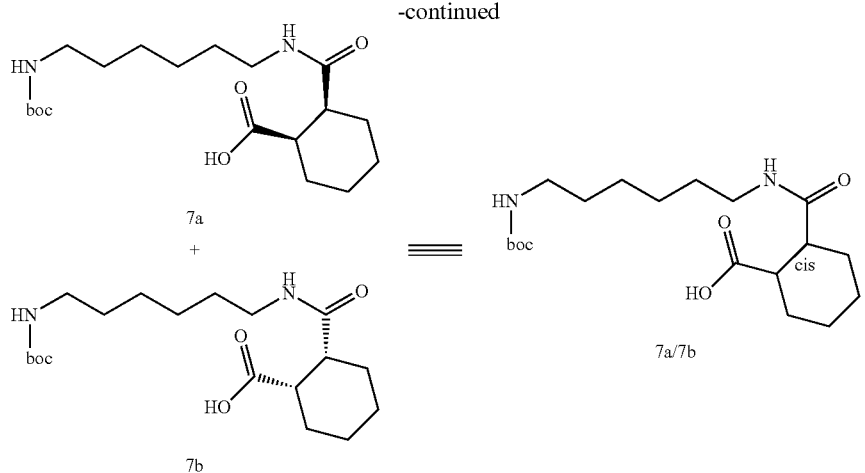

N-Boc-1,6-hexanediamine (270 mg, 1.25 mmol) was dissolved in DMF (2 ml) and cis-1,2-cyclohexanedicarboxylic anhydride (231 mg, 1.50 mmol) was added to the reaction mixture at RT. DIPEA (0.65 mL, 3.76 mmol) was added and the mixture was stirred at RT until consumption of N-Boc-1,6-hexanediamine (LC/MS). The reaction mixture was diluted with $H_2O$/MeCN (9:1) and the product was purified by RP-HPLC (solvent A: $H_2O$ with 0.05% TFA, solvent B: MeCN with 0.05% TFA, gradient: 10-80% B over 16 min, flow: 40 ml/min). The pooled fractions were neutralized with sat. $NaHCO_3$ soln. (pH approx. 6) and the organic solvents were removed in vacuo. The remaining aqueous phase was extracted several times with DCM. The organic layers were dried with $MgSO_4$ and the solvent was removed in vacuo obtaining 7a/7b as a racemic mixture.

Yield: 410 mg (88%).

MS: m/z 371.39=[M+H]$^+$ (MW+H calculated=371.27 g/mol).

Example 8

Synthesis of Dmob Protected Treprostinil 8:

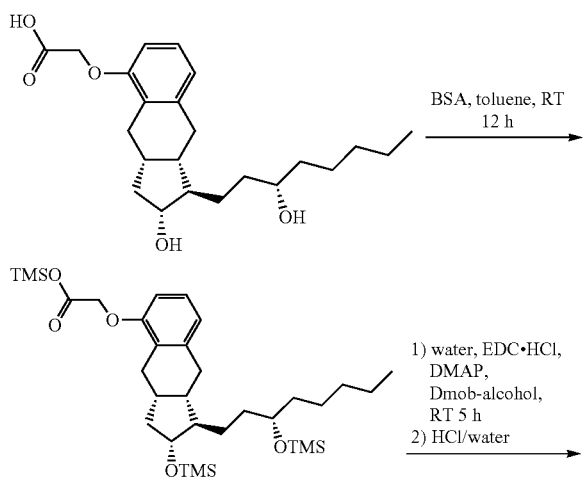

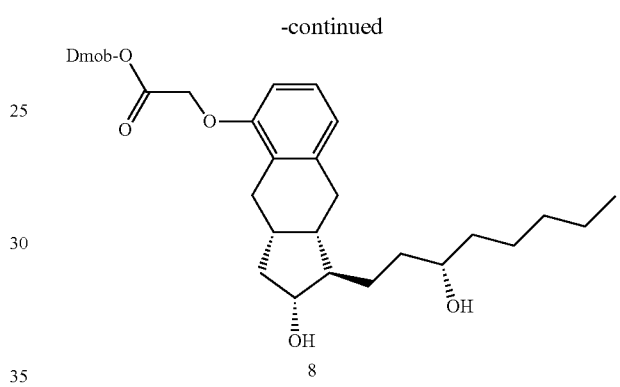

Treprostinil (61 mg, 0.156 mmol) was dissolved in toluene (dry, molecular sieve, 2.5 ml) and silylation reagent BSA (0.6 mL, 0.245 mmol) was added. The reaction mixture was stirred for 12 h at RT. Volatile solvents were removed in vacuo and the TMS protected treprostinil was used without further purification.

TMS protected treprostinil was dissolved in DCM (2.5 mL) and $H_2O$ (60 µL). DMAP (76 mg, 0.624 mmol), EDC.HCl (119 mg, 0.624 mmol) and Dmob-alcohol (105 mg, 0.624 mmol) dissolved in DCM (1 ml) were added. The reaction mixture was stirred at RT until reaction was complete (LC/MS). The solution was diluted with DCM and quenched by addition of 0.1 N HCl solution saturated with NaCl. The aqueous phase was extracted several times with DCM. Combined organic layers were dried with $MgSO_4$ and the solvent was removed in vacuo obtaining crude product 8. Crude product was purified using RP-HPLC (solvent A: $H_2O$ with 0.05% TFA, solvent B: MeCN with 0.05% TFA, gradient: 35-85% B over 16 min, flow: 40 ml/min). Combined HPLC fractions were adjusted to a pH of approx. 7 by adding sat. $NaHCO_3$ soln. MeCN was removed in vacuo. The remaining $H_2O$ layer was extracted several times with DCM and the combined organic phases were dried with $MgSO_4$, filtered and the solvent was removed in vacuo obtaining product 8 as colorless solid.

Yield: 69 mg (82%).

MS: m/z 563.20 g/mol=[M+Na]$^+$ (MW+Na calculated=563.67 g/mol).

Example 9

Synthesis of Treprostinil Linker Thiol

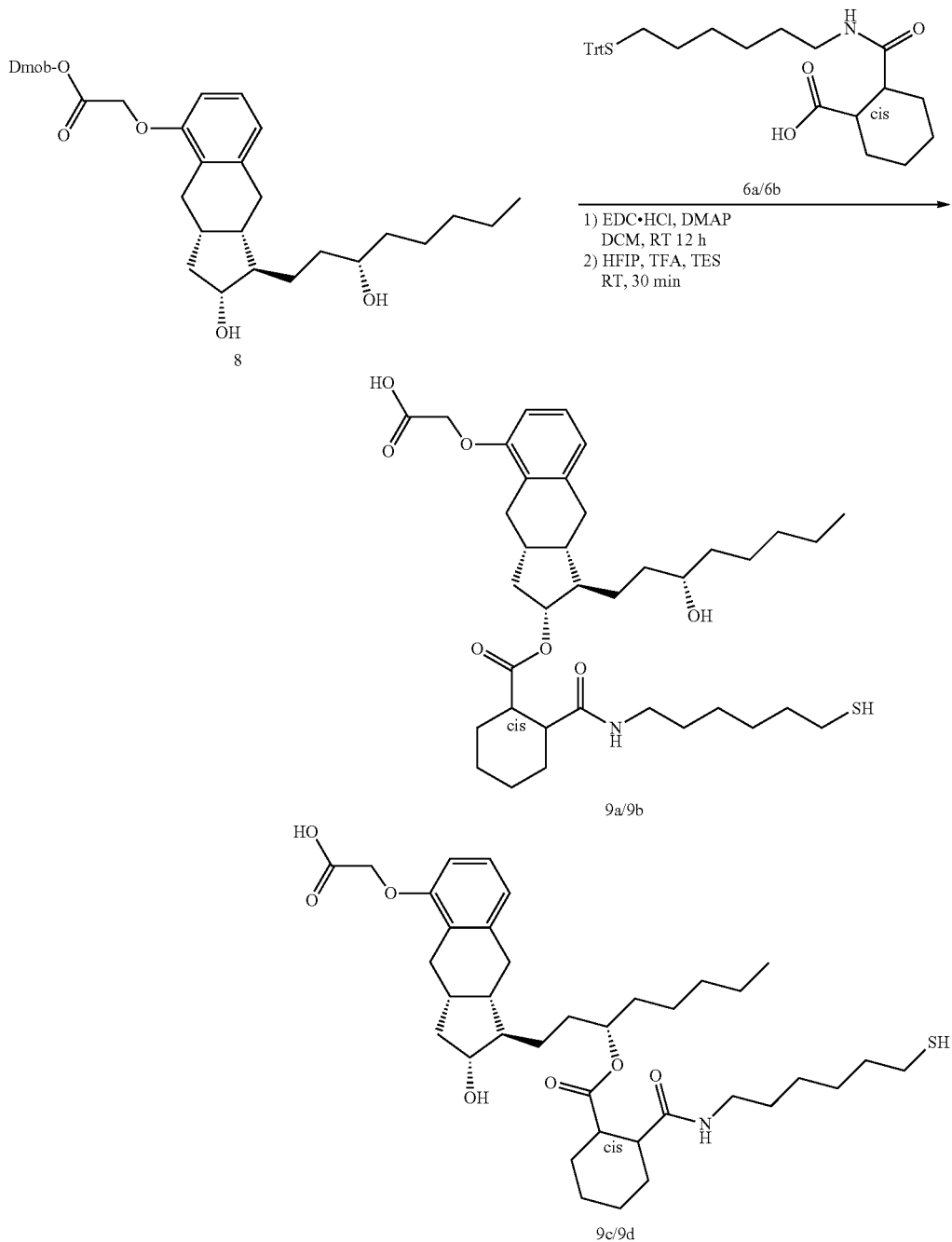

Carboxylic acid 6a/6b (147 mg, 0.277 mmol), EDC.HCl (53 mg, 0.277 mmol) and DMAP (34 mg, 0.277 mmol) were dissolved in 0.5 mL DCM. Dmob protected treprostinil 8 (43 mg, 0.08 mmol) was dissolved in 0.5 mL DCM and added to the reaction mixture. The mixture was stirred at RT until consumption of 8 was complete (over night, LC/MS). Volatile solvents were removed in vacuo. The residue was dissolved in HFIP (2 mL), TFA (100 μL) and TES (50 μL) and stirred for 30 min at RT (LC/MS). Volatiles were removed in vacuo. The residue was dissolved in H$_2$O/MeCN (9/1, 0.05% TFA, 2 mL) and the mixture of four possible isomers was purified by RP-HPLC (solvent A: H$_2$O with 0.05% TFA, solvent B: MeCN with 0.05% TFA, gradient: 60-85% B over 16 min, flow: 6 mL/min). Product isomers eluted as three separable peaks. Fractions containing the peak with the shortest elution time (compound "9x") were pooled and used in the PEGylation step without further processing. Structural assignment of 9x to the possible isomers 9a, 9b, 9c or 9d was not performed in this experiment. Yield of 9x was determined by using Ellman test.

Yield: 8.1 mg (26%)

MS: m/z 682.21 g/mol=[M+Na]$^+$ (MW+Na calculated=682.40 g/mol).

Example 10

Synthesis of Treprostinil Linker Amine

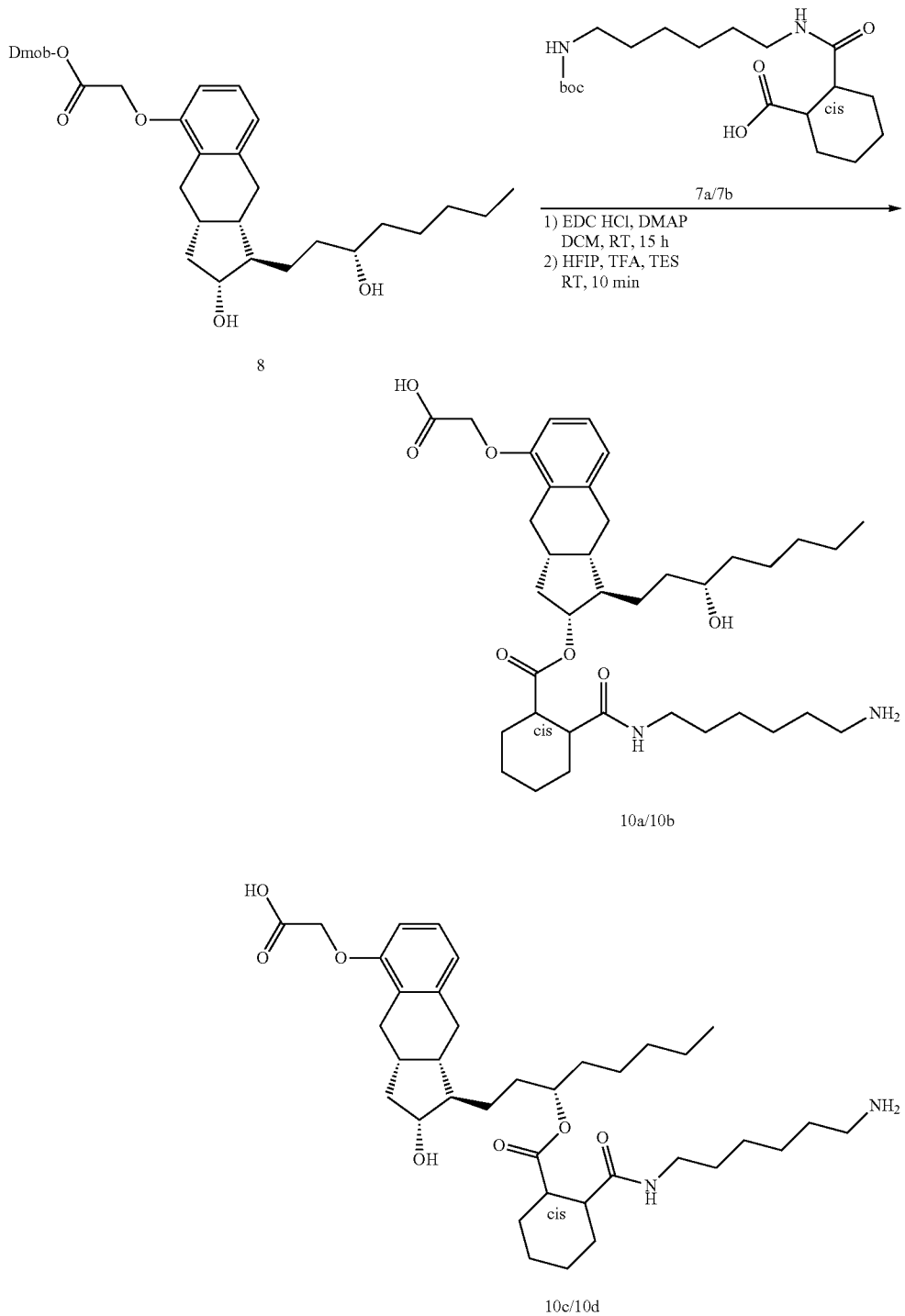

Carboxylic acid 7a/7b (50 mg, 0.134 mmol), EDC HCl (26 mg, 0.134 mmol) and DMAP (16 mg, 0.134 mmol) were dissolved in DCM (0.3 mL). Dmob protected treprostinil 8 (36 mg, 0.066 mmol) was dissolved in DCM (0.5 mL) and added to the reaction mixture. The mixture was stirred at RT until the consumption was complete (LC/MS). Volatile solvents were removed in vacuo. The residue was dissolved in $H_2O$/MeCN (9/1, 0.05% TFA, 2 mL) and the mono coupling products (treprostinil coupled to one 7a/7b molecule) were separated from the double coupling products (treprostinil coupled to two 7a/7b molecules) by RP-HPLC: Thermo Fisher Hypersil Gold PFP column, 150×10 mm, solvent A: $H_2O$ with 0.05% TFA, solvent B: MeCN with 0.05% TFA, gradient: 35-55% B over 16 min, flow: 6 mL/min. HPLC fractions containing mono coupling products were pooled and lyophilized. Lyophilizate was dissolved in HFIP (0.9 mL), DCM (0.1 mL), TFA (100 μL) and TES (20 μL) and stirred for 10 min at RT. Volatiles were removed in vacuo, the residue was dissolved in H$_2$O/MeCN (9/1, 0.05% TFA, 2 mL) and the and the mixture of four possible isomers was purified by RP-HPLC (solvent A: H$_2$O with 0.05% TFA, solvent B: MeCN with 0.05% TFA, gradient: 35-55% B over 16 min, flow: 6 mL/min). Product isomers eluted as three separable peaks. Fractions containing the peak with the shortest elution time (compound "10x") were pooled and used in the PEGylation step without further processing.

Structural assignment of the 10x to the possible isomers 10a, 10b, 10c or 10d was not performed in this experiment. Yield of 10x was estimated by HPLC by using a treprostinil calibration curve (280 nm).

Yield: 3.0 mg

MS: m/z 643.28 g/mol=[M+Na]$^+$ (MW+Na calculated=643.45 g/mol).

Example 11

PEGylation Reaction of Treprostinil Linker Amine with Linear PEG 5 kDa NHS

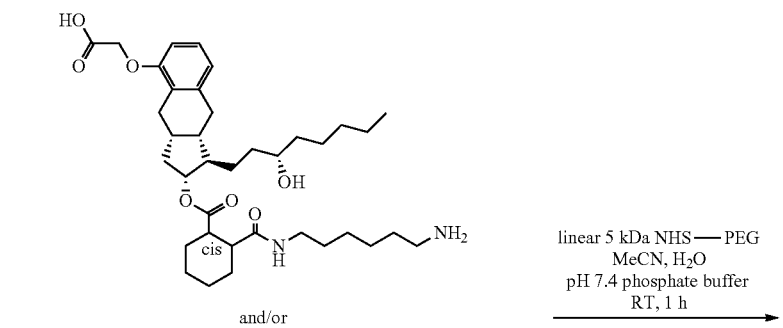

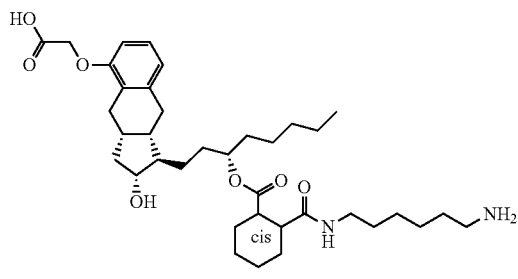

10x

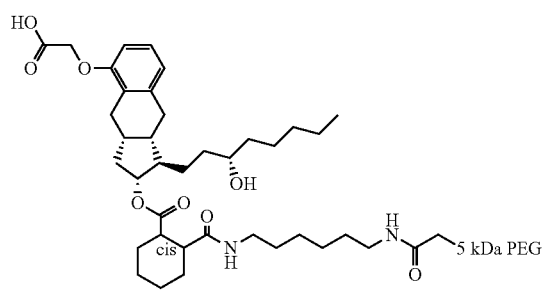

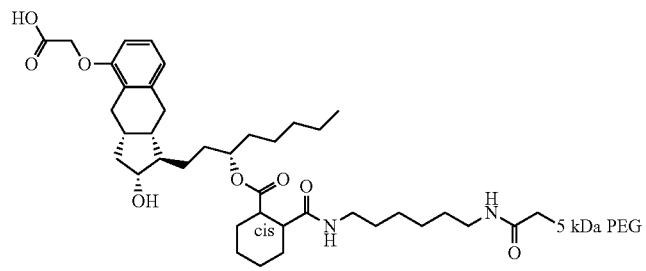

11

To treprostinil linker amine 10× (0.6 mg, 1 µmol in solution, MeCN/H₂O, 0.05% TFA, 5 mL) linear PEG 5 kDa NHS (23 mg, 4.6 µmol) was added. The solution was neutralized by addition of 0.5 M pH 7.4 buffer (0.5 M phosphate, 0.6 mL). H₂O (1 mL) was added for obtaining a clear solution, and reaction mixture was incubated at RT for 1 h. Then the reaction mixture was purified by RP-HPLC (solvent A: H₂O with 0.01% HCl, solvent B: MeCN with 0.01% HCl, gradient: 10-70% B over 16 min, flow: 6 mL/min) to obtain after lyophilization TransCon linear 5 kDa PEG treprostinil 11.

Yield: 3 mg

Example 12

PEGylation Reaction of Treprostinil Linker Thiol with Linear PEG 40 kDa Maleimide

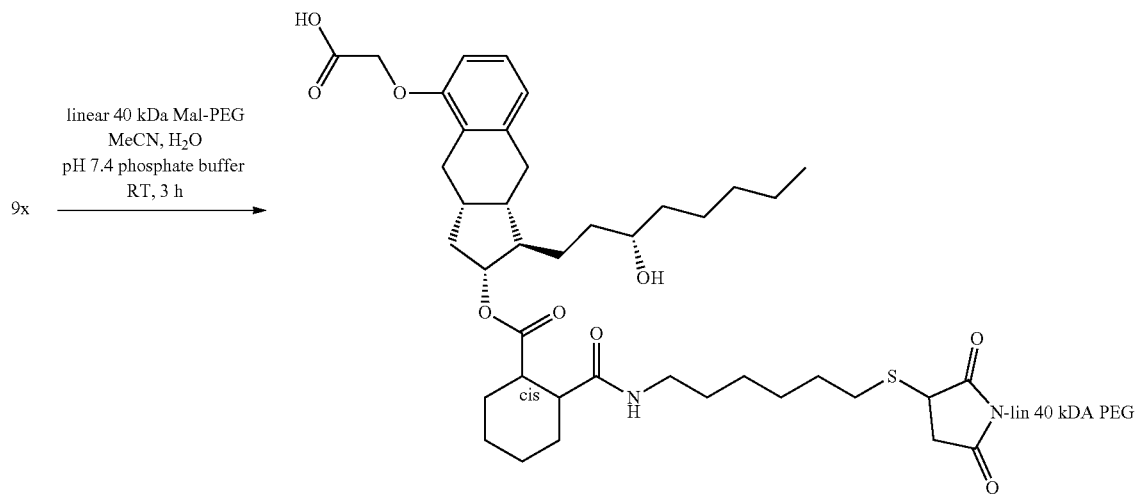

or

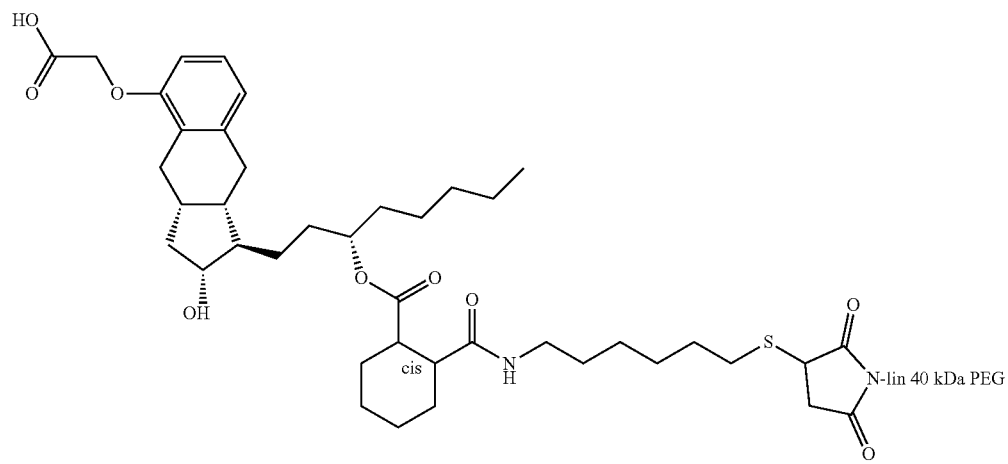

To the treprostinil linker thiol 9× (6.2 mg, 9.42 µmol) solution in MeCN/H$_2$O (0.05% TFA, 87 mL) linear PEG 40 kDa maleimide (463 mg, 11.3 µmol) was added. The solution was neutralized by addition of pH 7.4 buffer (0.5 M phosphate, 4.4 mL). After 1 h incubation time another portion of linear 40 kDa Mal-PEG (73 mg, 178 µmol) and H$_2$O (5 mL) was added and the reaction solution was incubated for another 1.5 h. The reaction mixture was purified by RP-HPLC (solvent A: H$_2$O with 0.01% HCl, solvent B: MeCN with 0.01% HCl, gradient: 30-50% B over 16 min, flow: 40 mL/min) to obtain after lyophilization TransCon linear 40 kDa PEG treprostinil 12.

Yield: 321 mg (82%)

Example 13

PEGylation Reaction of Treprostinil Linker Thiol with 4-Arm PEG 20 kDa Maleimide

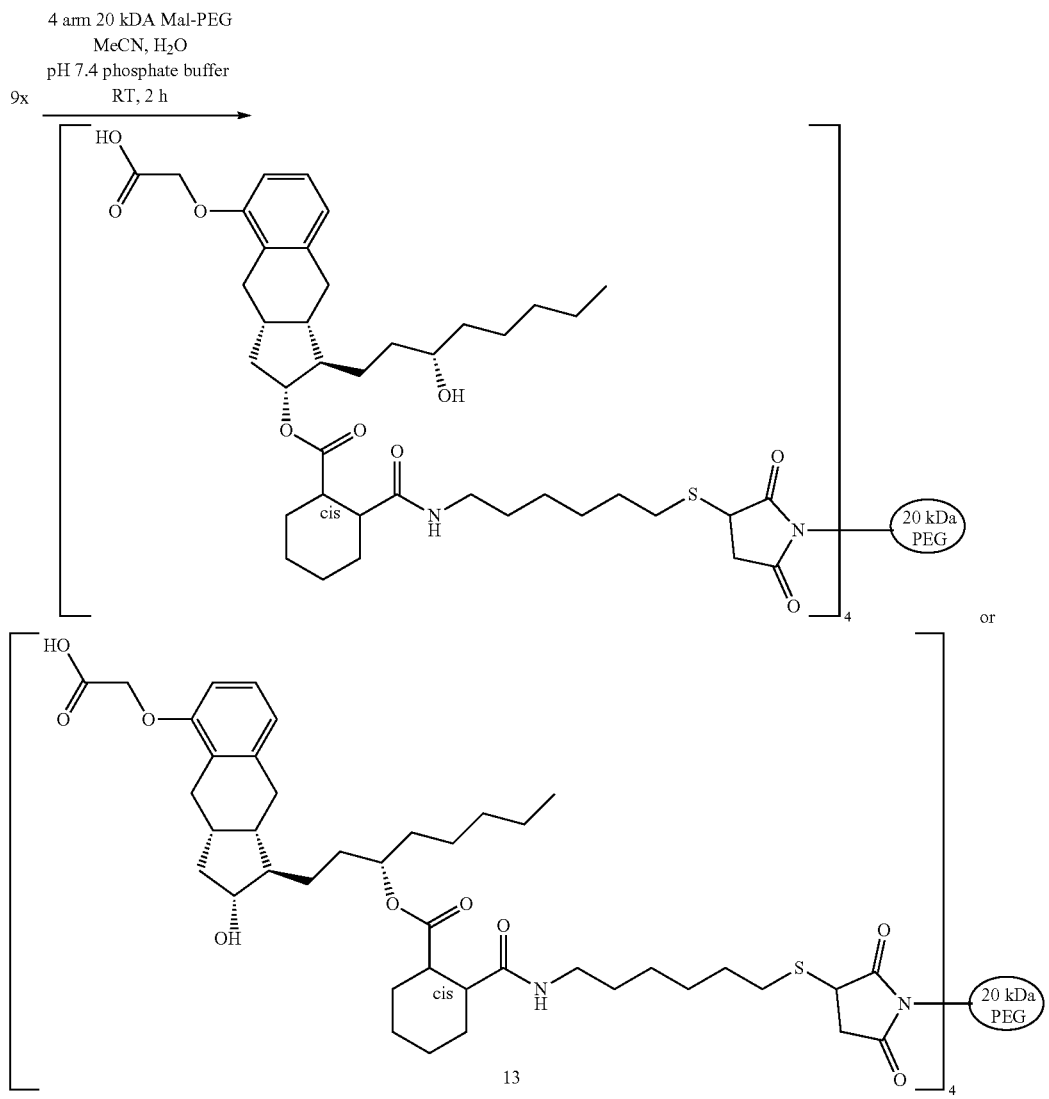

To the treprostinil linker thiol 9× (2.54 mg, 3.84 µmol) solution in MeCN/H$_2$O (0.05% TFA, 5.7 mL) 4-arm PEG 20 kDa maleimide (21 mg, 0.98 µmol) was added. The solution was neutralized by addition of pH 7.4 buffer (0.5 M phosphate, 3.0 mL). H$_2$O (3 mL) was added until the reaction mixture became a clear solution again. The reaction mixture was incubated at RT for 2 h and then purified by RP-HPLC (solvent A: H$_2$O with 0.01% HCl, solvent B: MeCN with 0.01% HCl, gradient: 45-85% B over 16 min, flow: 40 mL/min) to obtain after lyophilization TransCon 4-arm PEG 20 kDa treprostinil 13.

Yield: 14 mg (66%).

Example 14

Treprostinil Release Kinetics of TransCon PEG Linker Treprostinil Compounds 11 and 12:

Release kinetics were determined according to Example 5. A treprostinil release half life time of 4.3 days (±0.7 days) was obtained for compounds 11 and 12.

Example 15

Treprostinil Release Kinetics of TransCon PEG Linker Treprostinil Compound 13

TransCon PEG linker treprostinil 13 (2.5 mg) was incubated in pH 7.4 hydrolysis buffer (60 mM sodium phosphate, 3 mM EDTA, 0.05% Tween-20, 1 mL) at 37° C. and aliquots were analyzed by UPLC at various time points for released treprostinil. The percentage of released treprostinil was determined in relation to the area of treprostinil after total hydrolysis of an aliquot (50 µl hydrolysis solution and 25 µl 5 N NaOH were mixed for 20 min. 25 µl AcOH was added and the resulting solution was analyzed by LCMS).

By using a first order kinetics fit, a half life of 5 d for treprostinil release from 13 was obtained.

Example 16

Synthesis of Building Block 14

Building block 14 was synthesized according to the following scheme:

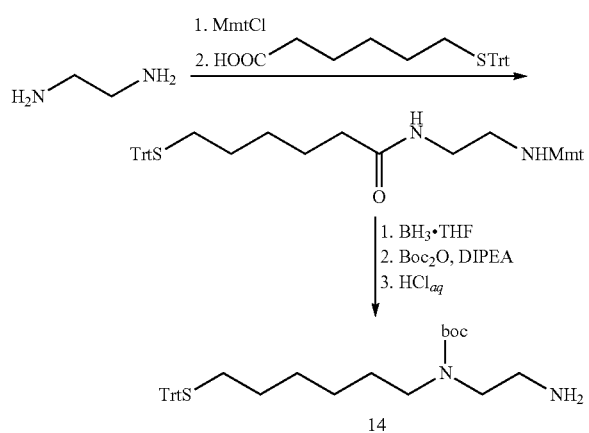

Mmt-chloride (3 g, 9.71 mmol) was dissolved in DCM (20 mL) and added dropwise to a solution of ethylenediamine (6.5 mL, 97.1 mmol) in DCM (20 mL). After two hours the solution was poured into diethyl ether (300 mL) and washed three times with 30/1 (v/v) brine/0.1 M NaOH solution (50 ml each) and once with brine (50 mL). The organic phase was dried over $Na_2SO_4$ and volatiles were removed under reduced pressure. Mmt-protected amine (3.18 g, 9.56 mmol) was used in the next step without further purification.

The Mmt-protected amine (3.18 g, 9.56 mmol) was dissolved in anhydrous DCM (30 mL). 6-(S-Tritylmercapto)hexanoic acid (4.48 g, 11.47 mmol), PyBOP (5.96 g, 11.47 mmol) and DIPEA (5.0 mL, 28.68 mmol) were added and the mixture was agitated for 30 min at RT. The solution was diluted with diethyl ether (250 mL) and washed three times with 30/1 (v/v) brine/0.1 M NaOH solution (50 mL each) and once with brine (50 mL). The organic phase was dried over $Na_2SO_4$ and volatiles were removed under reduced pressure. Amide was purified by flash chromatography eluting with heptane/ethyl acetate containing 0.02% (v/v) diethylmethylamine.

Yield: 5.69 g (8.07 mmol).

MS: m/z 705.4=[M+H]⁺ (MW=705.0).

Amide (3.19 g, 4.53 mmol) was dissolved in anhydrous THF (50 mL) and $BH_3$.THF (1 M solution, 8.5 mL, 8.5 mmol) was added. Solution was stirred for 16 h at RT. Further $BH_3$.THF (1 M solution, 14 mL, 14 mmol) was added and stirred for further 16 h at RT. The reaction was quenched by addition of methanol (8.5 mL). N,N-dimethylethylenediamine (3 mL, 27.2 mmol) was added, the solution was heated to reflux and stirred for 3 h. Reaction mixture was allowed to cool down to RT and was then diluted with ethyl acetate (300 mL), washed with saturated, aqueous $Na_2CO_3$ solution (2×100 mL) and saturated, aqueous $NaHCO_3$ solution (2×100 mL). The organic phase was dried over $Na_2SO_4$ and volatiles were removed under reduced pressure to obtain crude amine intermediate (3.22 g).

The amine intermediate (3.22 g) was dissolved in DCM (5 mL). $Boc_2O$ (2.97 g, 13.69 mmol) dissolved in DCM (5 mL) and DIPEA (3.95 mL, 22.65 mmol) were added and the mixture was agitated at RT for 30 min. Boc- and Mmt-protected intermediate was purified by flash chromatography.

Yield: 3.00 g (3.79 mmol).

MS: m/z 791.4=[M+H]⁺, 519.3=[M−Mmt+H]⁺ (MW calculated=791.1).

0.4 M aqueous HCl (48 mL) was added to a solution of the Boc- and Mmt-protected intermediate in acetonitrile (45 mL). The mixture was diluted with acetonitrile (10 mL) and stirred for 1 h at RT. Subsequently, the pH value of the reaction mixture was adjusted to 5.5 by addition of an aqueous 5 M NaOH solution. Acetonitrile was removed under reduced pressure and the aqueous solution was extracted with DCM (4×100 mL). The combined organic phases were dried over $Na_2SO_4$ and volatiles were removed under reduced pressure. Crude amine 14 was used without further purification.

Yield: 2.52 g (3.19 mmol). A MW of 791.1 g/mol of crude amine 14 was assumed

MS: m/z 519.3=[M+H]⁺ (MW calculated=519.8 g/mol).

Example 17

Synthesis of Linker Building Blocks 15a, 15b, and 15c

Linker building block 15a was synthesized according to the following scheme:

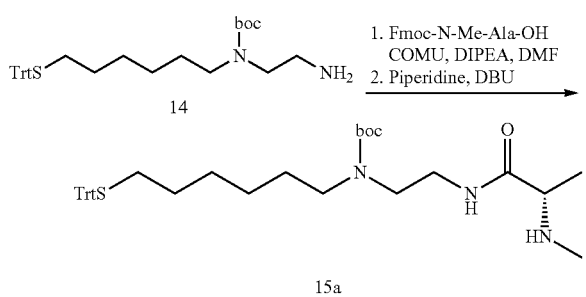

Amine 14 (503 mg, 0.635 mmol, assuming a MW of 791.1 g/mol of crude 1) was dissolved in 4 mL DMF (anhydrous, mol. sieve). Fmoc-N-Me-Ala-OH (310 mg, 0.953 mmol), COMU (408 mg, 0.953 mmol) and DIPEA (332 µl, 1.906 mmol) were added and the reaction was allowed to stir for 3 h at RT. 150 µl piperidine and 150 µl DBU were added to the mixture and stirring was continued for further 60 min. 400 µl acetic acid were added and product was purified by HPLC. HPLC fractions containing product 15a were neutralized with a saturated NaHCO$_3$ solution and extracted twice with DCM. Combined organic phases were dried over Na$_2$SO$_4$ and volatiles were removed under reduced pressure.

Yield: 203 mg (0.336 mmol).

MS: m/z 604.1=[M+H]$^+$ (MW calculated=603.9 g/mol).

Linker Building Block 15b

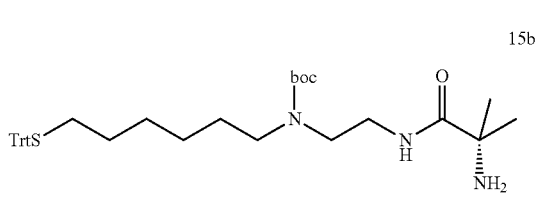

15b

Linker building block 15b was synthesized as described for 15a except that Fmoc-Aib-OH was used instead of Fmoc-N-Me-Ala-OH.

Yield: 95 mg (0.161 mmol).

MS: m/z 604.2=[M+H]$^+$ (MW calculated=603.9 g/mol).

Linker Building Block 15c

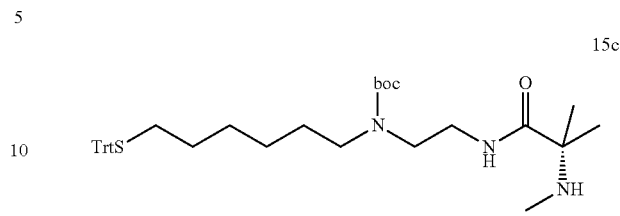

15c

Linker building block 15c was synthesized as described for 15a except that Fmoc-N-Me-Aib-OH was used instead of Fmoc-N-Me-Ala-OH.

Yield: 149 mg (0.241 mmol).

MS: m/z 619.0=[M+H]$^+$ (MW calculated=617.9 g/mol).

Example 18

Synthesis of Treprostinil-Linker Thiols 16a, 16b, 16c, 16d, 16e and 16f

Treprostinil-linker thiols 16a/16b were synthesized according to the following scheme:

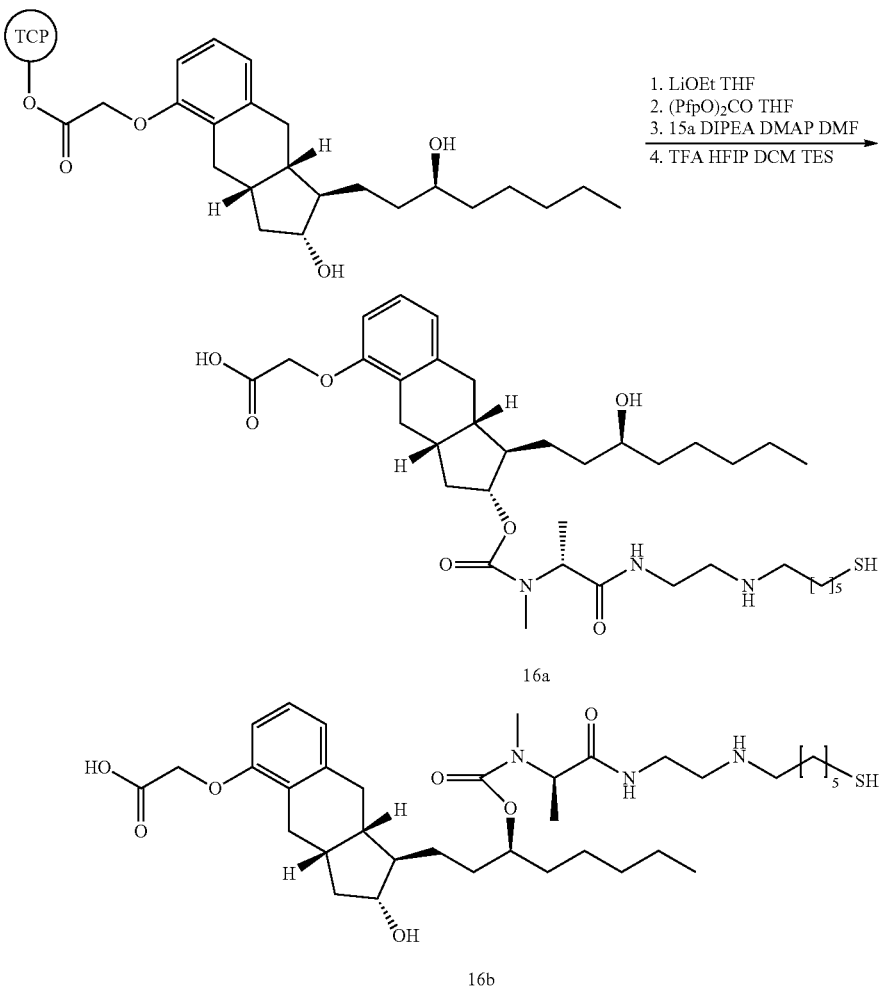

1. LiOEt THF
2. (PfpO)$_2$CO THF
3. 15a DIPEA DMAP DMF
4. TFA HFIP DCM TES

16a

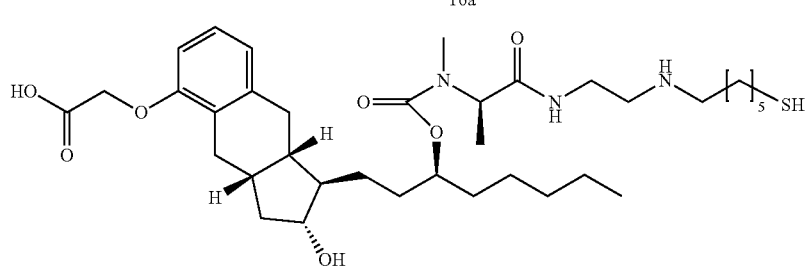

16b

A 10 mL single use syringe reactor equipped with a PE frit was loaded with 2-chlorotrityl chloride (TCP) resin (153 mg, loading 1.22 mmol/g, 0.186 mmol). A solution of treprostinil (54 mg, 0.138 mmol) and DIPEA (60 µl, 0.346 mmol) in DCM (anhydrous, mol. sieve) was drawn into the reactor. Reactor was agitated for 2 h at RT. 200 µl methanol were added and reactor was agitated for further 10 min. Solution was dispelled and resin was washed with DCM (5×), DMF (5×) and DCM (10×). Resin was dried under vacuum (1 mbar). Based on weight, a treprostinil loading of 0.72 mmol/g TCP resin was obtained.

900 µl THF (anhydrous, mol. sieve) and 300 µl of a 1 M LiOEt solution in THF (300 µmol) were drawn to 30 mg treprostinil loaded TCP resin (21.6 µmol) in a single use 2 mL syringe reactor equipped with a PE frit. Reactor was agitated for 40 min at RT. Solution was dispelled and resin was washed with THF (2×). A solution of bis(pentafluorophenyl)carbonate (100 mg, 254 µmol) in 1 mL THF was drawn into the syringe which was agitated for 90 min at RT. Solution was dispelled and resin was washed with THF (5×) and DMF (5×). A solution of linker building block 15a (50 mg, 83 µmol), DIPEA (50 µl, 287 µmol) and DMAP (1 mg, 8 µmol) in 300 µl DMF (anhydrous, mol. sieve) was drawn into the syringe. Syringe was agitated for 3 h at RT. Solution was dispelled and resin was washed with DMF (10×) and DCM (10×). Product was cleaved from resin by incubation with 500 µl of cleavage cocktail HFIP/DCM/TES 90/10/2 v/v/v for 10 min (3×). Resin was washed with 500 µl DCM (2×). TFA (250 µL) was added to the combined cleavage and washing solutions and the mixture was incubated at RT for 10 min. Volatiles were removed under reduced pressure. Residue was subjected to HPLC purification which gave thiols 16a/16b as a mixture of the two regioisomers. HPLC eluate was used in the next step without further processing.

MS: m/z 678.1=[M+H]$^+$ (MW calculated=678.0 g/mol).

Treprostinil Linker Thiols 16c/16d

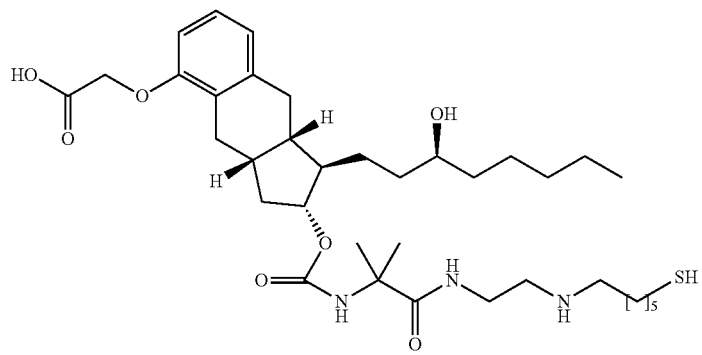

16c

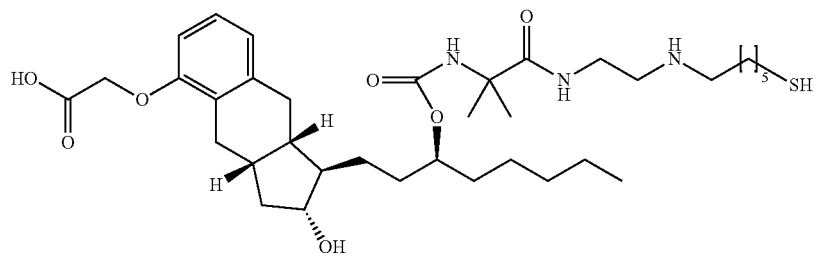

16d

Treprostinil linker thiols 16c/16d were synthesized as described for 16a/16b except that linker building block 15b was used instead of 15a. Thiols 16c/16d were obtained as a mixture of isomers. HPLC eluate was used in the next step without further processing.

MS: m/z 678.1=[M+H]$^+$ (MW calculated=678.0 g/mol).

Treprostinil Linker Thiols 16e and 16f

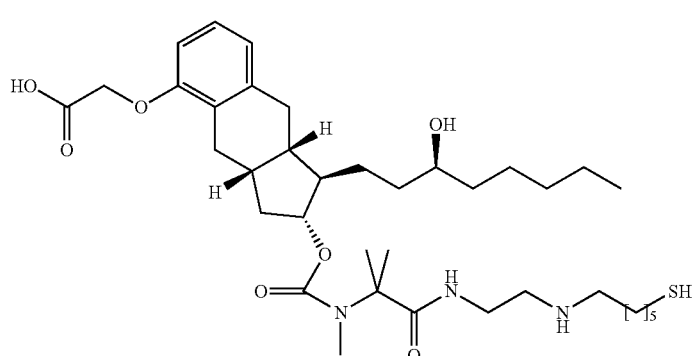

16e

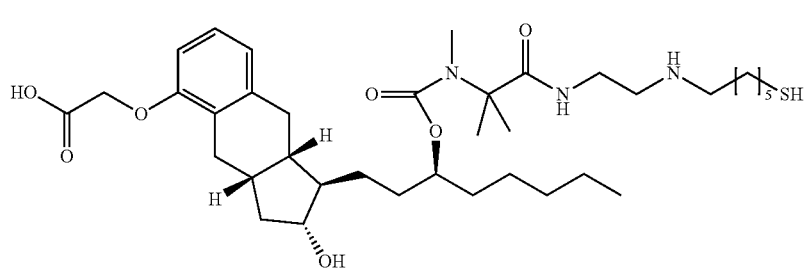

16f

Treprostinil linker thiols 16e and 16f were synthesized as described for 16a/16b except that linker building block 15c was used instead of 15a. Two isomers assigned to structures 16e and 16f were separated by HPLC. HPLC eluates were used in the next step without further processing.

15e MS: m/z 693.0=[M+H]$^+$ (MW calculated=692.0 g/mol).

15f MS: m/z 693.0=[M+H]$^+$ (MW calculated=692.0 g/mol).

Example 19

Synthesis of Linker Building Blocks 17a☐ and 17b

Linker building blocks 17a and 17b were synthesized according to the following scheme:

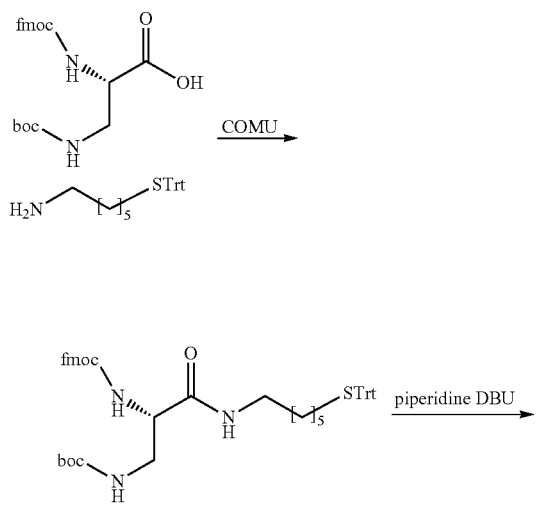

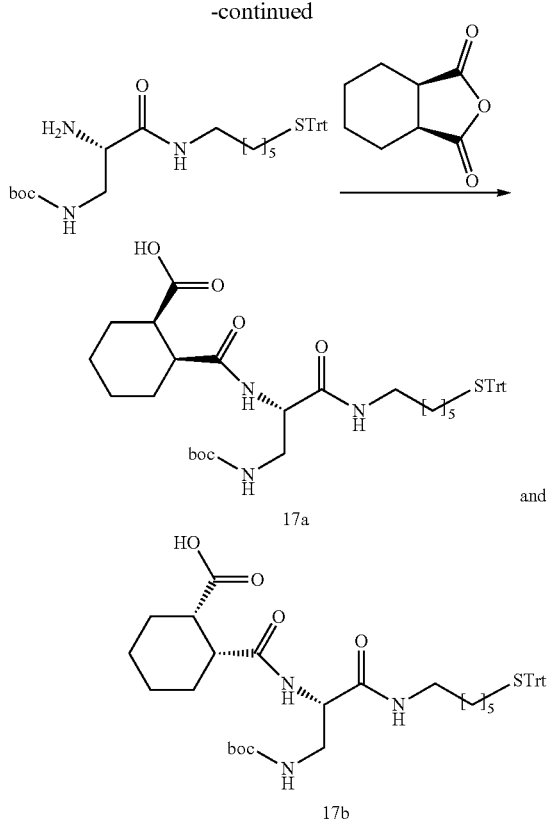

L-Fmoc-Dpr(Boc)-OH (100 mg, 0.234 mmol) was dissolved in 0.5 mL DMF (anhydrous, mol. sieve). 6-(S-Tritylsulfanyl)-hexaneamine (71 mg, 0.189 mmol), COMU (97 mg, 0.227 mmol) and DIPEA (66 µl, 0.378 mmol) were added and mixture was stirred for 1 h at RT. Piperidine (50

μl, 0.505 mmol) and DBU (40 μl, 0.336 mmol) were added and stirring was continued for 10 h. ds-Cyclohexanedicarboxylic anhydride (600 mg, 3.89 mmol) was added and stirring was continued for 1 h. Solution was quenched with water/acetonitrile and acidified with acetic acid Building blocks were purified by RP-HPLC. Structures assignment of the earlier eluting diastereomer 17a and the later eluting diastereomer 17b was done arbitrarily and could also be reverse.

Yield: 17a 30 mg (0.042 mmol), 17b 42 mg (0.059 mmol)
MS: m/z 716.2=[M+H]$^+$ (MW calculated=716.0 g/mol).

Example 20

Synthesis of Treprostinil Linker Thiols 18a/18b

Linker building block 17a (11 mg, 12 μmol), EDC HCl (7.4 mg, 38.5 μmol) and DMAP (4.7 mg, 38.5 μmol) were dissolved in 300 μl DCM (anhydrous, mol. sieve). Solution was drawn to 15 mg treprostinil loaded TCP resin (10.8 μmol, 0.72 mmol/g see Example 3) in a single use 2 mL syringe reactor equipped with a frit. Reactor was agitated for 15 h at RT. Solution was dispelled and resin was washed with DCM (10×). Product was cleaved by incubating resin with 500 μl HFIP/DCM 30/70 v/v for 10 min (3×). Resin was washed with 500 μl DCM (2×). To the combined cleavage and washing solutions were added 250 μl TFA and the mixture was incubated at RT for 10 min. Volatiles were removed under reduced pressure. Residue was subjected to RP-HPLC purification which gave thiols 18a/18b as a mix-

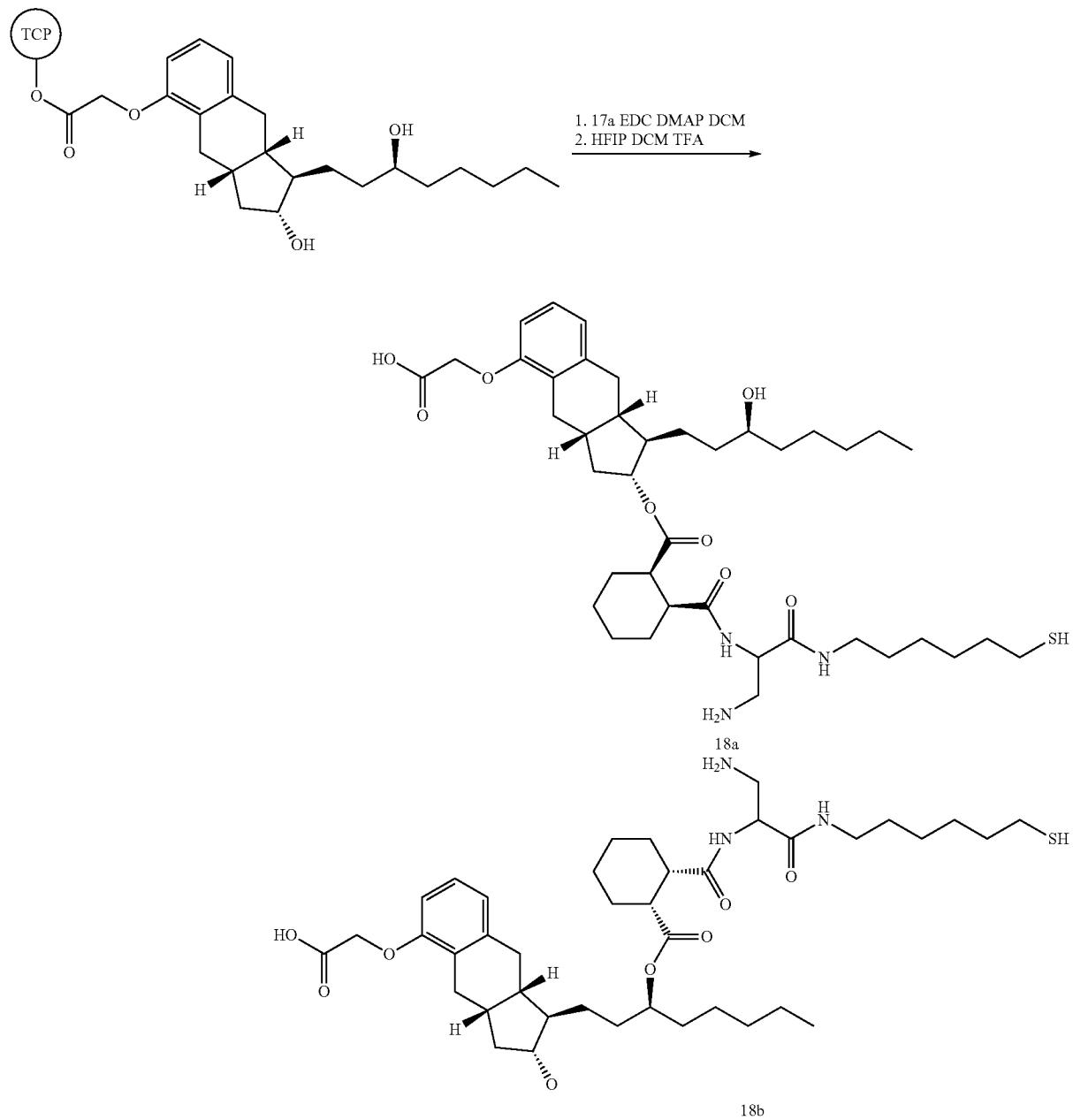

ture of the two regioisomers. HPLC eluate was used in the next step without further processing.

Yield: 18a/18b 1.5 mg (2 µmol) as determined by thiol quantification by Ellman Test.

MS: m/z 746.2=[M+H]⁺ (MW calculated=746.0 g/mol).

Example 21

Synthesis of PEG-Linker-Drug Conjugates 19a/b, 19c/6d, 19e, 19f and 19g/19h

PEG-linker-drug conjugates were prepared according to the following scheme:

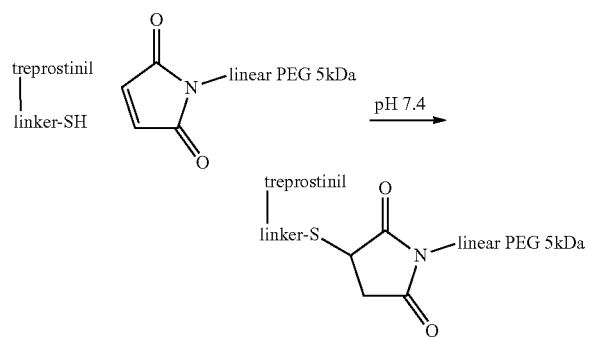

To HPLC eluates of treprostinil linker thiols 16a/16b, 16c/16d, 16e, 16f and 18a/18b was given an excess of linear PEG 5 kDa maleimide. Mixtures were neutralized by addition of pH 7.4 buffer (0.5 M phosphate) and incubated at RT. After complete consumption of thiol (approx. 1 h) mixtures were acidified with acetic acid and separated from excess PEG-maleimide by RP-HPLC. HPLC eluates were lyophilized to yield PEG-linker-drug conjugates 19a/b, 19c/19d, 19e, 19f and 19g/19h respectively.

Example 22

Determination of Drug Release Half Life Time from PEG Conjugates 19a/b, 19c/19d, 19e, 19f and 19g/19h:

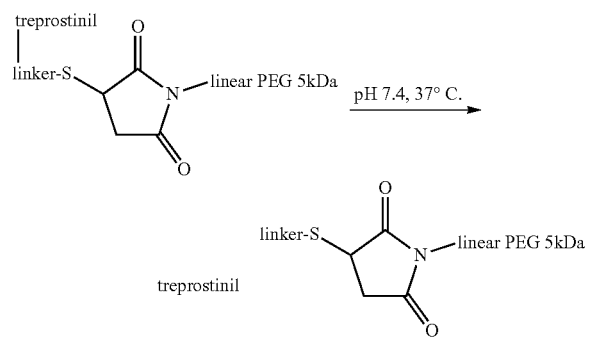

PEG-linker-drug conjugates 19a/b, 19c/19d, 19e, 19f and 19g/19h were dissolved in pH 7.4 buffer (60 mM sodium phosphate, 3 mM EDTA, 0.05% Tween-20, 1 mL) and incubated at 37° C. At various time points aliquots were analyzed by UPLC to determine the amount of released treprostinil which was plotted against time. Drug release was found to follow first order kinetics. Curve fitting software was used to determine half life time of drug release from the respective conjugates (Table 1)

TABLE 2

| entry | PEG-linker-drug conjugate | drug release half life time |
|---|---|---|
| 1 | 19a/b | 31 d |
| 2 | 19c/19d | 17 d |
| 3 | 19e | 24 d |
| 4 | 19f | 37 d |
| 5 | 19g/19h | 35 min |

Example 23

Synthesis of Intermediate 20:

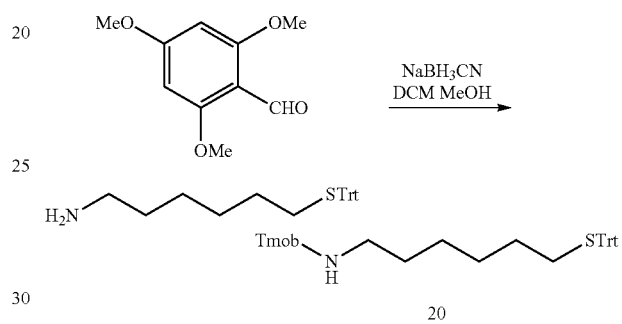

The amino group of 6-(S-Tritylsulfanyl)-hexaneamine was Tmob (2,4,6-Trimethoxybenzyl) protected by dropwise addition of a solution of 2,4,6-trimethoxybenzaldehyde (4.22 g, 21.51 mmol) in 88 mL methanol/DCM 1/1 (v/v) to 6-(S-tritylsulfanyl)-hexaneamine (6.74 g, 17.95 mmol) and sodium cyanoborohydride (1.58 g, 25.14 mmol) in 44 mL methanol. The mixture was stirred for 1.5 h at RT and quenched with 95 mL of 0.4 N aqueous HCl solution. After further stirring at RT for 30 min mixture was extracted with ethyl acetate (4×). Combined organic layers were washed with sat. aqueous NaHCO₃ solution (2×) and brine. The organic layer was dried over Na₂SO₄ and the solvent was removed under reduced pressure. Tmob protected amine 20 was purified by flash chromatography eluting with DCM/methanol containing 0.1% (v/v) triethylamine.

Yield: 5.88 g (55%).

MS: m/z 556.3⁼[M+H]⁺ (MW calculated=555.79 g/mol).

Example 24

Synthesis of Intermediate 21:

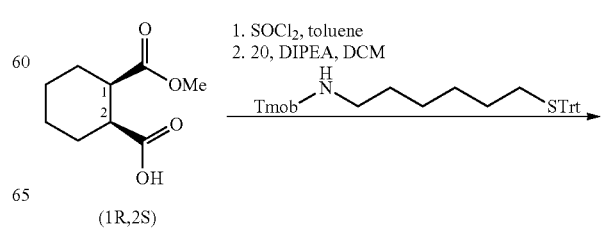

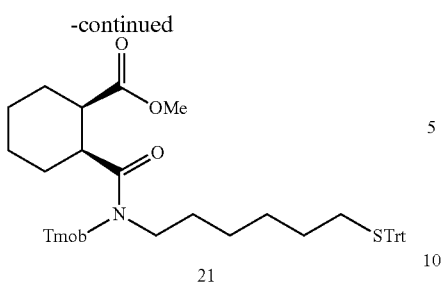

(1R,2S)-Cyclohexanedicarboxylic acid 1-methyl ester, CAS no. 88335-92-6 (for synthesis see R. Manzano et al. *J. Org. Chem.* 2010, 75(15), 5417-5420) (506 mg, 2.72 mmol) was dissolved in toluene (11 ml, anhydrous). Thionyl chloride (1.09 mL, 15.0 mmol) was added and mixture was heated for 1 h at 60° C. in a pressure tube. Volatiles were removed in vacuo. A solution of Tmob protected amine 20 (1.66 g, 2.99 mmol) and DIPEA (1.12 mL, 6.43 mmol) in DCM (30 mL, anhydrous) was added and mixture was stirred for 2 h at RT. Ethyl acetate was added and the organic layer was washed with 0.1 N aqueous HCl (2×). The organic layer was dried over $Na_2SO_4$ and the solvent was removed under reduced pressure. Methyl ester 21 was purified by flash chromatography eluting with ethyl acetate/heptane.

Yield: 1.55 g (79%).

MS: m/z 746.1=[M+Na]$^+$ (MW calculated=723.98 g/mol).

Example 25

Synthesis of Intermediate 22:

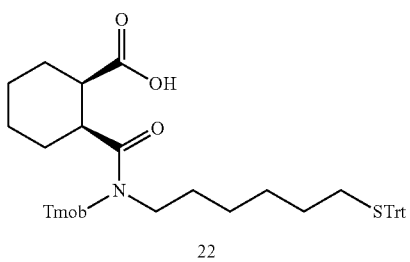

Methyl ester 21 (3.12 g, 4.31 mmol) was dissolved in isopropanol (10 ml). 35 mL of a 1 M aqueous LiOH solution were added and the mixture was stirred for 5 d at RT. Ethyl acetate was added and the organic layer was washed with 0.05 N aqueous HCl (2×) and brine. The organic layer was dried over $Na_2SO_4$ and the solvent was removed under reduced pressure. 22 was purified by flash chromatography eluting with ethyl acetate/heptane containing 0.1% formic acid (v/v).

Yield: 2.41 g (79%).

MS: m/z 710.1=[M+H]$^+$ (MW calculated=709.95 g/mol).

Example 26

Synthesis of Intermediate 6a:

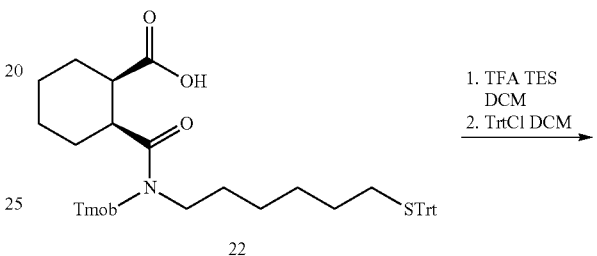

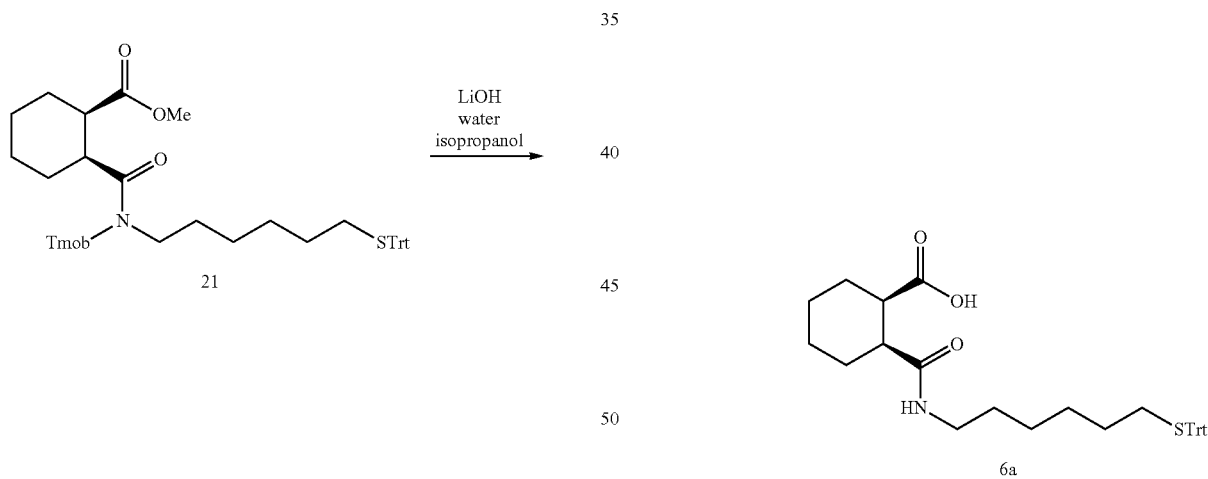

Compound 22 (1.23 g, 1.74 mmol) was dissolved in DCM (18 ml). TFA (2 mL) and TES (600 µl) were added and the mixture was stirred for 40 min at RT. Volatiles were removed in vacuo. The residue was dissolved in DCM (20 mL) and tritylchloride (728 mg, 2.61 mmol) was added. The mixture was stirred for 2 h at RT. DCM was removed under reduced pressure. Carboxylic acid 6a was purified by flash chromatography using ethyl acetate/heptane containing 0.1% formic acid (v/v) as eluent, followed by RP-HPLC purification.

Yield: 615 mg (67%).

MS: m/z 552.2=[M+Na]$^+$ (MW calculated=529.75 g/mol).

Example 27

Synthesis of Treprostinil Linker Thiol 24a

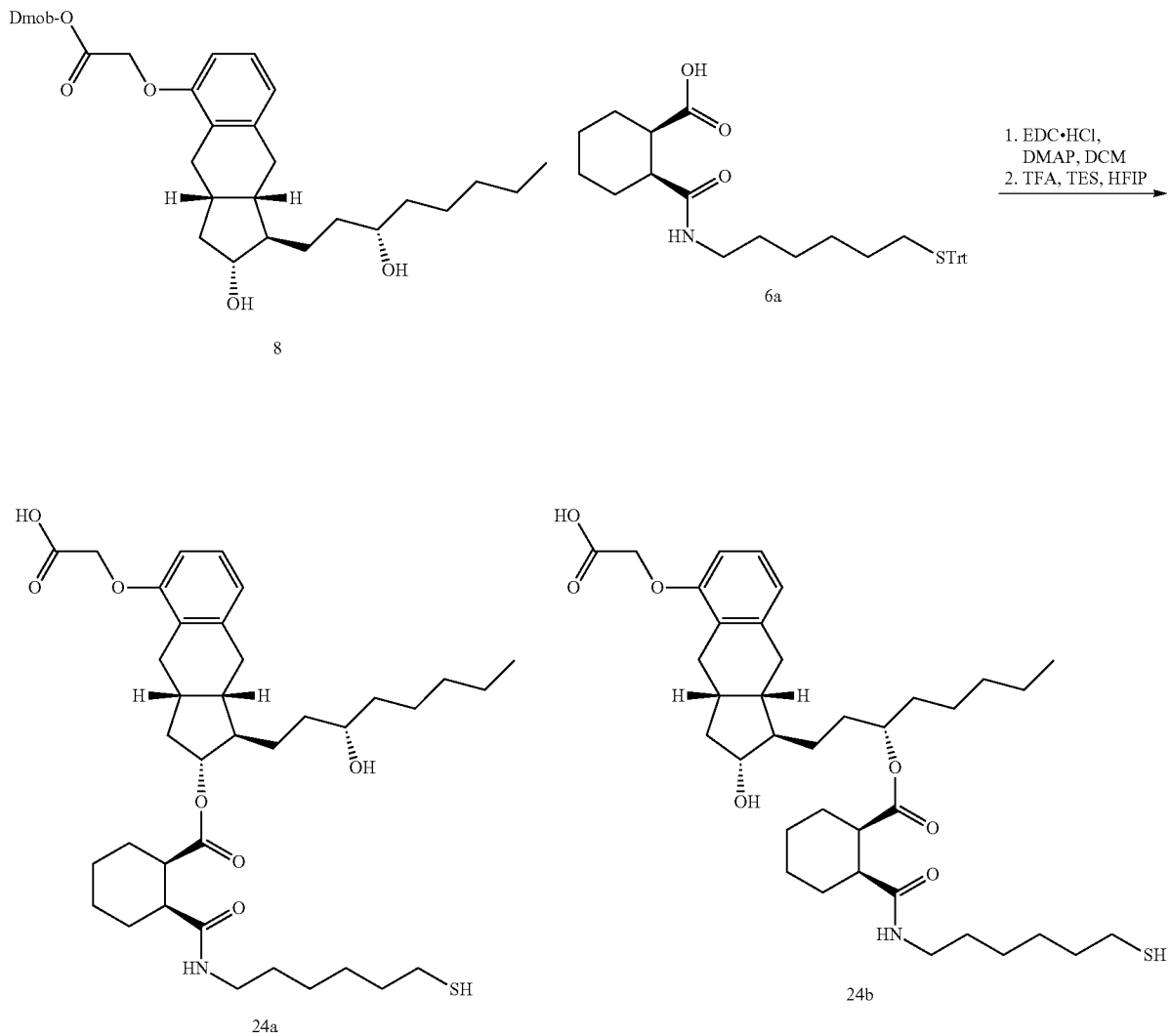

Dmob protected treprostinil 8 (100 mg, 0.185 mmol), carboxylic acid 6a (195 mg, 0.368 mmol), EDC.HCl (72 mg, 0.376 mmol) and DMAP (43 mg, 0.352 mmol) were dissolved in DCM (1.8 mL, anhydrous, mol. sieve). The mixture was stirred at RT for 1 d. Ethyl acetate was added and the organic layer was washed with 0.1 N aqueous HCl (3×) and brine. The organic layer was dried over $Na_2SO_4$ and the solvent was removed under reduced pressure. The residue was dissolved in HFIP (5 mL), TFA (250 µL) and TES (250 µL) and stirred for 30 min at RT. The precipitate was filtered off and the filtrate was evaporated in vacuo.

UPLC analysis revealed a 4/1 ratio of regioisomers 24a and 24b (column: Kinetex 100×2.1 mm, 1.7 µm XB-C18 silica, pore size 100 Å, Phenomonex Ltd, Aschaffenburg, Germany; flow rate 0.25 mL/min; solvent A: water+0.05% TFA (v/v), solvent B: acetonitrile+0.04% TFA; gradient: 30-58% B (10 min), 58% B isocratic (10 min), 58-80% B (5 min), 80-99% (5 min), wavelength 280 nm). 24a turned out to be identical with compound 9x.

The residue was taken up in acetonitrile/water and 24a was purified by RP-HPLC (solvent A: $H_2O$+0.01% HCl, solvent B: MeCN+0.01% HCl, gradient: 60-85% B over 16 min). Isomer 24a eluted first, followed by isomer 24b. Fractions containing pure 24a were combined and lyophilized. Mixed fractions containing 24a and 24b were subjected to repurification.

Yield 24a: 29.5 mg (24%)

MS: m/z 660.3=[M+H]$^+$ (MW calculated=659.9 g/mol).

$^1$H-NMR (CDCl$_3$, δ [ppm]): 7.07 (t, 1H), 6.80 (d, 1H), 6.71 (d, 1H), 5.86 (bs, 1H), 4.78-4.63 (m, 3H), 3.53 (bs, 1H), 3.14-3.03 (m, 1H), 3.03-2.83 (m, 2H), 2.82-2.66 (m, 2H), 2.66-2.58 (m, 1H), 2.58-2.46 (m, 4H), 2.46-2.31 (m, 1H), 2.31-2.13 (m, 1H), 2.13-1.92 (m, 2H), 1.92-1.81 (m, 1H), 1.75-1.51 (m, 7H), 1.51-1.21 (m, 21H), 1.21-1.08 (m, 1H), 0.90 (t, 3H).

$^{13}$C-NMR (126 MHz, CDCl$_3$, δ [ppm]): 174.7, 174.2, 171.7, 155.2, 140.6, 127.5, 126.3, 121.8, 109.71, 78.8, 72.4, 65.8, 48.3, 43.9, 42.5, 40.4, 39.7, 37.4, 37.3, 35.4, 34.00, 33.0, 32.9, 32.1, 29.3, 28.4, 28.1, 27.0, 26.4, 25.5, 24.6, 24.2, 23.2, 22.8, 14.2.

Example 28

PEGylation Reaction of Treprostinil Linker Thiol 24a with 4-Arm PEG 20 kDa Maleimide

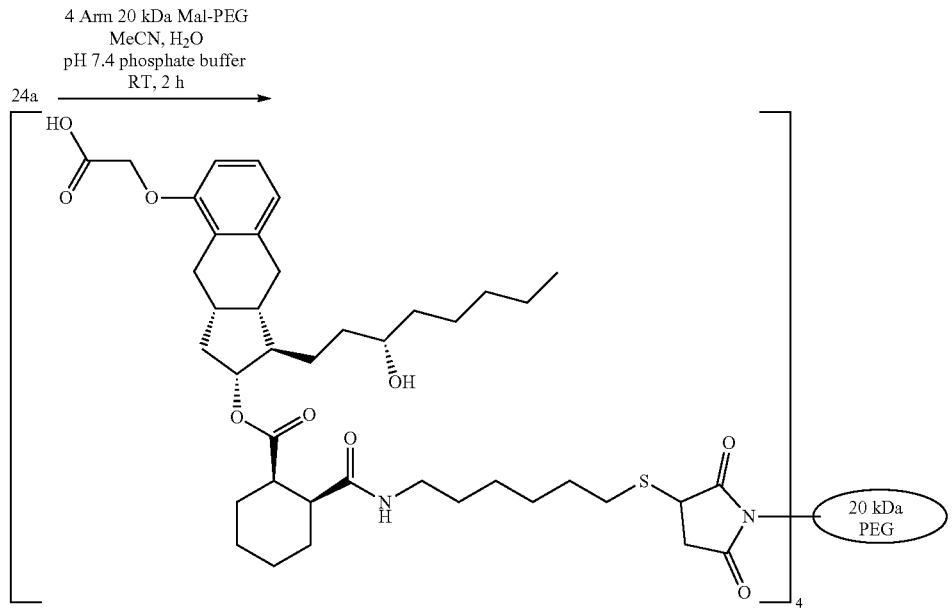

A solution of treprostinil linker thiol 24a (7.5 mg, 11.3 µmol) in 2 mL of acetonitrile/water 9/1 (v/v) was mixed with a solution of 4-arm PEG 20 kDa maleimide (53.5 mg, 2.54 µmol) in 2 mL of acetonitrile/water 1/1 (v/v). The pH was adjusted to 7.0 by addition of pH 7.4 buffer (50 mM phosphate, 0.8 mL). The reaction mixture was stirred at RT for 1.5 h and then purified by RP-HPLC (solvent A: $H_2O$ with 0.01% HCl, solvent B: MeCN with 0.01% HCl, gradient: 45-85% B over 16 min). Product containing fractions were pooled and acetonitrile was removed under reduced pressure. The solution was neutralized by addition of pH 7.4 buffer (phosphate, 0.5 M). The solution was concentrated and the buffer was exchanged with 10 mM pH 7.0 phosphate containing 46 g/l mannitol by ultrafiltration (Vivaspin centrifugal concentrator, PES membrane with 10 kDa cut off) to obtain 8.5 mL of the final solution of 25. UPLC and SEC analysis revealed a uniform material. The concentration was determined by quantification of treprostinil content after basic hydrolysis: 30 µL aliquots were treated with 35 µL 0.5 M NaOH. After 30 min incubation at RT 35 µL acetic acid was added. The trerostinil content was determined by UPLC by using a treprostinil calibration curve. A total treprostinil content of 2.0 mg was found, corresponding to 30 mg 25. Yield: 50% based on PEG starting material.

Example 29

Treprostinil Release Kinetics of TransCon PEG Linker Treprostinil Compound 25

Treprostinil release kinetics from 25 was determined as described in example 15 and compared with the results obtained from compound 13. No difference in half life time (5 d) was observed.

Example 30

Treprostinil Release Kinetics of TransCon PEG Linker Treprostinil Compound 13 in Rat Plasma 150 µl of a pH 7.5 HEPES buffer (1 M HEPES, 3 mM EDTA) were mixed with 1.2 mL rat plasma (WISTAR rat Li heparin plasma, Innovative Research, Novi, Mich., USA). 150 µl of a of TransCon PEG linker treprostinil 13 solution (0.15 mg 13 in 1.5 mL 10 mM phosphate 46 g/l mannitol buffer pH 7.0) were added. A pH of 7.4 of the mixture was confirmed by means of a pH electrode. Mixture was incubated at 37° C. At given time points 100 µl aliquots were withdrawn. 100 µl aliquots were analyzed for released and total treprostinil content.

For analysis of released treprostinil, 100 µl aliquots were spiked with 20 µl internal standard (2.8 µg/mL tolbutamide in methanol/water 1/1 (v/v)) and transferred to a Ostro 96 well plate (Waters GmbH, Eschborn, Germany). Plasma proteins were precipitated by addition of three volumes of pre-cooled (0-5° C.) acetonitrile containing 1% formic acid. Positive pressure was applied (4 bar, Waters Positive Pressure-96 Processor) and eluate was lyophilized. Lyophilizate was dissolved in 40 µl of 10 mM ammonium formiate pH 4.0/acetonitrile 7/3 (v/v). Solution was centrifuged and supernatant was assayed for released treprostinil by UPLC-MS/MS.

For analysis of total treprostinil content (sum of released and carrier bound treprostinil), 100 µl aliquots were spiked with 20 µl internal standard (2.8 µg/mL tolbutamide in methanol/water 1/1 (v/v)) and 50 µl of 0.5 M LiOH were added. Mixture was incubated in a shaker for 2 h at room temperature. After addition 25 µL 1 M HCl the mixture was transferred to a Ostro 96 well plate (Waters GmbH, Eschborn, Germany). Plasma proteins were precipitated by addition of three volumes of pre-cooled (0-5° C.) acetonitrile containing 1% formic acid. Positive pressure was applied (4 bar, Waters Positive Pressure-96 Processor) and eluate was lyophilized. Lyophilizate was dissolved in 100 µl of 10 mM ammonium formiate pH 4.0/acetonitrile 7/3 (v/v). Solution was centrifuged and supernatant was assayed for total treprostinil content by UPLC-MS/MS.

UPLC-MS/MS method for determination of treprostinil content:

The quantification of plasma treprostinil concentrations were carried out using a Waters Acquity UPLC coupled to a Thermo LTQ Orbitrap Discovery mass spectrometer via an ESI probe and with Waters BEH C18 (50×2.1 mm I.D., 1.7 µm particle size) as analytical column (mobile phase A: 10 mM ammonium formate pH 4.6, mobile phase B: methanol, T=22° C.). The gradient system comprised a linear gradient from 0.1% B to 95% B in 4 min, an isocratic washing phase with 95% B (0.5 min), and a reconditioning phase (2.4 min) with a flow rate of 0.25 mL/min. Detection of the ions was performed in the selected reaction monitoring (SRM, negative ionization) mode, monitoring the transition pairs at the m/z 389.2 precursor ions to the m/z 331.2 product ions for treprostinil and m/z 269.1 precursor ions to the m/z 170.0 product ions for the internal standard (IS) tolbutamide.

The calibration curve was acquired by plotting the extracted peak area ratio area$_{treprostinil}$/area$_{tolbutamide}$ against the nominal treprostinil concentrations of calibration standards. The results were fitted to linear regression using standard software.

The extracted peak area ratio area$_{treprostinil}$/area$_{tolbutamide}$ of the quantification experiments at different time points were used to calculate the treprostinil content according to the calibration curve.

Treprostinil release at time points was expressed as % treprostinil release compared to total treprostinil content (see FIG. 1). By using a first order kinetics fit a half life of 4.5 d for the release kinetics of treprostinil from 25 in buffered rat plasma at 37° C. was obtained, which is in good agreement to release kinetics in pH 7.4 buffer at 37° C. (Example 15).

Example 31

PK of PEG Treprostinil Conjugate 25 in Monkeys 25 (3 mg/mL in 10 mM pH 7.0 phosphate, 46 g/L mannitol) was given at a dose level of 0.5 mg/kg as a single dose by sc and iv injection in three male cynomolgus monkeys each. Blood samples were collected at given time points over two weeks. The plasma was assayed for PEG content and total treprostinil content (sum of released and carrier bound treprostinil). Due to the fast elimination of free treprostinil compared to carrier bound treprostinil, treprostinil plasma levels reflect the presence of treprostinil conjugate rather than free treprostinil levels.

For the analysis of total treprostinil content, 100 µL plasma samples and treprostinil standards in cynomolgus monkey plasma were spiked with 20 µL internal standard (2.8 µg/mL tolbutamide in methanol/water 1/1 (v/v)) and 50 µl of 0.5 M LiOH were added. The mixture was incubated in a shaker at RT for 2.5 h. After addition of 25 µL 1 M HCl the mixture was transferred to an Ostro 96 well plate (Waters GmbH, Eschborn, Germany). Plasma proteins were precipitated by addition of three volumes of pre-cooled (0-5° C.) acetonitrile containing 1% formic acid. Positive pressure was applied (4 bar, Waters Positive Pressure-96 Processor) and the eluate was lyophilized. The lyophilizate was dissolved in 100 µl of 10 mM ammonium formiate pH 4.0/acetonitrile 7/3 (v/v). The solution was centrifuged and the supernatant was assayed for total treprostinil content by UPLC-MS/MS.

UPLC-MS/MS method for determination of treprostinil content:

The quantification of plasma treprostinil concentrations were carried out using a Waters Acquity UPLC coupled to a Thermo LTQ Orbitrap Discovery mass spectrometer via an ESI probe and with a Waters BEH C18 (50×2.1 mm I.D., 1.7 µm particle size) as analytical column (mobile phase A: 10 mM ammonium formate pH 4.6, mobile phase B: methanol, T=22° C.). The gradient system comprised a linear gradient from 0.1% B to 95% B in 4 min, an isocratic washing phase with 95% B (0.5 min), and a reconditioning phase (2.4 min) with a flow rate of 0.25 mL/min. Detection of the ions was performed in the selected reaction monitoring (SRM, negative ionization) mode, monitoring the transition pairs at the m/z 389.2 precursor ions to the m/z 331.2 product ions for treprostinil and m/z 269.1 precursor ions to the m/z 170.0 product ions for the internal standard (IS) tolbutamide.

The calibration curve was acquired by plotting the extracted peak area ratio area$_{treprostinil}$/area$_{tolbutamide}$ against the nominal treprostinil concentrations of calibration standards which were prepared in cynomolgus monkey plasma. The results were fitted to a linear regression using standard software.

The extracted peak area ratio area$_{treprostinil}$/area$_{tolbutamide}$ of the quantification experiments at different time points were used to calculate the treprostinil content according to the calibration curve.

For analysis of total PEG content, plasma samples underwent basic preincubation in order to generate a uniform PEG material from 25. This was based on the fact that after injection of 25 different treprostinil carrier species are generated due to the sequential release of 4 treprostinils from carrier molecule over time.

50 µl plasma samples and 25 PEG treprostinil conjugate standards in cynomolgus monkey plasma were diluted with 50 µL of 200 mM HEPES solution (pH 7.5) and 50 µl of 0.5 M LiOH were added. Mixture was incubated in a shaker for 2 h at room temperature. After addition of 50 µL 1 M HCl the mixture was assayed using the high sensitivity PEG ELISA kit P-0003 from Life Diagnostics Inc. West Chester, Pa., USA, according to the manufacturer's instructions.

The calibration curve was acquired by plotting the absorption values at 450 nm against the nominal PEG concentrations of calibration standards. The results were fitted to a sigmoidal curve using standard software.

The absorption values at 450 nm of the quantification experiments at different time points were used to calculate the PEG content according to the calibration curve.

Figure 2:
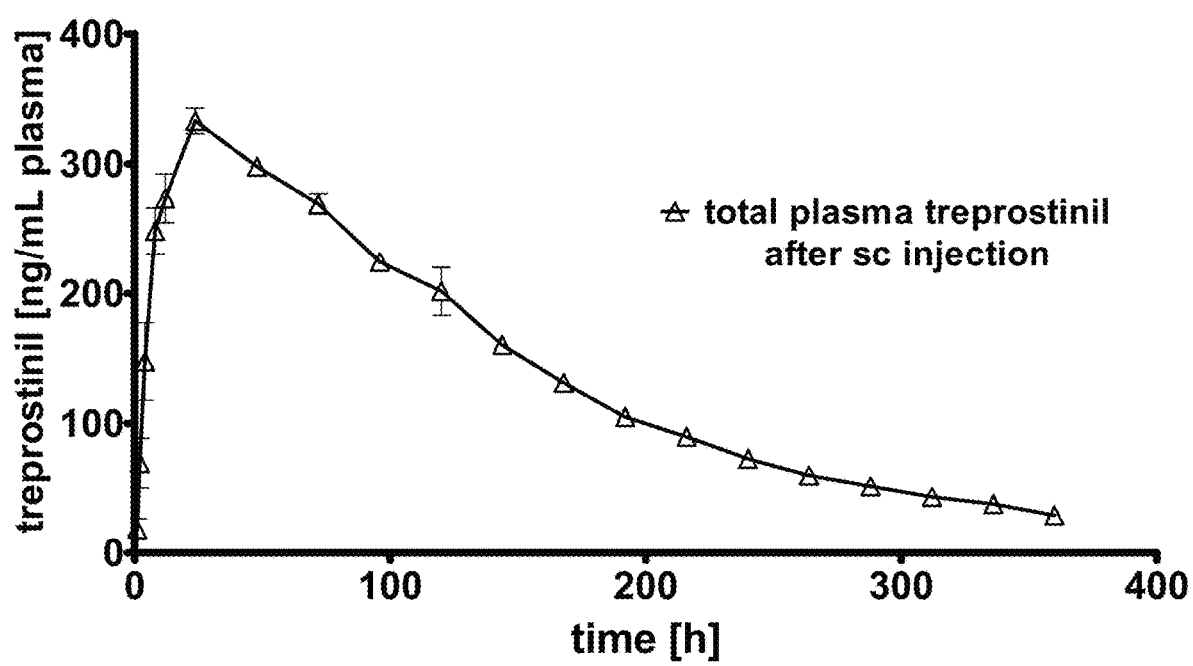
FIG. 2 shows a prolonged duration of circulation of treprostinil conjugate 25 for more than two weeks in monkeys after subcutaneous injection (see Example 30).

Result: Total treprostinil content analysis after a single dose sc injection of 25 reveals a prolonged duration of circulation of treprostinil conjugate for more than two weeks in monkeys. (FIG. 2)

Figure 3:
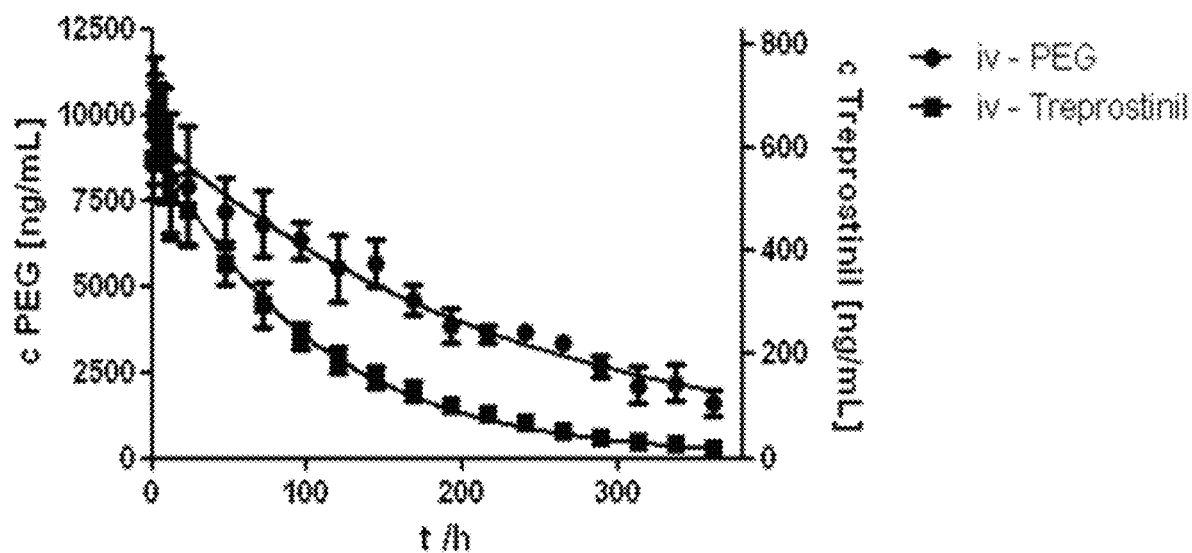
FIG. 3 shows a single dose iv injection of compound 25 and subsequent plasma analysis for total treprostinil and carrier content (see Example 30).

Single dose iv injection of 25 and plasma analysis for total treprostinil content revealed similar duration of circulation (FIG. 3). An apparent first order total treprostinil elimination half life time of 2.9 days (rate constant $k_{apparent}$: 0.239 $d^{-1}$) was obtained by using standard software.

In contrast plasma analysis for PEG carrier content revealed a much slower elimination (FIG. 3). By fitting as a first order kinetics using standard software an PEG carrier elimination half life time of 6.6 d (rate constant $k_{PEGelim}$: 0.105 $d^{-1}$) was obtained.

Equal elimination rate constant of different treprostinil carrier species e.g. generated by sequential linker hydrolysis/release of one to four treprostinils from PEG carrier are assumed.

The apparent faster elimination half life time of total treprostinil compared to PEG carrier is based on the combination of elimination of the PEG carrier and treprostinil release by linker hydrolysis. From the determined rate constant values of $k_{apparent}$ (0.239 $d^{-1}$) and $k_{PEGelim}$ (0.105 $d^{-1}$) a first order treprostinil release by linker cleavage rate constant $k_{linker}$ can be calculated:

$$\exp(-k_{apparent}t) = \exp(-k_{PEGelim}t) \cdot \exp(-k_{linker}t) = \exp(-t[k_{PEGelim} + k_{linker}])$$

After logmarithizing and rearrangement $k_{linker}$ can be calculated according to:

$$k_{linker} = k_{apparent} - k_{PEGelim};\ k_{linker} = 0.239\ d^{-1} - 0.105\ d^{-1} = 0.134\ d^{-1}$$

By help of the equation $t_{half\ life\ time} = \ln(2)/k$ the half life time of treprostinil release by linker hydrolysis was calculated as 5.2 d, which is in good agreement with the 5 d linker treprostinil release half life time determined in vitro.

Example 32

PK of PEG Treprostinil Conjugate 25 and Free Treprostinil in Rats 25 (3 mg/mL buffer (10 mM pH 7.0 phosphate, 46 g/L mannitol)) was injected at a dose level of 5.5 mg/kg as a single dose in male Wistar rats each. Three animals received sc injection and three animals received iv injection. Blood samples were collected at given time points over two weeks. Blood samples (250 µL) were given directly into collection tubes containing 50 µL acidic citrate buffer (0.5 M sodium citrate, pH 4.0). The plasma was assayed for free treprostinil content and total treprostinil content (sum of free and carrier bound treprostinil).

For the analysis of free treprostinil, 50 µL plasma were thawed on ice and mixed with 5 µl acidic citrate buffer and 10 µL internal standard (0.28 µg/mL tolbutamide in methanol/water 1/1 (v/v)). Samples were transferred to Ostro 96 well plates (Waters GmbH, Eschborn, Germany), and plasma proteins were precipitated by rapid addition of 400 µL pre-cooled (0-5° C.) acetonitrile containing 1% formic acid. Positive pressure was applied (4 bar, Waters Positive Pressure-96 Processor) and the eluates were collected. Subsequently, the well plates were rinsed two times with 100 µL ice-cold acetonitrile containing 1 vol. % formic acid. The eluates were transferred into 2 mL vials, placed into an Eppendorf Thermomixer (at 10° C.) and eluates were concentrated under a soft stream of nitrogen over 45 min to a final volume of 60-80 µL. 30 µl solvent mixture (10 mM aqueous ammonium formiate adjusted to pH 4.0 with formic acid/acetonitrile 7/3 (v/v)) were added to each vial and the solutions were analyzed by UHPLC-MS/MS.

For preparation of calibration standards, blank plasma samples were spiked with treprostinil and treated likewise.

UHPLC-MS/MS method for determination of free treprostinil content:

The quantification of plasma treprostinil concentrations were carried out using an Agilent 1290 UHPLC coupled to an Agilent Triplequad 6460 system (MassHunter Xcalibur software) in the ES-mode. As analytical column a Waters BEH C18 was used (50×2.1 mm I.D., 1.7 µm particle size. Mobile phase A: 10 mM ammonium formate pH 5.7, mobile phase B: methanol. The gradient system comprised a linear gradient from 35% B to 99% B in 8 min, an isocratic washing phase with 99% B (0.9 min), and a reconditioning phase (3 min) with a flow rate of 0.200 mL/min (T=40° C.).

Detection of the ions was performed in the SRM mode, monitoring the transition pairs at the m/z 389.1 precursor ions to the m/z 331.1 product ions for treprostinil and m/z 269.0 precursor ions to the m/z 169.9 product ions for the internal standard (IS) tolbutamide. The calibration curve was acquired by plotting the extracted peak area ratio area treprostinil/area tolbutamide against the nominal trepostinil concentrations of calibration standards. The results were fitted to a linear regression using standard software.

The extracted peak area ratio area treprostinil/area tolbutamide of the quantification experiments at different time points were used to calculate the treprostinil content according to the calibration curve.

Total treprostinil plasma content was determined as given in Example 31.

Figure 4:
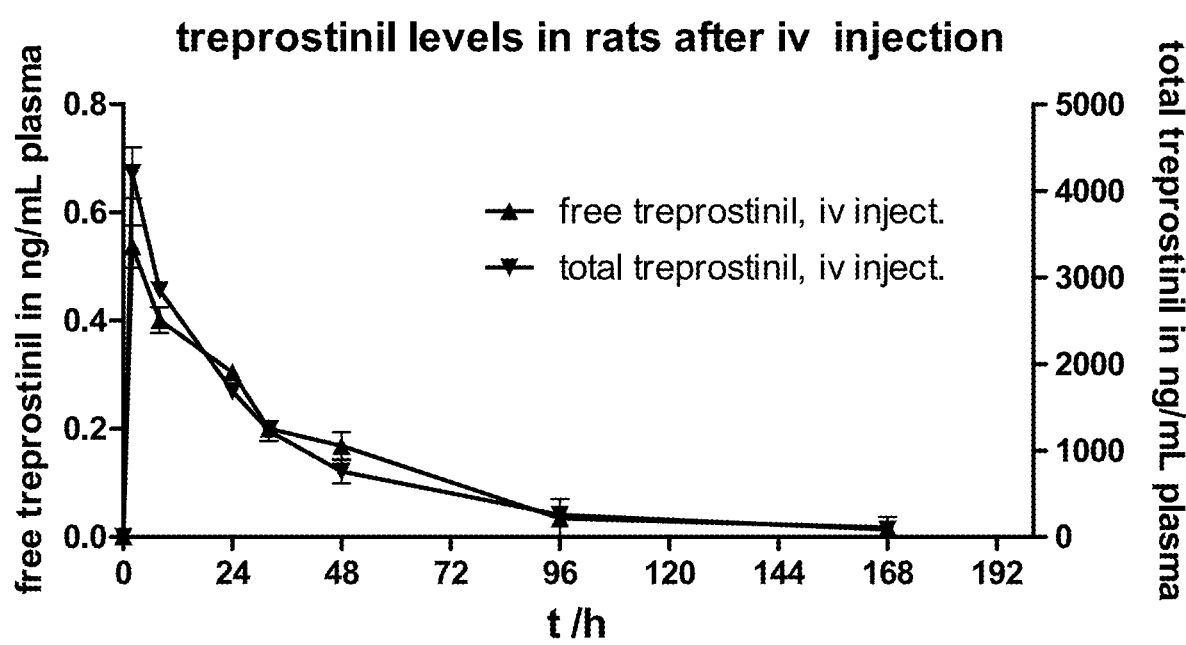
FIG. 4 shows a single dose iv injection of compound 25 and subsequent plasma analysis for free treprostinil (see Example 32).
Figure 5:
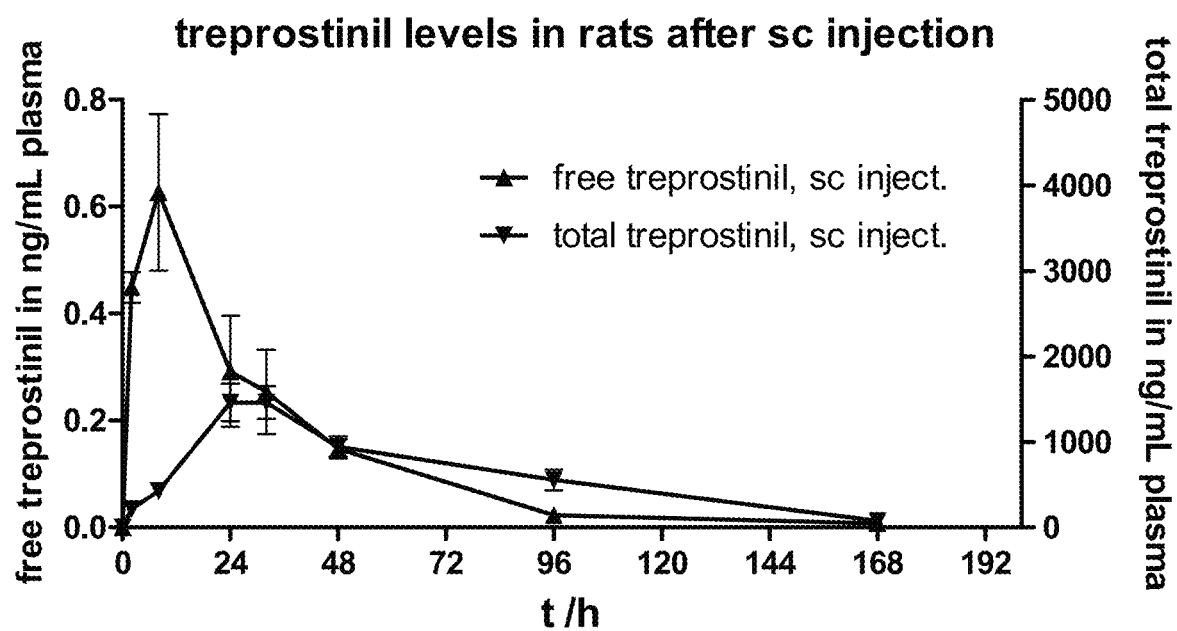
FIG. 5 shows a single dose subcutaneous injection of compound 25 and subsequent plasma analysis for free treprostinil (see Example 32).

Result: Free and total treprostinil content analysis after a single dose sc injection of 25 reveals a prolonged circulation of treprostinil conjugate and a burstless release of free treprostinil for more than four days in rats after iv (FIG. 4) or sc injection (FIG. 5).

Example 33

Isolation of Intermediate 6a by Enantioseparation of Racemic Mixture 6a/6b

Racemic mixture 6a/6b (107 g) was separated on a Chiralpak IA column (250×76 mm, 20 µm, flow rate 270 mL/min) using acetonitrile/acetic acid 1000/1 (v/v) as eluent. Combined eluates of second eluting enantiomer (6a) were mixed with 5 vol % water and evaporated under reduced pressure. The residue was taken up in DCM (500 mL) and extracted with 0.1 M HCl (500 mL, 2×) and brine (500 mL). The organic phase was dried over $Na_2SO_4$ and the solvent was removed under reduced pressure.

Yield: 28.9 g (27%).

MS: m/z 552.2=$[M+Na]^+$ (MW calculated=$529$ 0.7$^5$ g/mol).

Enantiomeric ratio of 6a/6b as determined by Chiralpak IC column (4.5×250 mm, 5 µm, eluent acetonitrile/acetic acid 1000/1 (v/v), flow rate 1 mL/min, 230 nm): 97.5/2.5

Example 34

Improved Synthesis of Treprostinil Linker Thiol 24a

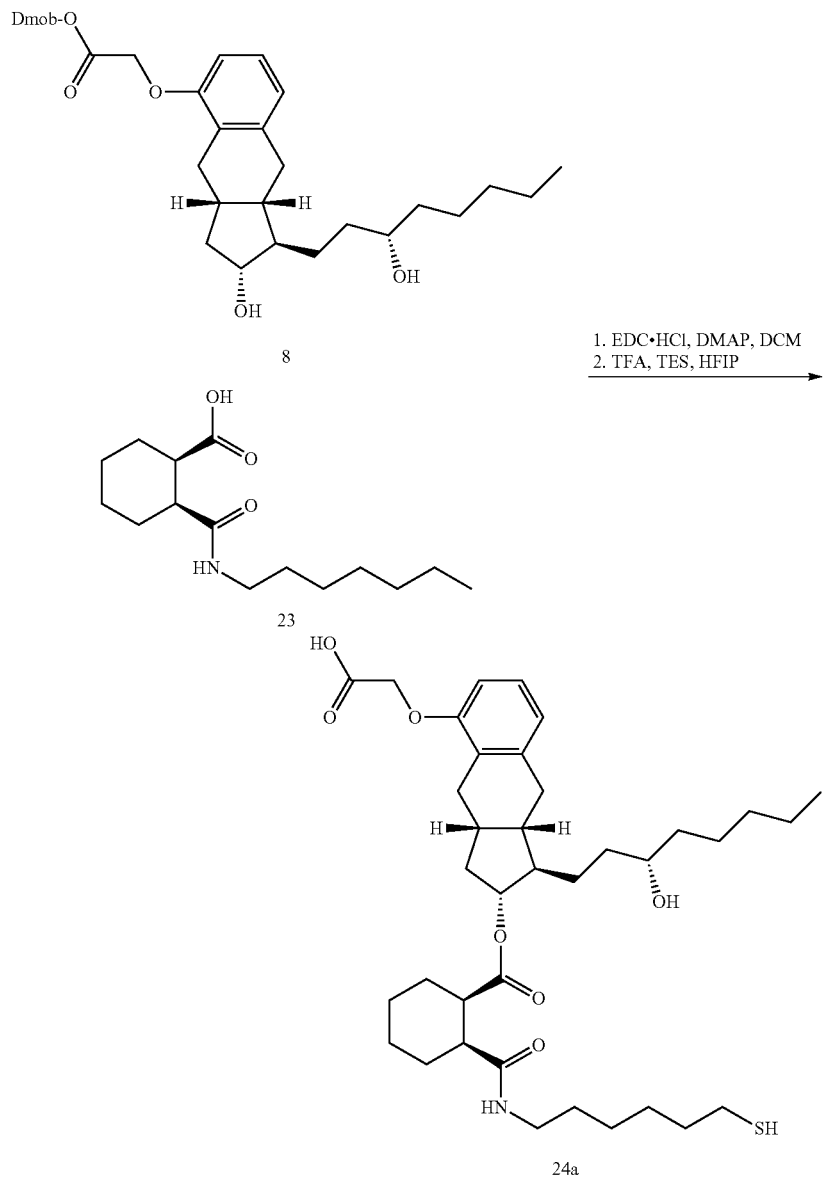

Dmob protected treprostinil 8 (200 mg, 0.370 mmol), carboxylic acid 23 (294 mg, 0.555 mmol), EDC.HCl (248 mg, 1.295 mmol) and DMAP (158 mg, 1.295 mmol) were dissolved in DCM (2.9 mL, anhydrous, mol. sieve). The mixture was stirred at RT for 1 d. Ethyl acetate was added and the organic layer was washed with 0.1 N aqueous HCl (3×) and brine. The organic layer was dried over $Na_2SO_4$ and the solvent was removed under reduced pressure.

The residue was dissolved in HFIP (8 mL). After addition of TFA (200 μL) and TES (200 μL) the mixture was stirred for 30 min at RT. The solution was extracted with heptane (16 mL, 6×) and diluted with DCM (16 mL). Solution was extracted with water (16 mL, 3×). Combined water phases were back extracted with DCM (8 mL). The combined DCM phases were evaporated under reduced pressure.

UPLC analysis revealed a 9/1 ratio of regioisomers 24a and 24b (column: Kinetex 100×2.1 mm, 1.7 μm XB-C18 silica, pore size 100 Å, Phenomonex Ltd, Aschaffenburg, Germany; flow rate 0.25 mL/min; solvent A: water+0.05% TFA (v/v), solvent B: acetonitrile+0.04% TFA; gradient: 30-58% B (10 min), 58% B isocratic (10 min), 58-80% B (5 min), 80-99% B (5 min), wavelength 280 nm).

The residue was taken up in acetonitrile/water and 24a was isolated by RP-HPLC (solvent A: $H_2O$+0.01% HCl, solvent B: MeCN+0.01% HCl, gradient: 57-62% B over 15 min). Mixed fractions were subjected to repurification. Fractions containing pure 24a were combined and lyophilized.

Yield 24a: 98 mg (39%)

MS: m/z 660.3=$[M+H]^+$ (MW calculated=659.9 g/mol).

Abbreviations

AcOH acetic acid
AIB 2-Aminoisobutyric acid

BnBr benzylbromide
Boc tert-Butoxycarbonyl-
BSA N,O-Bis-(trimethylsilyl)-acetamide
COMU (1-Cyano-2-ethoxy-2-oxoethylidenaminooxy)dimethylamino-morpholino-carbenium hexafluorophosphate Abbreviations d day
DIPEA diisopropylethylamine
DCM dichloromethane
DMAP 4-(Dimethylamino)pyridine
DMF N,N-Dimethylformamide
Dmob 2,4-dimethoxybenzyl
DMSO dimethyl sulfoxide
Dpr 2,3-Diaminopropionic acid
EDC N-(3-Dimethylaminopropyl)-N'-ethylcarbodiimide
EDTA ethylenediamine tetraacetic acid disodium salt dihydrate
EtOAc ethyl acetate
eq equivalent
h Hour
HFIP 1,1,1,3,3,3-Hexafluoroisopropanol
HPLC high performance liquid chromatography
LC/MS mass spectrometry-coupled liquid chromatography
Mal maleimido
MeOH methanol
MeCN acetonitrile
min Minute
Mmt 4-Methoxytriphenylmethyl
mol. Molecular
m/z Mass/charge
NaOH Sodium hydroxide
NHS N-hydroxysuccinimide
PEG Polyethylene glycol
Pfp Pentafluorophenyl
PyBOB Benzotriazol-1-yl-oxytripyrrolidinophosphonium hexafluorophosphate
PP polypropylene Abbreviations RT room temperature
RP reversed phase
sat. saturated
soln. solution
T temperature
T3P propyl phosphonic anhydride
TCP 2-Chlorotrityl chloride resin
TES Triethylsilane
Trt Trityl
Tmob 2,4,6-trimethoxybenzyl
TMS trimethylsilyl
TransCon transiently conjugated
THF tetrahydrofuran
TFA trifluoroacetic acid
UPLC ultra performance liquid chromatography
UV ultra violet While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

The invention claimed is:

1. A method of treating, controlling, delaying, or preventing in a mammalian patient in need of the treatment of pulmonary arterial hypertension, comprising:

administering by inhalation to said patient a diagnostically and/or therapeutically effective amount of a carrier-linked treprostinil prodrug of formula (II), or a pharmaceutical salt thereof:

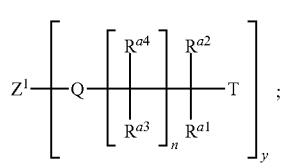

(II)

wherein each T is independently selected from structures (i) to (v):

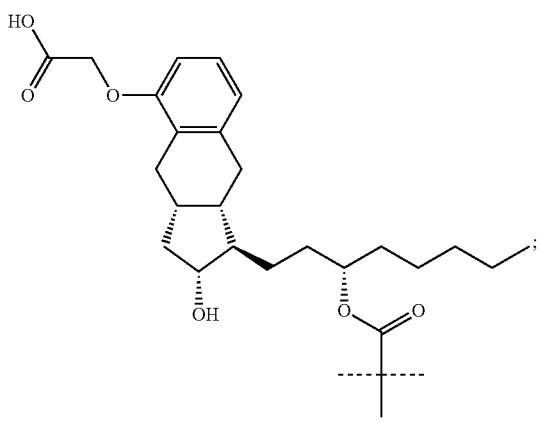

(i)

-continued (ii)

(iii)

(iv)

(v)

wherein:
dashed lines indicate attachment to the rest of the molecule;
y is an integer ranging of from 1 to 64;
$R^{a1}$ is selected from the group consisting of:
unsubstituted alkyl, substituted alkyl, unsubstituted phenyl, substituted phenyl, unsubstituted naphthyl, substituted naphthyl, unsubstituted indenyl, substituted indenyl, unsubstituted indanyl, substituted indanyl, unsubstituted tetralinyl, substituted tetralinyl, unsubstituted $C_{3-10}$ cycloalkyl, substituted $C_{3-10}$ cycloalkyl, unsubstituted 4- to 7-membered heterocyclyl, substituted 4- to 7-membered heterocycyl, unsubstituted 9- to 11-membered heterobicyclyl, and substituted 9- to 11-membered heterobicyclyl;
$R^{a2}$ is selected from the group consisting of:
H, unsubstituted alkyl, and substituted alkyl;
$R^{a3}$ and $R^{a4}$ are independently selected from the group consisting of:
H, unsubstituted alkyl, and substituted alkyl;
n is 0 or 1;
Q is a spacer moiety;
optionally, $R^{a1}$ and $R^{a3}$ are joined together with the atoms to which they are attached to form a ring A;
A is selected from the group consisting of:
phenyl, naphthyl, indenyl, indanyl, tetralinyl, $C_{3-10}$ cycloalkyl, 4- to 7-membered aliphatic heterocyclyl, and 9- to 11-membered aliphatic heterobicyclyl, wherein A is unsubstituted or substituted; and
$Z^1$ is a carrier comprising a covalently bound polymer; and
wherein $R^{a2}$ and $R^{a4}$ are absent if A is an aromatic ring.

2. The method of claim 1;
wherein $R^{a2}$ is H.

3. The method of claim 1;
wherein $R^{a4}$ is selected from H, $C_{1-6}$ alkyl or substituted $C_{1-6}$ alkyl.

4. The method of claim 1;
wherein $R^{a1}$ and $R^{a3}$ are joined together with the atoms to which they are attached to form a ring A;
wherein A is selected from the group consisting of: phenyl;
naphthyl, indenyl, indanyl, tetralinyl, $C_{3-10}$ cycloalkyl, 4- to 7-membered aliphatic heterocyclyl, and 9- to 11-membered aliphatic heterobicyclyl; and
wherein A is unsubstituted or substituted.

5. The method of claim 1;
wherein T is selected from structure (iii).

6. The method of claim 1;
wherein y is 4, 6, 8, 10, or 12.

7. The method of claim 1;
wherein the carrier-linked treprostinil prodrug has the structure of formula (II-A):

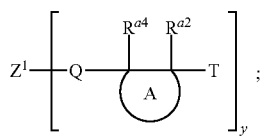
(II-A)

wherein:
each T is independently selected from structures (i) to (v):

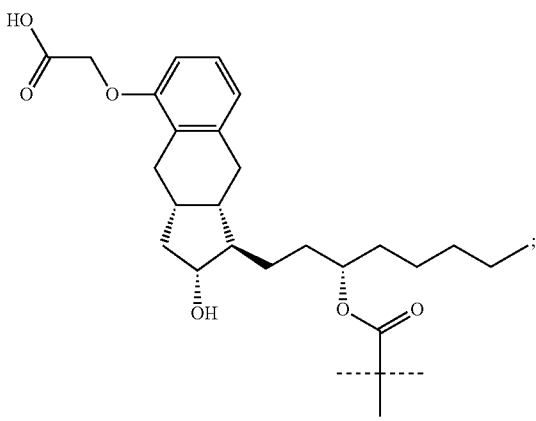
(i)

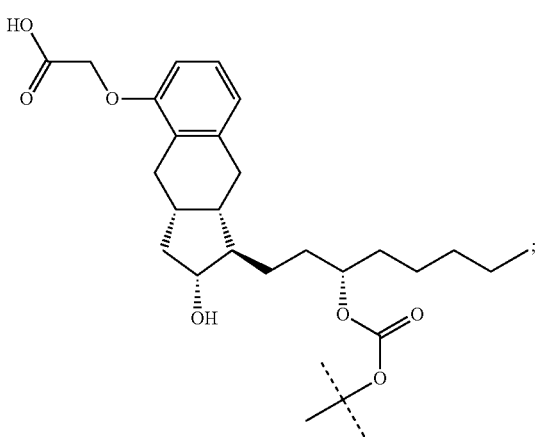
(ii)

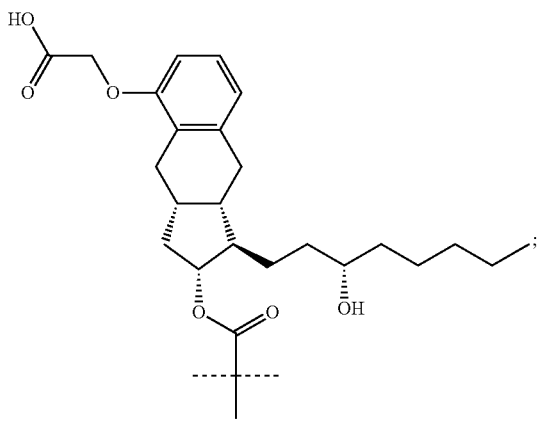
(iii)

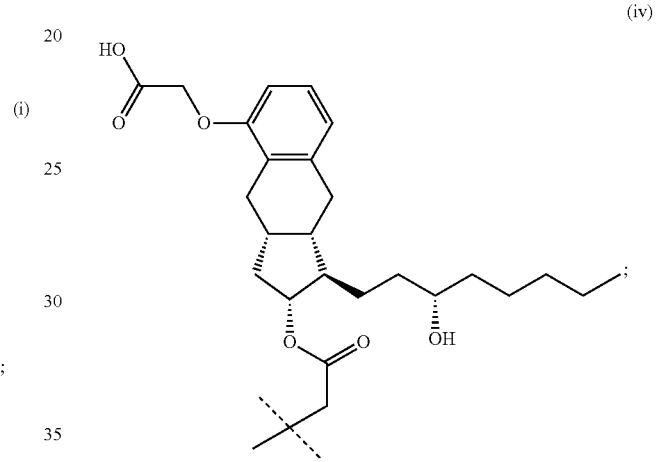
(iv)

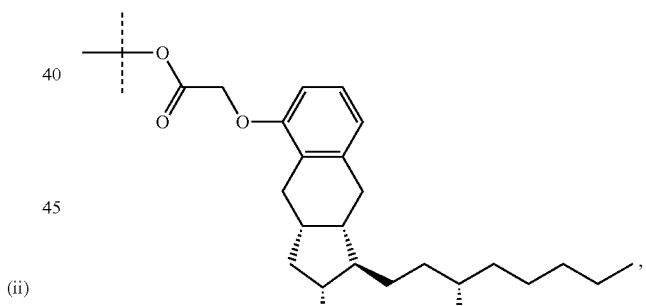
(v)

wherein:
dashed lines indicate attachment to the rest of the molecule;
y is an integer ranging of from 1 to 64;
$R^{a2}$ is selected from H, unsubstituted alkyl, and substituted alkyl;
$R^{a4}$ is selected from the group consisting of:
H, unsubstituted alkyl, and substituted alkyl;
A is selected from the group consisting of:
phenyl, naphthyl, indenyl, indanyl, tetralinyl, $C_{3-10}$ cycloalkyl, 4- to 7-membered aliphatic heterocyclyl, and 9- to 11-membered aliphatic heterobicyclyl, wherein A is unsubstituted or substituted;
Q is a spacer moiety; and
$Z^1$ is a carrier comprising a covalently bound polymer.

8. The method of claim 1;
wherein Q in formula (H) is selected from the group consisting of:
COOR$^{a9}$, OR$^{a9}$, C(O)R$^{a9}$, C(O)N(R$^{a9}$R$^{a9a}$), S(O)$_2$N(R$^{a9}$R$^{a9a}$), S(O)N(R$^{a9}$R$^{a9a}$), S(O)$_2$R$^{a9}$, S(O)R$^{a9}$, N(R$^{a9}$)S(O)$_2$N(R$^{a9a}$R$^{a9b}$), SR$^{a9}$, N(R$^{a9}$R$^{a9a}$), OC(O)R$^{a9}$, N(R$^{a9}$)C(O)R$^{a9a}$, N(R$^{a9}$)S(O)$_2$R$^{a9a}$, N(R$^{a9}$)S(O)R$^{a9a}$, N(R$^{a9}$)C(O)OR$^{a9a}$, N(R$^{a9}$)C(O)N(R$^{a9a}$R$^{a9b}$), OC(O)N(R$^{a9}$R$^{a9a}$), W; C$_{1-50}$ alkyl, C$_{2-50}$ alkenyl, and C$_{2-50}$ alkynyl;
wherein W, C$_{1-50}$ alkyl, C$_{2-50}$ alkenyl, and C$_{2-50}$ alkynyl are optionally substituted with one or more R$^{a10}$, which are the same or different;
wherein:
C$_{1-50}$ alkyl; C$_{2-50}$ alkenyl; and C$_{2-50}$ alkynyl are optionally interrupted by one or more groups selected from the group consisting of:
—W—, —C(O)O, —O—, —C(O)—, —C(O)N(R$^{a11}$)—, —S(O)$_2$N(R$^{a11}$)—, —S(O)N(R$^{a11}$)—, —S(O)$_2$—; —S(O)—, —N(R$^{a11}$)S(O)$_2$N(R$^{a11a}$)—, —S—, —N(R$^{a11}$)—, —OC(O)R$^{a11}$, —N(R$^{a11}$)C(O)—, —N(R$^{a11}$)S(O)$_2$—, —N(R$^{a11}$)S(O)—, —N(R$^{a11}$)C(O)O—, —N(R$^{a11}$)C(O)N(R$^{a11a}$)—, and —OC(O)N(R$^{a11}$R$^{a11a}$);
R$^{a9}$, R$^{a9a}$, and R$^{a9b}$ are independently selected from the group consisting of:
H, W, and C$_{1-50}$ alkyl, C$_{2-50}$ alkenyl, and C$_{2-50}$ alkynyl;
wherein W, C$_{1-50}$ alkyl, C$_{2-50}$ alkenyl, and C$_{2-50}$ alkynyl are optionally substituted with one or more R$^{a10}$, which are the same or different;
wherein:
C$_{1-50}$ alkyl, C$_{2-50}$ alkenyl, and C$_{2-50}$ alkynyl are optionally interrupted by one or more groups selected from the group consisting of:
—W—, —C(O)O—, —O—, —C(O)—, —C(O)N(R$^{a11}$)—, —S(O)$_2$N(R$^{a11}$)—, —S(O)N(R$^{a11}$)—, —S(O)$_2$—, —S(O)—, —N(R$^{a11}$)S(O)$_2$N(R$^{a11a}$)—, —S—, —N(R$^{a11}$)—, —OC(O)R$^{a11}$, —N(R$^{a11}$)C(O)—, —N(R$^{a11}$)S(O)$_2$—, —N(R$^{a11}$)S(O)—, —N(R$^{a11}$)C(O)O—, —N(R$^{a11}$)C(O)N(R$^{a11a}$)—, and —OC(O)N(R$^{a11}$R$^{a11}$);
W is selected from the group consisting of:
phenyl, naphthyl, indenyl, indanyl, tetralinyl, C$_{3-10}$ cycloalkyl, 4- to 7-membered heterocyclyl, and 9- to 11-membered heterobicyclyl;
wherein W is optionally substituted with one or more R$^{a10}$, which are the same or different;
R$^{a10}$ is selected from the group consisting of:
halogen, CN, oxo (=O), COOR$^{a12}$, OR$^{a12}$, C(O)R$^{a12}$, C(O)N(R$^{a12}$R$^{a12a}$), S(O)$_2$N(R$^{a12}$R$^{a12a}$), S(O)N(R$^{a12}$R$^{a12a}$), S(O)$_2$R$^{a12}$, S(O)R$^{a12}$, N(R$^{a12}$)S(O)$_2$N(R$^{a12}$R$^{a12b}$), SR$^{a12}$; N(R$^{a12}$R$^{a12a}$) NO$_2$, OC(O)R$^{a12}$, N(R$^{a12}$)C(O)R$^{a12a}$, N(R$^{a12}$)S(O)$_2$R$^{a12a}$, N(R$^{a12}$)S(O)R$^{a12a}$, N(R$^{a12}$)C(O)R$^{a12a}$, N(R$^{a12}$)C(O)N(R$^{a12}$R$^{a12b}$), OC(O)N(R$^{a12}$R$^{a12a}$), and C$_{1-6}$ alkyl;
wherein C$_{1-6}$ alkyl is optionally substituted with one or more halogen, which are the same or different; and
R$^{a11}$, R$^{a11a}$, R$^{a12}$, R$^{a12a}$, and R$^{a12b}$ are independently selected from the group consisting of:
H, and C$_{1-6}$ alkyl;
wherein C$_{1-6}$ alkyl is optionally substituted with one or more halogen, which are the same or different.

9. The method of claim 8;
wherein each -Q- is independently -Q$^{1a}$-Q$^1$-*, wherein the asterisk indicates the connection to Z';
wherein:
Q$^{1a}$ is a bond selected from the group consisting of:
—C(O)O—, —O—, —C(O)—, —C(O)N(R$^{a9a}$)—, —S(O)$_2$N(R$^{a9a}$)—, —S(O)N(R$^{a9a}$)—, —S(O)$_2$—, —S(O)—, —N(R$^{a9a}$)S(O)$_2$N(R$^{a9a}$)—, —S—, —N(R$^{a9a}$)—, —OC(O)—, —N(R$^{a9a}$)C(O)—, —N(R$^{a9a}$)S(O)$_2$—, —N(R$^{a9a}$)S(O)—, —N(R$^{a9a}$)C(O)O—, —N(R$^{a9a}$)C(O)N(R$^{a9b}$)—, —OC(O)N(R$^{a9a}$)—, and —W—,
Q$^1$ is selected from the group consisting of:
C$_{1-50}$ alkyl, C$_{2-50}$ alkenyl, and C$_{2-50}$ alkynyl which are optionally substituted with one or more R$^{a10}$, which are optionally interrupted, provided that Q$^1$ is at least C$_2$, by one or more groups selected from the group consisting of:
C$_{3-7}$ cycloalkyl, 4- to 7-membered heterocyclyl,

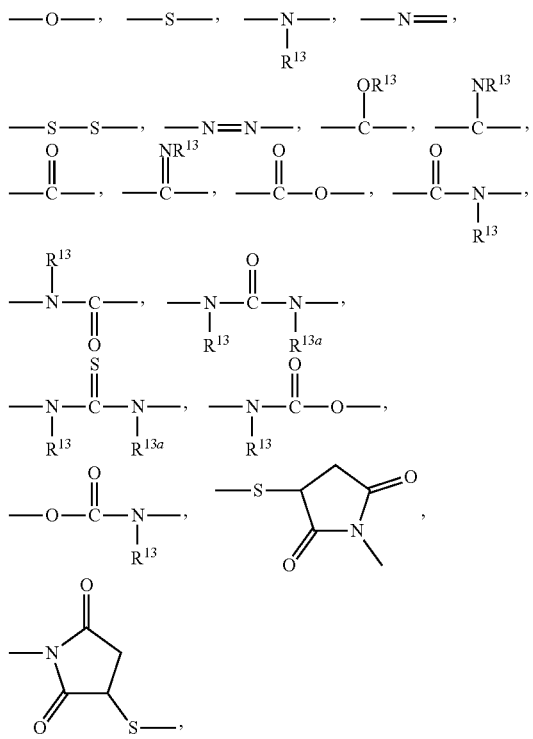

wherein each of said group may individually be present one or more times; and which C$_{1-50}$ alkyl, C$_{2-50}$ alkenyl, and C$_{2-50}$ alkynyl may optionally be terminated at the end connected to Z$^1$ by a group selected from C$_{3-7}$ cycloalkyl, 4- to 7-membered heterocyclyl,

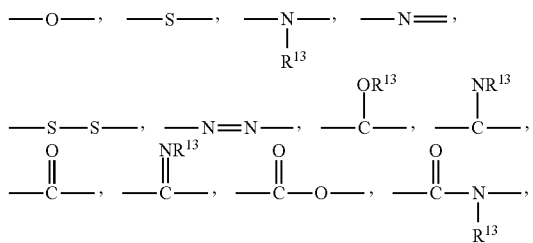

-continued

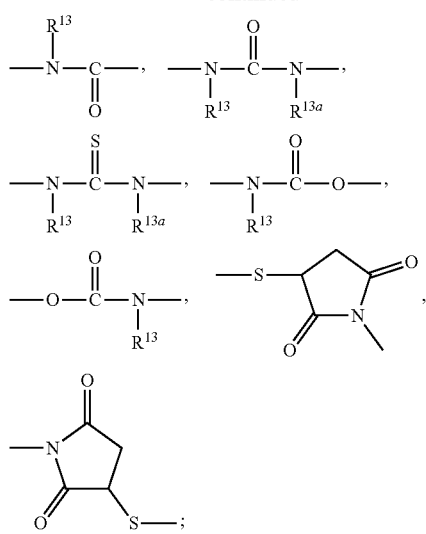

wherein:

$R^{a9a}$ is as defined in claim 8;

$R^{a10}$ is selected from the group consisting of:

halogen, CN, oxo (=O), $COOR^{a12}$, $OR^{a12}$, $C(O)R^{a12}$, $C(O)N(R^{a12}R^{a12a})$, $S(O)_2N(R^{a12}R^{a12a})$, $S(O)N(R^{a12}R^{a12a})$, $S(O)_2R^{a12}$, $S(O)R^{a12}$, $N(R^{a12})S(O)_2N(R^{a12a}R^{a12b})$, $SR^{a12}$, $N(R^{a12}R^{a12a})$, $NO_2$, $OC(O)R^{a12}$, $N(R^{a12})C(O)R^{a12a}$, $N(R^{a12})S(O)_2R^{a12a}$, $N(R^{a12})S(O)R^{a12a}$, $N(R^{a12})C(O)OR^{a12a}$, $N(R^{a12})C(O)N(R^{a12a}R^{a12B})$, $OC(O)N(R^{a12}R^{a12a})$, and $C_{1-6}$ alkyl;

wherein $C_{1-6}$ alkyl is optionally substituted with one or more halogen, which are the same or different;

$R^{a12}$, $R^{a12a}$ and $R^{a12b}$ are independently selected from the group consisting of:

H; and $C_{1-6}$ alkyl;

wherein $C_{1-6}$ alkyl is optionally substituted with one or more halogen, which are the same or different; and $R^{13}$ and $R^{13a}$ are independently selected from the group consisting of:

H, $C_{1-6}$ alkyl, $C_{2-6}$ alkenyl, and $C_{2-6}$ alkynyl.

10. The method of claim 1;

wherein the carrier-linked treprostinil prodrug is of formula (IIaa):

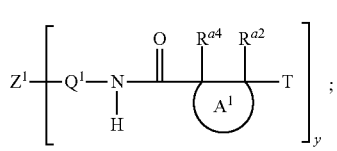

(IIaa)

wherein:

each T is independently selected from structures (i) or (iii):

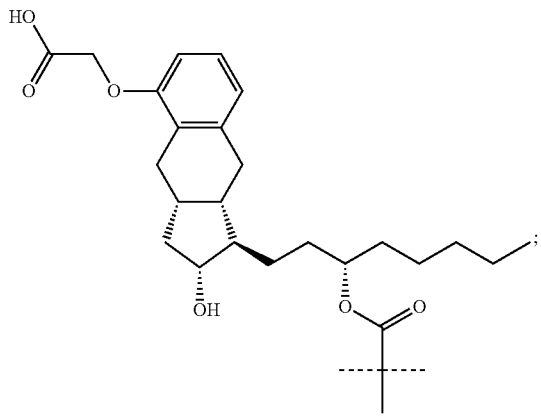

(i)

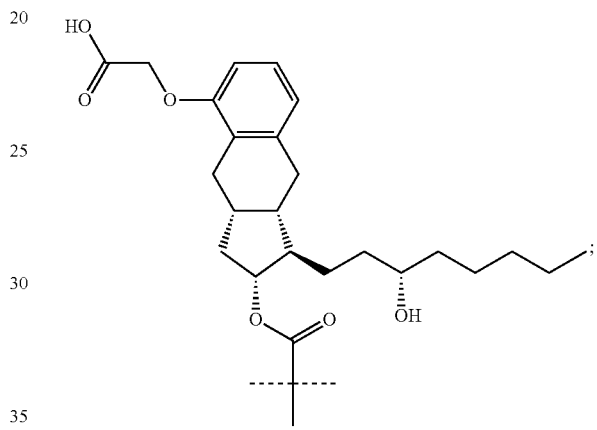

(iii)

wherein:
dashed lines indicate attachment to the rest of the molecule;
y is an integer ranging of from 1 to 64;
$R^{a2}$ is selected from H, unsubstituted alkyl, and substituted alkyl;
$R^{a4}$ is selected from H, unsubstituted alkyl, and substituted alkyl;
ring $A^1$ is a $C_{3-10}$ cycloalkyl; 4- to 7-membered aliphatic heterocyclyl; or 9- to 11-membered aliphatic heterobicyclyl;
wherein $A^1$ is unsubstituted or substituted;
$Q^1$ is selected from $C_{1-50}$ alkyl, $C_{2-50}$ alkenyl, and $C_{2-50}$ alkynyl which are optionally substituted with one or more $R^{a10}$, which are optionally interrupted, provided that $Q^1$ is at least $C_2$, by one or more groups selected from the group consisting of:
$C_{3-7}$ cycloalkyl, 4- to 7-membered heterocyclyl,

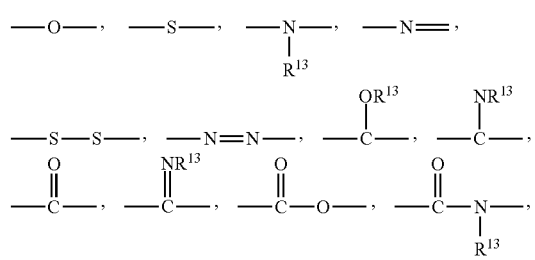

149

-continued

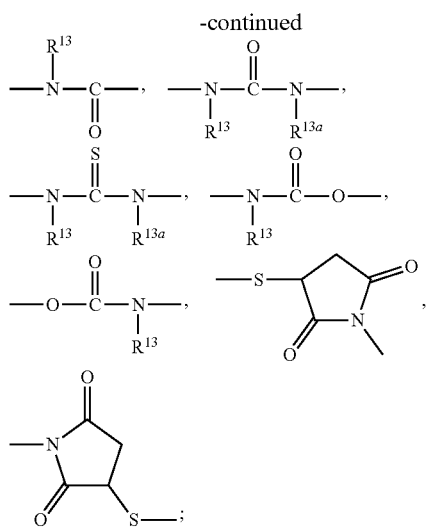

wherein each of said group may individually be present one or more times; and which $C_{1-50}$ alkyl, $C_{2-50}$ alkenyl, and $C_{2-50}$ alkynyl may optionally be terminated at the end connected to $Z^1$ by a group selected from $C_{3-7}$ cycloalkyl, 4- to 7-membered heterocyclyl,

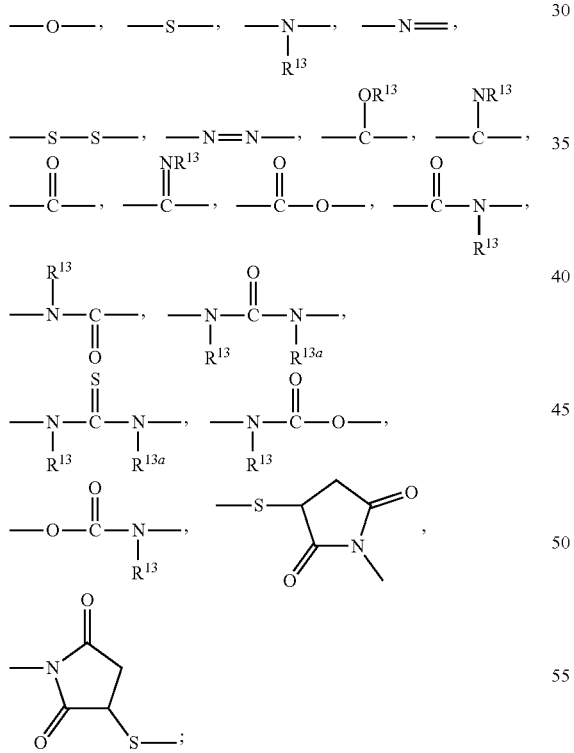

wherein:
$R^{a10}$ is selected from the group consisting of:
halogen, CN, oxo (=O), $COOR^{a12}$, $OR^{a12}$, $C(O)R^{a12}$, $C(O)N(R^{a12}R^{a12a})$, $S(O)_2N(R^{a12}R^{a12a})$, $S(O)N(R^{a12}R^{a12a})$, $S(O)_2R^{a12}$, $S(O)R^{a12}$, $N(R^{a12})S(O)_2R^{a12a}$, $SR^{a12}$, $N(R^{a12}R^{a12a})$, $NO_2$, $OC(O)R^{a12}$, $N(R^{a12})C(O)R^{a12a}$, $N(R^{a12})S(O)_2R^{a12a}$, $N(R^{a12})S(O)R^{a12a}$, $N(R^{a12})C(O)OR^{a12a}$, $N(R^{a12})C(O)N(R^{a12a}R^{a12b})$, $OC(O)N(R^{a12}R^{a12a})$, and $C_{1-6}$ alkyl;

wherein $C_{1-6}$ alkyl is optionally substituted with one or more halogen, which are the same or different;

$R^{a12}$, $R^{a12a}$ and $R^{a12b}$ are independently selected from the group consisting of:
H, and $C_{1-6}$ alkyl;
wherein $C_{1-6}$ alkyl is optionally substituted with one or more halogen, which are the same or different;

$R^{13}$ and $R^{13a}$ are independently selected from H, $C_{1-6}$ alkyl, $C_{2-6}$ alkenyl, or $C_{2-6}$ alkynyl; and $Z^1$ is a carrier comprising a covalently bound polymer.

11. The method of claim 1;
wherein the carrier-linked treprostinil prodrug is of formula (IIab):

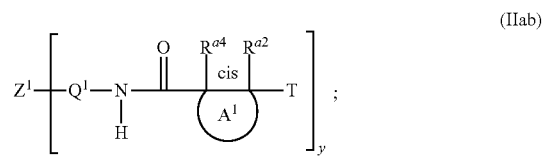

wherein:
each T is independently selected from structures (i) or (iii):

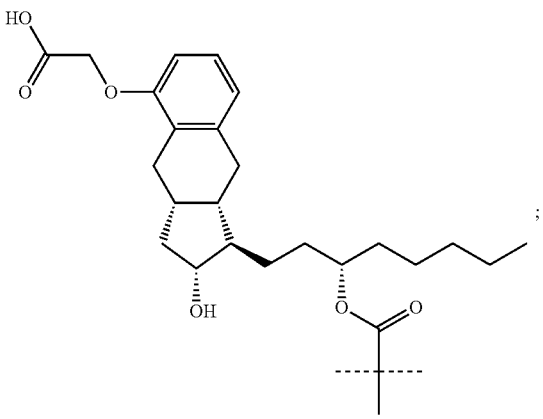

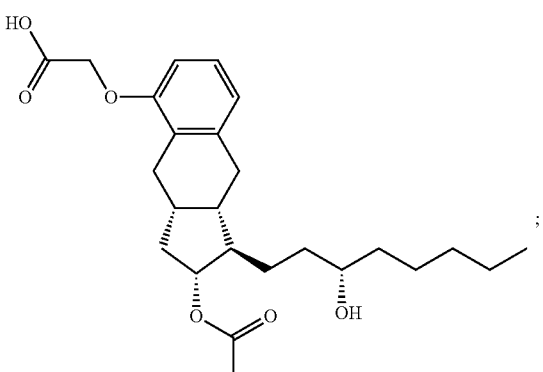

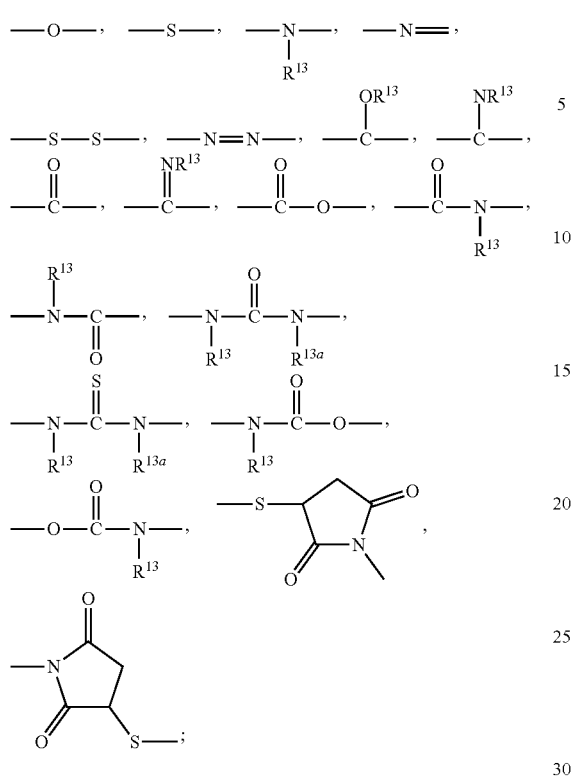

wherein:
dashed lines indicate attachment to the rest of the molecule;
y is an integer ranging of from 1 to 64;
$R^{a2}$ is selected from H, unsubstituted alkyl, and substituted alkyl;
$R^{a4}$ is selected from H, unsubstituted alkyl, and substituted alkyl;
ring $A^1$ is a $C_{3-10}$ cycloalkyl; 4- to 7-membered aliphatic heterocyclyl; or 9- to 11-membered aliphatic heterobicyclyl;
wherein $A^1$ is unsubstituted or substituted;
$Q^1$ is selected from $C_{1-50}$ alkyl, $C_{2-50}$ alkenyl, and $C_{2-50}$ alkynyl which are optionally substituted with one or more $R^{a10}$, which are optionally interrupted, provided that $Q^1$ is at least $C_2$, by one or more groups selected from the group consisting of:
$C_{3-7}$ cycloalkyl, 4- to 7-membered heterocyclyl,

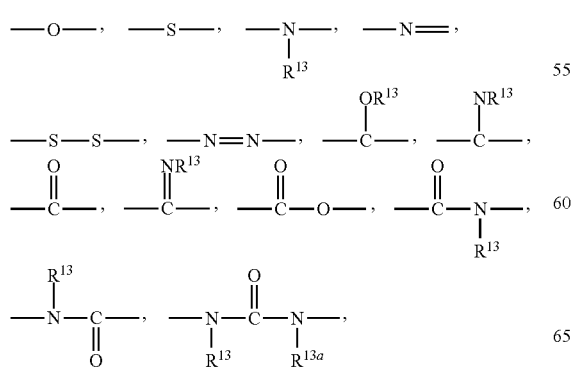

wherein each of said group may individually be present one or more times; and which $C_{1-50}$ alkyl, $C_{2-50}$ alkenyl, and $C_{2-50}$ alkynyl may optionally be terminated at the end connected to $Z^1$ by a group selected from $C_{3-7}$ cycloalkyl, 4- to 7-membered heterocyclyl,

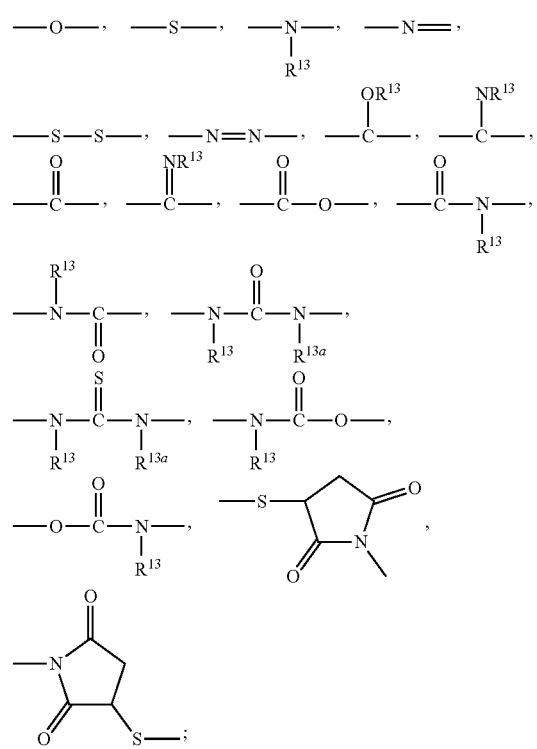

wherein:
$R^{a10}$ is selected from the group consisting of:
halogen, CN, oxo (=O), $COOR^{a12}$, $OR^{a12}$, $C(O)R^{a12}$, $C(O)N(R^{a12}R^{a12a})$, $S(O)_2N(R^{a12}R^{a12a})$, $S(O)N(R^{a12}R^{a12a})$, $S(O)_2R^{a12}$, $S(O)R^{a12}$, $N(R^{a12})S(O)_2N(R^{a12a}R^{a12b})$, $SR^{a12}$, $N(R^{a12}R^{a12a})$, $NO_2$, $OC(O)R^{a12}$, $N(R^{a12})C(O)R^{a12a}$, $N(R^{a12})S(O)_2R^{a12a}$, $N(R^{a12})S(O)R^{a12a}$, $N(R^{a12})C(O)OR^{a12a}$, $N(R^{a12})C(O)N(R^{a12a}R^{a12b})$, $OC(O)N(R^{a12}R^{a12a})$, and $C_{1-6}$ alkyl;
wherein $C_{1-6}$ alkyl is optionally substituted with one or more halogen, which are the same or different;

R$^{a12}$, R$^{a12a}$ and R$^{a12b}$ are independently selected from the group consisting of:
  H, and C$_{1-6}$ alkyl;
    wherein C$_{1-6}$ alkyl is optionally substituted with one or more halogen, which are the same or different;
R$^{13}$ and R$^{13a}$ are independently selected from H, C$_{1-6}$ alkyl, C$_{2-6}$ alkenyl, or C$_{2-6}$ alkynyl; and
Z$^1$ is a carrier comprising a covalently bound polymer.

12. The method of claim 1;
wherein the carrier-linked treprostinil prodrug is of formula (IIac) or (IIad):

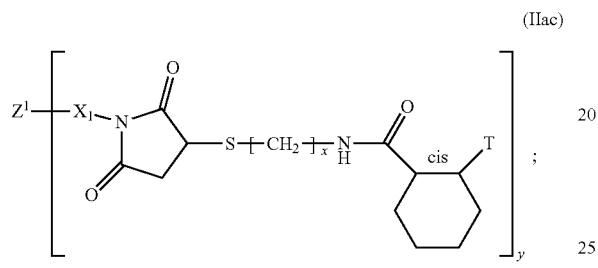
(IIac)

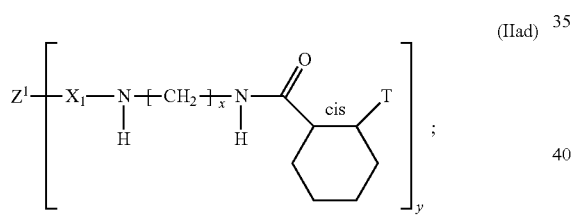
(IIad)

wherein:
  each T is independently selected from structures (i) or (iii):

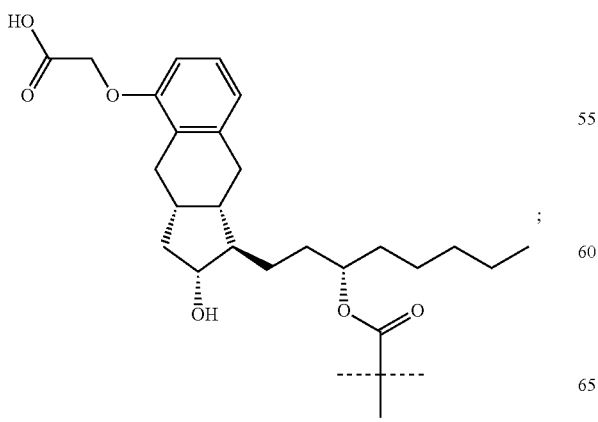
(i)

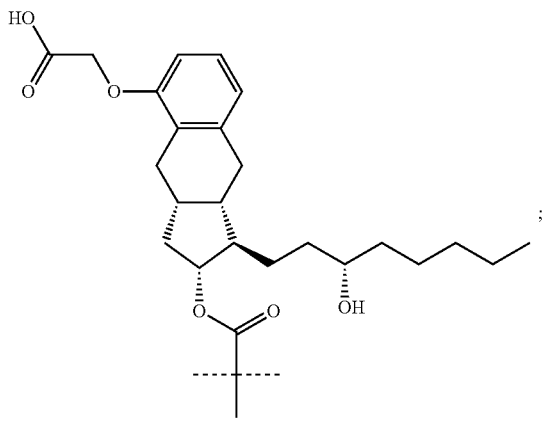
(iii)

Z$^1$ is a carrier comprising a covalently bound polymer;
y is an integer ranging of from 1 to 64;
x is selected from 2, 3, 4, 5, 6, 7 or 8; and
X$_1$ is selected from C$_{1-15}$ alkyl, C$_{2-15}$ alkenyl and C$_{2-15}$ alkynyl, which are optionally substituted or interrupted by one or more groups selected from the group consisting of:
  C$_{3-7}$ cycloalkyl, 4- to 7-membered heterocyclyl,

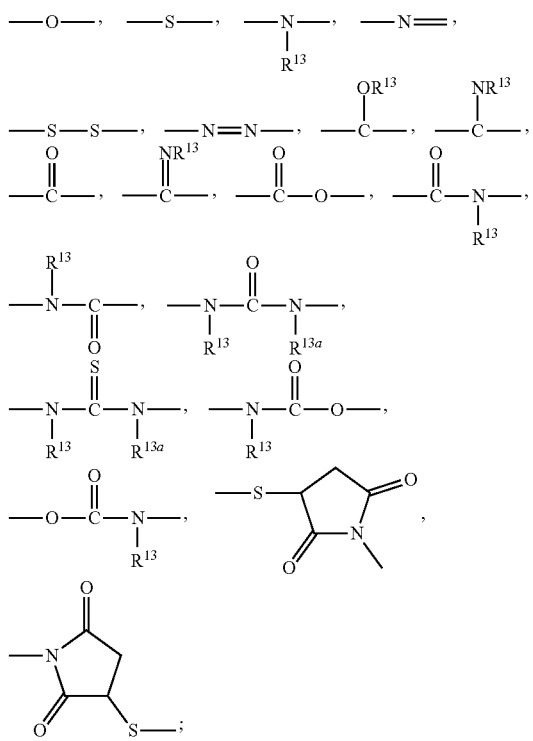

wherein R$^{13}$ and R$^{13a}$ are independently selected from H, C$_{1-6}$ alkyl, C$_{2-6}$ alkenyl, or C$_{2-6}$ alkynyl.

13. The method of claim 1;
wherein the carrier-linked treprostinil prodrug is of formula (IIb):

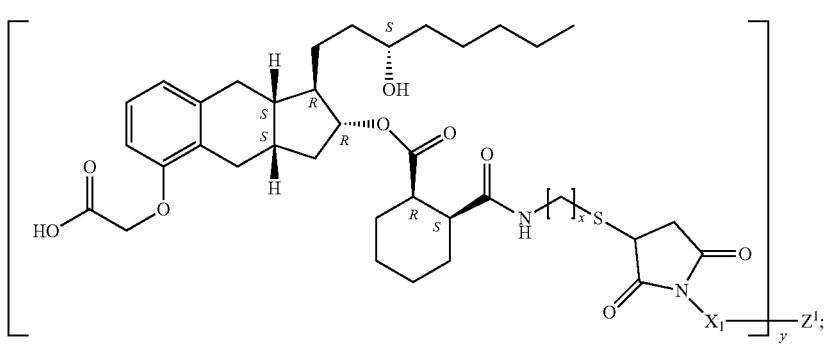

wherein:

X₁ is selected from $C_{1-15}$ alkyl, $C_{2-15}$ alkenyl and $C_{2-15}$ alkynyl, which are optionally substituted or interrupted by one or more groups selected from the group consisting of:

$C_{3-7}$ cycloalkyl, 4- to 7-membered heterocyclyl,

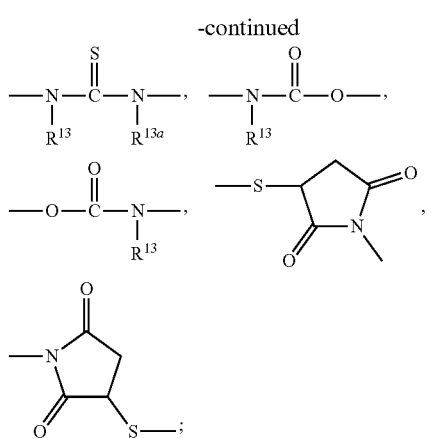

wherein:

$R^{13}$ and $R^{13a}$ are independently selected from H, $C_{1-6}$ alkyl, $C_{2-6}$ alkenyl, or $C_{2-6}$ alkynyl;

y is an integer ranging of from 1 to 64;

x is selected from 2, 3, 4, 5, 6, 7 or 8; and $Z^1$ is a carrier comprising a covalently bound polymer.

14. The method of claim 12;

wherein x is 6.

15. The method of claim 1;

wherein the carrier-linked treprostinil prodrug has the structure of formula (IIba):

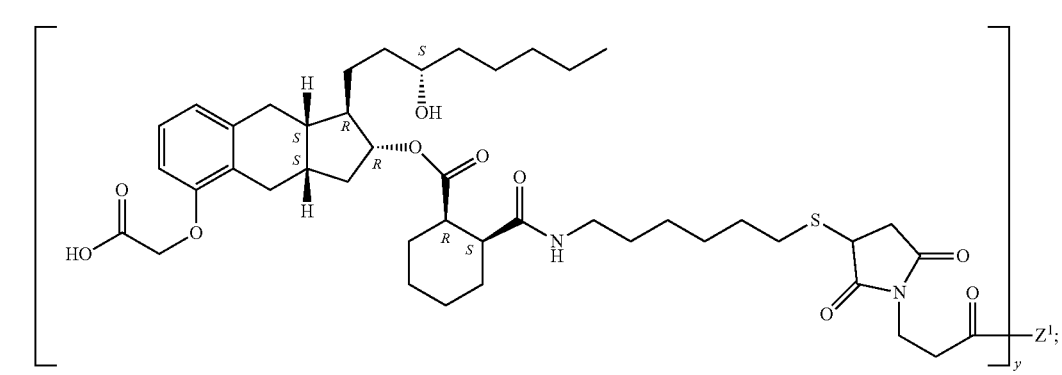

wherein:
  y is an integer ranging of from 1 to 64; and
  $Z^1$ is a carrier comprising a covalently bound polymer.

16. The method of claim 1;
wherein the carrier Z¹ has the structure of formula (VII):

B─(A)$_n$     (VII);

wherein:
  B is branching core;
  A is a poly(ethylene glycol)-based polymeric chain; and
  n is an integer of from 3 to 32.

17. The method of claim 1;
wherein $Z^1$ is of formula (IIca):

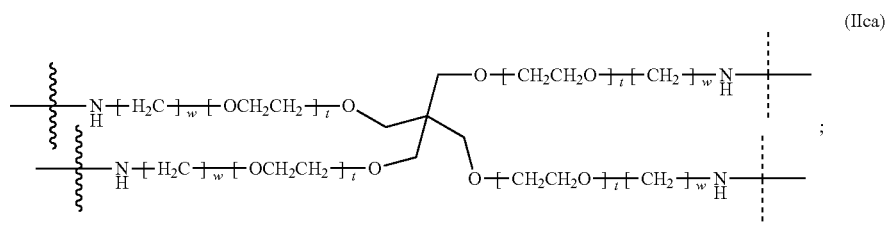

(IIca)

wherein:
  t ranges from 80 to 160;
  w ranges from 2 to 6; and
  dashed lines indicate attachment to the rest of the carrier-linked treprostinil prodrug.

18. The method of claim 17;
wherein w is 2 or 3.

19. The method of claim 1;
wherein the carrier-linked treprostinil prodrug is of formula (IIc), or a pharmaceutically acceptable salt thereof:

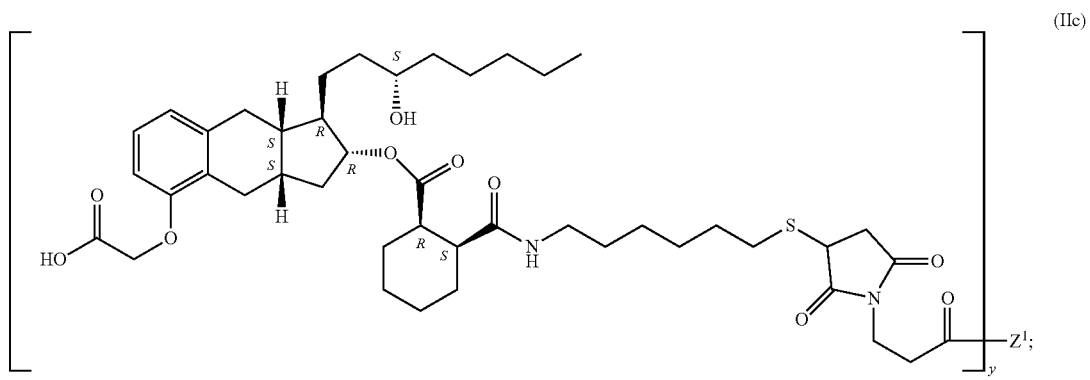

(IIc)

wherein y is 4 and $Z^1$ represents a moiety (IIca):

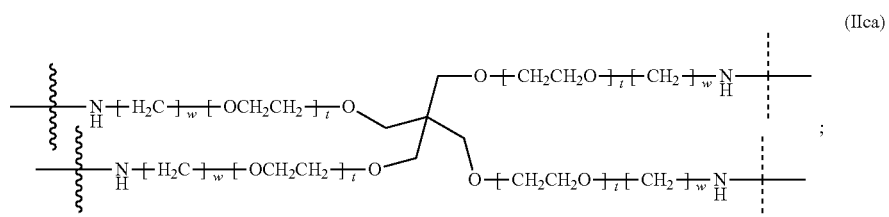

(IIca)

wherein:
dashed lines indicate attachment to the rest of the structure of formula (IIc);
t ranges from 80 to 160; and
w is 2 or 3.

20. The method of claim 1;
wherein $R^{a1}$ is $C_{1-6}$ alkyl or substituted $C_{1-6}$ alkyl.

21. The method of claim 1;
wherein $R^{a3}$ is H, $C_{1-6}$ alkyl or substituted $C_{1-6}$ alkyl.

22. The method of claim 1;
wherein the carrier-linked treprostinil prodrug, or a pharmaceutically acceptable salt thereof, as claimed in claim 1 is administered as part of a pharmaceutical composition that optionally further comprises one or more pharmaceutically acceptable excipients.

23. The method of claim 22;
(i) wherein the carrier-linked treprostinil prodrug is sufficiently dosed in the pharmaceutical composition to provide a therapeutically effective amount of treprostinil for at least 12 hours in one application; and/or
(ii) wherein a single dose of the pharmaceutical composition comprises about 2 to about 6 mg the treprostinil moiety T.

24. The method of claim 1;
wherein $R^{a1}$ and $R^{a3}$ are joined together with the atoms to which they are attached to form a ring A; and
wherein A is selected from the group consisting of:
cyclopropane, cyclobutane, cyclopentane, cyclohexane, and cycloheptane.

\* \* \* \* \*

SEQUENCE LISTING

```
<160> NUMBER OF SEQ ID NOS: 15

<210> SEQ ID NO 1
<211> LENGTH: 20
<212> TYPE: PRT
<213> ORGANISM: Artificial Sequence
<220> FEATURE:
<223> OTHER INFORMATION: polymer cassette

<400> SEQUENCE: 1

Ala Ala Ala Ala Ser Ser Ala Ser Ser Ala Ser Ser Ser Ser Ser Ala
1               5                   10                  15

Ala Ala Ser Ala
            20

<210> SEQ ID NO 2
<211> LENGTH: 20
<212> TYPE: PRT
<213> ORGANISM: Artificial Sequence
<220> FEATURE:
<223> OTHER INFORMATION: polymer cassette

<400> SEQUENCE: 2

Ala Ala Ser Ala Ala Ala Ser Ser Ala Ala Ala Ser Ala Ala Ala Ala
1               5                   10                  15

Ser Ala Ser Ser
            20

<210> SEQ ID NO 3
<211> LENGTH: 20
```

```
<212> TYPE: PRT
<213> ORGANISM: Artificial Sequence
<220> FEATURE:
<223> OTHER INFORMATION: polymer cassette

<400> SEQUENCE: 3

Ala Ser Ala Ser Ala Ser Ala Ser Ala Ser Ala Ser Ser Ala Ala Ser
1               5                   10                  15

Ala Ala Ser Ala
            20

<210> SEQ ID NO 4
<211> LENGTH: 20
<212> TYPE: PRT
<213> ORGANISM: Artificial Sequence
<220> FEATURE:
<223> OTHER INFORMATION: polymer cassette

<400> SEQUENCE: 4

Ser Ala Ala Ser Ser Ser Ala Ser Ser Ser Ala Ala Ser Ser Ala
1               5                   10                  15

Ser Ala Ala Ala
            20

<210> SEQ ID NO 5
<211> LENGTH: 20
<212> TYPE: PRT
<213> ORGANISM: Artificial Sequence
<220> FEATURE:
<223> OTHER INFORMATION: polymer cassette

<400> SEQUENCE: 5

Ser Ser Ser Ser Ala Ala Ser Ala Ala Ser Ala Ala Ala Ala Ala Ser
1               5                   10                  15

Ser Ser Ala Ser
            20

<210> SEQ ID NO 6
<211> LENGTH: 20
<212> TYPE: PRT
<213> ORGANISM: Artificial Sequence
<220> FEATURE:
<223> OTHER INFORMATION: polymer cassette

<400> SEQUENCE: 6

Ser Ser Ala Ser Ser Ser Ala Ala Ser Ser Ser Ala Ser Ser Ser
1               5                   10                  15

Ala Ser Ala Ala
            20

<210> SEQ ID NO 7
<211> LENGTH: 20
<212> TYPE: PRT
<213> ORGANISM: Artificial Sequence
<220> FEATURE:
<223> OTHER INFORMATION: polymer cassette

<400> SEQUENCE: 7

Ser Ala Ser Ala Ser Ala Ser Ala Ser Ala Ser Ala Ala Ser Ser Ala
1               5                   10                  15

Ser Ser Ala Ser
            20

<210> SEQ ID NO 8
```

-continued

```
<211> LENGTH: 20
<212> TYPE: PRT
<213> ORGANISM: Artificial Sequence
<220> FEATURE:
<223> OTHER INFORMATION: polymer cassette

<400> SEQUENCE: 8

Ala Ser Ser Ala Ala Ala Ser Ala Ala Ala Ala Ser Ser Ala Ala Ser
1               5                   10                  15

Ala Ser Ser Ser
            20

<210> SEQ ID NO 9
<211> LENGTH: 20
<212> TYPE: PRT
<213> ORGANISM: Artificial Sequence
<220> FEATURE:
<223> OTHER INFORMATION: polymer cassette

<400> SEQUENCE: 9

Ala Ser Pro Ala Ala Pro Ala Pro Ala Ser Pro Ala Ala Pro Ala Pro
1               5                   10                  15

Ser Ala Pro Ala
            20

<210> SEQ ID NO 10
<211> LENGTH: 20
<212> TYPE: PRT
<213> ORGANISM: Artificial Sequence
<220> FEATURE:
<223> OTHER INFORMATION: polymer cassette

<400> SEQUENCE: 10

Ala Ala Pro Ala Ser Pro Ala Pro Ala Ala Pro Ser Ala Pro Ala Pro
1               5                   10                  15

Ala Ala Pro Ser
            20

<210> SEQ ID NO 11
<211> LENGTH: 20
<212> TYPE: PRT
<213> ORGANISM: Artificial Sequence
<220> FEATURE:
<223> OTHER INFORMATION: polymer cassette

<400> SEQUENCE: 11

Ala Pro Ser Ser Pro Ser Pro Ser Ala Pro Ser Ser Pro Ser Pro Ala
1               5                   10                  15

Ser Pro Ser Ser
            20

<210> SEQ ID NO 12
<211> LENGTH: 20
<212> TYPE: PRT
<213> ORGANISM: Artificial Sequence
<220> FEATURE:
<223> OTHER INFORMATION: polymer cassette

<400> SEQUENCE: 12

Ser Ser Pro Ser Ala Pro Ser Pro Ser Ser Pro Ala Ser Pro Ser Pro
1               5                   10                  15

Ser Ser Pro Ala
            20
```

```
<210> SEQ ID NO 13
<211> LENGTH: 24
<212> TYPE: PRT
<213> ORGANISM: Artificial Sequence
<220> FEATURE:
<223> OTHER INFORMATION: polymer cassette

<400> SEQUENCE: 13

Ala Ala Ser Pro Ala Ala Pro Ser Ala Pro Pro Ala Ala Ala Ser Pro
 1               5                  10                  15

Ala Ala Pro Ser Ala Pro Pro Ala
            20

<210> SEQ ID NO 14
<211> LENGTH: 20
<212> TYPE: PRT
<213> ORGANISM: Artificial Sequence
<220> FEATURE:
<223> OTHER INFORMATION: polymer cassette

<400> SEQUENCE: 14

Ala Ser Ala Ala Ala Pro Ala Ala Ala Ser Ala Ala Ala Ser Ala Pro
 1               5                  10                  15

Ser Ala Ala Ala
            20

<210> SEQ ID NO 15
<211> LENGTH: 20
<212> TYPE: PRT
<213> ORGANISM: Artificial Sequence
<220> FEATURE:
<223> OTHER INFORMATION: polymer cassette

<400> SEQUENCE: 15

Ser Ala Pro Ser Ser Pro Ser Pro Ser Ala Pro Ser Ser Pro Ser Pro
 1               5                  10                  15

Ala Ser Pro Ser
            20
```